(12) United States Patent
Sparks et al.

(10) Patent No.: US 11,952,367 B2
(45) Date of Patent: Apr. 9, 2024

(54) PYRIDINE AND PYRIDIMINE COMPOUNDS AS PI3K-GAMMA INHIBITORS

(71) Applicant: Incyte Corporation, Wilmington, DE (US)

(72) Inventors: Richard B. Sparks, Hockessin, DE (US); Stacey Shepard, Wilmington, DE (US); Andrew P. Combs, Kennett Square, PA (US); Andrew W. Buesking, Wilmington, DE (US); Lixin Shao, Wilmington, DE (US); Haisheng Wang, Hockessin, DE (US); Nikoo Falahatpisheh, Wilmington, DE (US)

(73) Assignee: Incyte Corporation, Wilmington, DE (US)

( * ) Notice: Subject to any disclaimer, the term of this patent is extended or adjusted under 35 U.S.C. 154(b) by 0 days.

(21) Appl. No.: 17/705,079

(22) Filed: Mar. 25, 2022

(65) Prior Publication Data

US 2022/0227736 A1 Jul. 21, 2022

Related U.S. Application Data

(63) Continuation of application No. 16/369,541, filed on Mar. 29, 2019, now Pat. No. 11,352,340, which is a continuation of application No. 15/398,121, filed on Jan. 4, 2017, now abandoned.

(60) Provisional application No. 62/274,942, filed on Jan. 5, 2016.

(51) Int. Cl.
| | |
|---|---|
| *C07D 401/14* | (2006.01) |
| *C07D 403/14* | (2006.01) |
| *C07D 405/14* | (2006.01) |
| *C07D 487/08* | (2006.01) |
| *C07D 487/10* | (2006.01) |
| *C07D 491/107* | (2006.01) |

(52) U.S. Cl.
CPC ......... *C07D 401/14* (2013.01); *C07D 403/14* (2013.01); *C07D 405/14* (2013.01); *C07D 487/08* (2013.01); *C07D 487/10* (2013.01); *C07D 491/107* (2013.01)

(58) Field of Classification Search
CPC .. C07D 401/14; C07D 403/14; C07D 405/14; C07D 487/08; C07D 487/10; C07D 491/107
See application file for complete search history.

(56) References Cited

U.S. PATENT DOCUMENTS

| | | | |
|---|---|---|---|
| 4,269,846 A | 5/1981 | Huang et al. |
| 5,521,184 A | 5/1996 | Zimmermann |
| 7,186,832 B2 | 3/2007 | Sun |
| 7,511,145 B2 | 3/2009 | Schmitz et al. |
| 8,680,108 B2 | 3/2014 | Li et al. |
| 8,759,359 B2 | 6/2014 | Combs et al. |
| 8,940,752 B2 | 1/2015 | Li et al. |
| 9,062,055 B2 | 6/2015 | Li et al. |
| 9,096,600 B2 | 8/2015 | Li et al. |
| 9,108,984 B2 | 8/2015 | Combs et al. |
| 9,126,948 B2 | 9/2015 | Combs et al. |
| 9,193,721 B2 | 11/2015 | Combs et al. |
| 9,199,982 B2 | 12/2015 | Li et al. |
| 9,586,949 B2 | 3/2017 | Zou et al. |
| 10,022,387 B2 | 7/2018 | Zou et al. |
| 10,065,963 B2 | 9/2018 | Shvartsbart et al. |
| 10,138,248 B2 | 11/2018 | Buesking et al. |
| 10,472,368 B2 | 11/2019 | Shvartsbart et al. |
| 10,479,795 B2 | 11/2019 | Buesking et al. |
| 10,596,184 B2 | 3/2020 | Zou et al. |
| 10,975,088 B2 | 4/2021 | Buesking et al. |
| 11,091,491 B2 | 8/2021 | Shvartsbart et al. |
| 11,352,340 B2 | 6/2022 | Sparks et al. |
| 2008/0019915 A1 | 1/2008 | Hadida-Ruah et al. |
| 2010/0298334 A1 | 11/2010 | Rodgers et al. |
| 2011/0015212 A1 | 1/2011 | Li et al. |
| 2011/0059951 A1 | 3/2011 | Rodgers et al. |
| 2011/0183985 A1 | 7/2011 | Li et al. |
| 2011/0224190 A1 | 9/2011 | Huang et al. |
| 2012/0149681 A1 | 6/2012 | Rodgers et al. |
| 2012/0149682 A1 | 6/2012 | Rodgers et al. |
| 2012/0157430 A1 | 6/2012 | Li et al. |
| 2012/0238564 A1 | 9/2012 | Luk et al. |
| 2013/0018034 A1 | 1/2013 | Yao et al. |
| 2013/0045963 A1 | 2/2013 | Rodgers et al. |
| 2013/0059835 A1 | 3/2013 | Li et al. |
| 2013/0261101 A1 | 10/2013 | Combs et al. |

(Continued)

FOREIGN PATENT DOCUMENTS

| | | |
|---|---|---|
| EP | 2044051 | 1/2010 |
| JP | 2015-512940 | 4/2015 |

(Continued)

OTHER PUBLICATIONS

Campa, Nature Communications, 2018, vol. 9:5232, 1-16. (Year: 2018).*

(Continued)

*Primary Examiner* — D Margaret M Seaman
(74) *Attorney, Agent, or Firm* — Fish & Richardson P.C.

(57) ABSTRACT

The present disclosure provides compounds of Formula I, or pharmaceutically acceptable salts thereof, that modulate the activity of phosphoinositide 3-kinases-gamma (PI3Kγ) and are useful in the treatment of diseases related to the activity of PI3Kγ including, for example, autoimmune diseases, cancer, cardiovascular diseases, and neurodegenerative diseases.

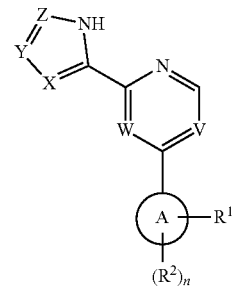

29 Claims, No Drawings

(56) References Cited

U.S. PATENT DOCUMENTS

| | | |
|---|---|---|
| 2014/0005166 A1 | 1/2014 | Rodgers et al. |
| 2014/0121198 A1 | 5/2014 | Li et al. |
| 2014/0249132 A1 | 9/2014 | Li et al. |
| 2014/0275127 A1 | 9/2014 | Combs et al. |
| 2014/0343030 A1 | 11/2014 | Li et al. |
| 2015/0284390 A1 | 10/2015 | Li et al. |
| 2015/0361094 A1 | 12/2015 | Li et al. |
| 2016/0000795 A1 | 1/2016 | Scherle et al. |
| 2016/0022685 A1 | 1/2016 | Li et al. |
| 2016/0024117 A1 | 1/2016 | Li et al. |
| 2017/0129899 A1 | 5/2017 | Shvartsbart et al. |
| 2017/0190689 A1 | 7/2017 | Sparks et al. |
| 2018/0009816 A1 | 1/2018 | Buesking et al. |
| 2019/0060331 A1 | 2/2019 | Zou et al. |
| 2019/0062336 A1 | 2/2019 | Shvartsbart et al. |
| 2019/0119287 A1 | 4/2019 | Buesking et al. |
| 2019/0359592 A1 | 11/2019 | Sparks et al. |
| 2020/0031837 A1 | 1/2020 | Shvartsbart et al. |
| 2020/0102315 A1 | 4/2020 | Buesking et al. |
| 2022/0251087 A1 | 8/2022 | Buesking et al. |

FOREIGN PATENT DOCUMENTS

| | | |
|---|---|---|
| WO | WO 00/09495 | 2/2000 |
| WO | WO 00/053595 | 9/2000 |
| WO | WO 01/014402 | 3/2001 |
| WO | WO 01/064655 | 9/2001 |
| WO | WO 01/85724 | 11/2001 |
| WO | WO 2002/000196 | 1/2002 |
| WO | WO 03/024967 | 3/2003 |
| WO | WO 03/035065 | 5/2003 |
| WO | WO 03/035644 | 5/2003 |
| WO | WO 03/037347 | 5/2003 |
| WO | WO 03/068225 | 8/2003 |
| WO | WO 03/099771 | 12/2003 |
| WO | WO 04/005281 | 1/2004 |
| WO | WO 04/046120 | 6/2004 |
| WO | WO 04/056786 | 7/2004 |
| WO | WO 04/080980 | 9/2004 |
| WO | WO 2004/078943 | 9/2004 |
| WO | WO 2005/012288 | 2/2005 |
| WO | WO 05/028444 | 3/2005 |
| WO | WO 2005/118580 | 12/2005 |
| WO | WO 2006/056399 | 6/2006 |
| WO | WO 2007/019416 | 2/2007 |
| WO | WO 2007/019417 | 2/2007 |
| WO | WO 2007/028051 | 3/2007 |
| WO | WO 2009/005551 | 1/2009 |
| WO | WO 2009/016118 | 2/2009 |
| WO | WO 2009/024585 | 2/2009 |
| WO | WO 2009/079011 | 6/2009 |
| WO | WO 2009/123776 | 10/2009 |
| WO | WO 2009/133127 | 11/2009 |
| WO | WO 2009/158118 | 12/2009 |
| WO | WO 2010/051245 | 5/2010 |
| WO | WO 2010/061903 | 6/2010 |
| WO | WO 2010/069684 | 6/2010 |
| WO | WO 2010/135014 | 11/2010 |
| WO | WO 2011/099832 | 8/2011 |
| WO | WO 2011/123609 | 10/2011 |
| WO | WO 2011/149856 | 12/2011 |
| WO | WO 2011/149874 | 12/2011 |
| WO | WO 2012/051410 | 4/2012 |
| WO | WO 2012/074126 | 6/2012 |
| WO | WO 2012/143796 | 10/2012 |
| WO | WO 2012/170867 | 12/2012 |
| WO | WO 2013/129674 | 9/2013 |
| WO | WO 2013/154878 | 10/2013 |
| WO | WO 2013/180193 | 12/2013 |
| WO | WO 2014/009295 | 1/2014 |
| WO | WO 2014/149207 | 9/2014 |
| WO | WO 2014/153529 | 9/2014 |
| WO | WO 2014/182954 | 11/2014 |
| WO | WO 2015/008872 | 1/2015 |
| WO | WO 2015/051241 | 4/2015 |
| WO | WO 2015/154878 | 10/2015 |
| WO | WO 2016/044342 | 3/2016 |
| WO | WO 2016/054491 | 4/2016 |
| WO | WO 2016/075130 | 5/2016 |

OTHER PUBLICATIONS

Chamcheu, Antioxidants Redox Signaling, vol. 26(2), 2017, 1-28. (Year: 2017).*

Jacot, J Opthalmology, vol. 2011, Article ID 589813, 1-19, 2011. (Year: 2011).*

Confettura, Translational Neurodegeneration, 2022, 11:2, 1-18. (Year: 2022).*

U.S. Appl. No. 60/578,491, Ren, filed Jun. 10, 2004.

Ameriks and Venable, "Small Molecule Inhibitors of Phosphoinositide 3-Kinase (PI3K) δand γ," Curr Topics Med Chem., 2009, 9:738-753.

Bala et al., "Highy efficient water-mediated approach to access benzazoles: metal catalyst and base-free synthesis of 2-substituted benzimidazoles, benzoxazoles, and benzothiazoles," Molecular Diversity, Mar. 2015, 19(2): 263-272.

Barber et al., "Class IB-Phosphatidylinositol 3-Kinase (PI3K) Deficiency Ameliorates IA-PI3K-Induces Systemic Lupus but Not T Cell Invasion," J Immunol., 2006, 176:589-593.

Barber et al., "PI3Kgamma inhibition blocks glomerulonephritis and extends lifespan in a mouse model of systemic lupus," Nat Med., Sep. 2005, 11(9): 933-5.

Berge, Journal of Pharmaceutical Science, 66, 2 (1977).

Berod et al., "PI3Kγ deficiency delays the onset of experimental autoimmune encephalomyelitis and ameliorates its clinical outcome," Eur J Immunol, Mar. 2011, 41(3): 833-44.

Blom et al., "Optimizing Preparative LC/MS Configurations and Methods for Parallel Synthesis Purification," J. Comb. Chem., 2003, 5: 670-683.

Blom et al., "Preparative LC-MS Purification: Improved Compound-Specific Method Optimization," J. Comb. Chem., 2004, 6: 874-883.

Blom, "Two-Pump at-col. Dilution Configuration for Preparative Liquid Chromatography-Mass Spectrometry," J. Comb. Chem., 2002, 4: 295-301.

Brock et al., "Roles of G beta gamma in membrane recruitment and activation of p110 gamma/p101 phosphoinositide 3-kinase gamma," J Cell Biol, Jan. 2003, 160(1): 89-99.

Camps et al., "Blockade of PI3Kγ suppresses joint inflammation and damage in mouse models of rheumatoid arthritis," Nature Medicine, Sep. 2005, 11(9): 936-943.

Cantley, "The phosphoinositide 3-kinase pathway," Science, May 2002, 296(5573): 1655-7.

Carter et al., "Prioritization of driver mutations in pancreatic cancer using cancer-specific high-throughput annotation of somatic mutations (CHASM)," Cancer Biol Ther, Sep. 2010, 10(6): 582-7.

Collier et al., "Discovery of Highly Isoform Selective Thiazolopiperidine Inhibitors of Phosphoinositide 3-Kinase γ," Journal of Medicinal Chemistry, 2015, 58: 5684-5688.

Collier et al., "Structural Basis for Isoform Selectivity in a Class of Benzothiazole Inhibitors of Phosphoinositide 3-Kinase [gamma]," Journal of Medicinal Chemistry, Jan. 2015, 58(1): 517-521.

Comerford et al., "PI3Kγ drives priming and survival of autoreactive CD4(+) T cells during experimental autoimmune encephalomyelitis," PLoS One, 2012, 7(9): e45095.

Cossy et al., "Formation of optically active 3-hydroxypiperidines," Tetrahedron Letters, Jan. 23, 1995, 36(4):549-552.

Cushing et al., "PI3Kδ and PI3Kγ as Targets for Autoimmune and Inflammatory Diseases," Journal of Medicinal Chemistry, 2012, 55: 8559-8581.

Database Registry [online], Chemical Abstracts Service, Columbus, OH, US; Aug. 2012, CAS client services: XP002755356, Database accession No. 1391828-67-3.

Database Registry [online], Chemical Abstracts Service, Columbus, OH, US; Dec. 2011, Chemical Catalog; Supplier: Ukrorgsyntez ltd.: XP002755357, Database accession No. 1347088-14-5.

(56) References Cited

OTHER PUBLICATIONS

Database Registry [online], Chemical Abstracts Service, Columbus, OH, US; Dec. 2012, Chemical Catalog; Supplier: Aurora Fine Chemicals: XP002755355, Database accession No. 1411464-90-8.
Database Registry [online], Chemical Abstracts Service, Columbus, OH, US; Feb. 2014, Chemical Catalog; Supplier: Aurora Fine Chemicals: XP002755346, Database accession No. 1554931-95-1.
Database Registry [online], Chemical Abstracts Service, Columbus, OH, US; Feb. 2014, Chemical Catalog; Supplier: Aurora Fine Chemicals: XP002755347, Database accession No. 1540856-06-1.
Database Registry [online], Chemical Abstracts Service, Columbus, OH, US; Feb. 2014, Chemical Catalog; Supplier: Aurora Fine Chemicals: XP002755349, Database accession No. 1538237-68-1.
Database Registry [online], Chemical Abstracts Service, Columbus, OH, US; Feb. 2014, Chemical Catalog; Supplier: Aurora Fine Chemicals: XP002755350, Database accession No. 1536955-67-5.
Database Registry [online], Chemical Abstracts Service, Columbus, OH, US; Jan. 2014, Chemical Catalog; Supplier: Aurora Fine Chemicals: XP002755351, Database accession No. 1528719-88-1.
Database Registry [online], Chemical Abstracts Service, Columbus, OH, US; Jan. 2014, Chemical Catalog; Supplier: Aurora Fine Chemicals: XP002755352, Database accession No. 1526778-80-2.
Database Registry [online], Chemical Abstracts Service, Columbus, OH, US; Jan. 2014, Chemical Catalog; Supplier: Aurora Fine Chemicals: XP002755353, Database accession No. 1522493-70-4.
Database Registry [online], Chemical Abstracts Service, Columbus, OH, US; Jan. 2014, Chemical Catalog; Supplier: Aurora Fine Chemicals: XP002755354, Database accession No. 1520181-20-7.
Database Registry [online], Chemical Abstracts Service, Columbus, OH, US; Oct. 2005, Chemical Library; Supplier: interchim: XP002755358, Database accession No. 866138-38-7.
Database Registry [online], Chemical Abstracts Service, Columbus, OH, US; Oct. 2005, Chemical Library; Supplier: interchim: XP002755359, Database accession No. 864939-76-4.
Database Registry [online], Chemical Abstracts Service, Columbus, Ohio, US, Feb. 2010, Chemical Catalog; Supplier: Aurora Fine Chemicals: XP002755348, Database accession No. 1540777-22-7.
Database Registry [online], Chemical Abstracts Service, Columbus, OH, US, May 29, 2015, Chemical Catalog; Supplier: Aurora Fine Chemicals: XP002755360, Database Accession No. 1715195-44-0.
Database Registry [online], Chemical Abstracts Service, Columbus, OH, US, Jun. 1, 2015, Chemical Catalog; Supplier: Aurora Fine Chemicals: XP002755361, Database Accession No. 1770353-29-1.
Database Registry [online], Chemical Abstracts Service, Columbus, OH, US, Jun. 4, 2015, Chemical Catalog; Supplier: Aurora Fine Chemicals: XP002755362, Database Accession No. 1773443-64-3.
Dorwald et al., "Side reactions in Organic Synthesis," Wiley: VCH Weinheinn Preface, 2005, pp. 1-15, Chapter 8, pp. 279-308.
Doukas et al., "Aerosolized phosphoinositide 3-kinase gamma/delta inhibitor TG100-115 [3-[2,4-diamino-6-(3-hydroxyphenyl)pteridin-7-yl]phenol] as a therapeutic candidate for asthma and chronic obstructive pulmonary disease," J Pharmacol Exp Ther, Mar. 2009, 328(3): 758-65.
Doukas et al., "Phosphoinositide 3-kinase gamma/delta inhibition limits infarct size after myocardial ischemia/reperfusion injury," Proc Natl Acad Sci USA, Dec. 2006, 103(52): 19866-71.
El Khoury et al., "Ccr2 deficiency impairs microglial accumulation and accelerates progression of Alzheimer-like disease," Nat Med, Apr. 2007, 13(4): 432-8.
Elger et al., "Novel alpha-amino-3-hydroxy-5-methyl-4-isoxazole propionate (AMPA) receptor antagonists of 2,3-benzodiazepine type: chemical synthesis, in vitro characterization, and in vivo prevention of acute neurodegeneration," J. Med. Chem., Jul. 2005, 48(14): 4618-4627.
European Office Action in European Application No. 16805238.9, dated Mar. 27, 2020, 5 pages.
European Search Report in European Application No. 20187907.9, dated Jan. 20, 2021, 6 pages.
European Office Action in European Application No. 20187907.9, dated Jun. 27, 2022, 3 pages.

Falasca and Maffucci, "Targeting p110gamma in gastrointestinal cancers: attack on multiple fronts," Frontiers in Physiology, 2014, 5: 1-10.
Giri et al., "Mechanism of amyloid peptide induced CCR5 expression in monocytes and its inhibition by siRNA for Egr-1," Am J Physiol Cell Physiol, Aug. 2005, 289(2): C264-76.
Gonzalez-Garcia et al., "Phosphatidylinositol 3-Kinase Inhibition Ameliorates Inflammation and Tumor Growth in a Model of Colitis-Associated Cancer," Gastroenterology, 2010, 138: 1373-1384.
Hanahan and Weinberg, "Hallmarks of Cancer: The Next Generation," Cell, 2011, 144: 646-674.
Hayer et al., "PI3Kgamma regulates cartilage damage in chronic inflammatory arthritis," FASEB J, Dec. 2009, 23(12): 4288-98.
International Search Report and Written Opinion in International Application No. PCT/US2016/017073, dated Apr. 15, 2016, 21 pages.
International Search Report and Written Opinion in International Application No. PCT/US2016/060468, dated Jan. 25, 2017, 14 pages.
International Search Report and Written Opinion in International Application No. PCT/US2017/038955, dated Aug. 8, 2017, 15 pages.
International Search Report and Written Opinion in International Application No. PCT/US2017/012135, dated May 19, 2017, 17 pages.
International Preliminary Report on Patentability in International Application No. PCT/US2017/038955, dated Dec. 25, 2018, 8 pages.
International Preliminary Report on Patentability in International Application No. PCT/US2016/017073, dated Aug. 15, 2017, 11 pages.
International Preliminary Report on Patentability in International Application No. PCT/US2016/060468, dated May 8, 2018, 9 pages.
International Preliminary Report on Patentability in International Application No. PCT/US2017/012135, dated Jul. 19, 2018, 10 pages.
Japanese Office Action in Japanese Application No. 2018-523015, dated Oct. 20, 2020, 7 pages.
Jimenez et al., "The p85 regulatory subunit controls sequential activation of phosphoinositide 3-kinase by Tyr kinases and Ras," J Biol Chem, Nov. 2002, 277(44): 41556-62.
Kaneda et al., "Abstract 3650: PI3-kinase gamma controls the macrophage M1-M2 switch, thereby promoting tumor immunosuppression and progression," Cancer Res., Oct. 2014, 74(Suppl 19), 2 pages.
Kumar et al., "Discovery and optimization of a new class of pyruvate kinase inhibitors as potential therapeutics for the treatment of methicillin-resistant *Staphylococcus aureus* infections," Bioorganic & Medicinal Chemistry, Jan. 2014, 22(5): 1708-1725.
Laffargue et al., "Phosphoinositide 3-kinase gamma is an essential amplifier of mast cell function," Immunity, Mar. 2002, 16(3): 441-51.
Li et al., "PI3Kγ inhibition alleviates symptoms and increases axon No. in experimental autoimmune encephalomyelitis mice," Neuroscience, Dec. 2013, 253: 89-99.
Liu et al., "Discovery of Novel Small Molecule Mer Kinase Inhibitors for the Treatment of Pediatric Acute Lymphoblastic Leukemia," ACS Med. Chem. Lett., Feb. 9, 2012, 3(2):129-134.
Lupia et al., "Ablation of phosphoinositide 3-kinase-gmma reduces the severity of acute pancreatitis," Am J Pathol, Dec. 2004, 165(6): 2003-11.
Mamedov et al., "Acid-catalyzed rearrangement of 3-(beta-2-aminostyryl)quinoxalin-2(1H)ones—a new and efficient method for the synthesis of 2-benzimidazol-2-ylquinolines," Tetrahedron Letters, Dec. 2010, 51(50): 6503-6506.
Martin et al., "PI3Kγ mediates Kaposi's sarcoma-associated herpes virus vGPCR-induced sarcomagenesis," Cancer Cell, Jun. 2011, 19(6): 805-13.
Mejdrova et al., "Highly selective Phosphatidylinositol 4-Kinase III[beta] Inhibitors and Structural Insight into Their Mode of Action," Journal of Medicinal Chemistry, May 2015, 58(9): 3767-3793.

(56) References Cited

OTHER PUBLICATIONS

Passos et al., "Involvement of phosphoinositide 3-kinase gamma in the neuro-inflammatory response and cognitive impairments induced by beta-amyloid 1-40 peptide in mice," Brain Behav Immun, Mar. 2010, 24(3): 493-501.
Park et al., "Homogenous proximity tyrosine kinase assays: scintillation proximity assay versus homogenous time-resolved fluorescence," Anal. Biochem., Apr. 1999, 269(1): 94-104.
Pinho et al., "Phosphoinositide-3 kinases critically regulate the recruitment and survival of eosinophils in vivo: importance for the resolution of allergic inflammation," J Leukoc Biol, May 2005, 77(5): 800-10.
Pomel et al., "Furan-2-ylmethylene thiazolidinediones as novel, potent, and selective inhibitors of phosphoinositide 3-kinase gamma," J. Med. Chem., Jun. 2006, 49(13): 3857-71.
Prete et al., "Defective dendritic cell migration and activation of adaptive immunity in PI3Kgamma-deficient mice," EMBO J, Sep. 2004, 23(17): 3505-15.
Randis et al., "Role of PI3Kdelta and PI3Kgamma in inflammatory arthritis and tissue localization of neutrophils," Eur J Immunol, May 2008, 38(5): 1215-24.
Remington's Pharmaceutical Sciences, 17th ed., Mack Publishing Company, Easton, Pa., 1985, p. 1418.
Rodrigues et al., "Absence of PI3K gamma leads to increased leukocyte apoptosis and diminished severity of experimental autoimmune encephalomyelitis," J Neuroimmunol, May 2010, 222(1-2)90-4.
Rommel et al., "PI3Kδ and PI3Kγ: partners in crime in inflammation in rheumatoid arthritis and beyond?" Nature Rev Immunol., 2007, 7:191-201.
Ruckle et al., "PI3Kgamma inhibition: towards an 'aspirin of the 21st century'?" Nat Rev Drug Discov, Nov. 2006, 5(11): 903-18.
Schmid et al., "Receptor tyrosine kinases and TLR/ILIRs unexpectedly activate myeloid cell PI3Kγ, a single convergent point promoting tumor inflammation and progression," Cancer Cell, Jun. 2011, 19(6): 715-27.
Schmidt et al., Cancer Res. 2012, 72 (Suppl 1: Abstract, 411).
Subramaniam et al., "Targeting nonclassical oncogenes for therapy in T-ALL," Cancer Cell, Apr. 2012, 21(4): 459-72.

Taiwan Office Action in Taiwan Application No. 105136055, dated Aug. 8, 2020, 14 pages.
T. W. Greene and P. G. M. Wuts, Protective Groups in Organic Synthesis, 3rd Ed., Wiley & Sons, Inc., New York (1999), 799 pages.
Thomas et al., "Airway inflammation: chemokine-induced neutrophilia and the class I phosphoinositide 3-kinases," Eur J Immunol, Apr. 2005, 35(4): 1283-91.
Vaillard et al., "Synthesis of 6-substituted 2-pyrrolyl and Indolyl Benzoxazoles by Intramolecular O-Arylation in Photostimulated Reactions," The Journal of Organic Chemistry, Feb. 2012, 77(3): 1507-1519.
Vanhaesebroeck et al., "Signalling by PI3K isoforms: insights from gene-targeted mice," Trends Biochem Sci, Apr. 2005, 30(4): 194-204.
Vecchione et al., "Protection from angiotensin II-mediated vasculotoxic and hypertensive response in mice lacking PI3Kgamma," J Exp Med, Apr. 2005, 201(8): 1217-28.
Venable et al., "Phosphoinositide 3-Kinase Gamma (PI3K[gamma]) Inhibitors for the Treatment of Inflammation and Autoimmune Disease," Recent Patents on Inflammation & Allergy Drug Discovery, Jan. 2010, 4(1): 1-15.
Cheung et al., "Future therapeutic targets in rheumatoid arthritis?" Semin Immunopathol., 2017, 39:487-500.
Campa et al., "Inhalation of the prodrug PI3K inhibitor CL27c improves lung function in asthma and fibrosis," Nature Communications,, 2018, 9:5232.
Chamcheu et al., "Dual Inhibition of PI3K/Akt and mTOR by the Dietary Antioxidant, Delphinidin, Ameliorates Psoriatic Features In Vitro and in an Imiquimod-Induced Psoriasis-Like Disease in Mice," Antioxidants Redox Signaling, 2017, 26(2):49-69.
Jacot et al., "Potential Therapeutic Roles for Inhibition of the PI3K/Akt/mTOR Pathway in the Pathophysiology of Diabetic Retinopathy," J Ophthalmology, 2011, ID:589813.
European Search Report in European Application No. 22162035.4, dated Jul. 27, 2022, 9 pages.
Office Action in European Appln. No. 20187907.9, dated Mar. 30, 2023, 5 pages.

* cited by examiner

PYRIDINE AND PYRIDIMINE COMPOUNDS AS PI3K-GAMMA INHIBITORS

CROSS REFERENCE TO RELATED APPLICATIONS

This application is a continuation of U.S. Ser. No. 16/369,541, filed Mar. 29, 2019, which is a continuation of U.S. Ser. No. 15/398,121, filed Jan. 4, 2017, which claims the benefit of U.S. Ser. No. 62/274,942, filed Jan. 5, 2016, the disclosures of each which are incorporated herein by reference in their entirety.

TECHNICAL FIELD

The present disclosure provides pyridine and pyrmidine compounds that modulate the activity of phosphoinositide 3-kinases-gamma (PI3Kγ) and are useful in the treatment of diseases related to the activity of PI3Kγ including, for example, autoimmune diseases, cancer, cardiovascular diseases, and neurodegenerative diseases.

BACKGROUND

The phosphoinositide 3-kinases (PI3Ks) belong to a large family of lipid signaling kinases that phosphorylate phosphoinositides at the D3 position of the inositol ring (Cantley, Science, 2002, 296(5573):1655-7). PI3Ks are divided into three classes (class I, II, and III) according to their structure, regulation and substrate specificity. Class I PI3Ks, which include PI3Kα, PI3Kβ, PI3Kγ, and PI3Kδ are a family of dual specificity lipid and protein kinases that catalyze the phosphorylation of phosphatidylinosito-4,5-bisphosphate ($PIP_2$) giving rise to phosphatidylinosito-3,4,5-trisphosphate ($PIP_3$). $PIP_3$ functions as a second messenger that controls a number of cellular processes, including growth, survival, adhesion and migration. All four class I PI3K isoforms exist as heterodimers composed of a catalytic subunit (p110) and a tightly associated regulatory subunit that controls their expression, activation, and subcellular localization. PI3Kα, PI3Kβ and PI3Kδ associate with a regulatory subunit known as p85 and are activated by growth factors and cytokines through a tyrosine kinase-dependent mechanism (Jimenez, et al., J Biol Chem., 2002, 277(44):41556-62) whereas PI3Kγ associates with two regulatory subunits (p101 and p84) and its activation is driven by the activation of G-protein-coupled receptors (Brock, et al., J Cell Biol., 2003, 160(1):89-99). PI3Kα and PI3Kβ are ubiquitously expressed. In contrast, PI3Kγ and PI3Kδ are predominantly expressed in leukocytes (Vanhaesebroeck, et al., Trends Biochem Sci., 2005, 30(4):194-204).

Expression of PI3Kγ is mainly restricted to hematopoietic system, although it can be also detected at lower level in endothelium, heart and brain. PI3Kγ knock-out or kinase dead knock in mice are normal and fertile and do not present any overt adverse phenotypes. Analysis at the cellular level indicates that PI3Kγ is required for GPCR ligand-induced PtdINs (3,4,5)P3 production, chemotaxis and respiratory burst in neutrophils. PI3Kγ-null macrophages and dendritic cell exhibit reduced migration towards various chemoattractants. T-cells deficient in PI3Kγ show impaired cytokine production in response to anti-CD3 or Con A stimulation. PI3Kγ working downstream of adenosine A3A receptor is critical for sustained degranulation of mast cells induced by FCεRI cross-linking with IgE. PI3Kγ is also essential for survival of eosinophils (Ruckle et al., Nat. Rev. Drug Discovery, 2006, 5, 903-918)

Given its unique expression pattern and cellular functions, the potential role of PI3Kγ in various autoimmune and inflammatory disease models has been investigated with genetic and pharmacological tools. In asthma and allergy models, PI3Kγ$^{-/-}$ mice or mice treated with PI3Kγ inhibitor showed a defective capacity to mount contact hypersensitivity and delayed-type hypersensitivity reactions. In these models, PI3Kγ was shown to be important for recruitment of neutrophils and eosinopohils to airways and degranulation of mast cells (see e.g. Laffargue et al., Immunity, 2002, 16, 441-451; Prete et al., The EMBO Journal, 2004, 23, 3505-3515; Pinho et al., L. Leukocyte Biology, 2005, 77, 800-810; Thomas et al., Eur. J. Immunol. 2005, 35, 1283-1291; Doukas et al., J. Pharmacol. Exp Ther. 2009, 328, 758-765).

In two different acute pancreatitis models, genetic ablation of PI3Kγ significantly reduced the extent of acinar cell injury/necrosis and neutrophil infiltration without any impact on secretive function of isolated pancreatic acini (Lupia et al., Am. J. Pathology, 2004, 165, 2003-2011). PI3Kγ$^{-/-}$ mice were largely protected in four different models of rheumatoid arthritis (CIA, α-CII-IA, K/B×N serum transfer and TNF transgenic) and PI3Kγ inhibition suppressed the progression of joint inflammation and damage in the CIA and α-CII-IA models (see e.g., Camps et al., Nat. Medicine, 2005, 11, 939-943; Randis et al., Eur. J. Immunol, 2008, 38, 1215-1224; Hayer et al., FASB J., 2009, 4288-4298). In the MRL-lpr mouse model of human systemic lupus erythematous, inhibition of PI3Kγ reduced glomerulonephritis and prolonged life span (Barber et al., Nat. Medicine, 2005, 9, 933-935).

There is evidence suggesting that chronic inflammation due to infiltration by myeloid-derived cells is a key component in the progression of neurodegeneration diseases, such as Alzheimer's disease (AD) (Giri et al., Am. J. Physiol. Cell Physiol., 2005, 289, C264-C276; El Khoury et al., Nat. Med., 2007, 13, 432-438). In line with this suggestion, PI3Kγ inhibition was shown to attenuate Aβ(1-40)-induced accumulation of activated astrocytes and microglia in the hippocampus and prevent the peptide-induced cognitive deficits and synaptic dysfunction in a mouse model of AD (Passos et al., Brain Behav. Immun. 2010, 24, 493-501). PI3Kγ deficiency or inhibition also was shown to delay onset and alleviate symptoms in experimental autoimmune encephalomyelitis in mice, a mouse model of human multiple sclerosis, which is another form of neurodegeneration disease (see e.g., Rodrigues et al., J. Neuroimmunol. 2010, 222, 90-94; Berod et al., Euro. J. Immunol. 2011, 41, 833-844; Comerford et al., PLOS one, 2012, 7, e45095; Li et al., Neuroscience, 2013, 253, 89-99).

Chronic inflammation has been formally recognized as one of the hallmarks for many different types of cancers. Accordingly, selective anti-inflammatory drugs represent a novel class of anti-cancer therapies (Hanahan and Weinberg, Cell, 2011, 144, 646-674). Since PI3Kγ is reported to mediate various inflammatory processes, its role as an immune oncology target has also been investigated. A recent study reported that PI3Kγ deficiency suppressed tumor growth in the syngeneic models of lung cancer, pancreatic cancer and melanoma (LLC, PAN02 and B16). PI3Kγ deficiency or inhibition also inhibited tumor growth in a spontaneous breast cancer model (Schmid et al., Cancer Cell, 2011, 19, 715-727). A further study reported that PI3Kγ deficiency could ameliorate inflammation and tumor growth in mice having colitis-associated colon cancer, (Gonzalez-Garcia et al., Gastroenterology, 2010, 138, 1373-1384). Detailed mechanistic analysis indicates that tumor infiltration by CD11b$^+$ myeloid cells can cause protumorigenic inflammation at tumor sites and PI3Kγ in the myeloid cells is critical in mediating signaling of various chemoattractants in bring the cells to the tumor (Schmid et al., *Cancer Cell*, 2011, 19, 715-727). Other studies suggest that PI3Kγ is also required for differentiation of naïve myeloid cells into M2 macrophges at tumor sites. M2 macrophages promote tumor growth and progression by secreting immunosuppressive factors such arginase 1, which depletes the tumor microenvironment of arginine, thereby promoting T-cell death and NK cell inhibition (Schmidt et al., *Cancer Res.* 2012, 72 (Suppl 1: Abstract, 411; Kaneda et al., *Cancer Res.*, 74 (Suppl 19: Abstract 3650)).

In addition to its potential role in promoting protumorigenic microenvironment, PI3Kγ may play a direct role in cancer cells. PI3Kγ is reported to be required for signaling from the Kaposi's sarcoma-associated herpevirus encoded vGPCR oncogene and tumor growth in a mouse model of sarcoma (Martin et al., *Cancer Cell*, 2011, 19, 805-813). PI3Kγ was also suggested to be required for growth of T-ALL (Subramanjam et al., *Cancer Cell*, 2012, 21, 459-472), PDAC and HCC cells (Falasca and Maffucci, *Frontiers in Physiology*, 2014, 5, 1-10). Moreover, in a survey of driver mutations in pancreatic cancer, PI3Kγ gene was found to contain second highest scoring predicted driven mutation (R839C) among the set of genes not previously identified as a driver in pancreatic cancer (Carter et al., *Cancer Biol. Ther.* 2010, 10, 582-587).

Finally, PI3Kγ deficiency also has been reported to offer protection to experimental animals in different cardiovascular disease models. For examples, lack of PI3Kγ would reduce angiotension-evoked smooth muscle contraction and, therefore, protect mice from angiotension-induced hypertension (Vecchione et al., *J. Exp. Med.* 2005, 201, 1217-1228). In rigorous animal myocardial infarction models, PI3Kγ inhibition provided potent cardioprotection, reducing infarct development and preserving myocardial function (Doukas et al., *Proc. Natl. Acad. Sci. USA*, 2006, 103, 19866-19871).

For these reasons, there is a need to develop new PI3Kγ inhibitors that can be used for the treatment of diseases such as cancer, autoimmune disorders, and inflammatory and cardiac diseases. This application is directed to this need and others.

SUMMARY

The present disclosure relates to, inter alia, compounds of Formula I:

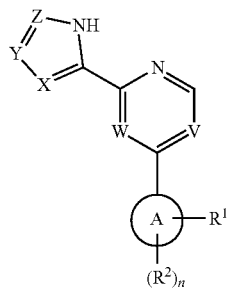

wherein X, Y, Z, V, W, A, $R^1$, $R^2$, and n are described herein.

The present disclosure further provides pharmaceutical compositions comprising a compound of Formula I, or a pharmaceutically acceptable salt thereof, and a pharmaceutically acceptable carrier.

The present disclosure further provides methods of inhibiting an activity of PI3Kγ kinase comprising contacting the kinase with a compound of Formula I, or a pharmaceutically acceptable salt thereof.

The present disclosure further provides methods of treating a disease or a disorder associated with abnormal PI3Kγ kinase expression or activity in a patient by administering to a patient a therapeutically effective amount of a compound of Formula I, or a pharmaceutically acceptable salt thereof.

The present disclosure further provides a compound of Formula I, or a pharmaceutically acceptable salt thereof, for use in any of the methods described herein.

The present disclosure further provides use of a compound of Formula I, or a pharmaceutically acceptable salt thereof, for the preparation of a medicament for use in any of the methods described herein.

DETAILED DESCRIPTION

The present disclosure provides, inter alia, a compound of Formula I:

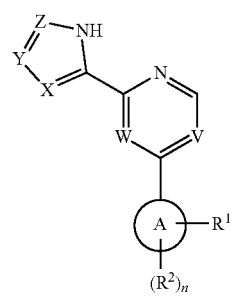

or a pharmaceutically acceptable salt thereof or tautomer thereof, wherein:
W is CH and V is CH; or
W is N and V is CH; or
W is CH and V is N;
X is CH, Y is N, and Z is N or $CR^4$; or
X is N, Y is N or $CR^3$, and Z is N or $CR^4$;
provided that no more than two of X, Y and Z are N;
ring A is a monocyclic 4-6 membered azaheterocycloalkyl ring or a monocyclic 5-6 membered azaheteroaryl ring, each of which has 1, 2, or 3 nitrogen ring members;
n is 0 or 1;
$R^1$ is independently selected from halo, CN, $NO_2$, $C_{1-6}$ alkyl, $C_{2-6}$ alkenyl, $C_{2-6}$ alkynyl, $C_{1-4}$ haloalkyl, $Cy^{1a}$, —$C_{1-4}$ alkylene-Cy, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cOR^d$, $NR^cC(O)R^b$, $NR^cC(O)OR^b$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$; wherein said $C_{1-6}$ alkyl, $C_{2-6}$ alkenyl, $C_{2-6}$ alkynyl, and $C_{1-4}$ haloalkyl are optionally substituted with 1, 2, or 3 independently selected $R^{11}$ groups;
$R^2$ is halo, OH, CN, $C_{1-4}$ alkyl, $C_{1-4}$ haloalkyl, $C_{1-4}$ alkoxy, $C_{1-4}$ haloalkoxy, amino, $C_{1-4}$ alkylamine, di($C_{1-4}$ alkyl)amino, cyano-$C_{1-4}$ alkyl, HO—$C_{1-4}$ alkyl, $C_{1-3}$ alkoxy-$C_{1-4}$ alkyl, $C_{1-6}$ alkylsulfonyl, or phenylsulfonyl, wherein the phenyl is optionally substituted with 1, 2, or 3 independently selected $R^g$ groups;
$R^3$ and $R^4$ are each independently selected from H, halo, CN, $C_{1-6}$ alkyl, $C_{2-6}$ alkenyl, $C_{2-6}$ alkynyl, $C_{1-4}$ haloalkyl, $Cy^1$, —$C_{1-4}$ alkylene-$Cy^1$, $OR^{a1}$, $SR^{a1}$, $C(O)R^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$OR$^{d1}$, NR$^{c1}$C(O)R$^{b1}$, NR$^{c1}$C(O)OR$^{b1}$, NR$^{c1}$C(O)NR$^{c1}$R$^{d1}$, NR$^{c1}$S(O)R$^{b1}$, NR$^{c1}$S(O)$_2$R$^{b1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, and S(O)$_2$NR$^{c1}$R$^{d1}$, wherein said C$_{1-6}$ alkyl, C$_{2-6}$ alkenyl, C$_{2-6}$ alkynyl, and C$_{1-4}$ haloalkyl are each optionally substituted with 1, 2, or 3 independently selected R$^{13}$ groups;

provided that when both R$^3$ and R$^4$ are present, then one of R$^3$ and R$^4$ is selected from H, halo, OH, CN, C$_{1-4}$ alkyl, C$_{1-4}$ haloalkyl, C$_{1-4}$ alkoxy, C$_{1-4}$ haloalkoxy, amino, C$_{1-4}$ alkylamine, di(C$_{1-4}$ alkyl)amino, cyano-C$_{1-4}$ alkyl, HO—C$_{1-4}$ alkyl, and C$_{1-3}$ alkoxy-C$_{1-4}$ alkyl;

alternatively, R$^3$ and R$^4$, taken together with the carbon atoms to which they are attached form a monocyclic 4-7 membered cycloalkyl ring, a phenyl ring, a monocyclic 4-6 membered heterocycloalkyl ring, or a monocyclic 5-6 membered heteroaryl ring, each of which is optionally substituted by 1, 2 or 3 independently selected R$^{13}$ groups;

each R$^{11}$ is independently selected from halo, CN, NO$_2$, C$_{1-6}$ alkyl, C$_{2-6}$ alkenyl, C$_{2-6}$ alkynyl, C$_{1-4}$ haloalkyl, Cy$^2$, —C$_{1-4}$ alkylene-Cy$^2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$OR$^{d2}$, NR$^{c2}$C(O)R$^{b2}$, NR$^{c2}$C(O)OR$^{a2}$, NR$^{c2}$C(O)NR$^{c2}$R$^{d2}$, NR$^{c2}$S(O)R$^{b2}$, NR$^{c2}$S(O)$_2$R$^{b2}$, NR$^{c2}$S(O)$_2$NR$^{c2}$R$^{d2}$, S(O)R$^{b2}$, S(O)NR$^{c2}$R$^{d2}$, S(O)$_2$R$^{b2}$, and S(O)$_2$NR$^{c2}$R$^{d2}$; wherein said C$_{1-6}$ alkyl, C$_{2-6}$ alkenyl, C$_{2-6}$ alkynyl, and C$_{1-4}$ haloalkyl are each optionally substituted with 1, 2, 3, or 4 independently selected R$^g$ groups;

each R$^{13}$ is independently selected from halo, CN, NO$_2$, C$_{1-6}$ alkyl, C$_{2-6}$ alkenyl, C$_{2-6}$ alkynyl, C$_{1-4}$ haloalkyl, Cy$^3$, —C$_{1-4}$ alkylene-Cy$^3$, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$OR$^{d3}$, NR$^{c3}$C(O)R$^{b3}$, NR$^{c3}$C(O)OR$^{a3}$, NR$^{c3}$C(O)NR$^{c3}$R$^{d3}$, NR$^{c3}$S(O)R$^{b3}$, NR$^{c3}$S(O)$_2$R$^{b3}$, NR$^{c3}$S(O)$_2$NR$^{c3}$R$^{d3}$, S(O)R$^{b3}$, S(O)NR$^{c3}$R$^{d3}$, S(O)$_2$R$^{b3}$, and S(O)$_2$NR$^{c3}$R$^{d3}$; wherein said C$_{1-6}$ alkyl, C$_{2-6}$ alkenyl, C$_{2-6}$ alkynyl, and C$_{1-4}$ haloalkyl are each optionally substituted with 1, 2, 3, or 4 independently selected R$^g$ groups;

Cy$^{1a}$ is selected from 3-10 membered cycloalkyl and 4-10 membered heterocycloalkyl, each of which is optionally substituted by 1, 2, 3, or 4 independently selected R$^{11}$ groups;

each Cy is independently selected from 3-10 membered cycloalkyl, 6-10 membered aryl, 5-10 membered heteroaryl, and 4-10 membered heterocycloalkyl, each of which is optionally substituted by 1, 2, 3, or 4 independently selected R$^{11}$ groups;

each Cy$^1$ is independently selected from 3-10 membered cycloalkyl, 6-10 membered aryl, 5-10 membered heteroaryl, and 4-10 membered heterocycloalkyl, each of which is optionally substituted by 1, 2, 3, or 4 independently selected R$^{13}$ groups;

each Cy$^2$ is independently selected from 3-10 membered cycloalkyl, 6-10 membered aryl, 5-10 membered heteroaryl, and 4-10 membered heterocycloalkyl, each of which is optionally substituted by 1, 2, 3, or 4 independently selected R$^g$ groups;

each Cy$^3$ is independently selected from 3-10 membered cycloalkyl, 6-10 membered aryl, 5-10 membered heteroaryl, and 4-10 membered heterocycloalkyl, each of which is optionally substituted by 1, 2, 3, or 4 independently selected R$^g$ groups;

R$^a$, R$^c$, and R$^d$ is independently selected from H, C$_{1-6}$ alkyl, C$_{2-6}$ alkenyl, C$_{2-6}$ alkynyl, C$_{1-4}$ haloalkyl, Cy, and —C$_{1-4}$ alkylene-Cy; wherein said C$_{1-6}$ alkyl, C$_{2-6}$ alkenyl, C$_{2-6}$ alkynyl, and C$_{1-4}$ haloalkyl are each optionally substituted with 1, 2, 3, or 4 independently selected R$^{11}$ groups;

R$^b$ is independently selected from C$_{1-6}$ alkyl, C$_{2-6}$ alkenyl, C$_{2-6}$ alkynyl, C$_{1-4}$ haloalkyl, Cy, and —C$_{1-4}$ alkylene-Cy; wherein said C$_{1-6}$ alkyl, C$_{2-6}$ alkenyl, C$_{2-6}$ alkynyl, and C$_{1-4}$ haloalkyl are each optionally substituted with 1, 2, 3, or 4 independently selected R$^{11}$ groups;

alternatively, any R$^c$ and R$^d$ attached to the same N atom, together with the N atom to which they are attached, form a 4-10 membered heterocycloalkyl group or a 5-6 membered heteroaryl group, each optionally substituted with 1, 2, or 3 independently selected R$^{11}$ groups;

R$^{a1}$, R$^{c1}$, and R$^{d1}$ are each independently selected from H, C$_{1-6}$ alkyl, C$_{2-6}$ alkenyl, C$_{2-6}$ alkynyl, C$_{1-4}$ haloalkyl, Cy$^1$, and —C$_{1-4}$ alkylene-Cy$^1$; wherein said C$_{1-6}$ alkyl, C$_{2-6}$ alkenyl, C$_{2-6}$ alkynyl, and C$_{1-4}$ haloalkyl are each optionally substituted with 1, 2, 3, or 4 independently selected R$^{13}$ groups;

R$^{b1}$ is independently selected from C$_{1-6}$ alkyl, C$_{2-6}$ alkenyl, C$_{2-6}$ alkynyl, C$_{1-4}$ haloalkyl, Cy$^1$, and —C$_{1-4}$ alkylene-Cy$^1$; wherein said C$_{1-6}$ alkyl, C$_{2-6}$ alkenyl, C$_{2-6}$ alkynyl, and C$_{1-4}$ haloalkyl are each optionally substituted with 1, 2, 3, or 4 independently selected R$^{13}$ groups; or alternatively, any R$^{c1}$ and R$^{d1}$ attached to the same N atom, together with the N atom to which they are attached, form a 4-, 5-, 6- or 7-membered heterocycloalkyl group optionally substituted with 1, 2 or 3 independently selected R$^{13}$ groups;

each R$^{a2}$, R$^{c2}$, and R$^{d2}$ are independently selected from H, C$_{1-6}$ alkyl, C$_{2-6}$ alkenyl, C$_{2-6}$ alkynyl, C$_{1-4}$ haloalkyl, Cy$^2$, and —C$_{1-4}$ alkylene-Cy$^2$; wherein said C$_{1-6}$ alkyl, C$_{2-6}$ alkenyl, C$_{2-6}$ alkynyl, and C$_{1-4}$ haloalkyl are each optionally substituted with 1, 2, 3, or 4 independently selected R$^g$ groups;

each R$^{b2}$ is independently selected from C$_{1-6}$ alkyl, C$_{2-6}$ alkenyl, C$_{2-6}$ alkynyl, C$_{1-4}$ haloalkyl, Cy$^2$, and —C$_{1-4}$ alkylene-Cy$^2$; wherein said C$_{1-6}$ alkyl, C$_{2-6}$ alkenyl, C$_{2-6}$ alkynyl, and C$_{1-4}$ haloalkyl are each optionally substituted with 1, 2, 3, or 4 independently selected R$^g$ groups; or alternatively, any R$^{c2}$ and R$^{d2}$ attached to the same N atom, together with the N atom to which they are attached, form a 4-, 5-, 6- or 7-membered heterocycloalkyl group optionally substituted with 1, 2 or 3 independently selected R$^g$ groups;

each R$^{a3}$, R$^{c3}$, and R$^{d3}$ are independently selected from H, C$_{1-6}$ alkyl, C$_{2-6}$ alkenyl, C$_{2-6}$ alkynyl, C$_{1-4}$ haloalkyl, Cy$^3$, and —C$_{1-4}$ alkylene-Cy$^3$; wherein said C$_{1-6}$ alkyl, C$_{2-6}$ alkenyl, C$_{2-6}$ alkynyl, and C$_{1-4}$ haloalkyl are each optionally substituted with 1, 2, 3, or 4 independently selected R$^g$ groups;

each R$^{b3}$ is independently selected from C$_{1-6}$ alkyl, C$_{2-6}$ alkenyl, C$_{2-6}$ alkynyl, C$_{1-4}$ haloalkyl, Cy$^3$, and —C$_{1-4}$ alkylene-Cy$^3$; wherein said C$_{1-6}$ alkyl, C$_{2-6}$ alkenyl, C$_{2-6}$ alkynyl, and C$_{1-4}$ haloalkyl are each optionally substituted with 1, 2, 3, or 4 independently selected R$^g$ groups; or alternatively, any R$^{c3}$ and R$^{d3}$ attached to the same N atom, together with the N atom to which they are attached, form a 4-, 5-, 6- or 7-membered heterocycloalkyl group optionally substituted with 1, 2 or 3 independently selected R$^g$ groups; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl) amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, the compound is a compound of Formula I, or a pharmaceutically acceptable salt thereof.

In some embodiments of compounds provided herein (e.g., compounds of Formula I), $R^1$ is selected from halo, $C_{1-6}$ alkyl, $C_{2-6}$ alkenyl, $C_{2-6}$ alkynyl, $C_{1-4}$ haloalkyl, $Cy^{1a}$, —$C_{1-4}$ alkylene-Cy, $OR^a$, $C(O)R^b$, $C(O)NR^cR^d$, $C(O)OR^a$, $OC(O)R^b$, $OC(O)NR^cR^d$, $NR^cR^d$, $NR^cOR^d$, $NR^cC(O)R^b$, $NR^cC(O)OR^b$, $NR^cC(O)NR^cR^d$, $NR^cS(O)_2R^b$, $NR^cS(O)_2NR^cR^d$, $S(O)_2R^b$, and $S(O)_2NR^cR^d$; wherein said $C_{1-6}$ alkyl, $C_{2-6}$ alkenyl, $C_{2-6}$ alkynyl, and $C_{1-4}$ haloalkyl are optionally substituted with 1, 2, or 3 independently selected $R^{11}$ groups.

In some embodiments, $R^1$ is selected from halo, $C_{1-6}$ alkyl, $C_{1-4}$ haloalkyl, $Cy^{1a}$, —$C_{1-4}$ alkylene-Cy, $OR^a$, $C(O)R^b$, $C(O)NR^cR^d$, $C(O)OR^a$, $NR^cR^d$, $NR^cOR^d$, $NR^cC(O)R^b$, $NR^cC(O)OR^b$, $NR^cC(O)NR^cR^d$, $NR^cS(O)_2R^b$, $NR^cS(O)_2NR^cR^d$, $S(O)_2R^b$, and $S(O)_2NR^cR^d$; wherein said $C_{1-6}$ alkyl and $C_{1-4}$ haloalkyl are optionally substituted with 1, 2, or 3 independently selected $R^{11}$ groups.

In some embodiments, $R^1$ is selected from halo, $C_{1-6}$ alkyl, $C_{1-4}$ haloalkyl, $Cy^{1a}$, —$C_{1-4}$ alkylene-Cy, $OR^a$, $C(O)R^b$, $C(O)NR^cR^d$, $C(O)OR^a$, $NR^cR^d$, $NR^cC(O)R^b$, $NR^cC(O)OR^b$, $NR^cC(O)NR^cR^d$, $NR^cS(O)_2R^b$, and $S(O)_2R^b$; wherein said $C_{1-6}$ alkyl and $C_{1-4}$ haloalkyl are optionally substituted with 1, 2, or 3 independently selected $R^{11}$ groups.

In some embodiments, $R^1$ is selected from halo, $C_{1-6}$ alkyl, $C_{1-4}$ haloalkyl, $Cy^{1a}$, —$C_{1-4}$ alkylene-Cy, $OR^a$, $C(O)R^b$, $C(O)NR^cR^d$, $C(O)OR^a$, $NR^cR^d$, $NR^cC(O)R^b$, $NR^cC(O)OR^b$, $NR^cC(O)NR^cR^d$, $NR^cS(O)_2R^b$, $S(O)_2R^b$, and $S(O)_2NR^cR^d$; wherein said $C_{1-6}$ alkyl and $C_{1-4}$ haloalkyl are optionally substituted with 1, 2, or 3 independently selected $R^{11}$ groups.

In some embodiments, $R^1$ is $C_{1-6}$ alkyl, $Cy^{1a}$, —$C_{1-4}$ alkylene-Cy, $OR^a$, $C(O)R^b$, $C(O)NR^cR^d$, $C(O)OR^a$, $NR^cR^d$, $NR^cC(O)R^b$, $NR^cC(O)OR^b$, or $S(O)_2R^b$.

In some embodiments, $R^1$ is $C_{1-6}$ alkyl, $Cy^{1a}$, $OCH_3$, $C(O)R^b$, $C(O)NR^cR^d$, $C(O)OR^a$, $NR^d$, $NHC(O)R^b$, or $S(O)_2R^b$.

In some embodiments, $R^1$ is methyl, ethyl, $OCH_3$, morpholinyl, $S(O)_2R^b$, $C(O)R^b$, or $C(O)NR^cR^d$. In some embodiments, $R^1$ is $OCH_3$. In some embodiments, $R^1$ is morpholinyl. In some embodiments, $R^1$ is $SO_2CH_3$. In some embodiments, $R^1$ is $C(O)R^b$, where $R^b$ is $C_{1-6}$ alkyl or Cy. In some embodiments, $R^1$ is $C(O)NR^cR^d$, where R and $R^d$ are independently selected from H, $C_{1-6}$ alkyl, and Cy, or $R^c$ and $R^d$ together with the N atom to which they are attached, a 4-6 membered heterocycloalkyl group or a 5-6 membered heteroaryl group.

In some embodiments, $R^1$ is $C_{1-6}$ alkyl, optionally substituted by 1, 2, or 3 independently selected $R^{11}$ groups.

In some embodiments, $R^1$ is $S(O)_2NR^cR^d$.

In some embodiments, $R^a$, $R^c$, and $R^d$ are each independently selected from H, $C_{1-6}$ alkyl, Cy, and —$C_{1-4}$ alkylene-Cy; wherein said $C_{1-6}$ alkyl is optionally substituted with 1 or 2 independently selected $R^{11}$ groups; $R^b$ is independently selected from $C_{1-6}$ alkyl, Cy, and —$C_{1-4}$ alkylene-Cy; wherein said $C_{1-6}$ alkyl is optionally substituted with 1 or 2 independently selected $R^{11}$ groups; alternatively, any $R^c$ and $R^d$ attached to the same N atom, together with the N atom to which they are attached, form a 4-10 membered heterocycloalkyl group, which is optionally substituted with 1 or 2 independently selected $R^{11}$ groups.

In some embodiments, $R^c$ and $R^d$ attached to the same N atom, together with the N atom to which they are attached, form an azetidine ring, a pyrrolidine ring, an azabiyclo [2.2.1]-heptane ring, a piperidine ring, a piperazine ring, a morpholine ring, an azepane ring, a decahydroisoquinoline ring, a 2,8-diazaspiro[4.5]decan-1-one ring, a 3-oxa-9-azaspiro[5.5]undecane ring, a 2-oxa-7-azaspiro[3.5]nonane ring, or a 5-azaspiro[2.4]heptane ring, each of which is optionally substituted with 1 or 2 independently selected $R^{11}$ groups.

In some embodiments, each Cy is independently 3-7 membered cycloalkyl, 4-6 membered heterocycloalkyl, phenyl or 5-6 membered heteroaryl, each of which is optionally substituted by 1, 2, 3, or 4 independently selected $R^{11}$ groups.

In some embodiments, each Cy is independently 3-7 membered cycloalkyl, 4-6 membered heterocycloalkyl, or phenyl, each of which is optionally substituted by 1, 2, 3, or 4 independently selected $R^{11}$ groups.

In some embodiments, each Cy is independently cyclopropyl, cyclobutyl, cyclopentyl,

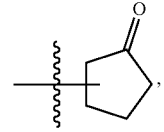

tetrahydrofuranyl, tetrahydropyranyl, morpholinyl, or phenyl, each of which is optionally substituted by 1 or 2 independently selected $R^{11}$ groups.

In some embodiments, each Cy is 4-6 membered heterocycloalkyl, which is optionally substituted by 1 or 2 independently selected $R^{11}$ groups.

In some embodiments, each Cy is independently 3-7 membered cycloalkyl, which is optionally substituted by 1 or 2 independently selected $R^{11}$ groups.

In some embodiments, each Cy is phenyl, which is optionally substituted by 1 or 2 independently selected $R^{11}$ groups.

In some embodiments, each Cy is independently 4-10 membered heterocycloalkyl, which is optionally substituted by 1, 2, 3, or 4 independently selected $R^{11}$ groups. In some embodiments, Cy is morpholinyl.

In some embodiments, $Cy^{1a}$ is 4-10 membered heterocycloalkyl, which is optionally substituted by 1, 2, 3, or 4 independently selected $R^{11}$ groups.

In some embodiments, $Cy^{1a}$ is 5-6 membered heterocycloalkyl, which is optionally substituted by 1, 2, 3, or 4 independently selected $R^{11}$ groups.

In some embodiments, $Cy^{1a}$ is a pyrrolidine ring, a dihydropyrrole ring, a morpholine ring, a piperidine ring, a piperazine ring, a tetrahydrofuran ring, or a tetrahydropyran ring, each of which is optionally substituted by 1 or 2 independently selected $R^{11}$ groups.

In some embodiments, each $R^{11}$ is independently selected from halo, CN, $C_{1-6}$ alkyl, $C_{2-6}$ alkenyl, $C_{2-6}$ alkynyl, $C_{1-4}$ haloalkyl, $Cy^2$, —$C_{1-4}$ alkylene-$Cy^2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}OR^{d2}$, $NR^{c2}C(O)R^{b2}$, $NR^{c2}C(O)OR^{a2}$, $NR^{c2}C(O)NR^{c2}R^{d2}$, $NR^{c2}S(O)_2R^{b2}$, $NR^{c2}S(O)_2NR^{c2}R^{d2}$, $S(O)_2R^{b2}$, and $S(O)_2NR^{c2}R^{d2}$; wherein said $C_{1-6}$ alkyl, $C_{2-6}$ alkenyl, $C_{2-6}$ alkynyl, and $C_{1-4}$ haloalkyl are each optionally substituted with 1, 2, 3, or 4 independently selected $R^g$ groups.

In some embodiments, each $R^{11}$ is independently selected from halo, CN, $C_{1-6}$ alkyl, $C_{1-4}$ haloalkyl, $Cy^2$, —$C_{1-4}$ alkylene-$Cy^2$, $OR^{a2}$, $SR^{a2}$, $C(O)R^{b2}$, $C(O)NR^{c2}R^{d2}$, $C(O)OR^{a2}$, $NR^{c2}R^{d2}$, $NR^{c2}OR^{d2}$, $NR^{c2}C(O)R^{b2}$, $NR^{c2}C(O)OR^{a2}$, $NR^{c2}C(O)NR^{c2}R^{d2}$, $NR^{c2}S(O)_2R^{b2}$, $NR^{c2}S(O)_2NR^{c2}R^{d2}$, $S(O)_2R^{b2}$, and $S(O)_2NR^{c2}R^{d2}$; wherein said $C_{1-6}$ alkyl and $C_{1-4}$ haloalkyl are each optionally substituted with 1, 2, 3, or 4 independently selected $R^g$ groups.

In some embodiments, each $R^{11}$ is independently selected from halo, CN, $C_{1-6}$ alkyl, $C_{1-4}$ haloalkyl, $Cy^2$, —$C_{1-4}$ alkylene-$Cy^2$, $OR^{a2}$, $C(O)R^{b2}$, $C(O)NR^{c2}R^{d2}$, $C(O)OR^{a2}$, $NR^{c2}R^{d2}$, and $S(O)_2R^{b2}$; wherein said $C_{1-6}$ alkyl is optionally substituted with 1, 2, 3, or 4 independently selected $R^g$ groups.

In some embodiments, each $R^{a2}$, $R^{c2}$, and $R^{d2}$ are independently selected from H, $C_{1-6}$ alkyl, $Cy^2$; wherein said $C_{1-6}$ alkyl is optionally substituted with 1 or 2 independently selected $R^g$ groups; each $R^{b2}$ is independently selected from $C_{1-6}$ alkyl and $Cy^2$; wherein said $C_{1-6}$ alkyl is optionally substituted with 1 or 2 independently selected $R^g$ groups; alternatively, any $R^{c2}$ and $R^{d2}$ attached to the same N atom, together with the N atom to which they are attached, form a 5-6-membered heterocycloalkyl group optionally substituted with 1 or 2 independently selected $R^g$ groups.

In some embodiments, any $R^{c2}$ and $R^{d2}$ attached to the same N atom, together with the N atom to which they are attached, form a pyrrolidine or a morpholine ring, each of which is optionally substituted with 1 or 2 independently selected $R^g$ groups.

In some embodiments, each $R^{11}$ is independently $Cy^2$.

In some embodiments, each $Cy^2$ is independently 6-10 membered aryl.

In some embodiments, each $Cy^2$ is independently 4-10 membered heterocycloalkyl.

In some embodiments, each $Cy^2$ is independently selected from 3-10 membered cycloalkyl, 6-10 membered aryl, and 4-10 membered heterocycloalkyl, each of which is optionally substituted by 1, 2, 3, or 4 independently selected $R^g$ groups.

In some embodiments, each $Cy^2$ is independently selected from 3-7 membered cycloalkyl, phenyl, and 4-6 membered heterocycloalkyl, each of which is optionally substituted by 1 or 2 independently selected $R^g$ groups.

In some embodiments, each $Cy^2$ is independently phenyl, cyclopentyl, piperidinyl, morpholinyl, pyridyl, or pyrazinyl.

In some embodiments of compounds provided herein (e.g., compounds of Formula I), n is 1.

In some embodiments of compounds provided herein (e.g., compounds of Formula I), n is O.

In some embodiments of compounds provided herein (e.g., compounds of Formula I), $R^2$ is halo, OH, $C_{1-4}$ alkyl, $C_{1-4}$ haloalkyl, $C_{1-4}$ alkoxy, $C_{1-4}$ haloalkoxy, amino, $C_{1-4}$ alkylamine, di($C_{1-4}$ alkyl)amino, HO—$C_{1-4}$ alkyl, or $C_{1-3}$ alkoxy-$C_{1-4}$ alkyl.

In some embodiments, $R^2$ is halo, $C_{1-4}$ alkyl, $C_{1-4}$ haloalkyl, $C_{1-4}$ alkoxy, $C_{1-4}$ haloalkoxy, amino, $C_{1-4}$ alkylamine, di($C_{1-4}$ alkyl)amino, or $C_{1-3}$ alkoxy-$C_{1-4}$ alkyl.

In some embodiments, $R^2$ is halo, $C_{1-4}$ alkyl, $C_{1-4}$ haloalkyl, $C_{1-4}$ alkoxy, $C_{1-4}$ haloalkoxy, or $C_{1-3}$ alkoxy-$C_{1-4}$ alkyl.

In some embodiments, $R^2$ is $C_{1-4}$ alkyl, or $C_{1-4}$ haloalkyl.

In some embodiments, $R^2$ is $C_{1-4}$ alkyl.

In some embodiments, $R^2$ is methyl.

In some embodiments of compounds provided herein (e.g., compounds of Formula I), $R^3$ and $R^4$ are each independently selected from H, halo, $C_{1-6}$ alkyl, $C_{2-6}$ alkenyl, $C_{2-6}$ alkynyl, $C_{1-4}$ haloalkyl, $Cy^1$, —$C_{1-4}$ alkylene-$Cy^1$, $OR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}OR^{d1}$, $NR^{c1}C(O)R^{b1}$, $NR^{c1}C(O)OR^{b1}$, $NR^{c1}C(O)NR^{c1}R^{d1}$, $NR^{c1}S(O)_2R^{b1}$, $NR^{c1}S(O)_2NR^{c1}R^{d1}$, $S(O)_2R^{b1}$, and $S(O)_2NR^{c1}R^{d1}$, wherein said $C_{1-6}$ alkyl, $C_{2-6}$ alkenyl, $C_{2-6}$ alkynyl, and $C_{1-4}$ haloalkyl are each optionally substituted with 1, 2, or 3 independently selected $R^{13}$ groups;
  provided that when both $R^3$ and $R^4$ are present, then one of $R^3$ and $R^4$ is selected from H, halo, OH, CN, $C_{1-4}$ alkyl, $C_{1-4}$ haloalkyl, $C_{1-4}$ alkoxy, $C_{1-4}$ haloalkoxy, amino, $C_{1-4}$ alkylamine, di($C_{1-4}$ alkyl)amino, cyano-$C_{1-4}$ alkyl, HO—$C_{1-4}$ alkyl, and $C_{1-3}$ alkoxy-$C_{1-4}$ alkyl;
  alternatively, $R^3$ and $R^4$, taken together with the carbon atoms to which they are attached form a monocyclic 4-7 membered cycloalkyl ring, a phenyl ring, a monocyclic 4-6 membered heterocycloalkyl ring, or a monocyclic 5-6 membered heteroaryl ring, each of which is optionally substituted by 1, 2 or 3 independently selected $R^{13}$ groups.

In some embodiments, $R^3$ and $R^4$ are each independently selected from H, halo, $C_{1-6}$ alkyl, $C_{2-6}$ alkenyl, $C_{2-6}$ alkynyl, $C_{1-4}$ haloalkyl, $Cy^1$, —$C_{1-4}$ alkylene-$Cy^1$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{b1}$, $NR^{c1}C(O)NR^{c1}R^{d1}$, $S(O)_2R^{b1}$, and $S(O)_2NR^{c1}R^{d1}$, wherein said $C_{1-6}$ alkyl, $C_{2-6}$ alkenyl, $C_{2-6}$ alkynyl, and $C_{1-4}$ haloalkyl are each optionally substituted with 1, 2, or 3 independently selected $R^{13}$ groups;
  provided that when both $R^3$ and $R^4$ are present, then one of $R^3$ and $R^4$ is selected from H, $C_{1-4}$ alkyl, and $C_{1-4}$ haloalkyl;
  alternatively, $R^3$ and $R^4$, taken together with the carbon atoms to which they are attached form a monocyclic 4-7 membered cycloalkyl ring or a phenyl ring, each of which is optionally substituted by 1, 2 or 3 independently selected $R^{13}$ groups.

In some embodiments, $R^3$ and $R^4$ are each independently selected from H, $C_{1-6}$ alkyl, $C_{1-4}$ haloalkyl, $Cy^1$, —$C_{1-4}$ alkylene-$Cy^1$, $C(O)R^{b1}$, $C(O)NR^{c1}R^{d1}$, $C(O)OR^{a1}$, $NR^{c1}R^{d1}$ and $NR^{c1}C(O)R^{b1}$ wherein said $C_{1-6}$ alkyl is optionally substituted with 1, 2, or 3 independently selected $R^{13}$ groups;
  provided that when both $R^3$ and $R^4$ are present, then one of $R^3$ and $R^4$ is selected from H, $C_{1-4}$ alkyl, and $C_{1-4}$ haloalkyl;
  alternatively, $R^3$ and $R^4$, taken together with the carbon atoms to which they are attached form a monocyclic 4-7 membered cycloalkyl ring or a phenyl ring.

In some embodiments, $R^3$ and $R^4$ are each independently selected from H, CN, $C_{1-6}$ alkyl, $C_{1-4}$ haloalkyl, $Cy^1$, —$C_{1-4}$ alkylene-$Cy^1$, $C(O)R^{b1}$, $C(O)NR^{c1}R^{d1}$, $C(O)OR^{a1}$, $NR^{c1}R^{d1}$ and $NR^{c1}C(O)R^{b1}$ wherein said $C_{1-6}$ alkyl is optionally substituted with 1, 2, or 3 independently selected $R^{13}$ groups;
  provided that when both $R^3$ and $R^4$ are present, then one of $R^3$ and $R^4$ is selected from H, $C_{1-4}$ alkyl, and $C_{1-4}$ haloalkyl;
  alternatively, $R^3$ and $R^4$, taken together with the carbon atoms to which they are attached form a monocyclic 4-7 membered cycloalkyl ring or a phenyl ring.

In some embodiments of compounds provided herein (e.g., compounds of Formula I), $R^3$ is selected from H, $C_{1-6}$ alkyl, $C_{1-4}$ haloalkyl, $Cy^1$, $C(O)NR^{c1}R^{d1}$, and $C(O)OR^{a1}$, wherein said $C_{1-6}$ alkyl is optionally substituted with 1, 2, or 3 independently selected $R^{13}$ groups.

In some embodiments of compounds provided herein (e.g., compounds of Formula I), $R^3$ is selected from H, CN, $C_{1-6}$ alkyl, $C_{1-4}$ haloalkyl, $Cy^1$, $C(O)NR^{c1}R^{d1}$, and $C(O)OR^{a1}$, wherein said $C_{1-6}$ alkyl is optionally substituted with 1, 2, or 3 independently selected $R^{13}$ groups.

In some embodiments of compounds provided herein (e.g., compounds of Formula I), $R^4$ is selected from H, $C_{1-6}$ alkyl, $C_{1-4}$ haloalkyl, $Cy^1$, —$C_{1-4}$ alkylene-$Cy^1$, $NR^{c1}R^{d1}$ and $NR^{c1}C(O)R^{b1}$, wherein said $C_{1-6}$ alkyl is optionally substituted with 1, 2, or 3 independently selected $R^{13}$ groups.

In some embodiments, $R^3$ is H or $C_{1-4}$ alkyl, and $R^4$ is $C_{1-6}$ alkyl or $Cy^1$.

In some embodiments, $R^3$ is H or methyl, and $R^4$ is methyl or phenyl.

In some embodiments, $R^3$ is H and $R^4$ is phenyl.

In some embodiments, $R^3$ is methyl and $R^4$ is methyl.

In some embodiments, $R^3$ and $R^4$, taken together with the carbon atoms to which they are attached form a phenyl ring.

In some embodiments, $R^3$ and $R^4$, taken together with the carbon atoms to which they are attached form a cyclopentyl ring.

In some embodiments, $R^3$ is H, $C_{1-6}$ alkyl or $C(O)NR^{c1}R^{d1}$.

In some embodiments, $R^3$ is H or methyl.

In some embodiments, $R^3$ is $C(O)NR^{c1}R^{d1}$.

In some embodiments, $R^3$ is $C(O)NR^{c1}R^{d1}$, where $R^{c1}$ and $R^{d1}$ are independently selected from H, $C_{1-6}$ alkyl, and $Cy^1$, or $R^{c1}$ and $R^{d1}$ together with the N atom to which they are attached, form a 4-, 5-, 6- or 7-membered heterocycloalkyl group.

In some embodiments, $R^3$ is H, $C_{1-6}$ alkyl, $C(O)OR^{b1}$, or $C(O)NR^{c1}R^{d1}$.

In some embodiments, $R^3$ is H or methyl.

In some embodiments, $R^3$ is $C(O)OR^{b1}$.

In some embodiments, $R^3$ is CN.

In some embodiments, $R^{a1}$, $R^{c1}$, and $R^{d1}$ are each independently selected from H, $C_{1-6}$ alkyl, $Cy^1$, and —$C_{1-4}$ alkylene-$Cy^1$; wherein said $C_{1-6}$ alkyl is optionally substituted with 1, 2, 3, or 4 independently selected $R^{13}$ groups; $R^{b1}$ are each independently selected from $C_{1-6}$ alkyl, $Cy^1$, and —$C_{1-4}$ alkylene-$Cy^1$; wherein said $C_{1-6}$ alkyl is optionally substituted with 1, 2, 3, or 4 independently selected $R^{13}$ groups; alternatively, any $R^{c1}$ and $R^{d1}$ attached to the same N atom, together with the N atom to which they are attached, form a 4-, 5-, 6- or 7-membered heterocycloalkyl group optionally substituted with 1, 2 or 3 independently selected $R^{13}$ groups.

In some embodiments, any $R^{c1}$ and $R^{d1}$ attached to the same N atom, together with the N atom to which they are attached, form an azetidine ring, a pyrrolidine ring, or a morpholine ring, each of which is optionally substituted with 1, 2 or 3 independently selected $R^{13}$ groups.

In some embodiments, each $Cy^1$ is independently selected from 3-10 membered cycloalkyl, 4-6 membered heterocycloalkyl, 5-6 membered heteroaryl, and phenyl, each of which is optionally substituted by 1, 2, 3, or 4 independently selected $R^{13}$ groups.

In some embodiments, each $Cy^1$ is independently cyclopropyl, cyclobutyl, cyclopentyl, cyclohexyl, admantyl, indenyl, phenyl, piperidinyl, morpholinyl, tetrahydrofuranyl, tetrahydropyranyl, thiomorpholinyl, and pyridyl, each of which is optionally substituted by 1, 2, 3, or 4 independently selected $R^{13}$ groups.

In some embodiments, each $Cy^1$ is independently 4-10 membered heterocycloalkyl, which is optionally substituted by 1, 2, 3, or 4 independently selected $R^{13}$ groups.

In some embodiments, each $Cy^1$ is independently 4-6 membered heterocycloalkyl, which is optionally substituted by 1, 2, 3, or 4 independently selected $R^{13}$ groups In some embodiments, each $Cy^1$ is independently azetidinyl, pyrrolidinyl, or morpholinyl.

In some embodiments, each $Cy^1$ is independently 3-10 membered cycloalkyl, which is optionally substituted by 1, 2, 3, or 4 independently selected $R^{13}$ groups.

In some embodiments, each $Cy^1$ is independently 6-10 membered aryl, which is optionally substituted by 1, 2, 3, or 4 independently selected $R^{13}$ groups.

In some embodiments, each $Cy^1$ is independently phenyl, pyridyl, cyclopropyl, cyclopentyl, or cyclohexyl.

In some embodiments, $R^4$ is methyl, ethyl, $CF_3$, phenyl, or $NHR^{d1}$.

In some embodiments, $R^4$ is methyl.

In some embodiments, $R^4$ is $CF_3$.

In some embodiments, $R^4$ is phenyl.

In some embodiments, $R^4$ is $NHR^{d1}$, wherein $R^{d1}$ is selected from H, $C_{1-6}$ alkyl, $C_{2-6}$ alkenyl, $C_{2-6}$ alkynyl, $C_{1-4}$ haloalkyl, $Cy^1$, and —$C_{1-4}$ alkylene-$Cy^1$; wherein said $C_{1-6}$ alkyl, $C_{2-6}$ alkenyl, $C_{2-6}$ alkynyl, and $C_{1-4}$ haloalkyl are each optionally substituted with 1, 2, 3, or 4 independently selected $R^{13}$ groups.

In some embodiments, $R^4$ is $NHR^{d1}$, wherein $R^{d1}$ is selected from H, $C_{1-6}$ alkyl, $C_{1-4}$ haloalkyl, $Cy^1$, and —$C_{1-4}$ alkylene-$Cy^1$; wherein said $C_{1-6}$ alkyl and $C_{1-4}$ haloalkyl are each optionally substituted with 1, 2, 3, or 4 independently selected $R^{13}$ groups.

In some embodiments, $R^4$ is $C_{1-4}$ alkyl, $C_{1-4}$ haloalkyl, $Cy^1$, or $NR^{c1}R^{d1}$.

In some embodiments, each $R^{13}$ is independently selected from halo, CN, $C_{1-6}$ alkyl, $C_{2-6}$ alkenyl, $C_{2-6}$ alkynyl, $C_{1-4}$ haloalkyl, $Cy^3$, —$C_{1-4}$ alkylene-$Cy^3$, $OR^{a3}$, $C(O)R^{b3}$, $C(O)NR^{c3}R^{d3}$, $C(O)OR^{a3}$, $NR^{c3}R^{d3}$, $NR^{c3}OR^{a3}$, $NR^{c3}C(O)R^{b3}$, $NR^{c3}C(O)OR^{a3}$, $NR^{c3}C(O)NR^{c3}R^{d3}$, $S(O)_2R^{b3}$, and $S(O)_2NR^{c3}R^{d3}$; wherein said $C_{1-6}$ alkyl, $C_{2-6}$ alkenyl, $C_{2-6}$ alkynyl, and $C_{1-4}$ haloalkyl are each optionally substituted with 1, 2, 3, or 4 independently selected $R^g$ groups.

In some embodiments, each $R^{13}$ is independently selected from halo, CN, $C_{1-6}$ alkyl, $C_{1-4}$ haloalkyl, $Cy^3$, —$C_{1-4}$ alkylene-$Cy^3$, $OR^{a3}$, $C(O)R^{b3}$, $C(O)NR^{c3}R^{d3}$, $C(O)OR^{a3}$, $NR^{c3}R^{d3}$, $NR^{c3}OR^{a3}$, $NR^{c3}C(O)R^{b3}$, $NR^{c3}C(O)OR^{a3}$, and $NR^{c3}C(O)NR^{c3}R^{d3}$; wherein said $C_{1-6}$ alkyl is optionally substituted by 1 or 2 independently selected $R^g$ groups.

In some embodiments, each $R^{13}$ is selected from halo, CN, $C_{1-6}$ alkyl, $C_{1-4}$ haloalkyl, —$C_{1-4}$ alkylene-$Cy^3$, $OR^{a3}$, $NR^{c3}R^{d3}$, $NR^{c3}C(O)OR^{a3}$, and $S(O)_2NR^{c3}R^{d3}$; wherein said $C_{1-6}$ alkyl is optionally substituted by 1 or 2 independently selected $R^g$ groups.

In some embodiments, each $R^{13}$ is selected from halo, CN, $C_{1-6}$ alkyl, $C_{1-4}$ haloalkyl, —$C_{1-4}$ alkylene-$Cy^3$, $OR^{a3}$, $NR^{c3}R^{d3}$, $NR^{c3}C(O)OR^{a3}$, $C(O)R^{b3}$, $NR^{c3}C(O)OR^{a3}$, $S(O)_2R^{b3}$, and $S(O)_2NR^{c3}R^{d3}$; wherein said $C_{1-6}$ alkyl is optionally substituted by 1 or 2 independently selected $R^g$ groups.

In some embodiments, each $R^{a3}$, $R^{c3}$, and $R^{d3}$ are independently selected from H and $C_{1-6}$ alkyl; wherein said $C_{1-6}$ alkyl is optionally substituted with 1, 2, 3, or 4 independently selected $R^g$ groups; each $R^{b3}$ is independently selected from $C_{1-6}$ alkyl, which is optionally substituted with 1, 2, 3, or 4 independently selected $R^g$ groups; alternatively, any $R^{c3}$ and $R^{d3}$ attached to the same N atom, together with the N atom to which they are attached, form a 4-, 5-, 6- or 7-membered heterocycloalkyl group optionally substituted with 1, 2 or 3 independently selected $R^g$ groups.

In some embodiments, any $R^{c3}$ and $R^{d3}$ attached to the same N atom, together with the N atom to which they are attached, form a morpholine ring.

In some embodiments, each $Cy^3$ is independently selected from 3-7 membered cycloalkyl and 4-6 membered heterocycloalkyl, each of which is optionally substituted by 1 or 2 independently selected $R^g$ groups.

In some embodiments, each $Cy^3$ is independently cyclopentyl, tetrahydrofuranyl, or tetrahydropyranyl, or phenyl.

In some embodiments, each $R^g$ is independently selected from OH, CN, halo, $C_{1-6}$ alkyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, and di($C_{1-6}$ alkyl)amino.

In some embodiments, each $R^g$ is independently selected from OH, methoxy, and methyl.

In some embodiments,

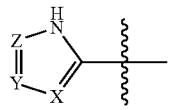

is

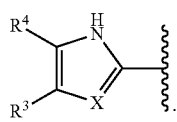

In some embodiments,

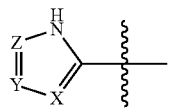

is

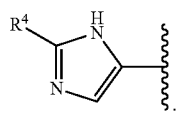

In some embodiments,

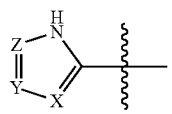

is

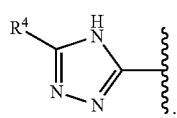

In some embodiments, W is CH and V is CH. In some embodiments, W is N and V is CH. In some embodiments, W is CH and V is N.

In some embodiments of compounds provided herein (e.g., compounds of Formula I), ring A is a monocyclic 5-6 membered azaheterocycloalkyl ring or a 5-6 membered azaheteroaryl ring.

In some embodiments, ring A is a monocyclic 5-6 membered azaheteroaryl ring.

In some embodiments, ring A is a pyrazole ring, a pyridine ring, an imidazole ring, a tetrahydropyridine ring, a dihydropyrrolyl ring, or a pyrrole ring. In some embodiments, ring A is a pyrazole ring, a pyridine ring, an imidazole ring, a tetrahydropyridine ring, or a dihydropyrrolyl ring. In some embodiments, ring A is a pyrazole ring or a pyridine ring. In some embodiments, ring A is a tetrahydropyridine ring or a dihydropyrrolyl ring. In some embodiments, ring A is pyrazol-3-yl, pyrazol-5-yl, imidazol-2-yl, pyridin-3-yl, piperidin-3-yl, 1,2,5,6-tetrahydropyridin-4-yl, or 2,5-dihydropyrrol-3-yl.

In some embodiments:

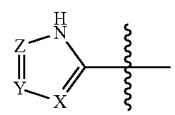

is

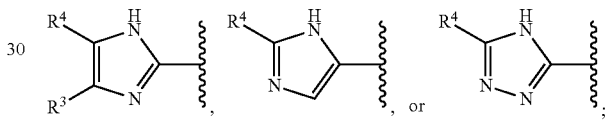

ring A is a monocyclic 5-6 membered azaheterocycloalkyl ring or a 5-6 membered azaheteroaryl ring;

$R^1$ is selected from halo, $C_{1-6}$ alkyl, $C_{2-6}$ alkenyl, $C_{2-6}$ alkynyl, $C_{1-4}$ haloalkyl, $Cy^{1a}$, —$C_{1-4}$ alkylene-Cy, $OR^a$, $C(O)R^b$, $C(O)NR^cR^d$, $C(O)OR^a$, $OC(O)R^b$, $OC(O)NR^cR^d$, $NR^cR^d$, $NR^cOR^d$, $NR^cC(O)R^b$, $NR^cC(O)OR^b$, $NR^cC(O)NR^cR^d$, $NR^cS(O)_2R^b$, $NR^cS(O)_2NR^cR^d$, $S(O)_2R^b$, and $S(O)_2NR^cR^d$; wherein said $C_{1-6}$ alkyl, $C_{2-6}$ alkenyl, $C_{2-6}$ alkynyl, and $C_{1-4}$ haloalkyl are optionally substituted with 1, 2, or 3 independently selected $R^{11}$ groups;

$R^2$ is halo, OH, $C_{1-4}$ alkyl, $C_{1-4}$ haloalkyl, $C_{1-4}$ alkoxy, $C_{1-4}$ haloalkoxy, amino, $C_{1-4}$ alkylamine, di($C_{1-4}$ alkyl) amino, HO—$C_{1-4}$ alkyl, or $C_{1-3}$ alkoxy-$C_{1-4}$ alkyl;

$R^3$ and $R^4$ are independently selected from H, halo, $C_{1-6}$ alkyl, $C_{2-6}$ alkenyl, $C_{2-6}$ alkynyl, $C_{1-4}$ haloalkyl, $Cy^1$, —$C_{1-4}$ alkylene-$Cy^1$, $OR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}OR^{d1}$, $NR^{c1}C(O)R^{b1}$, $NR^{c1}C(O)OR^{b1}$, $NR^{c1}C(O)NR^{c1}R^{d1}$, $NR^{c1}S(O)_2R^{b1}$, $NR^{c1}S(O)_2NR^{c1}R^{d1}$, $S(O)_2R^{b1}$, and $S(O)_2NR^{c1}R^{d1}$, wherein said $C_{1-6}$ alkyl, $C_{2-6}$ alkenyl, $C_{2-6}$ alkynyl, and $C_{1-4}$ haloalkyl are each optionally substituted with 1, 2, or 3 independently selected $R^{13}$ groups;

provided that when both $R^3$ and $R^4$ are present, then one of $R^3$ and $R^4$ is selected from H, halo, OH, CN, $C_{1-4}$ alkyl, $C_{1-4}$ haloalkyl, $C_{1-4}$ alkoxy, $C_{1-4}$ haloalkoxy, amino, $C_{1-4}$ alkylamine, di($C_{1-4}$ alkyl)amino, cyano-$C_{1-4}$ alkyl, HO—$C_{1-4}$ alkyl, and $C_{1-3}$ alkoxy-$C_{1-4}$ alkyl; and alternatively, $R^3$ and $R^4$, taken together with the carbon atoms to which they are attached form a monocyclic 4-7 membered cycloalkyl ring, a phenyl ring, a monocyclic 4-6 membered heterocycloalkyl ring, or a monocyclic 5-6 membered heteroaryl ring, each of which is optionally substituted by 1, 2 or 3 independently selected $R^{13}$ groups.

In some embodiments:

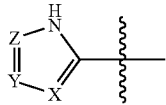

is

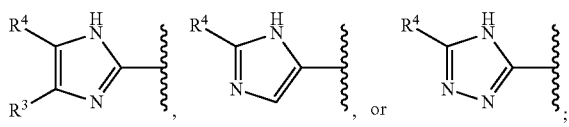

ring A is a monocyclic 5-6 membered azaheterocycloalkyl ring or a 5-6 membered azaheteroaryl ring;

$R^1$ is selected from halo, $C_{1-6}$ alkyl, $C_{2-6}$ alkenyl, $C_{2-6}$ alkynyl, $C_{1-4}$ haloalkyl, $Cy^{1a}$, —$C_{1-4}$ alkylene-Cy, $OR^a$, $C(O)R^b$, $C(O)NR^cR^d$, $C(O)OR^a$, $NR^cR^d$, $NR^cOR^d$, $NR^cC(O)R^b$, $NR^cC(O)OR^b$, $NR^cC(O)NR^c R^d$, $NR^cS(O)_2R^b$, $NR^cS(O)_2NR^cR^d$, $S(O)_2R^b$, and $S(O)_2NR^cR^d$; wherein said $C_{1-6}$ alkyl, $C_{2-6}$ alkenyl, $C_{2-6}$ alkynyl, and $C_{1-4}$ haloalkyl are optionally substituted with 1, 2, or 3 independently selected $R^{11}$ groups;

$R^2$ is halo, OH, $C_{1-4}$ alkyl, $C_{1-4}$ haloalkyl, $C_{1-4}$ alkoxy, $C_{1-4}$ haloalkoxy, amino, $C_{1-4}$ alkylamine, di($C_{1-4}$ alkyl)amino, or $C_{1-3}$ alkoxy-$C_{1-4}$ alkyl;

$R^3$ and $R^4$ are independently selected from H, halo, $C_{1-6}$ alkyl, $C_{2-6}$ alkenyl, $C_{2-6}$ alkynyl, $C_{1-4}$ haloalkyl, $Cy^1$, —$C_{1-4}$ alkylene-$Cy^1$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{b1}$, $NR^{c1}C(O)NR^{c1}R^{d1}$, $S(O)_2R^{b1}$, and $S(O)_2NR^{c1}R^{d1}$, wherein said $C_{1-6}$ alkyl, $C_{2-6}$ alkenyl, $C_{2-6}$ alkynyl, and $C_{1-4}$ haloalkyl are each optionally substituted with 1, 2, or 3 independently selected $R^{13}$ groups;

provided that when both $R^3$ and $R^4$ are present, then one of $R^3$ and $R^4$ is selected from H, halo, OH, CN, $C_{1-4}$ alkyl, $C_{1-4}$ haloalkyl, $C_{1-4}$ alkoxy, $C_{1-4}$ haloalkoxy, amino, $C_{1-4}$ alkylamine, di($C_{1-4}$ alkyl)amino, cyano-$C_{1-4}$ alkyl, HO—$C_{1-4}$ alkyl, and $C_{1-3}$ alkoxy-$C_{1-4}$ alkyl; and alternatively, $R^3$ and $R^4$, taken together with the carbon atoms to which they are attached form a monocyclic 4-7 membered cycloalkyl ring, a phenyl ring, a monocyclic 4-6 membered heterocycloalkyl ring, or a monocyclic 5-6 membered heteroaryl ring, each of which is optionally substituted by 1, 2 or 3 independently selected $R^{13}$ groups.

In some embodiments:

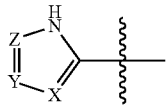

is

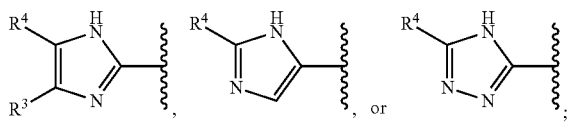

W is CH and V is CH; or
W is N and V is CH; or
W is CH and V is N;

ring A is a monocyclic 5-6 membered azaheterocycloalkyl ring or a 5-6 membered azaheteroaryl ring;

$R^1$ is selected from halo, $C_{1-6}$ alkyl, $C_{2-6}$ alkenyl, $C_{2-6}$ alkynyl, $C_{1-4}$ haloalkyl, $Cy^{1a}$, —$C_{1-4}$ alkylene-Cy, $OR^a$, $C(O)R^b$, $C(O)NR^cR^d$, $C(O)OR^a$, $OC(O)R^b$, $OC(O)NR^cR^d$, $NR^cR^d$, $NR^cOR^d$, $NR^cC(O)R^b$, $NR^cC(O)OR^b$, $NR^cC(O)NR^cR^d$, $NR^cS(O)_2R^b$, $NR^cS(O)_2NR^cR^d$, $S(O)_2R^b$, and $S(O)_2NR^cR^d$; wherein said $C_{1-6}$ alkyl, $C_{2-6}$ alkenyl, $C_{2-6}$ alkynyl, and $C_{1-4}$ haloalkyl are optionally substituted with 1, 2, or 3 independently selected $R^{11}$ groups;

$R^2$ is halo, OH, $C_{1-4}$ alkyl, $C_{1-4}$ haloalkyl, $C_{1-4}$ alkoxy, $C_{1-4}$ haloalkoxy, amino, $C_{1-4}$ alkylamine, di($C_{1-4}$ alkyl)amino, HO—$C_{1-4}$ alkyl, or $C_{1-3}$ alkoxy-$C_{1-4}$ alkyl;

$R^3$ and $R^4$ are independently selected from H, halo, $C_{1-6}$ alkyl, $C_{2-6}$ alkenyl, $C_{2-6}$ alkynyl, $C_{1-4}$ haloalkyl, $Cy^1$, —$C_{1-4}$ alkylene-$Cy^1$, $OR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}OR^{d1}$, $NR^{c1}C(O)R^{b1}$, $NR^{c1}C(O)OR^{b1}$, $NR^{c1}C(O)NR^{c1}R^{d1}$, $NR^{c1}S(O)_2R^{b1}$, $NR^{c1}S(O)_2NR^{c1}R^{d1}$, $S(O)_2R^{b1}$, and $S(O)_2NR^{c1}R^{d1}$, wherein said $C_{1-6}$ alkyl, $C_{2-6}$ alkenyl, $C_{2-6}$ alkynyl, and $C_{1-4}$ haloalkyl are each optionally substituted with 1, 2, or 3 independently selected $R^{13}$ groups;

provided that when both $R^3$ and $R^4$ are present, then one of $R^3$ and $R^4$ is selected from H, halo, OH, CN, $C_{1-4}$ alkyl, $C_{1-4}$ haloalkyl, $C_{1-4}$ alkoxy, $C_{1-4}$ haloalkoxy, amino, $C_{1-4}$ alkylamine, di($C_{1-4}$ alkyl)amino, cyano-$C_{1-4}$ alkyl, HO—$C_{1-4}$ alkyl, and $C_{1-3}$ alkoxy-$C_{1-4}$ alkyl;

alternatively, $R^3$ and $R^4$, taken together with the carbon atoms to which they are attached form a monocyclic 4-7 membered cycloalkyl ring, a phenyl ring, a monocyclic 4-6 membered heterocycloalkyl ring, or a monocyclic 5-6 membered heteroaryl ring, each of which is optionally substituted by 1, 2 or 3 independently selected $R^{13}$ groups;

each $R^{11}$ is independently selected from halo, CN, $C_{1-6}$ alkyl, $C_{2-6}$ alkenyl, $C_{2-6}$ alkynyl, $C_{1-4}$ haloalkyl, $Cy^2$, —$C_{1-4}$ alkylene-$Cy^2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^2OR^{d2}$, $NR^{c2}C(O)R^{b2}$, $NR^{c2}C(O)OR^{a2}$, $NR^{c2}C(O)NR^{c2}R^{d2}$, $NR^{c2}S(O)_2R^{b2}$, $NR^{c2}S(O)_2NR^{c2}R^{d2}$, $S(O)_2R^{b2}$, and $S(O)_2NR^{c2}R^{d2}$; wherein said $C_{1-6}$ alkyl, $C_{2-6}$ alkenyl, $C_{2-6}$ alkynyl, and $C_{1-4}$ haloalkyl are each optionally substituted with 1, 2, 3, or 4 independently selected $R^g$ groups;

each $R^{13}$ is independently selected from halo, CN, $C_{1-6}$ alkyl, $C_{2-6}$ alkenyl, $C_{2-6}$ alkynyl, $C_{1-4}$ haloalkyl, $Cy^3$, —$C_{1-4}$ alkylene-$Cy^3$, $OR^{a3}$, $C(O)R^{b3}$, $C(O)NR^{c3}R^{d3}$, $C(O)OR^{a3}$, $NR^{c3}R^{d3}$, $NR^{c3}OR^{d3}$, $NR^{c3}C(O)R^{b3}$, $NR^{c3}C(O)OR^{a3}$, $NR^{c3}C(O)NR^{c3}R^{d3}$, $S(O)_2R^{b3}$, and $S(O)_2NR^{c3}R^{d3}$; wherein said $C_{1-6}$ alkyl, $C_{2-6}$ alkenyl, $C_{2-6}$ alkynyl, and $C_{1-4}$ haloalkyl are each optionally substituted with 1, 2, 3, or 4 independently selected $R^g$ groups;

each $R^{13}$ is selected from halo, CN, $C_{1-6}$ alkyl, $C_{1-4}$ haloalkyl, —$C_{1-4}$ alkylene-$Cy^3$, $OR^{a3}$, $NR^{c3}R^{d3}$, $NR^{c3}C(O)OR^{a3}$, and $S(O)_2NR^{c3}R^{d3}$; wherein said $C_{1-6}$ alkyl is optionally substituted by 1 or 2 independently selected $R^g$ groups;

$R^a$, $R^c$, and $R^d$ are each independently selected from H, $C_{1-6}$ alkyl, $C_{1-4}$ haloalkyl, Cy, and —$C_{1-4}$ alkylene-Cy; wherein said $C_{1-6}$ alkyl is optionally substituted with 1 or 2 independently selected $R^{11}$ groups;

$R^b$ is independently selected from $C_{1-6}$ alkyl, $C_{1-4}$ haloalkyl, Cy, and —$C_{1-4}$ alkylene-Cy; wherein said $C_{1-6}$ alkyl is optionally substituted with 1 or 2 independently selected $R^{11}$ groups;

alternatively, any $R^c$ and $R^d$ attached to the same N atom, together with the N atom to which they are attached, form a 4-10 membered heterocycloalkyl group, which is optionally substituted with 1 or 2 independently selected $R^{11}$ groups;

$R^{a1}$, $R^{c1}$, and $R^{d1}$ are each independently selected from H, $C_{1-6}$ alkyl, $C_{1-4}$ haloalkyl, $Cy^1$, and —$C_{1-4}$ alkylene-$Cy^1$; wherein said $C_{1-6}$ alkyl is optionally substituted with 1, 2, 3, or 4 independently selected $R^{13}$ groups;

$R^{b1}$ are each independently selected from $C_{1-6}$ alkyl, $C_{1-4}$ haloalkyl, $Cy^1$, and —$C_{1-4}$ alkylene-$Cy^1$; wherein said $C_{1-6}$ alkyl is optionally substituted with 1, 2, 3, or 4 independently selected $R^{13}$ groups;

alternatively, any $R^{c1}$ and $R^{d1}$ attached to the same N atom, together with the N atom to which they are attached, form a 4-, 5-, 6- or 7-membered heterocycloalkyl group optionally substituted with 1, 2 or 3 independently selected $R^{13}$ groups;

each $R^{a3}$, $R^{c3}$, and $R^{d3}$ are independently selected from H, $C_{1-6}$ alkyl, and $C_{1-4}$ haloalkyl; wherein said $C_{1-6}$ alkyl is optionally substituted with 1, 2, 3, or 4 independently selected $R^g$ groups;

each $R^{b3}$ is independently selected from $C_{1-6}$ alkyl and $C_{1-4}$ haloalkyl; wherein said $C_{1-6}$ alkyl is optionally substituted with 1, 2, 3, or 4 independently selected $R^g$ groups;

alternatively, any $R^{c3}$ and $R^{d3}$ attached to the same N atom, together with the N atom to which they are attached, form a 4-, 5-, 6- or 7-membered heterocycloalkyl group optionally substituted with 1, 2 or 3 independently selected $R^g$ groups;

each Cy is independently 3-7 membered cycloalkyl, 4-6 membered heterocycloalkyl, phenyl, or 5-6 membered heteroaryl, each of which is optionally substituted by 1, 2, 3, or 4 independently selected $R^{11}$ group;

$Cy^{1a}$ is 3-7 membered cycloalkyl, 4-6 membered heterocycloalkyl, phenyl, or 5-6 membered heteroaryl, which is optionally substituted by 1, 2, 3, or 4 independently selected $R^{11}$ groups;

each $Cy^1$ is independently selected from 3-10 membered cycloalkyl, 4-6 membered heterocycloalkyl, 5-6 membered heteroaryl, and phenyl, each of which is optionally substituted by 1, 2, 3, or 4 independently selected $R^{13}$ groups;

each $Cy^3$ is independently selected from –7 membered cycloalkyl, 4-6 membered heterocycloalkyl, phenyl, or 5-6 membered heteroaryl, each of which is optionally substituted by 1 or 2 independently selected $R^g$ groups;

n is 0 or 1; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments:

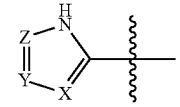

is

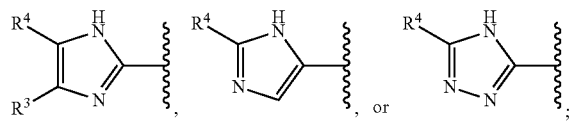

W is CH and V is CH; or
W is N and V is CH; or
W is CH and V is N;

ring A is a monocyclic 5-6 membered azaheterocycloalkyl ring or a 5-6 membered azaheteroaryl ring;

$R^1$ is selected from halo, $C_{1-6}$ alkyl, $C_{2-6}$ alkenyl, $C_{2-6}$ alkynyl, $C_{1-4}$ haloalkyl, $Cy^{1a}$, —$C_{1-4}$ alkylene-Cy, $OR^a$, $C(O)R^b$, $C(O)NR^cR^d$, $C(O)OR^a$, $NR^cR^d$, $NR^cOR^d$, $NR^cC(O)R^b$, $NR^cC(O)OR^b$, $NR^cC(O)NR^cR^d$, $NR^cS(O)_2R^b$, $NR^cS(O)_2NR^cR^d$, $S(O)_2R^b$, and $S(O)_2NR^cR^d$; wherein said $C_{1-6}$ alkyl, $C_{2-6}$ alkenyl, $C_{2-6}$ alkynyl, and $C_{1-4}$ haloalkyl are optionally substituted with 1, 2, or 3 independently selected $R^{11}$ groups;

$R^2$ is halo, $C_{1-4}$ alkyl, $C_{1-4}$ haloalkyl, $C_{1-4}$ alkoxy, $C_{1-4}$ haloalkoxy, amino, $C_{1-4}$ alkylamine, di($C_{1-4}$ alkyl)amino, or $C_{1-3}$ alkoxy-$C_{1-4}$ alkyl;

$R^3$ and $R^4$ are independently selected from H, halo, $C_{1-6}$ alkyl, $C_{2-6}$ alkenyl, $C_{2-6}$ alkynyl, $C_{1-4}$ haloalkyl, $Cy^1$, —$C_{1-4}$ alkylene-$Cy^1$, $OR^{a1}$, $C(O)R^{b1}$, $C(O)NR^{c1}R^{d1}$, $C(O)OR^{a1}$, $NR^{c1}R^{d1}$, $NR^{cc}C(O)R^{b1}$, $NR^{c1}C(O)OR^{b1}$, $NR^{c1}C(O)NR^{c1}R^{d1}$, $S(O)_2R^{b1}$, and $S(O)_2NR^{c1}R^{d1}$, wherein said $C_{1-6}$ alkyl, $C_{2-6}$ alkenyl, $C_{2-6}$ alkynyl, and $C_{1-4}$ haloalkyl are each optionally substituted with 1, 2, or 3 independently selected $R^{13}$ groups;

provided that when both $R^3$ and $R^4$ are present, then one of $R^3$ and $R^4$ is selected from H, halo, OH, CN, $C_{1-4}$ alkyl, $C_{1-4}$ haloalkyl, $C_{1-4}$ alkoxy, $C_{1-4}$ haloalkoxy, amino, $C_{1-4}$ alkylamine, di($C_{1-4}$ alkyl)amino, cyano-$C_{1-4}$ alkyl, HO—$C_{1-4}$ alkyl, and $C_{1-3}$ alkoxy-$C_{1-4}$ alkyl;

alternatively, $R^3$ and $R^4$, taken together with the carbon atoms to which they are attached form a monocyclic 4-7 membered cycloalkyl ring, a phenyl ring, a monocyclic 4-6 membered heterocycloalkyl ring, or a monocyclic 5-6 membered heteroaryl ring, each of which is optionally substituted by 1, 2 or 3 independently selected $R^{13}$ groups;

each $R^{11}$ is independently selected from halo, CN, $C_{1-6}$ alkyl, $C_{1-4}$ haloalkyl, $Cy^2$, —$C_{1-4}$ alkylene-$Cy^2$, $OR^{a2}$, $SR^{a2}$, $C(O)R^{b2}$, $C(O)NR^{c2}R^{d2}$, $C(O)OR^{a2}$, $NR^{c2}R^{d2}$, $NR^{c2}OR^{d2}$, $NR^{c2}C(O)R^{b2}$, $NR^{c2}C(O)OR^{a2}$, $NR^{c2}C(O)NR^{c2}R^{d2}$, $NR^{c2}S(O)_2R^{b2}$, $NR^{c2}S(O)_2NR^{c2}R^{d2}$, $S(O)_2R^{b2}$, and $S(O)_2NR^{c2}R^{d2}$; wherein said $C_{1-6}$ alkyl and $C_{1-4}$ haloalkyl are each optionally substituted with 1, 2, 3, or 4 independently selected $R^g$ groups;

each $R^{13}$ is independently selected from halo, CN, $C_{1-6}$ alkyl, $C_{1-4}$ haloalkyl, $Cy^3$, —$C_{1-4}$ alkylene-$Cy^3$, $OR^{a3}$, $C(O)R^{b3}$, $C(O)NR^{c3}R^{d3}$, $C(O)OR^{a3}$, $NR^{c3}R^{d3}$, $NR^{c3}OR^{a3}$, $NR^{c3}C(O)R^{b3}$, $NR^{c3}C(O)OR^{a3}$, and NR$^{c3}$C(O)NR$^{c3}$R$^{d3}$, wherein said C$_{1-6}$ alkyl is optionally substituted by 1 or 2 independently selected R$^g$ groups;

R$^a$, R$^c$, and R$^d$ are each independently selected from H, C$_{1-6}$ alkyl, C$_{1-4}$ haloalkyl, Cy, and —C$_{1-4}$ alkylene-Cy; wherein said C$_{1-6}$ alkyl is optionally substituted with 1 or 2 independently selected R$^{11}$ groups;

R$^b$ is independently selected from C$_{1-6}$ alkyl, C$_{1-4}$ haloalkyl, Cy, and —C$_{1-4}$ alkylene-Cy; wherein said C$_{1-6}$ alkyl is optionally substituted with 1 or 2 independently selected R$^{11}$ groups;

alternatively, any R$^c$ and R$^d$ attached to the same N atom, together with the N atom to which they are attached, form a 4-10 membered heterocycloalkyl group, which is optionally substituted with 1 or 2 independently selected R$^{11}$ groups;

R$^{a1}$, R$^{c1}$, and R$^{d1}$ are each independently selected from H, C$_{1-6}$ alkyl, C$_{1-4}$ haloalkyl, Cy$^1$, and —C$_{1-4}$ alkylene-Cy$^1$; wherein said C$_{1-6}$ alkyl is optionally substituted with 1, 2, 3, or 4 independently selected R$^{13}$ groups;

R$^{b1}$ are each independently selected from C$_{1-6}$ alkyl, C$_{1-4}$ haloalkyl, Cy$^1$, and —C$_{1-4}$ alkylene-Cy$^1$; wherein said C$_{1-6}$ alkyl is optionally substituted with 1, 2, 3, or 4 independently selected R$^{13}$ groups;

alternatively, any R$^{c1}$ and R$^{d1}$ attached to the same N atom, together with the N atom to which they are attached, form a 4-, 5-, 6- or 7-membered heterocycloalkyl group optionally substituted with 1, 2 or 3 independently selected R$^{13}$ groups;

each R$^{a3}$, R$^{c3}$, and R$^{d3}$ are independently selected from H, C$_{1-6}$ alkyl, and C$_{1-4}$ haloalkyl; wherein said C$_{1-6}$ alkyl is optionally substituted with 1, 2, 3, or 4 independently selected R$^g$ groups;

each R$^{b3}$ is independently selected from C$_{1-6}$ alkyl and C$_{1-4}$ haloalkyl; wherein said C$_{1-6}$ alkyl is optionally substituted with 1, 2, 3, or 4 independently selected R$^g$ groups;

alternatively, any R$^{c3}$ and R$^{d3}$ attached to the same N atom, together with the N atom to which they are attached, form a 4-, 5-, 6- or 7-membered heterocycloalkyl group optionally substituted with 1, 2 or 3 independently selected R$^g$ groups;

each Cy is independently 3-7 membered cycloalkyl, 4-6 membered heterocycloalkyl, phenyl, or 5-6 membered heteroaryl, each of which is optionally substituted by 1, 2, 3, or 4 independently selected R$^{11}$ group;

Cy$^{1a}$ is 3-7 membered cycloalkyl, 4-6 membered heterocycloalkyl, phenyl, or 5-6 membered heteroaryl, which is optionally substituted by 1, 2, 3, or 4 independently selected R$^{11}$ groups;

each Cy$^1$ is independently selected from 3-10 membered cycloalkyl, 4-6 membered heterocycloalkyl, 5-6 membered heteroaryl, and phenyl, each of which is optionally substituted by 1, 2, 3, or 4 independently selected R$^{13}$ groups;

each Cy$^3$ is independently selected from 3-7 membered cycloalkyl and 4-6 membered heterocycloalkyl, each of which is optionally substituted by 1 or 2 independently selected R$^g$ groups;

n is 0 or 1; and each R$^g$ is independently selected from OH, CN, halo, C$_{1-6}$ alkyl, C$_{1-4}$ haloalkyl, C$_{1-6}$ alkoxy, C$_{1-6}$ haloalkoxy, cyano-C$_{1-3}$ alkyl, HO—C$_{1-3}$ alkyl, amino, C$_{1-6}$ alkylamino, and di(C$_{1-6}$ alkyl)amino.

In some embodiments:

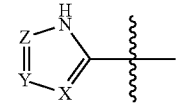

is

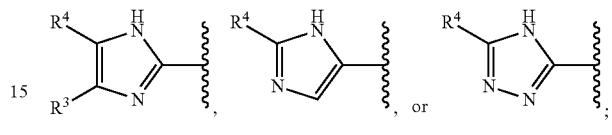

ring A is a pyrazole ring, a pyridine ring, an imidazole ring, a tetrahydropyridine ring, or a dihydropyrrolyl ring;

W is CH and V is CH; or
W is N and V is CH; or
W is CH and V is N;

R$^1$ is selected from halo, C$_{1-6}$ alkyl, C$_{1-4}$ haloalkyl, Cy$^{1a}$, —C$_{1-4}$ alkylene-Cy, OR$^a$, C(O)R$^b$, C(O)NR$^c$R$^d$, C(O)OR$^a$, NR$^c$R$^d$, NR$^c$C(O)R$^b$, NR$^c$C(O)OR$^b$, NR$^c$C(O)NR$^c$R$^d$, NR$^c$S(O)$_2$R$^b$, S(O)$_2$R$^b$, and S(O)$_2$NR$^c$R$^d$; wherein said C$_{1-6}$ alkyl and C$_{1-4}$ haloalkyl are optionally substituted with 1, 2, or 3 independently selected R$^{11}$ groups;

R$^2$ is C$_{1-4}$ alkyl;

R$^3$ and R$^4$ are each independently selected from H, CN, C$_{1-6}$ alkyl, C$_{1-4}$ haloalkyl, Cy$^1$, —C$_{1-4}$ alkylene-Cy$^1$, C(O)R$^{b1}$, C(O)NR$^{c1}$R$^{d1}$, C(O)OR$^{a1}$, NR$^{c1}$R$^{d1}$, and NR$^{c1}$C(O)R$^{b1}$ wherein said C$_{1-6}$ alkyl is optionally substituted with 1, 2, or 3 independently selected R$^{13}$ groups;

provided that when both R$^3$ and R$^4$ are present, then one of R$^3$ and R$^4$ is selected from H, C$_{1-4}$ alkyl, and C$_{1-4}$ haloalkyl;

alternatively, R$^3$ and R$^4$, taken together with the carbon atoms to which they are attached form a monocyclic 4-7 membered cycloalkyl ring, and a phenyl ring each R$^{11}$ is independently selected from halo, CN, C$_{1-6}$ alkyl, C$_{1-4}$ haloalkyl, Cy$^2$, —C$_{1-4}$ alkylene-Cy$^2$, OR$^{a2}$, C(O)R$^{b2}$, C(O)NR$^{c2}$R$^{d2}$, C(O)OR$^{a2}$, NR$^{c2}$R$^{d2}$ and S(O)$_2$R$^{b2}$; wherein said C$_{1-6}$ alkyl is optionally substituted with 1, 2, 3, or 4 independently selected R$^g$ groups;

each R$^{13}$ is selected from halo, CN, C$_{1-6}$ alkyl, C$_{1-4}$ haloalkyl, —C$_{1-4}$ alkylene-Cy$^3$, OR$^{a3}$, NR$^{c3}$R$^{d3}$, C(O)R$^{b3}$, NR$^{c3}$C(O)OR$^{a3}$ S(O)$_2$R$^{b3}$, and S(O)$_2$NR$^{c3}$R$^{d3}$; wherein said C$_{1-6}$ alkyl is optionally substituted by 1 or 2 independently selected R$^g$ groups;

R$^a$, R$^c$, and R$^d$ are each independently selected from H, C$_{1-6}$ alkyl, Cy, and —C$_{1-4}$ alkylene-Cy; wherein said C$_{1-6}$ alkyl is optionally substituted with 1 or 2 independently selected R$^{11}$ groups;

R$^b$ is independently selected from C$_{1-6}$ alkyl, Cy, and —C$_{1-4}$ alkylene-Cy; wherein said C$_{1-6}$ alkyl is optionally substituted with 1 or 2 independently selected R$^{11}$ groups;

alternatively, any R$^c$ and R$^d$ attached to the same N atom, together with the N atom to which they are attached, form a 4-10 membered heterocycloalkyl group, which is optionally substituted with 1 or 2 independently selected R$^{11}$ groups;

$R^{a1}$, $R^{c1}$, and $R^{d1}$ are each independently selected from H, $C_{1-6}$ alkyl, $Cy^1$, and $-C_{1-4}$ alkylene-$Cy^1$; wherein said $C_{1-6}$ alkyl is optionally substituted with 1, 2, 3, or 4 independently selected $R^{13}$ groups;

$R^{b1}$ are each independently selected from $C_{1-6}$ alkyl, $Cy^1$, and $-C_{1-4}$ alkylene-$Cy^1$; wherein said $C_{1-6}$ alkyl is optionally substituted with 1, 2, 3, or 4 independently selected $R^{13}$ groups;

alternatively, any $R^{c1}$ and $R^{d1}$ attached to the same N atom, together with the N atom to which they are attached, form a 4-, 5-, 6- or 7-membered heterocycloalkyl group optionally substituted with 1, 2 or 3 independently selected $R^{13}$ groups;

each $R^{a3}$, $R^{c3}$, and $R^{d3}$ are independently selected from H, $C_{1-6}$ alkyl, and phenyl; wherein said $C_{1-6}$ alkyl is optionally substituted with 1, 2, 3, or 4 independently selected $R^g$ groups;

each $R^{b3}$ is independently selected from $C_{1-6}$ alkyl and phenyl; wherein said $C_{1-6}$ alkyl is optionally substituted with 1, 2, 3, or 4 independently selected $R^g$ groups;

alternatively, any $R^{c3}$ and $R^{d3}$ attached to the same N atom, together with the N atom to which they are attached, form a 4-, 5-, 6- or 7-membered heterocycloalkyl group optionally substituted with 1, 2 or 3 independently selected $R^g$ groups;

each Cy is independently 3-7 membered cycloalkyl, 4-6 membered heterocycloalkyl, or phenyl, each of which is optionally substituted by 1, 2, 3, or 4 independently selected $R^{11}$ group;

$Cy^{1a}$ is 5-6 membered heterocycloalkyl, which is optionally substituted by 1, 2, 3, or 4 independently selected $R^{11}$ groups;

each $Cy^1$ is independently selected from 3-10 membered cycloalkyl, 4-6 membered heterocycloalkyl, 5-6 membered heteroaryl, and phenyl, each of which is optionally substituted by 1, 2, 3, or 4 independently selected $R^{13}$ groups;

each $Cy^3$ is independently selected from 3-7 membered cycloalkyl and 4-6 membered heterocycloalkyl, each of which is optionally substituted by 1 or 2 independently selected $R^g$ groups;

n is 0 or 1; and each $R^g$ is independently selected from OH, $C_{1-3}$ alkoxy, and $C_{1-3}$ alkyl.

In some embodiments:

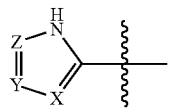

is

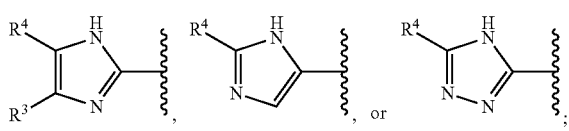

W is CH and V is CH; or
W is N and V is CH; or
W is CH and V is N;
ring A is a pyrazole ring, a pyridine ring, an imidazole ring, a tetrahydropyridine ring, or a dihydropyrrolyl ring;

$R^1$ is selected from halo, $C_{1-6}$ alkyl, $C_{1-4}$ haloalkyl, $Cy^{1a}$, $-C_{1-4}$ alkylene-Cy, $OR^a$, $C(O)R^b$, $C(O)NR^cR^d$, $C(O)OR^a$, $NR^cR^d$, $NR^cC(O)R^b$, $NR^cC(O)OR^b$, $NR^cC(O)NR^cR^d$, $NR^cS(O)_2R^b$, $S(O)_2R^b$, and $S(O)_2NR^cR^d$; wherein said $C_{1-6}$ alkyl and $C_{1-4}$ haloalkyl are optionally substituted with 1, 2, or 3 independently selected $R^{11}$ groups;

$R^2$ is $C_{1-4}$ alkyl;

$R^3$ and $R^4$ are each independently selected from H, CN, $C_{1-6}$ alkyl, $C_{1-4}$ haloalkyl, $Cy^1$, $-C_{1-4}$ alkylene-$Cy^1$, $C(O)R^{b1}$, $C(O)NR^{c1}R^{d1}$, $C(O)OR^{a1}$, $NR^{c1}R^{d1}$, and $NR^{c1}C(O)R^{b1}$, wherein said $C_{1-6}$ alkyl is optionally substituted with 1, 2, or 3 independently selected $R^{13}$ groups;

provided that when both $R^3$ and $R^4$ are present, then one of $R^3$ and $R^4$ is selected from H, $C_{1-4}$ alkyl, and $C_{1-4}$ haloalkyl;

alternatively, $R^3$ and $R^4$, taken together with the carbon atoms to which they are attached form a monocyclic 4-7 membered cycloalkyl ring, and a phenyl ring each $R^{11}$ is independently selected from halo, CN, $C_{1-6}$ alkyl, $C_{1-4}$ haloalkyl, $Cy^2$, $-_{1-4}$ alkylene-$Cy^2$, $OR^{a2}$, $C(O)R^{b2}$, $C(O)NR^{c2}R^{d2}$, $C(O)OR^{a2}$, $NR^{c2}R^{d2}$ and $S(O)_2R^{b2}$; wherein said $C_{1-6}$ alkyl is optionally substituted with 1, 2, 3, or 4 independently selected $R^g$ groups;

each $R^{13}$ is selected from halo, CN, $C_{1-6}$ alkyl, $C_{1-4}$ haloalkyl, $-C_{1-4}$ alkylene-$Cy^3$, $OR^{a3}$, $NR^{c3}R^{d3}$, $C(O)R^{b3}$, $NR^{c3}C(O)OR^{a3}$, $S(O)_2R^{b3}$, and $S(O)_2NR^{c3}R^{d3}$; wherein said $C_{1-6}$ alkyl is optionally substituted by 1 or 2 independently selected $R^g$ groups;

$R^a$, $R^c$, and $R^d$ are each independently selected from H, $C_{1-6}$ alkyl, Cy, and $-C_{1-4}$ alkylene-Cy; wherein said $C_{1-6}$ alkyl is optionally substituted with 1 or 2 independently selected $R^{11}$ groups;

$R^b$ is independently selected from $C_{1-6}$ alkyl, Cy, and $-C_{1-4}$ alkylene-Cy; wherein said $C_{1-6}$ alkyl is optionally substituted with 1 or 2 independently selected $R^{11}$ groups;

alternatively, any $R^c$ and $R^d$ attached to the same N atom, together with the N atom to which they are attached, form an azetidine ring, a pyrrolidine ring, an azabiyclo[2.2.1]-heptane ring, a piperidine ring, a piperazine ring, a morpholine ring, an azepane ring, a decahydroisoquinoline ring, a 2,8-diazaspiro[4.5]decan-1-one ring, a 3-oxa-9-azaspiro[5.5]undecane ring, a 2-oxa-7-azaspiro[3.5]nonane ring, or a 5-azaspiro[2.4]heptane ring, each of which is optionally substituted with 1 or 2 independently selected $R^{11}$ groups;

$R^{a1}$, $R^{c1}$, and $R^{d1}$ are each independently selected from H, $C_{1-6}$ alkyl, $Cy^1$, and $-C_{1-4}$ alkylene-$Cy^1$; wherein said $C_{1-6}$ alkyl is optionally substituted with 1, 2, 3, or 4 independently selected $R^{13}$ groups;

$R^{b1}$ are each independently selected from $C_{1-6}$ alkyl, $Cy^1$, and $-C_{1-4}$ alkylene-$Cy^1$; wherein said $C_{1-6}$ alkyl is optionally substituted with 1, 2, 3, or 4 independently selected $R^{13}$ groups;

alternatively, any $R^{c1}$ and $R^{d1}$ attached to the same N atom, together with the N atom to which they are attached, form an azetidine ring, a pyrrolidine ring, or a morpholine ring, each of which is optionally substituted with 1, 2 or 3 independently selected $R^{13}$ groups;

each $R^{a3}$, $R^{c3}$, and $R^{d3}$ are independently selected from H, $C_{1-6}$ alkyl, and phenyl; wherein said $C_{1-6}$ alkyl is optionally substituted with 1, 2, 3, or 4 independently selected $R^g$ groups;

each $R^{b3}$ is independently selected from $C_{1-6}$ alkyl and phenyl; wherein said $C_{1-6}$ alkyl is optionally substituted with 1, 2, 3, or 4 independently selected $R^g$ groups;

alternatively, any $R^{c3}$ and $R^{d3}$ attached to the same N atom, together with the N atom to which they are attached, form a morpholine ring;

each Cy is independently cyclopropyl, cyclobutyl, cyclopentyl, cyclohexyl,

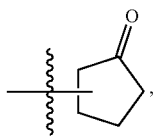

tetrahydrofuranyl, tetrahydropyranyl, morpholinyl, or phenyl, each of which is optionally substituted by 1 or 2 independently selected $R^{11}$ groups;

$Cy^{1a}$ is a pyrrolidine ring, a dihydropyrrole ring, a morpholine ring, a piperidine ring, a piperazine ring, a tetrahydrofuran ring, or a tetrahydropyran ring, each of which is optionally substituted by 1 or 2 independently selected $R^{11}$ groups;

each $Cy^1$ is independently cyclopropyl, cyclobutyl, cyclopentyl, cyclohexyl, admantyl, indenyl, phenyl, piperidinyl, morpholinyl, tetrahydrofuranyl, tetrahydropyranyl, thiomorpholinyl, and pyridyl, each of which is optionally substituted by 1, 2, 3, or 4 independently selected $R^{13}$ groups;

each $Cy^3$ is independently cyclopentyl, tetrahydrofuranyl, or tetrahydropyranyl, or phenyl;

n is 0 or 1; and each $R^g$ is independently selected from OH, methoxy, and methyl.

In some embodiments:

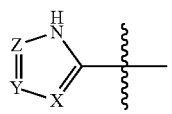

is

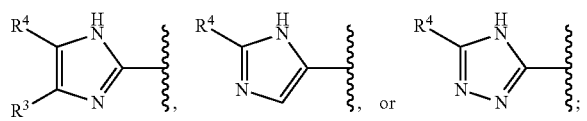

ring A is a pyrazole ring, a pyridine ring, an imidazole ring, a tetrahydropyridine ring, or a dihydropyrrolyl ring;

W is CH and V is CH; or

W is N and V is CH; or

W is CH and V is N;

$R^1$ is selected from halo, $C_{1-6}$ alkyl, $C_{1-4}$ haloalkyl, $Cy^{1a}$, —$C_{1-4}$ alkylene-Cy, $OR^a$, $C(O)R^b$, $C(O)NR^cR^d$, $C(O)OR^a$, $NR^cR^d$, $NR^cC(O)R^b$, $NR^cC(O)OR^b$, $NR^cC(O)NR^cR^d$, $NR^cS(O)_2R^b$, and $S(O)_2R^b$; wherein said $C_{1-6}$ alkyl and $C_{1-4}$ haloalkyl are optionally substituted with 1, 2, or 3 independently selected $R^{11}$ groups;

$R^2$ is $C_{1-4}$ alkyl;

$R^3$ and $R^4$ are each independently selected from H, $C_{1-6}$ alkyl, $C_{1-4}$ haloalkyl, $Cy^1$, —$C_{1-4}$ alkylene-$Cy^1$, $C(O)R^{b1}$, $C(O)NR^{c1}R^{d1}$, $C(O)OR^{a1}$, $NR^{c1}R^{d1}$ and $NR^{c1}C(O)R^{b1}$ wherein said $C_{1-6}$ alkyl is optionally substituted with 1, 2, or 3 independently selected $R^{13}$ groups;

provided that when both $R^3$ and $R^4$ are present, then one of $R^3$ and $R^4$ is selected from H, $C_{1-4}$ alkyl, and $C_{1-4}$ haloalkyl;

alternatively, $R^3$ and $R^4$, taken together with the carbon atoms to which they are attached form a monocyclic 4-7 membered cycloalkyl ring, and a phenyl ring each $R^{11}$ is independently selected from halo, CN, $C_{1-6}$ alkyl, $C_{1-4}$ haloalkyl, $Cy^2$, —$C_{1-4}$ alkylene-$Cy^2$, $OR^{a2}$, $C(O)R^{b2}$, $C(O)NR^{c2}R^{d2}$, $C(O)OR^{a2}$, $NR^{c2}R^{d2}$, and $S(O)_2R^{b2}$; wherein said $C_{1-6}$ alkyl is optionally substituted with 1, 2, 3, or 4 independently selected $R^g$ groups;

each $R^{13}$ is selected from halo, CN, $C_{1-6}$ alkyl, $C_{1-4}$ haloalkyl, —$C_{1-4}$ alkylene-$Cy^3$, $OR^{a3}$, $NR^{c3}R^{d3}$, $NR^{c3}C(O)OR^{a3}$, and $S(O)_2NR^{c3}R^{d3}$; wherein said $C_{1-6}$ alkyl is optionally substituted by 1 or 2 independently selected $R^g$ groups;

$R^a$, $R^c$, and $R^d$ are each independently selected from H, $C_{1-6}$ alkyl, Cy, and —$C_{1-4}$ alkylene-Cy; wherein said $C_{1-6}$ alkyl is optionally substituted with 1 or 2 independently selected $R^{11}$ groups;

$R^b$ is independently selected from $C_{1-6}$ alkyl, Cy, and —$C_{1-4}$ alkylene-Cy; wherein said $C_{1-6}$ alkyl is optionally substituted with 1 or 2 independently selected $R^{11}$ groups;

alternatively, any $R^c$ and $R^d$ attached to the same N atom, together with the N atom to which they are attached, form a 4-10 membered heterocycloalkyl group, which is optionally substituted with 1 or 2 independently selected $R^{11}$ groups;

$R^{a1}$, $R^{c1}$, and $R^{d1}$ are each independently selected from H, $C_{1-6}$ alkyl, $Cy^1$, and —$C_{1-4}$ alkylene-$Cy^1$; wherein said $C_{1-6}$ alkyl is optionally substituted with 1, 2, 3, or 4 independently selected $R^{13}$ groups;

$R^{b1}$ are each independently selected from $C_{1-6}$ alkyl, $Cy^1$, and —$C_{1-4}$ alkylene-$Cy^1$; wherein said $C_{1-6}$ alkyl is optionally substituted with 1, 2, 3, or 4 independently selected $R^{13}$ groups;

alternatively, any $R^{c1}$ and $R^{d1}$ attached to the same N atom, together with the N atom to which they are attached, form a 4-, 5-, 6- or 7-membered heterocycloalkyl group optionally substituted with 1, 2 or 3 independently selected $R^{13}$ groups;

each $R^{a3}$, $R^{b3}$, and $R^{d3}$ are independently selected from H and $C_{1-6}$ alkyl; wherein said $C_{1-6}$ alkyl is optionally substituted with 1, 2, 3, or 4 independently selected $R^g$ groups;

each $R^{b3}$ is independently selected from $C_{1-6}$ alkyl; wherein said $C_{1-6}$ alkyl is optionally substituted with 1, 2, 3, or 4 independently selected $R^g$ groups;

alternatively, any $R^{c3}$ and $R^{d3}$ attached to the same N atom, together with the N atom to which they are attached, form a 4-, 5-, 6- or 7-membered heterocycloalkyl group optionally substituted with 1, 2 or 3 independently selected $R^g$ groups;

each Cy is independently 3-7 membered cycloalkyl, 4-6 membered heterocycloalkyl, or phenyl, each of which is optionally substituted by 1, 2, 3, or 4 independently selected $R^{11}$ group;

Cy$^{1a}$ is 5-6 membered heterocycloalkyl, which is optionally substituted by 1, 2, 3, or 4 independently selected R$^{11}$ groups;

each Cy$^1$ is independently selected from 3-10 membered cycloalkyl, 4-6 membered heterocycloalkyl, 5-6 membered heteroaryl, and phenyl, each of which is optionally substituted by 1, 2, 3, or 4 independently selected R$^{13}$ groups;

each Cy$^3$ is independently selected from 3-7 membered cycloalkyl and 4-6 membered heterocycloalkyl, each of which is optionally substituted by 1 or 2 independently selected R$^g$ groups;

n is 0 or 1; and each R$^g$ is independently selected from OH, C$_{1-3}$ alkoxy, and C$_{1-3}$ alkyl.

In some embodiments:

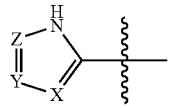

is

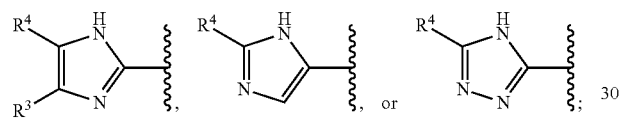

W is CH and V is CH; or
W is N and V is CH; or
W is CH and V is N;

ring A is a pyrazole ring, a pyridine ring, an imidazole ring, a tetrahydropyridine ring, or a dihydropyrrolyl ring;

R$^1$ is selected from halo, C$_{1-6}$ alkyl, C$_{1-4}$ haloalkyl, Cy$^{1a}$, —C$_{1-4}$ alkylene-Cy, OR$^a$, C(O)R$^b$, C(O)NR$^c$R$^d$, C(O)OR$^a$, NR$^c$R$^d$, NR$^c$C(O)R$^b$, NR$^c$C(O)OR$^b$, NR$^c$C(O)NR$^c$R$^d$, NR$^c$S(O)$_2$R$^b$, and S(O)$_2$R$^b$; wherein said C$_{1-6}$ alkyl and C$_{1-4}$ haloalkyl are optionally substituted with 1, 2, or 3 independently selected R$^{11}$ groups;

R$^2$ is C$_{1-4}$ alkyl;

R$^3$ and R$^4$ are each independently selected from H, C$_{1-6}$ alkyl, C$_{1-4}$ haloalkyl, Cy$^1$, —C$_{1-4}$ alkylene-Cy$^1$, C(O)R$^{b1}$, C(O)NR$^{c1}$R$^{d1}$, C(O)OR$^{a1}$, NR$^{c1}$R$^{d1}$, and NR$^{c1}$C(O)R$^{b1}$ wherein said C$_{1-6}$ alkyl is optionally substituted with 1, 2, or 3 independently selected R$^{13}$ groups;

provided that when both R$^3$ and R$^4$ are present, then one of R$^3$ and R$^4$ is selected from H, C$_{1-4}$ alkyl, and C$_{1-4}$ haloalkyl;

alternatively, R$^3$ and R$^4$, taken together with the carbon atoms to which they are attached form a monocyclic 4-7 membered cycloalkyl ring, and a phenyl ring each R$^{11}$ is independently selected from halo, CN, C$_{1-6}$ alkyl, C$_{1-4}$ haloalkyl, Cy$^2$, —C$_{1-4}$ alkylene-Cy$^2$, OR$^{a2}$, C(O)R$^{b2}$, C(O)NR$^{c2}$R$^{d2}$, C(O)OR$^{a2}$, NR$^{c2}$R$^{d2}$, and S(O)$_2$R$^{b2}$; wherein said C$_{1-6}$ alkyl is optionally substituted with 1, 2, 3, or 4 independently selected R$^g$ groups;

each R$^{13}$ is selected from halo, CN, C$_{1-6}$ alkyl, C$_{1-4}$ haloalkyl, —C$_{1-4}$ alkylene-Cy$^3$, OR$^{a3}$, NR$^{c3}$R$^{d3}$, NR$^{c3}$C(O)OR$^{a3}$, and S(O)$_2$NR$^{c3}$R$^{d3}$; wherein said C$_{1-6}$ alkyl is optionally substituted by 1 or 2 independently selected R$^g$ groups;

R$^a$, R$^c$, and R$^d$ are each independently selected from H, C$_{1-6}$ alkyl, Cy, and —C$_{1-4}$ alkylene-Cy; wherein said C$_{1-6}$ alkyl is optionally substituted with 1 or 2 independently selected R$^{11}$ groups;

R$^b$ is independently selected from C$_{1-6}$ alkyl, Cy, and —C$_{1-4}$ alkylene-Cy; wherein said C$_{1-6}$ alkyl is optionally substituted with 1 or 2 independently selected R$^{11}$ groups;

alternatively, any R$^c$ and R$^d$ attached to the same N atom, together with the N atom to which they are attached, form an azetidine ring, a pyrrolidine ring, an azabiclo[2.2.1]-heptane ring, a piperidine ring, a piperazine ring, a morpholine ring, an azepane ring, a decahydroisoquinoline ring, a 2,8-diazaspiro[4.5]decan-1-one ring, a 3-oxa-9-azaspiro[5.5]undecane ring, a 2-oxa-7-azaspiro[3.5]nonane ring, or a 5-azaspiro[2.4]heptane ring, each of which is optionally substituted with 1 or 2 independently selected R$^{11}$ groups;

R$^{a1}$, R$^{c1}$, and R$^{d1}$ are each independently selected from H, C$_{1-6}$ alkyl, Cy$^1$, and —C$_{1-4}$ alkylene-Cy$^1$; wherein said C$_{1-6}$ alkyl is optionally substituted with 1, 2, 3, or 4 independently selected R$^{13}$ groups;

R$^{b1}$ are each independently selected from C$_{1-6}$ alkyl, Cy$^1$, and —C$_{1-4}$ alkylene-Cy$^1$; wherein said C$_{1-6}$ alkyl is optionally substituted with 1, 2, 3, or 4 independently selected R$^{13}$ groups;

alternatively, any R$^{c1}$ and R$^{d1}$ attached to the same N atom, together with the N atom to which they are attached, form an azetidine ring, a pyrrolidine ring, or a morpholine ring, each of which is optionally substituted with 1, 2 or 3 independently selected R$^{13}$ groups;

each R$^{a3}$, R$^{c3}$, and R$^{d3}$ are independently selected from H and C$_{1-6}$ alkyl; wherein said C$_{1-6}$ alkyl is optionally substituted with 1, 2, 3, or 4 independently selected R$^g$ groups;

each R$^{b3}$ is independently selected from C$_{1-6}$ alkyl; wherein said C$_{1-6}$ alkyl is optionally substituted with 1, 2, 3, or 4 independently selected R$^g$ groups;

alternatively, any R$^{c3}$ and R$^{d3}$ attached to the same N atom, together with the N atom to which they are attached, form a morpholine ring;

each Cy is independently cyclopropyl, cyclobutyl, cyclopentyl,

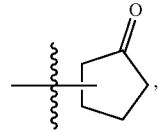

tetrahydrofuranyl, tetrahydropyranyl, morpholinyl, or phenyl, each of which is optionally substituted by 1 or 2 independently selected R$^{11}$ groups;

Cy$^{1a}$ is a pyrrolidine ring, a dihydropyrrole ring, a morpholine ring, a piperidine ring, a piperazine ring, a tetrahydrofuran ring, or a tetrahydropyran ring, each of which is optionally substituted by 1 or 2 independently selected R$^{11}$ groups;

each Cy$^1$ is independently cyclopropyl, cyclobutyl, cyclopentyl, cyclohexyl, admantyl, indenyl, phenyl, piperidinyl, morpholinyl, tetrahydrofuranyl, tetrahydropyranyl, thiomorpholinyl, and pyridyl, each of which is optionally substituted by 1, 2, 3, or 4 independently selected R$^{13}$ groups;

each Cy³ is independently cyclopentyl, tetrahydrofuranyl, or tetrahydropyranyl, or phenyl;
n is 0 or 1; and
each R$^g$ is independently selected from OH, methoxy, and methyl.

In some embodiments:

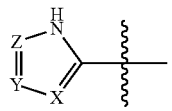

is

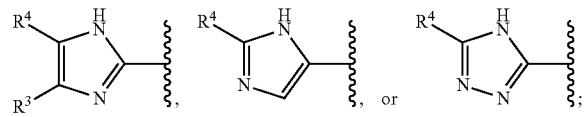

W is CH and V is CH;
ring A is a pyrazolyl or pyridyl;
R¹ is selected from halo, $C_{1-6}$ alkyl, $C_{1-4}$ haloalkyl, Cy$^{1a}$, —$C_{1-4}$ alkylene-Cy, OR$^a$, C(O)R$^b$, C(O)NR$^c$R$^d$, C(O)OR$^a$, NR$^c$R$^d$, NR$^c$C(O)R$^b$, NR$^c$C(O)OR$^b$, NR$^c$C(O)NR$^c$R$^d$, NR$^c$S(O)$_2$R$^b$, and S(O)$_2$R$^b$; wherein said $C_{1-6}$ alkyl and $C_{1-4}$ haloalkyl are optionally substituted with 1, 2, or 3 independently selected R¹¹ groups;
R² is $C_{1-4}$ alkyl or $C_{1-4}$ haloalkyl;
one of R³ and R⁴ is selected from H, $C_{1-6}$ alkyl, $C_{1-4}$ haloalkyl, Cy¹, —$C_{1-4}$ alkylene-Cy¹, C(O)R$^{b1}$, C(O)NR$^{c1}$R$^{d1}$, C(O)OR$^{a1}$, NR$^{c1}$R$^{d1}$, NR$^{c1}$C(O)R$^{b1}$, S(O)$_2$R$^{b1}$, and S(O)$_2$NR$^{c1}$R$^{d1}$, wherein said $C_{1-6}$ alkyl is optionally substituted with 1, 2, or 3 independently selected R¹³ groups;
and the other of R³ and R⁴ is selected from H, halo, OH, CN, $C_{1-4}$ alkyl, $C_{1-4}$ haloalkyl, $C_{1-4}$ alkoxy, $C_{1-4}$ haloalkoxy, amino, $C_{1-4}$ alkylamine, di($C_{1-4}$ alkyl) amino, cyano-$C_{1-4}$ alkyl, HO—$C_{1-4}$ alkyl, or $C_{1-3}$ alkoxy-$C_{1-4}$ alkyl;
alternatively, R³ and R⁴, taken together with the carbon atoms to which they are attached form a monocyclic 4-7 membered cycloalkyl ring, a phenyl ring, a monocyclic 4-6 membered heterocycloalkyl ring, or a monocyclic 5-6 membered heteroaryl ring, each of which is optionally substituted by 1, 2 or 3 independently selected R¹³ groups;
each R¹¹ is independently selected from halo, CN, $C_{1-6}$ alkyl, Cy², —$C_{1-4}$ alkylene-Cy², OR$^{a2}$, C(O)R$^{b2}$, C(O)NR$^{c2}$R$^{d2}$, C(O)OR$^{a2}$, NR$^{c2}$R$^{d2}$ and S(O)$_2$R$^{b2}$; wherein said $C_{1-6}$ alkyl is optionally substituted with 1, 2, 3, or 4 independently selected R$^g$ groups;
each R¹³ is independently selected from halo, CN, $C_{1-6}$ alkyl, $C_{1-4}$ haloalkyl, Cy³, —$C_{1-4}$ alkylene-Cy³, OR$^{a3}$, C(O)R$^{b3}$, C(O)OR$^{a3}$, NR$^{c3}$R$^{d3}$, NR$^{c3}$C(O)R$^{b3}$, NR$^{c3}$C(O)OR$^{a3}$, and S(O)$_2$NR$^{c3}$R$^{d3}$; wherein said $C_{1-6}$ alkyl and $C_{1-4}$ haloalkyl are each optionally substituted with 1, 2, 3, or 4 independently selected R$^g$ groups;
Cy$^{1a}$ is selected from 4-10 membered heterocycloalkyl, which is optionally substituted by 1, 2, 3, or 4 independently selected R¹¹ groups;
each Cy is independently selected from 3-10 membered cycloalkyl, 6-10 membered aryl, and 4-10 membered heterocycloalkyl, each of which is optionally substituted by 1, 2, 3, or 4 independently selected R¹³ groups;
each Cy¹ is independently selected from 3-10 membered cycloalkyl, 6-10 membered aryl, 5-10 membered heteroaryl, and 4-10 membered heterocycloalkyl, each of which is optionally substituted by 1, 2, 3, or 4 independently selected R¹³ groups;
each Cy² is independently selected from 6-10 membered aryl and 4-10 membered heterocycloalkyl, each of which is optionally substituted by 1, 2, 3, or 4 independently selected R$^g$ groups;
each Cy³ is independently selected from 3-10 membered cycloalkyl and 4-10 membered heterocycloalkyl, each of which is optionally substituted by 1, 2, 3, or 4 independently selected R$^g$ groups;
each R$^a$, R$^c$, and R$^d$ is independently selected from H, $C_{1-6}$ alkyl, Cy, and —$C_{1-4}$ alkylene-Cy; wherein said $C_{1-6}$ alkyl is optionally substituted with 1, 2, 3, or 4 independently selected R¹¹ groups;
each R$^b$ is independently selected from $C_{1-6}$ alkyl, Cy, and —$C_{1-4}$ alkylene-Cy; wherein said $C_{1-6}$ alkyl is optionally substituted with 1, 2, 3, or 4 independently selected R¹¹ groups;
alternatively, any R$^c$ and R$^d$ attached to the same N atom, together with the N atom to which they are attached, form a 4-6 membered heterocycloalkyl group, which is optionally substituted with 1, 2, or 3 independently selected R¹¹ groups;
R$^{a1}$, R$^{c}$, and R$^{d1}$ are each independently selected from H, $C_{1-6}$ alkyl, Cy¹, and —$C_{1-4}$ alkylene-Cy¹; wherein said $C_{1-6}$ alkyl is optionally substituted with 1, 2, 3, or 4 independently selected R¹³ groups;
R$^{b1}$ is independently selected from Cy¹, and —$C_{1-4}$ alkylene-Cy¹; or
alternatively, any R$^{c1}$ and R$^{d1}$ attached to the same N atom, together with the N atom to which they are attached, form a 4-, 5-, 6- or 7-membered heterocycloalkyl group optionally substituted with 1, 2 or 3 independently selected R¹³ groups;
each R$^{a2}$, R$^{c2}$, and R$^{d2}$ are independently selected from H, $C_{1-6}$ alkyl, Cy², and —$C_{1-4}$ alkylene-Cy²; wherein said $C_{1-6}$ alkyl is optionally substituted with 1, 2, 3, or 4 independently selected R$^g$ groups;
each R$^{b2}$ is independently selected from $C_{1-6}$ alkyl, $C_{1-4}$ haloalkyl, Cy², and —$C_{1-4}$ alkylene-Cy²; wherein said $C_{1-6}$ alkyl and $C_{1-4}$ haloalkyl are each optionally substituted with 1, 2, 3, or 4 independently selected R$^g$ groups; or
alternatively, any R$^{c2}$ and R$^{d2}$ attached to the same N atom, together with the N atom to which they are attached, form a 5- or 6-membered heterocycloalkyl group optionally substituted with 1, 2 or 3 independently selected R$^g$ groups;
each R$^{a3}$, R$^{c3}$, and R$^{d3}$ are independently selected from H, $C_{1-6}$ alkyl, Cy³, and —$C_{1-4}$ alkylene-Cy³; wherein said $C_{1-6}$ alkyl is optionally substituted with 1, 2, 3, or 4 independently selected R$^g$ groups;
each R$^{b3}$ is independently selected from $C_{1-6}$ alkyl, Cy³, and —$C_{1-4}$ alkylene-Cy³; wherein said $C_{1-6}$ alkyl is optionally substituted with 1, 2, 3, or 4 independently selected R$^g$ groups; or
alternatively, any R$^{c3}$ and R$^{d3}$ attached to the same N atom, together with the N atom to which they are attached, form a 4-, 5-, 6- or 7-membered heterocycloalkyl group optionally substituted with 1, 2 or 3 independently selected R$^g$ groups; and
each R$^g$ is independently selected from OH, CN, halo, $C_{1-6}$ alkyl, and $C_{1-6}$ alkoxy.

In any of the previous embodiments, the compound is a compound of Formula II:

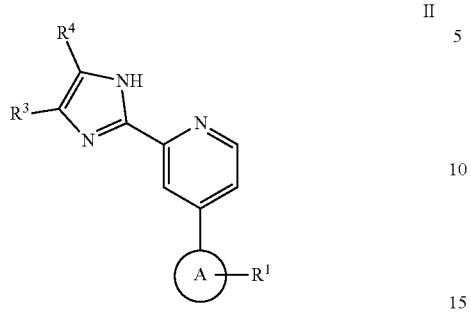
II or a pharmaceutically acceptable salt thereof.

In any of the previous embodiments, the compound is a compound of Formula III:

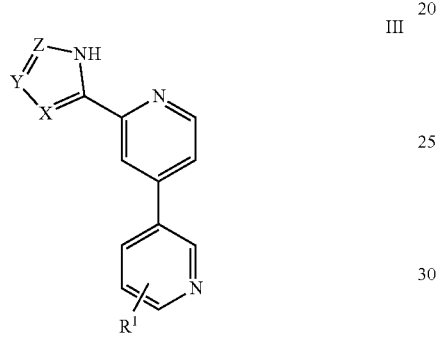
III or a pharmaceutically acceptable salt thereof.

In any of the previous embodiments, the compound is a compound of Formula IV:

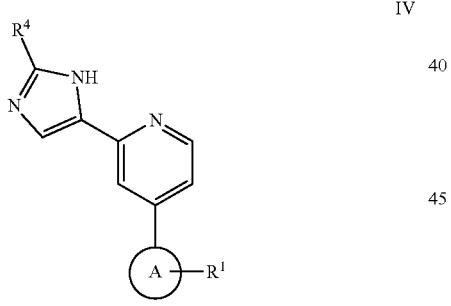
IV or a pharmaceutically acceptable salt thereof.

In any of the previous embodiments, the compound is a compound of Formula V:

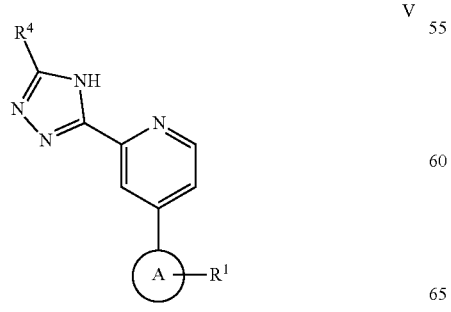
V or a pharmaceutically acceptable salt thereof.

In any of the previous embodiments, the compound is a compound of Formula IIa, Formula IIb, or Formula IIc:

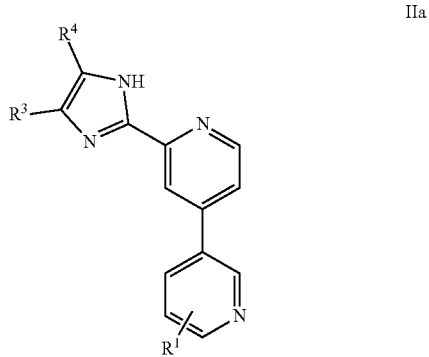
IIa

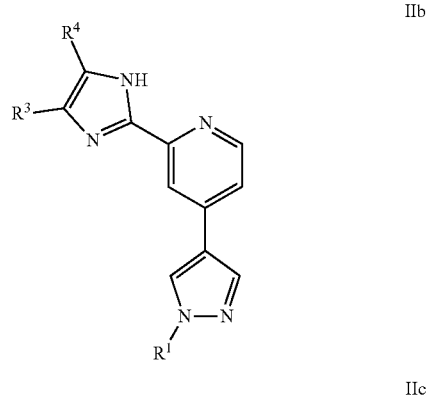
IIb

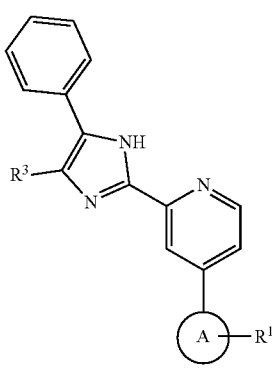
IIc or a pharmaceutically acceptable salt thereof.

In any of the previous embodiments, the compound is a compound of Formula IIa1, Formula IIa2, or Formula IIa3:

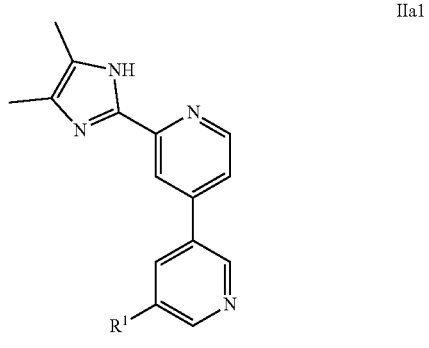
IIa1

-continued

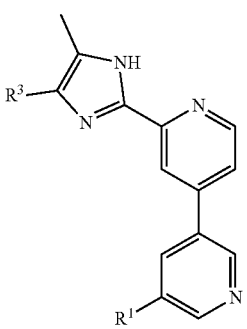

IIa2

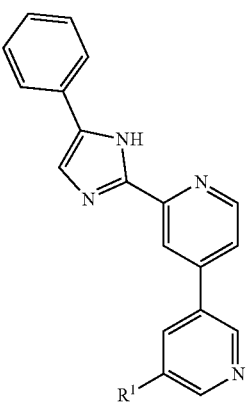

IIa3 or a pharmaceutically acceptable salt thereof.

In any of the previous embodiments, the compound is a compound of Formula IIb1:

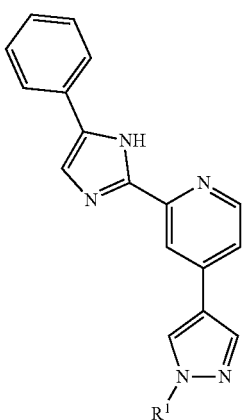

IIb1 or a pharmaceutically acceptable salt thereof.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

As used herein, the phrase "optionally substituted" means unsubstituted or substituted. The substituents are independently selected, and substitution may be at any chemically accessible position. As used herein, the term "substituted" means that a hydrogen atom is removed and replaced by a substituent. A single divalent substituent, e.g., oxo, can replace two hydrogen atoms. It is to be understood that substitution at a given atom is limited by valency.

Throughout the definitions, the term "$C_{n-m}$" indicates a range which includes the endpoints, wherein n and m are integers and indicate the number of carbons. Examples include $C_{1-4}$, $C_{1-6}$, and the like.

As used herein, the term "$C_{n-m}$ alkyl", employed alone or in combination with other terms, refers to a saturated hydrocarbon group that may be straight-chain or branched, having n to m carbons. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, "$C_{n-m}$ alkenyl" refers to an alkyl group having one or more double carbon-carbon bonds and having n to m carbons. Example alkenyl groups include, but are not limited to, ethenyl, n-propenyl, isopropenyl, n-butenyl, sec-butenyl, and the like. In some embodiments, the alkenyl moiety contains 2 to 6, 2 to 4, or 2 to 3 carbon atoms.

As used herein, "$C_{n-m}$ alkynyl" refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains 2 to 6, 2 to 4, or 2 to 3 carbon atoms.

As used herein, the term "$C_{n-m}$ alkylene", employed alone or in combination with other terms, refers to a divalent alkyl linking group having n to m carbons. Examples of alkylene groups include, but are not limited to, ethan-1,1-diyl, ethan-1,2-diyl, propan-1,1,-diyl, propan-1,3-diyl, propan-1,2-diyl, butan-1,4-diyl, butan-1,3-diyl, butan-1,2-diyl, 2-methyl-propan-1,3-diyl, and the like. In some embodiments, the alkylene moiety contains 2 to 6, 2 to 4, 2 to 3, 1 to 6, 1 to 4, or 1 to 2 carbon atoms.

As used herein, the term "$C_{n-m}$ alkoxy", employed alone or in combination with other terms, refers to a group of formula —O-alkyl, wherein the alkyl group has n to m carbons. Example alkoxy groups include, but are not limited to, methoxy, ethoxy, propoxy (e.g., n-propoxy and isopropoxy), butoxy (e.g., n-butoxy and tert-butoxy), and the like. In some embodiments, the alkyl group has 1 to 6, 1 to 4, or 1 to 3 carbon atoms.

As used herein, the term "$C_{n-m}$ alkylamino" refers to a group of formula —NH(alkyl), wherein the alkyl group has n to m carbon atoms. In some embodiments, the alkyl group has 1 to 6, 1 to 4, or 1 to 3 carbon atoms. Examples of alkylamino groups include, but are not limited to, N-methylamino, N-ethylamino, N-propylamino (e.g., N-(n-propyl)amino and N-isopropylamino), N-butylamino (e.g., N-(n-butyl)amino and N-(tert-butyl)amino), and the like.

As used herein, the term "$C_{n-m}$ alkoxycarbonyl" refers to a group of formula —C(O)O-alkyl, wherein the alkyl group has n to m carbon atoms. In some embodiments, the alkyl group has 1 to 6, 1 to 4, or 1 to 3 carbon atoms. Examples of alkoxycarbonyl groups include, but are not limited to, methoxycarbonyl, ethoxycarbonyl, propoxycarbonyl (e.g., n-propoxycarbonyl and isopropoxycarbonyl), butoxycarbonyl (e.g., n-butoxycarbonyl and tert-butoxycarbonyl), and the like.

As used herein, the term "$C_{n-m}$ alkylcarbonyl" refers to a group of formula —C(O)-alkyl, wherein the alkyl group has n to m carbon atoms. In some embodiments, the alkyl group has 1 to 6, 1 to 4, or 1 to 3 carbon atoms. Examples of alkylcarbonyl groups include, but are not limited to, methylcarbonyl, ethylcarbonyl, propylcarbonyl (e.g., n-propylcarbonyl and isopropylcarbonyl), butylcarbonyl (e.g., n-butylcarbonyl and tert-butylcarbonyl), and the like.

As used herein, the term "$C_{n-m}$ alkylcarbonylamino" refers to a group of formula —NHC(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonylamino" refers to a group of formula —NHS(O)$_2$-alkyl, wherein the alkyl group has n to m carbon atoms. In some embodiments, the alkyl group has 1 to 6, 1 to 4, or 1 to 3 carbon atoms.

As used herein, the term "aminosulfonyl" refers to a group of formula —S(O)$_2$NH$_2$.

As used herein, the term "$C_{n-m}$ alkylaminosulfonyl" refers to a group of formula —S(O)$_2$NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonyl" refers to a group of formula —S(O)$_2$N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminosulfonylamino" refers to a group of formula —NHS(O)$_2$NH$_2$.

As used herein, the term "$C_{n-m}$ alkylaminosulfonylamino" refers to a group of formula —NHS(O)$_2$NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonylamino" refers to a group of formula —NHS(O)$_2$N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminocarbonylamino", employed alone or in combination with other terms, refers to a group of formula —NHC(O)NH$_2$.

As used herein, the term "$C_{n-m}$ alkylaminocarbonylamino" refers to a group of formula —NHC(O)NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminocarbonylamino" refers to a group of formula —NHC(O)N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "$C_{n-m}$ alkylcarbamyl" refers to a group of formula —C(O)—NH(alkyl), wherein the alkyl group has n to m carbon atoms. In some embodiments, the alkyl group has 1 to 6, 1 to 4, or 1 to 3 carbon atoms.

As used herein, the term "thio" refers to a group of formula —SH.

As used herein, the term "$C_{n-m}$ alkylthio" refers to a group of formula —S-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfinyl" refers to a group of formula —S(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonyl" refers to a group of formula —S(O)$_2$-alkyl, wherein the alkyl group has n to m carbon atoms. In some embodiments, the alkyl group has 1 to 6, 1 to 4, or 1 to 3 carbon atoms.

As used herein, the term "amino" refers to a group of formula —NH$_2$.

As used herein, the term "aryl," employed alone or in combination with other terms, refers to an aromatic hydrocarbon group, which may be monocyclic or polycyclic (e.g., having 2, 3 or 4 fused rings). The term "$C_{n-m}$ aryl" refers to an aryl group having from n to m ring carbon atoms. Aryl groups include, e.g., phenyl, naphthyl, anthracenyl, phenanthrenyl, indanyl, indenyl, and the like. In some embodiments, aryl groups have from 6 to 10 carbon atoms. In some embodiments, the aryl group is phenyl or naphtyl.

As used herein, the term "carbamyl" to a group of formula —C(O)NH$_2$.

As used herein, the term "carbonyl", employed alone or in combination with other terms, refers to a —C(=O)— group, which may also be written as C(O).

As used herein, the term "carboxy" refers to a —C(O)OH group.

As used herein, the term "cyano-$C_{1-3}$ alkyl" refers to a group of formula —($C_{1-3}$ alkylene)-CN.

As used herein, the term "HO—$C_{1-3}$ alkyl" refers to a group of formula —($C_{1-3}$ alkylene)-OH.

As used herein, the term "di($C_{n-m}$-alkyl)amino" refers to a group of formula —N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, the term "di($C_{n-m}$-alkyl)carbamyl" refers to a group of formula —C(O)N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, "halo" refers to F, Cl, Br, or I. In some embodiments, a halo is F, Cl, or Br.

As used herein, "$C_{n-m}$ haloalkoxy" refers to a group of formula —O-haloalkyl having n to m carbon atoms. An example haloalkoxy group is OCF$_3$. In some embodiments, the haloalkoxy group is fluorinated only. In some embodiments, the alkyl group has 1 to 6, 1 to 4, or 1 to 3 carbon atoms.

As used herein, the term "$C_{n-m}$ haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 6, 1 to 4, or 1 to 3 carbon atoms.

As used herein, "cycloalkyl" refers to non-aromatic cyclic hydrocarbons including cyclized alkyl and/or alkenyl groups. Cycloalkyl groups can include mono- or polycyclic (e.g., having 2, 3 or 4 fused rings) groups and spirocycles. Ring-forming carbon atoms of a cycloalkyl group can be optionally substituted by oxo or sulfido (e.g., C(O) or C(S)). Also included in the definition of cycloalkyl are moieties that have one or more aromatic rings fused (i.e., having a bond in common with) to the cycloalkyl ring, for example, benzo or thienyl derivatives of cyclopentane, cyclohexane, and the like. A cycloalkyl group containing a fused aromatic ring can be attached through any ring-forming atom including a ring-forming atom of the fused aromatic ring. Cycloalkyl groups can have 3, 4, 5, 6, 7, 8, 9, or 10 ring-forming carbons ($C_{3-10}$). In some embodiments, the cycloalkyl is a $C_{3-10}$ monocyclic or bicyclic cycloalkyl. In some embodiments, the cycloalkyl is a $C_{3-7}$ monocyclic cycloalkyl. Example cycloalkyl groups include cyclopropyl, cyclobutyl, cyclopentyl, cyclohexyl, cycloheptyl, cyclo pentenyl, cyclohexenyl, cyclohexadienyl, cycloheptatrienyl, norbornyl, norpinyl, norcaranyl, and the like. In some embodiments, cycloalkyl is cyclopropyl, cyclobutyl, cyclopentyl, or cyclohexyl.

As used herein, "heteroaryl" refers to a monocyclic or polycyclic aromatic heterocycle having at least one heteroatom ring member selected from sulfur, oxygen, and nitrogen. In some embodiments, the heteroaryl ring has 1, 2, 3, or 4 heteroatom ring members independently selected from nitrogen, sulfur and oxygen. In some embodiments, any ring-forming N in a heteroaryl moiety can be an N-oxide. In some embodiments, the heteroaryl is a 5-10 membered monocyclic or bicyclic heteroaryl having 1, 2, 3 or 4 heteroatom ring members independently selected from nitrogen, sulfur and oxygen. In some embodiments, the heteroaryl is a 5-6 monocyclic heteroaryl having 1 or 2 heteroatom ring members independently selected from nitrogen, sulfur and oxygen. In some embodiments, the heteroaryl is a five-membered or six-membered heteroaryl ring. A five-membered heteroaryl ring is a heteroaryl with a ring having five ring atoms wherein one or more (e.g., 1, 2, or 3) ring atoms are independently selected from N, O, and S. Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl. A six-membered heteroaryl ring is a heteroaryl with a ring having six ring atoms wherein one or more (e.g., 1, 2, or 3) ring atoms are independently selected from N, O, and S. Exemplary six-membered ring heteroaryls are pyridyl, pyrazinyl, pyrimidinyl, triazinyl and pyridazinyl.

As used herein, "heterocycloalkyl" refers to non-aromatic monocyclic or polycyclic heterocycles having one or more ring-forming heteroatoms selected from O, N, or S. Included in heterocycloalkyl are monocyclic 4-, 5-, 6-, 7-, 8-, 9- or 10-membered heterocycloalkyl groups. Heterocycloalkyl groups can also include spirocycles. Example heterocycloalkyl groups include pyrrolidin-2-one, 1,3-isoxazolidin-2-one, pyranyl, tetrahydropuran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, benzazapene, and the like. Ring-forming carbon atoms and heteroatoms of a heterocycloalkyl group can be optionally substituted by oxo or sulfido (e.g., C(O), S(O), C(S), or S(O)$_2$, etc.). The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the cycloalkyl ring, for example, benzo or thienyl derivatives of piperidine, morpholine, azepine, etc. A heterocycloalkyl group containing a fused aromatic ring can be attached through any ring-forming atom including a ring-forming atom of the fused aromatic ring. In some embodiments, the heterocycloalkyl is a monocyclic 4-6 membered heterocycloalkyl having 1 or 2 heteroatoms independently selected from nitrogen, oxygen, or sulfur and having one or more oxidized ring members. In some embodiments, the heterocycloalkyl is a monocyclic or bicyclic 4-10 membered heterocycloalkyl having 1, 2, 3, or 4 heteroatoms independently selected from nitrogen, oxygen, or sulfur and having one or more oxidized ring members.

As used herein, 4-6 membered azaheterocycloalkyl ring is a monocyclic 4-6 membered heterocycloalkyl ring, having 1, 2, or 3 nitrogen atoms as ring members and optionally having 1-2 additional heteroatoms independently selected from N, O, and S, provided valency rules are observed.

As used herein, 5-6 membered azaheterocycloaryl ring is a monocyclic 5-6 membered heteroaryl ring, having 1, 2, or 3 nitrogen atoms as ring members and optionally having 1-2 additional heteroatoms independently selected from N, O, and S, provided valency rules are observed and the ring remains aromatic.

As used herein, the term "oxo" refers to an oxygen atom as a divalent substituent, forming a carbonyl group when attached to a carbon (e.g., C=O), or attached to a heteroatom forming a sulfoxide or sulfone group.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas a pyridin-3-yl ring is attached at the 3-position.

The compounds described herein can be asymmetric (e.g., having one or more stereocenters). All stereoisomers, such as enantiomers and diastereomers, are intended unless otherwise indicated. Compounds of the present disclosure that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present disclosure. Cis and trans geometric isomers of the compounds of the present disclosure are described and may be isolated as a mixture of isomers or as separated isomeric forms. In some embodiments, the compound has the (R)-configuration. In some embodiments, the compound has the (S)-configuration.

Resolution of racemic mixtures of compounds can be carried out by any of numerous methods known in the art. An example method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

All compounds, and pharmaceutically acceptable salts thereof, can be found together with other substances such as water and solvents (e.g. hydrates and solvates) or can be isolated.

In some embodiments, preparation of compounds can involve the addition of acids or bases to affect, for example, catalysis of a desired reaction or formation of salt forms such as acid addition salts.

Example acids can be inorganic or organic acids and include, but are not limited to, strong and weak acids. Some example acids include hydrochloric acid, hydrobromic acid, sulfuric acid, phosphoric acid, p-toluenesulfonic acid, 4-nitrobenzoic acid, methanesulfonic acid, benzenesulfonic acid, trifluoroacetic acid, and nitric acid. Some weak acids include, but are not limited to acetic acid, propionic acid, butanoic acid, benzoic acid, tartaric acid, pentanoic acid, hexanoic acid, heptanoic acid, octanoic acid, nonanoic acid, and decanoic acid.

Example bases include lithium hydroxide, sodium hydroxide, potassium hydroxide, lithium carbonate, sodium carbonate, potassium carbonate, and sodium bicarbonate. Some example strong bases include, but are not limited to, hydroxide, alkoxides, metal amides, metal hydrides, metal dialkylamides and arylamines, wherein; alkoxides include lithium, sodium and potassium salts of methyl, ethyl and t-butyl oxides; metal amides include sodium amide, potassium amide and lithium amide; metal hydrides include sodium hydride, potassium hydride and lithium hydride; and metal dialkylamides include lithium, sodium, and potassium salts of methyl, ethyl, n-propyl, iso-propyl, n-butyl, tert-butyl, trimethylsilyl and cyclohexyl substituted amides.

In some embodiments, the compounds provided herein, or salts thereof, are substantially isolated. By "substantially isolated" is meant that the compound is at least partially or substantially separated from the environment in which it was formed or detected. Partial separation can include, for example, a composition enriched in the compounds provided herein. Substantial separation can include compositions containing at least about 50%, at least about 60%, at least about 70%, at least about 80%, at least about 90%, at least about 95%, at least about 97%, or at least about 99% by weight of the compounds provided herein, or salt thereof. Methods for isolating compounds and their salts are routine in the art.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present application also includes pharmaceutically acceptable salts of the compounds described herein. The present disclosure also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in *Remington's Pharmaceutical Sciences*, 17th ed., Mack Publishing Company, Easton, Pa., 1985, p. 1418 and *Journal of Pharmaceutical Science*, 66, 2 (1977), each of which is incorporated herein by reference in its entirety.

Synthesis

As will be appreciated, the compounds provided herein, including salts thereof, can be prepared using known organic synthesis techniques and can be synthesized according to any of numerous possible synthetic routes.

Compounds described herein, wherein W and Y are N, C—H, or C—$R^4$, can be prepared as shown in Scheme 1. Halo-containing starting materials (1-1) can be reacted with M-Cy, where M is a boronic acid, boronic ester, or an appropriately substituted metal such as $Sn(Bu)_4$ or Zn, under standard Suzuki conditions or standard Stille conditions (e.g., in the presence of a palladium(0) catalyst, such as tetrakis(triphenylphosphine)palladium(0) or 4-(di-tert-butylphosphino)-N,N-dimethylaniline-dichloropalladium (2:1) and a base (e.g., a bicarbonate or carbonate base, or CsF) or standard Negishi conditions (e.g., in the presence of a palladium(0) catalyst, such as tetrakis(triphenylphosphine) palladium(0)), to give derivative 1-2. The nitrile of intermediate 1-2 can be converted to a substituted imidazole as shown in 1-3 via several routes, some of which are outlined in Scheme 2. The order of steps can be reversed, such that imidazole formation to furnish 1-4 (by methods such as shown in Scheme 2) can precede the coupling to $R^1$. In this case, the NH of the heterocycle (1-4) can be optionally protected (e.g., SEM-Cl and base) to give a N-protected derivative (1-5) which can be coupled with M-Cy as described for the transformation from 1-1 to 1-2 above, to provide 1-6, which upon N-deprotection (e.g., reaction with a strong acid, such as TFA) will furnish compounds 1-3. This and all subsequent preparations in the Schemes can be contemplated as potentially proceeding by either route, the choice of which may be dictated by the compatibility of functional groups present in the intermediates. Alternatively, conversion of halide-containing intermediates such as 1-1 or 1-5 to a metal M (e.g., M is $B(OR)_2$, $SnR_3$, Zn) under standard conditions can give intermediates that can undergo Suzuki, Stille or Negishi couplings with appropriate halo-derivatives Cy-X as alternative ways to access compounds shown in 1-2 or 1-6. Where the nitrile is not present in starting material 1-1, it can be installed from a halo-substituent (such as Cl) at the same position in intermediate 1-2 via Negishi coupling with $Zn(CN)_2$ (e.g., in the presence of a Pd(0) catalyst, such as tetrakis(triphenylphosphine)palladium(0)).

Scheme 1

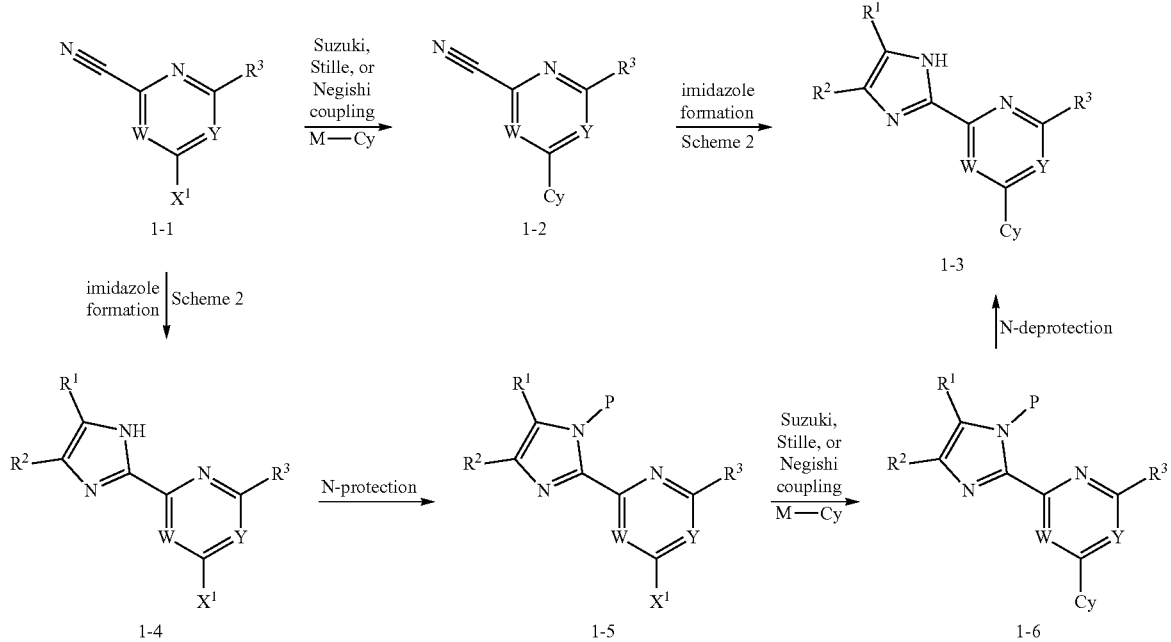

Useful methods for formation of the imidazole are outlined in Scheme 2, in which both nitriles and carboxylic acids serve as useful starting materials. Nitrile 2-1 can be converted to an imidate (e.g., by reacting with catalytic sodium methoxide in an alcohol or by reacting with HCl in an alcohol) and the intermediate imidate can be reacted with an amino ketal or amino acetal (2-2) in the presence of acid (e.g., AcOH or HCl) and heat to form imidazole 2-3. Alternatively, the intermediate imidate can be reacted with $NH_4Cl$ to afford an amidine, which can be alkylated with α-halo ketones (2-4) in the presence of base (e.g., $KHCO_3$, or $K_2CO_3$) in a solvent such as an alcohol, or preferably, DMF, to furnish imidazole 2-3. The imidate intermediate formed by reacting nitrile 2-1 with catalytic sodium methoxide can be treated with a diamine (2-5) (e.g., a phenylenediamine derivative) and cyclized under acidic conditions and heat to afford imidazole 2-3. Alternatively, carboxylic acid 2-6 can be coupled to a diamine (2-5) in the presence of a coupling reagent (e.g., HATU and the like) and base (e.g., Hunig's Base or triethylamine). The intermediate amide can be cyclized to imidazole 2-3 by heating in acid (e.g., AcOH). Carboxylic acid 2-6 can also be reacted with α-halo ketones (2-4) in the presence of base (e.g., $K_2CO_3$) to afford an ester intermediate that can be heated in the presence of $NH_4OAc$ to afford imidazole 2-3. The imidazole formations may be carried out with R=Cy or alternatively, with R=X (halo).

Scheme 2

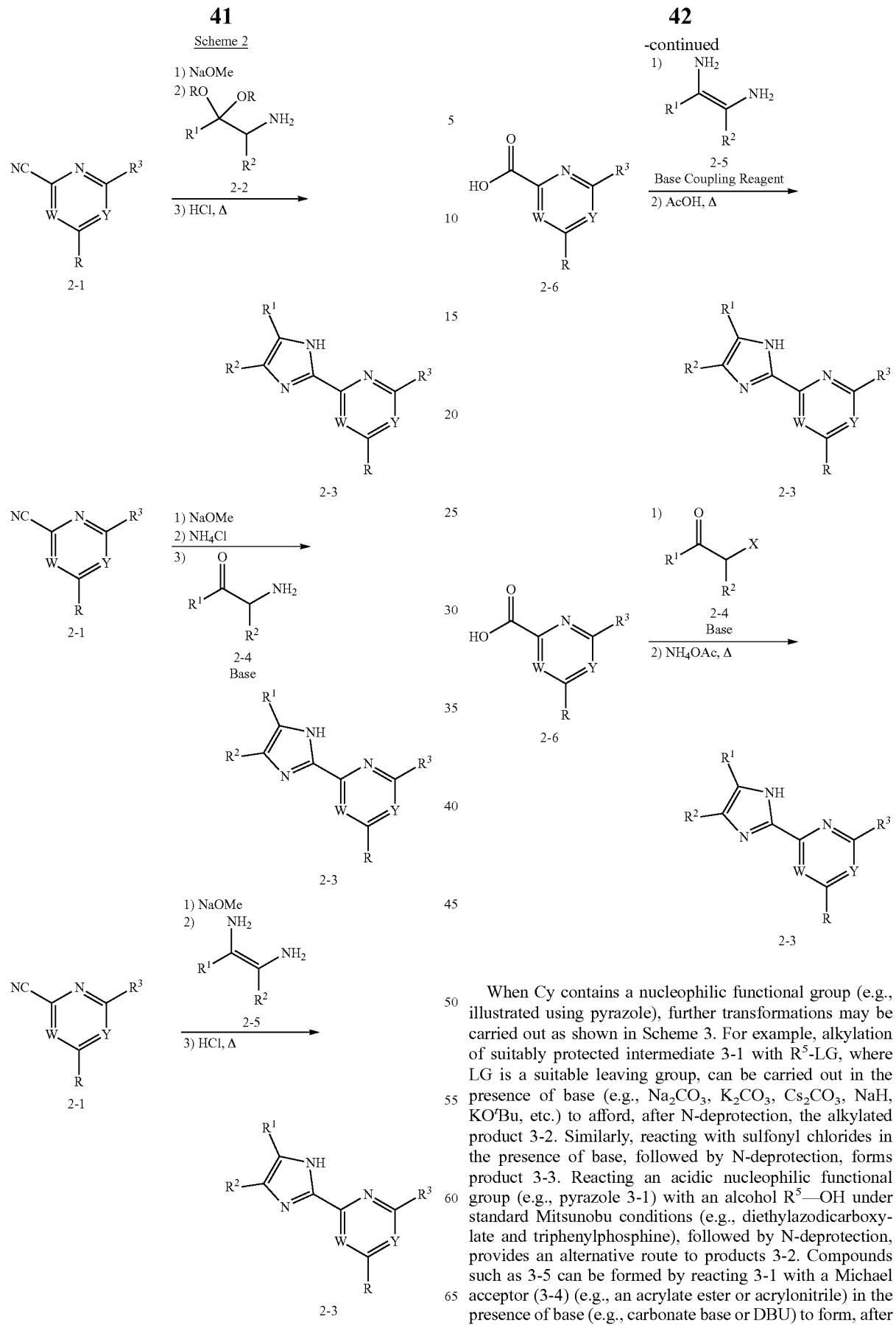

When Cy contains a nucleophilic functional group (e.g., illustrated using pyrazole), further transformations may be carried out as shown in Scheme 3. For example, alkylation of suitably protected intermediate 3-1 with $R^5$-LG, where LG is a suitable leaving group, can be carried out in the presence of base (e.g., $Na_2CO_3$, $K_2CO_3$, $Cs_2CO_3$, NaH, $KO^tBu$, etc.) to afford, after N-deprotection, the alkylated product 3-2. Similarly, reacting with sulfonyl chlorides in the presence of base, followed by N-deprotection, forms product 3-3. Reacting an acidic nucleophilic functional group (e.g., pyrazole 3-1) with an alcohol $R^5$—OH under standard Mitsunobu conditions (e.g., diethylazodicarboxylate and triphenylphosphine), followed by N-deprotection, provides an alternative route to products 3-2. Compounds such as 3-5 can be formed by reacting 3-1 with a Michael acceptor (3-4) (e.g., an acrylate ester or acrylonitrile) in the presence of base (e.g., carbonate base or DBU) to form, after N-deprotection, 3-5. Where desired, if $R^5$ of the alkylated product contains a manipulatable functional group, further transformations (e.g., hydrolysis, amide formation, reduction, alkylation, acylation, sulfonylation) are possible. Similar transformations may be carried out on suitable electron withdrawing groups (EWG, e.g. CO$_2$R, CN) of Michael adducts 3-5.

Alternative heterocycles may be installed in the compounds provided herein as shown in Schemes 4 to 7. In Scheme 4, a regioselective cross-coupling can be achieved with M-Cy at the 4-position of pyridine 4-1. This can be achieved by reacting M-Cy, where M is a boronic acid, boronic ester, or an appropriately substituted metal such as Sn(Bu)$_4$ or Zn, under standard Suzuki conditions or standard Stille conditions (e.g., in the presence of a palladium(0) catalyst, such as tetrakis(triphenylphosphine)palladium(0) or 4-(di-tert-butylphosphino)-N,N-dimethylaniline-dichloropalladium (2:1) and a base (e.g., a bicarbonate or carbonate base, or CsF) or standard Negishi conditions (e.g., in the presence of a palladium(0) catalyst, such as tetrakis(triphenylphosphine)palladium(0)), to give derivative 4-2. The desired heterocycle (e.g., imidazole isomer 4-3) can be coupled under Suzuki, Stille or Negishi conditions as described above to afford (on subsequent N-deprotection) compounds 4-4.

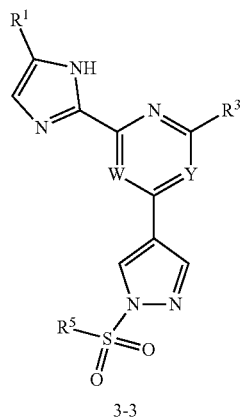

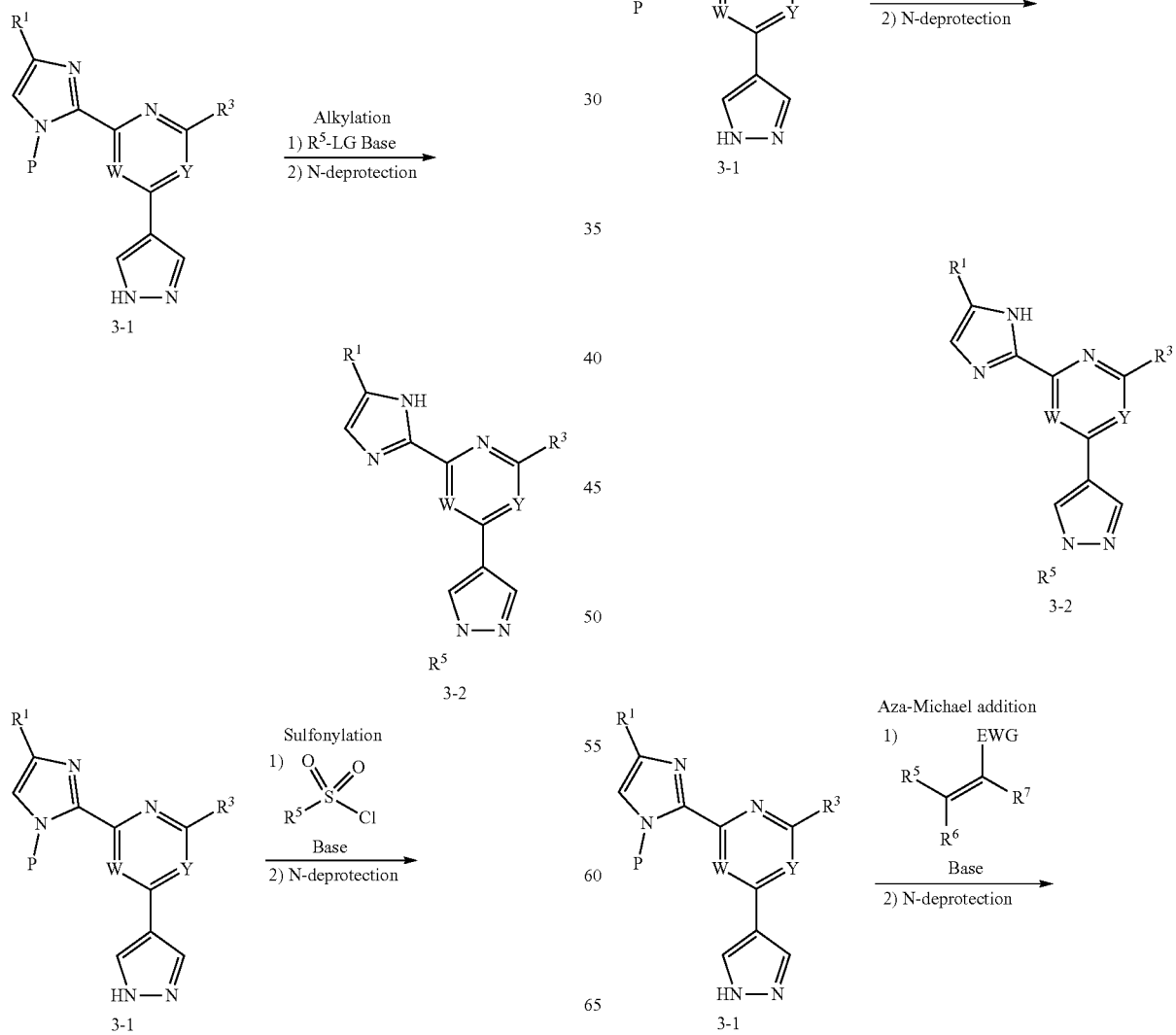

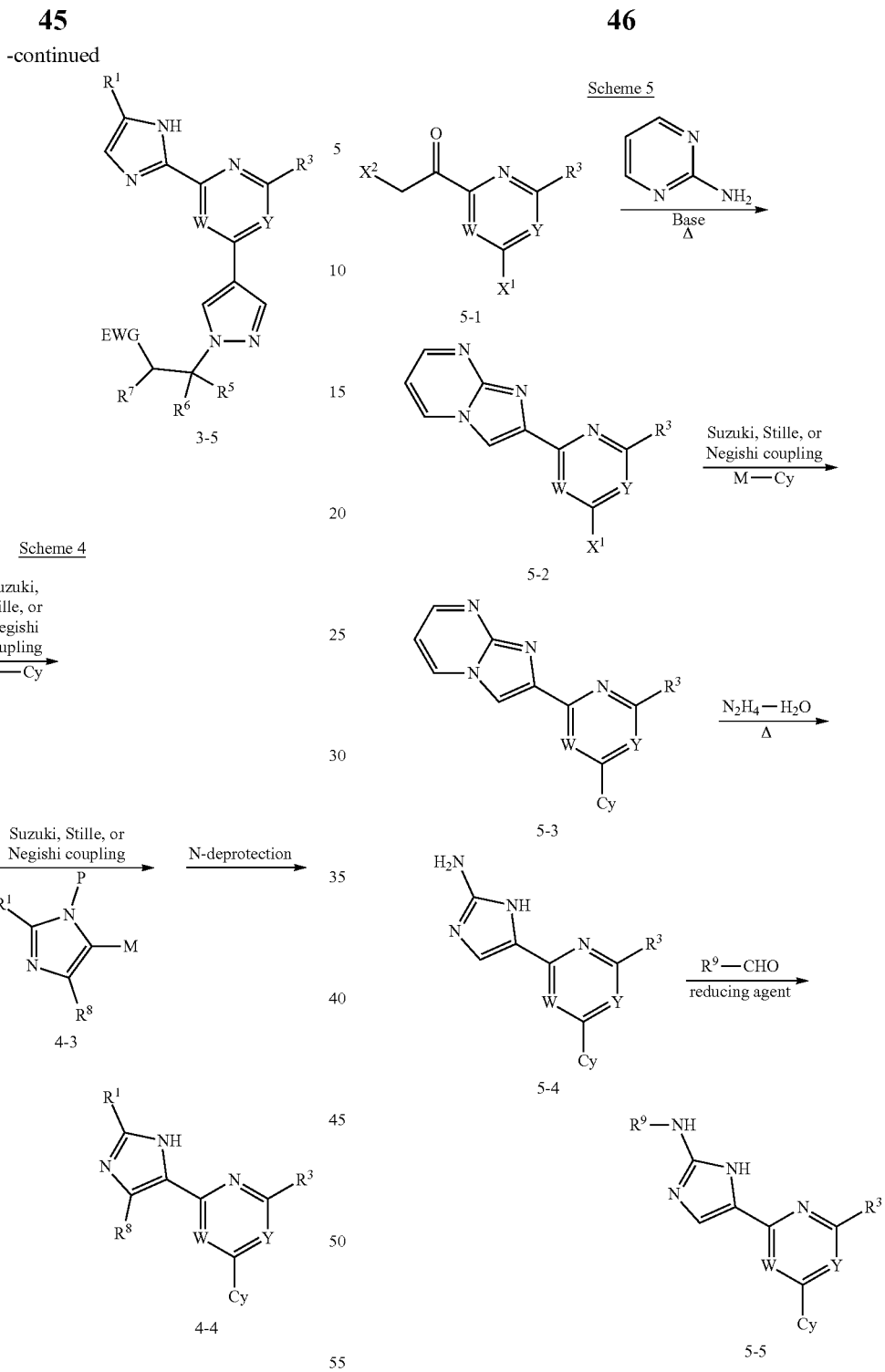

Compounds containing an amino-imidazole such as 5-5 can be accessed synthetically by reacting an α-halo ketone (5-1) with 2-aminopyrimidine to form intermediate 5-2. After coupling with M-Cy under standard Suzuki, Stille or Negishi conditions to afford 5-3, the aminoimidazole moiety can be liberated by reaction with hydrazine hydrate at elevated temperature (e.g., about 100° C.) to afford 5-4. The amine of 5-4 can be alkylated by reaction of the amine with an aldehyde (e.g., R⁹CHO) in the presence of a reducing agent (e.g., sodium cyanoborohydride or sodium triacetoxyborohydride) to give 5-5.

Compounds of provided herein containing an aminotriazole can be prepared by reacting an ester (6-2, prepared by Suzuki, Stille or Negishi coupling of 6-1 with M-Cy) with hydrazine hydrate at elevated temperature to form an acyl hydrazide 6-3. Intermediate 6-3 can be reacted with an alkylated thiourea (6-5) in the presence of heat and base (e.g., 2,6-lutidine) to afford aminotriazole product 6-6. When unavailable commercially, the requisite reactant 6-5 can be prepared by alkylating available thiourea 6-4 with methyl iodide.

Scheme 6

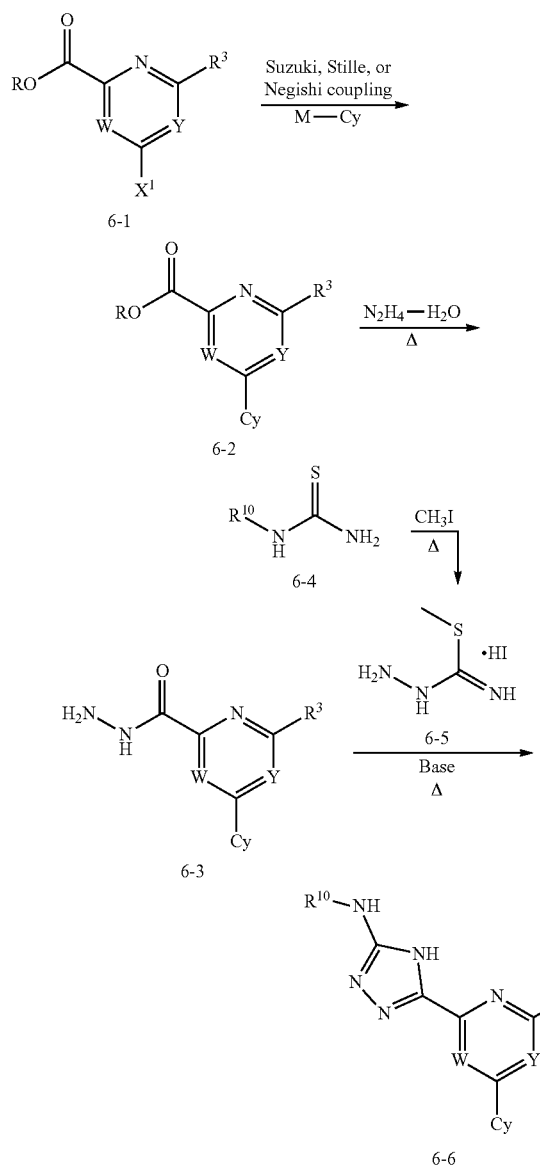

As shown in Scheme 7, triazoles can be formed from 7-2 by reacting the imidate intermediate derived therefrom (by treatment of the nitrile with catalytic sodium methoxide) with an acyl hydrazide (7-3) at elevated temperature to furnish triazoles 7-4.

Scheme 7

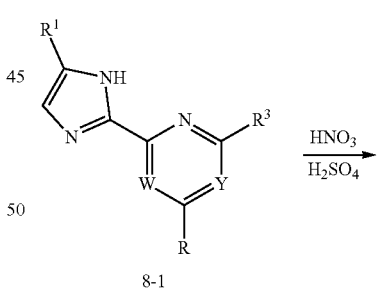

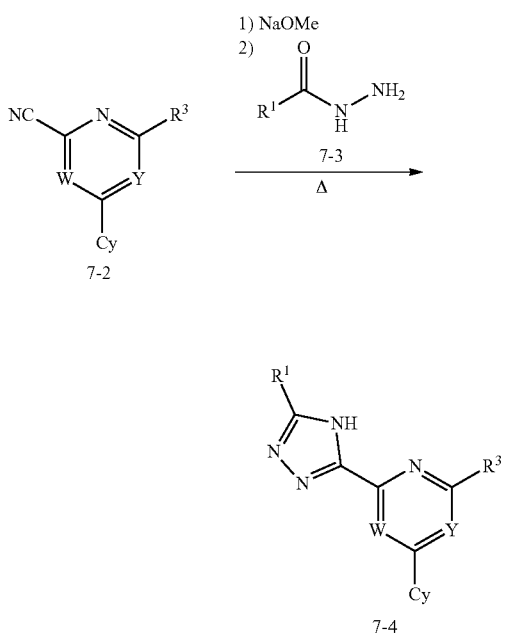

Compounds of provided herein containing imidazoles can be further functionalized as shown, for example, in Schemes 8 and 9. For example, an imidazole such as 8-1, containing an unfunctionalized carbon, can be nitrated (e.g., using $HNO_3$ in $H_2SO_4$) to provide nitro derivative 8-2, which can be reduced (e.g., using iron in AcOH or in aq. HCl and alcoholic solvent) to amino derivative 8-3. If R=Cy is not anticipated to be robust to the conditions, the synthesis may be carried out with R=X (halo), and the desired cyclic group (Cy) introduced by Suzuki, Stille, or Negishi conditions on intermediate 8-2.

Scheme 8

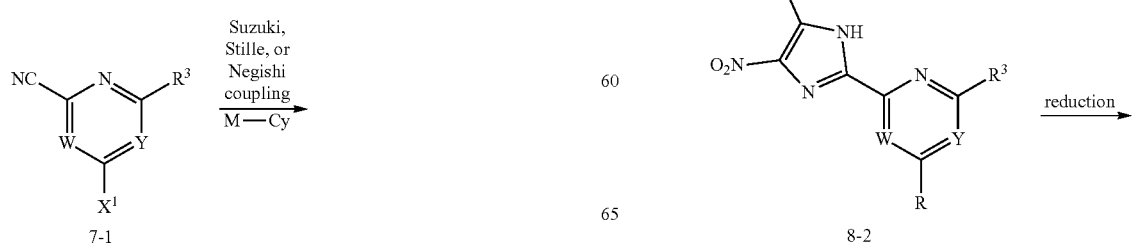

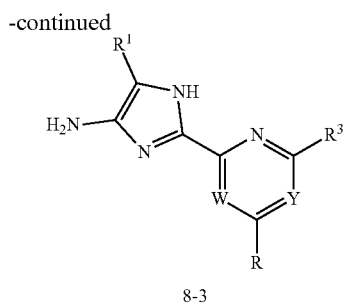

8-3

Compounds of provided herein, 9-3, wherein $R^2$ contains a carbonyl group (e.g., ester or aldehyde) may be prepared as shown in Scheme 9. Imidazole 9-1, containing an unfunctionalized carbon, can be treated with a halogenating reagent (e.g., N-iodosuccinimide or N-bromosuccinimide) to form intermediate 9-2. Subjection of an optionally protected intermediate 9-2 to a Pd-catalyzed cross-coupling reaction (e.g., CO insertion) can furnish intermediates 9-3, containing an ester or an aldehyde which may be further manipulated, for example, as shown in Scheme 10. Alternative transformations from the iodo-intermediate 9-2 are possible, such as Suzuki, Stille and Negishi couplings.

hydrolysis (e.g., aq. NaOH in THF and an alcohol) can be carried out. The resulting carboxylic acid can be coupled with amines $R^{11}R^{12}NH$ to form amides 10-3 under standard coupling conditions (e.g., HATU in the presence of Hunig's base or triethylamine). If the CO insertion on 10-1 is carried out in the absence of alcohol and in the presence of triethylsilane, aldehydes 10-4 can be prepared. The aldehyde can be converted to amines (10-5) by reductive amination with $R^{11}R^{12}NH$ in the presence of a reducing agent (e.g., sodium cyanoborohydride, sodium triacetoxyborohydride). Numerous other functional group transformations can be carried out on intermediates such as 10-4, such as Grignard addition, reduction, and fluorination (e.g., with Deoxo-Fluor®).

Scheme 9

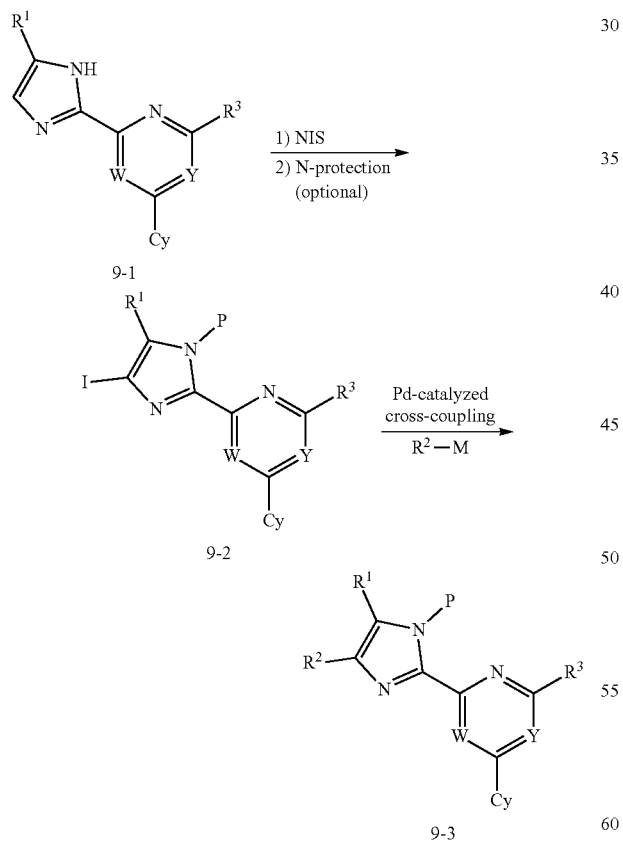

Scheme 10

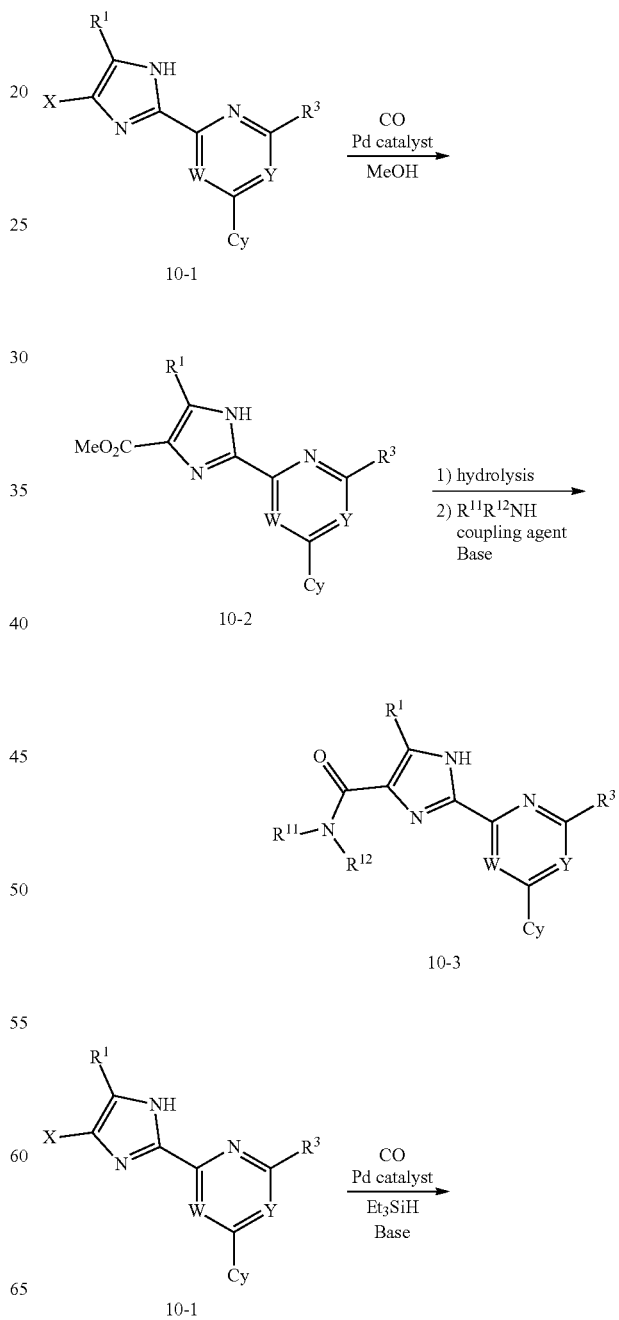

Following conversion of halo-containing derivative 10-1 (e.g., X=I or Br) to ester intermediate 10-2, using carbon monoxide in the presence of methanol and a Pd catalyst (e.g., [1,1'-bis(diphenylphosphino)ferrocene]dichloropalladium(II), complex with dichloromethane (1:1)), basic -continued

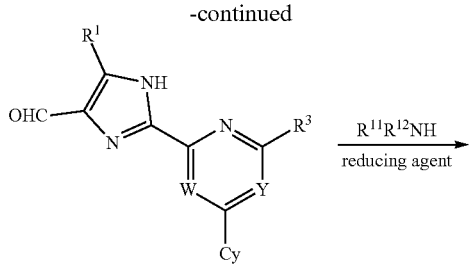

10-4

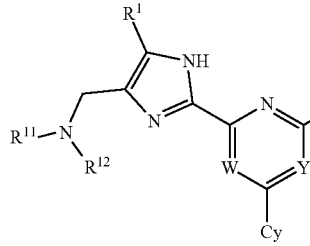

10-5

Further transformations can also be carried out on intermediates wherein Cy contains nucleophilic functionality, for example, an amine as in 11-1. As shown in Scheme 11, intermediate 11-1 can be treated with reagents $R^{13}$-L-X (where L is a linker and X is a suitable leaving group; e.g., acyl chlorides, sulfonyl chlorides, chloroformates) in the presence of base (e.g., triethylamine) to provide amides, sulfonamides, and carbamates of 11-2, respectively. Reaction of 11-1 with $R^{13}$NCO (an isocyanate) affords ureas, and reductive amination with $R^{13}$CHO in the presence of a reducing agent (e.g., sodium cyanoborohydride, sodium triacetoxyborohydride) affords alkylated amines.

Scheme 11

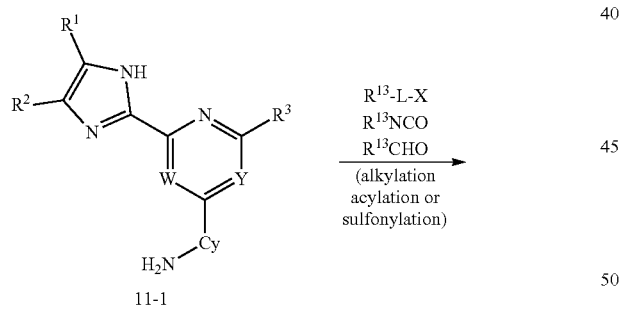

11-1

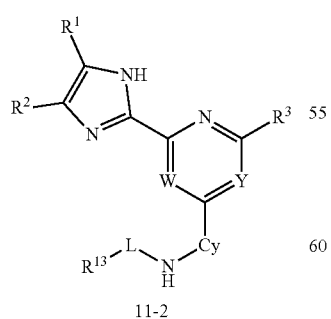

11-2

An alternative synthetic route for functionalizing Cy is illustrated in Scheme 12. A suitably protected halo-containing intermediate 12-1 (e.g., $X^1$=Br) can be coupled with a chloro-containing boronic acid or ester under Suzuki coupling conditions to provide 12-2. The chloro-containing intermediate 12-2 can be coupled with an amine $R^{11}R^{12}$NH by heating under Buchwald/Hartwig conditions (e.g., in the presence of a palladium catalyst, such as ᵗBuBrettPhos Pd G3, and a base (e.g., an alkoxide base or carbonate base)) to give derivative 12-3.

Scheme 12

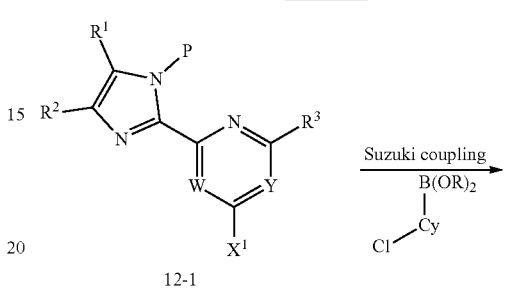

12-1

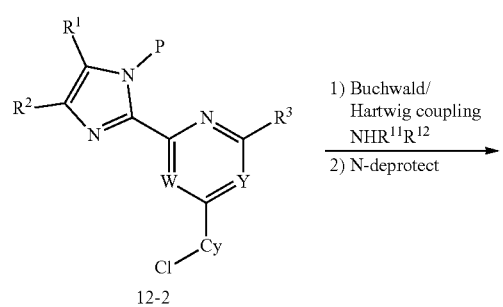

12-2

12-3

Similar chloro-containing intermediates (13-2), bearing nitrile as a precursor to later imidazole formation, find utility in Suzuki, Stille, or Negishi couplings to afford groups $R^{14}$ (e.g., heterocyclyl) which are C-linked in 13-3. In the case that M-$R^{14}$ is a heterocycle (where M is H and is attached to the amine nitrogen of amine-containing heterocycle $R^{14}$), coupling to the halide of 13-2 can be performed by heating under Buchwald/Hartwig conditions (e.g., in the presence of a palladium catalyst, such as ᵗBuBrettPhos Pd G3, and a base (e.g., an alkoxide base or a carbonate base)) to give a derivative 13-4, in which $R^{14}$ is N-linked to the pyridine. Where $R^{14}$ contains suitable functionality, further functional group manipulations can be carried out as desired and as outlined in examples set forth in the other Schemes.

Scheme 13

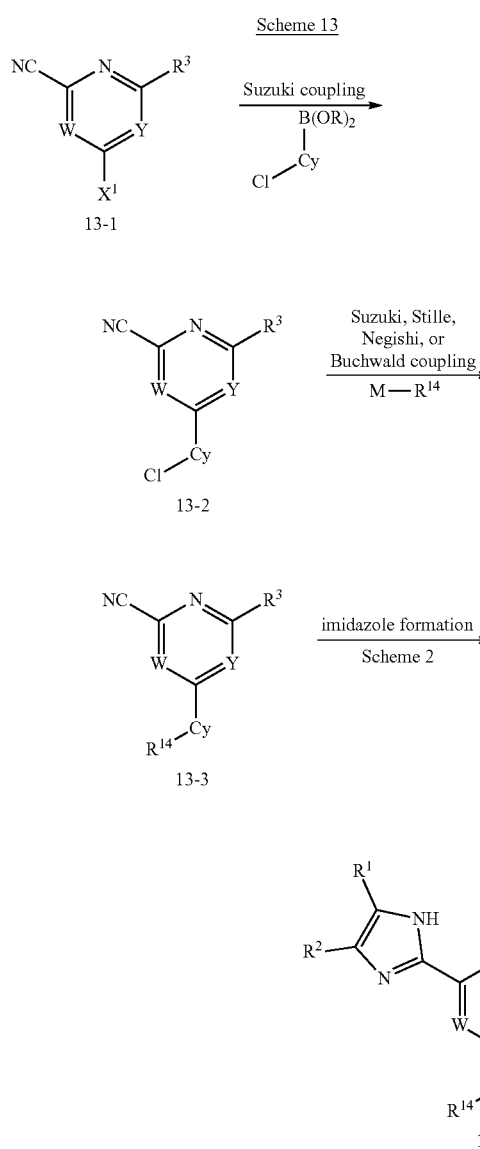

Further transformations can also be carried out on intermediates that contain carboxylate functionality on Cy, such as 14-1. The ester can be hydrolyzed (e.g., with aq. NaOH) and coupled with amines $R^{11}R^{12}NH$ under standard conditions (e.g., HATU and Hunig's base) to provide amides (14-2). Reduction to the alcohol can be carried out (e.g., using DIBAL), which can be followed by numerous subsequent transformations. For example, re-oxidation to the aldehyde (e.g., using Dess-Martin periodinane) can provide intermediate 14-3. Among other possible transformations, the aldehyde (14-3) can undergo reductive amination to afford amines (14-4) by reaction with $R^{11}R^{12}NH$ and a reducing agent (e.g., sodium cyanoborohydride, sodium triacetoxyborohydride).

When M-Cy of Scheme 1 is a partially saturated heterocycle, further synthetic transformations can be carried out on the coupled product as shown in Scheme 15. After N-deprotection of 15-1, the amine 15-2 can be converted to functionalized products 15-3. For example, 15-2 can be acylated or sulfonylated by reacting with $R^{13}$-L-X (where L is a linker and X is a suitable leaving group (e.g., acyl chlorides, sulfonyl chlorides, chloroformates) in the presence of a suitable base, to afford amide, sulfonamide, or carbamate products. Alternatively, products such as ureas can be formed by reacting with isocyanates $R^{13}NCO$, and alkylated products can be formed by reductive amination with aldehydes $R^{13}CHO$ in the presence of reducing agents. The double bond of the heterocyclic ring can be hydrogenated to afford the fully saturated compound 15-4 by reacting with $H_2$ over a catalyst (e.g., Palladium on Carbon). Similar transformations can be applied to heterocyclic rings installed by Suzuki coupling elsewhere on the compounds provided herein.

Scheme 14

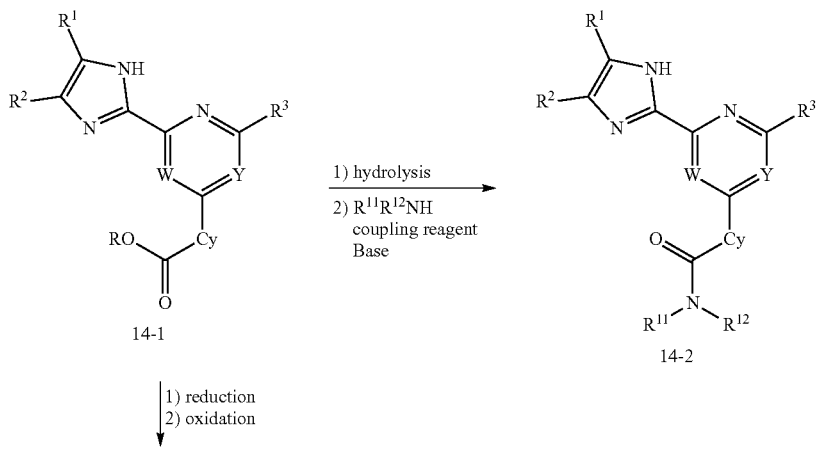

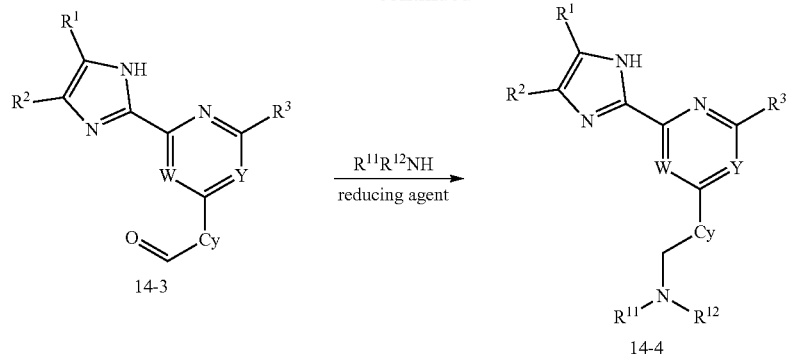

14-3 → 14-4

Scheme 15

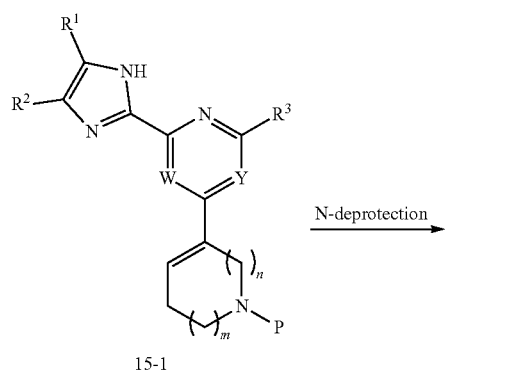

15-1

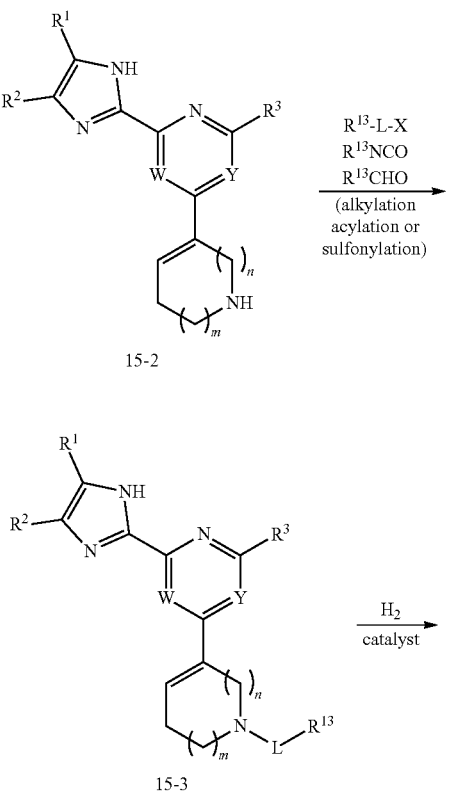

15-2

15-3

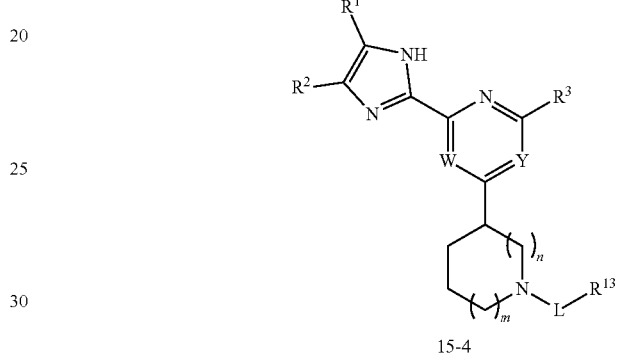

15-4

The reactions for preparing compounds described herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, (e.g., temperatures which can range from the solvent's freezing temperature to the solvent's boiling temperature). A given reaction can be carried out in one solvent or a mixture of more than one solvent. Depending on the particular reaction step, suitable solvents for a particular reaction step can be selected by the skilled artisan.

The expressions, "ambient temperature" and "room temperature" or "rt" as used herein, are understood in the art, and refer generally to a temperature, e.g. a reaction temperature, that is about the temperature of the room in which the reaction is carried out, for example, a temperature from about 20° C. to about 30° C.

Preparation of compounds described herein can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis*, 3$^{rd}$ Ed., Wiley & Sons, Inc., New York (1999).

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) and normal phase silica chromatography.

Methods of Use

The compounds or salts described herein inhibit activity of PI3Kγ kinase. Accordingly, the compounds or salts described herein can be used in methods of inhibiting PI3Kγ kinase by contacting the kinase with any one or more of the compounds, salts, or compositions described herein. In some embodiments, the compounds or salts can be used in methods of inhibiting activity of PI3Kγ in an individual in need of said inhibition by administering an inhibiting amount of a compound or salt thereof described herein. In some embodiments, the contacting is in vivo. In some embodiments, the contacting is ex vivo.

In some embodiments, the PI3Kγ includes a mutation. A mutation can be a replacement of one amino acid for another, or a deletion of one or more amino acids. In such embodiments, the mutation can be present in the kinase domain of the PI3Kγ.

In some embodiments, the compound or salt further inhibits PI3Kδ.

The compounds or salts described herein can be selective. By "selective" is meant that the compound binds to or inhibits PI3Kγ with greater affinity or potency, respectively, compared to at least one other kinase. In some embodiments, the compounds provided herein are selective inhibitors of PI3Kγ over PI3Kδ, PI3Kα, and PI3Kβ. In some embodiments, the compounds provided herein are selective inhibitors of PI3Kγ over PI3Kα and PI3Kβ. In some embodiments, selectivity can be at least about 2-fold, 3-fold, 5-fold, 10-fold, 20-fold, 50 fold, or 100 fold over PI3Kδ as measured by the assays described herein. In some embodiments, selectivity can be tested at the $K_m$ ATP concentration of each enzyme. In some embodiments, the selectivity of compounds provided herein can be determined by cellular assays associated with particular PI3K kinase activity.

Another aspect of the present disclosure pertains to methods of treating a kinase PI3Kγ-associated disease or disorder in an individual (e.g., patient) by administering to the individual in need of such treatment a therapeutically effective amount or dose of one or more compounds provided herein, or a pharmaceutically acceptable salt thereof, or a pharmaceutical composition thereof. A PI3Kγ-associated disease or disorder can include any disease, disorder or condition that is directly or indirectly linked to expression or activity of the PI3Kγ, including overexpression and/or abnormal activity levels.

In some embodiments, the disease or disorder is an autoimmune disease or disorder, cancer, cardiovascular disease, or neurodegenerative disease.

In some embodiments, the disease or disorder is lung cancer (e.g., non-small cell lung cancer), melanoma, pancreatic cancer, breast cancer, prostate cancer, liver cancer, color cancer, endometrial cancer, bladder cancer, skin cancer, cancer of the uterus, renal cancer, gastric cancer, or sarcoma. In some embodiments, the sarcoma is Askin's tumor, sarcoma botryoides, chondrosarcoma, Ewing's sarcoma, malignant hemangioendothelioma, malignant schwannoma, osteosarcoma, alveolar soft part sarcoma, angiosarcoma, cystosarcoma phyllodes, dermatofibrosarcoma protuberans, desmoid tumor, desmoplastic small round cell tumor, epithelioid sarcoma, extraskeletal chondrosarcoma, extraskeletal osteosarcoma, fibrosarcoma, gastrointestinal stromal tumor (GIST), hemangiopericytoma, hemangiosarcoma, Kaposi's sarcoma, leiomyosarcoma, liposarcoma, lymphangiosarcoma, lymphosarcoma, malignant peripheral nerve sheath tumor (MPNST), neurofibrosarcoma, rhabdomyosarcoma, synovial sarcoma, or undifferentiated pleomorphic sarcoma.

In some embodiments, the disease or disorder is acute myeloid leukemia (e.g., acute monocytic leukemia), small lymphocyctic lymphoma, chronic lymphocytic leukemia (CLL), chronic myelogenous leukemia (CML), multiple myeloma, T-cell actute lymphoblasic leukemia (T-ALL), cutaneous T-cell lymphoma, large granular lymphocytic leukemia, mature (peripheral) t-cell neoplasm (PTCL), anaplastic large cell lymphoma (ALCL), or lymphoblastic lymphoma. In some embodiments, the mature (peripheral) t-cell neoplasm (PTCL) is T-cell prolymphocytic leukemia, T-cell granular lymphocytic leukemia, aggressive NK-cell leukemia, mycosis fungoides/Sezary syndrome, naplastic large cell lymphoma (T-cell type), enteropathy type T-cell lymphoma, adult T-cell leukemia/lymphoma, or angioimmunoblastic T-cell lymphoma In some embodiments, the anaplastic large cell lymphoma (ALCL) is systemic ALCL or primary cutaneous ALCL.

In some embodiments, the disease or disorder is Burkitt's lymphoma, acute myeloblastic leukemia, chronic myeloid leukemia, non-Hodgkin's lymphoma, Hodgkin's lymphoma, hairy cell leukemia, Mantle cell lymphoma, small lymphocytic lymphoma, follicular lymphoma, lymphoplasmacytic lymphoma, extranodal marginal zone lymphoma, Waldenstrom's macroglobulinemia, prolymphocytic leukemia, acute lymphoblastic leukemia, myelofibrosis, mucosa-associated lymphatic tissue (MALT) lymphoma, mediastinal (thymic) large B-cell lymphoma, lymphomatoid granulomatosis, splenic marginal zone lymphoma, primary effusion lymphoma, intravascular large B-cell lymphoma, plasma cell leukemia, extramedullary plasmacytoma, smouldering myeloma (aka asymptomatic myeloma), monoclonal gammopathy of undetermined significance (MGUS), or diffuse large B cell lymphoma.

In some embodiments, the non-Hodgkin's lymphoma (NHL) is relapsed NHL, refractory NHL, recucurrent follicular NHL, indolent NHL (iNHL), or aggressive NHL (aNHL).

In some embodiments, the diffuse large B cell lymphoma is activated B-cell like (ABC) diffuse large B cell lymphoma, or germinal center B cell (GCB) diffuse large B cell lymphoma.

In some embodiments, the Burkitt's lymphoma is endemic Burkitt's lymphoma, sporadic Burkitt's lymphoma, or Burkitt's-like lymphoma In some embodiments, the disease or disorder is rheumatoid arthritis, multiple sclerosis, systemic lupus erythematous, asthma, allergy, pancreatitis, psoriasis, anaphylaxis, glomerulonephritis, inflammatory bowel disease (e.g., Crohn's disease and ulcerative colitis), thrombosis, meningitis, encephalitis, diabetic retinopathy, benign prostatic hypertrophy, myasthenia gravis, Sjögren's syndrome, osteoarthritis, restenosis, or atherosclerosis.

In some embodiments, disease or disorder is heart hypertropy, cardiac myocyte dysfunction, chronic obstructive pulmonary disease (COPD), elevated blood pressure, ischemia, ischemia-reperfusion, vasoconstriction, anemia (e.g., hemolytic anemia, aplastic anemia, or pure red cell anemia), bacterial infection, viral infection, graft rejection, kidney disease, anaphylactic shock fibrosis, skeletal muscle atrophy, skeletal muscle hypertrophy, angiogenesis, sepsis, graft rejection, glomerulosclerosis, progressive renal fibrosis, idiopathic thrombocytopenic purpura (ITP), autoimmune hemolytic anemia, vasculitis, systemic lupus erythematosus, lupus nephritis, pemphigus, or membranous nephropathy.

In some embodiments, the disease or disorder is Alzheimer's disease, central nervous system trauma, or stroke.

In some embodiments, the idiopathic thrombocytopenic purpura (ITP) is relapsed ITP or refractory ITP.

In some embodiments, the vasculitis is Behçet's disease, Cogan's syndrome, giant cell arteritis, polymyalgia rheumatica (PMR), Takayasu's arteritis, Buerger's disease (thromboangiitis obliterans), central nervous system vasculitis, Kawasaki disease, polyarteritis nodosa, Churg-Strauss syndrome, mixed cryoglobulinemia vasculitis (essential or hepatitis C virus (HCV)-induced), Henoch-Schonlein purpura (HSP), hypersensitivity vasculitis, microscopic polyangiitis, Wegener's granulomatosis, or anti-neutrophil cytoplasm antibody associated (ANCA) systemic vasculitis (AASV).

The present disclosure further provides a compound described herein, or a pharmaceutically acceptable salt thereof, for use in any of the methods described herein.

The present disclosure further provides use of a compound described herein, or a pharmaceutically acceptable salt thereof, for the preparation of a medicament for use in any of the methods described herein.

As used herein, the term "contacting" refers to the bringing together of indicated moieties in an in vitro system or an in vivo system. For example, "contacting" a PI3K with a compound of the disclosure includes the administration of a compound of the present disclosure to an individual or patient, such as a human, having a PI3K, as well as, for example, introducing a compound of the disclosure into a sample containing a cellular or purified preparation containing the PI3K.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

As used herein, the term "treating" or "treatment" can refer to one or more of (1) inhibiting the disease; for example, inhibiting a disease, condition or disorder in an individual who is experiencing or displaying the pathology or symptomatology of the disease, condition or disorder (i.e., arresting further development of the pathology and/or symptomatology); and (2) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

Combination Therapies

One or more additional pharmaceutical agents such as, for example, chemotherapeutics, anti-inflammatory agents, steroids, immunosuppressants, immune-oncology agents, metabolic enzyme inhibitors, chemokine receptor inhibitors, and phosphatase inhibitors, as well as Akt1, Akt2, Akt3, TGF-βR, PKA, PKG, PKC, CaM-kinase, phosphorylase kinase, MEKK, ERK, MAPK, mTOR, EGFR, HER2, HER3, HER4, INS-R, IGF-1R, IR-R, PDGFαR, PDGFβR, CSFIR, FLK-II, KDR/FLK-1, FLK-4, fit-1, FGFR1, FGFR2, FGFR3, FGFR4, Ron, Sea, TRKA, TRKB, TRKC, FLT3, VEGFR/Flt2, Flt4, EphA1, EphA2, EphA3, EphB2, EphB4, Tie2, Src, Fyn, Lck, Fgr, Btk, Fak, SYK, FRK, ABL, ALK, B-Raf, Bcr-Abl, Flt-3, EGFR, HER2, JAK, c-MET, VEGFR, PDGFR, cKit, IGF-1R, RAF and FAK kinase inhibitors such as, for example, those described in WO 2006/056399. Other agents such as therapeutic antibodies can be used in combination with the compounds provided herein for treatment of PI3K-associated diseases, disorders or conditions. The one or more additional pharmaceutical agents can be administered to a patient simultaneously or sequentially.

In some embodiments, the compounds of the present disclosure can be combined with one or more of the following inhibitors for the treatment of cancer and/or diseases or indications as described herein. Non-limiting examples of inhibitors that can be combined with the compounds of the present disclosure for treatment of cancer and/or diseases or indications as described herein include an FGFR inhibitor (FGFR1, FGFR2, FGFR3 or FGFR4, e.g., INCB54828, INCB62079 and INCB63904), a JAK inhibitor (JAK1 and/or JAK2, e.g., ruxolitinib, baricitinib or INCB39110), an IDO inhibitor (e.g., epacadostat and NLG919), an LSD1 inhibitor (e.g., INCB59872 and INCB60003), a TDO inhibitor, a PI3K-delta inhibitor (e.g., INCB50797 and INCB50465), a Pim inhibitor, a CSF1R inhibitor, a TAM receptor tyrosine kinases (Tyro-3, Axl, and Mer), an angiogenesis inhibitor, an interleukin receptor inhibitor, bromo and extra terminal family members inhibitors (for example, bromodomain inhibitors or BET inhibitors such as INCB54329 and INCB57643) and an adenosine receptor antagonist or combinations thereof.

In some embodiments, the compound or salt described herein is administered with a PI3Kδ inhibitor. In some embodiments, the compound or salt described herein is administered with a JAK inhibitor. In some embodiments, the compound or salt described herein is administered with a JAK1 or JAK2 inhibitor (e.g., baricitinib or ruxolitinib). In some embodiments, the compound or salt described herein is administered with a JAK1 inhibitor. In some embodiments, the compound or salt described herein is administered with a JAK1 inhibitor, which is selective over JAK2.

Example antibodies for use in combination therapy include but are not limited to Trastuzumab (e.g. anti-HER2), Ranibizumab (e.g. anti-VEGF-A), Bevacizumab (trade name Avastin, e.g. anti-VEGF, Panitumumab (e.g. anti-EGFR), Cetuximab (e.g. anti-EGFR), Rituxan (anti-CD20) and antibodies directed to c-MET.

One or more of the following agents may be used in combination with the compounds provided herein and are presented as a non-limiting list: a cytostatic agent, cisplatin, doxorubicin, taxotere, taxol, etoposide, irinotecan, camptostar, topotecan, paclitaxel, docetaxel, epothilones, tamoxifen, 5-fluorouracil, methoxtrexate, temozolomide, cyclophosphamide, SCH 66336, R115777, L778,123, BMS 214662, Iressa, Tarceva, antibodies to EGFR, Gleevec™, intron, ara-C, adriamycin, cytoxan, gemcitabine, Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, ELOXATIN™, Pentostatine, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17.alpha.-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, Hexamethylmelamine, Avastin, herceptin, Bexxar, Velcade, Zevalin, Trisenox, Xeloda, Vinorelbine, Porfimer, Erbitux, Liposomal, Thiotepa, Altretamine, Melphalan, Trastuzumab, Lerozole, Fulvestrant, Exemestane, Fulvestrant, Ifosfomide, Rituximab, C225, Campath, Clofarabine, cladribine, aphidicolon, rituxan, sunitinib, dasatinib, tezacitabine, Sml1, fludarabine, pentostatin, triapine, didox, trimidox, amidox, 3-AP, and MDL-101,731.

Additional examples of chemotherapeutics include proteosome inhibitors (e.g., bortezomib), thalidomide, revlimid, and DNA-damaging agents such as melphalan, doxorubicin, cyclophosphamide, vincristine, etoposide, carmustine, and the like.

Example steroids include corticosteroids such as dexamethasone or prednisone.

Example Bcr-Abl inhibitors include the compounds, and pharmaceutically acceptable salts thereof, of the genera and species disclosed in U.S. Pat. No. 5,521,184, WO 04/005281, and U.S. Ser. No. 60/578,491.

Example suitable Flt-3 inhibitors include compounds, and their pharmaceutically acceptable salts, as disclosed in WO 03/037347, WO 03/099771, and WO 04/046120.

Example suitable RAF inhibitors include compounds, and their pharmaceutically acceptable salts, as disclosed in WO 00/09495 and WO 05/028444.

Example suitable FAK inhibitors include compounds, and their pharmaceutically acceptable salts, as disclosed in WO 04/080980, WO 04/056786, WO 03/024967, WO 01/064655, WO 00/053595, and WO 01/014402.

In some embodiments, the compounds provided herein can be used in combination with one or more other kinase inhibitors including imatinib, particularly for treating patients resistant to imatinib or other kinase inhibitors.

In some embodiments, the compounds provided herein can be used in combination with a chemotherapeutic in the treatment of cancer, and may improve the treatment response as compared to the response to the chemotherapeutic agent alone, without exacerbation of its toxic effects. In some embodiments, the compounds provided herein can be used in combination with a chemotherapeutic provided herein. For example, additional pharmaceutical agents used in the treatment of multiple myeloma, can include, without limitation, melphalan, melphalan plus prednisone [MP], doxorubicin, dexamethasone, and Velcade (bortezomib). Further additional agents used in the treatment of multiple myeloma include Bcr-Abl, Flt-3, RAF and FAK kinase inhibitors. Additive or synergistic effects are desirable outcomes of combining a PI3K inhibitor of the present disclosure with an additional agent.

In some embodiments, the compounds provided herein can be used in combination with a targeted agent provided herein.

In some embodiments, the compounds provided herein can be used in combination with one or more immune-oncology agents. In some embodiments, the immune-oncology agent is selected from the group consisting of CTLA4, PD1, and PDL biologics.

In some embodiments, the compounds provided herein can be used in combination with one or more metabolic enzyme inhibitors. In some embodiments, the metabolic enzyme inhibitor is an inhibitor of IDO1, TDO, or arginase.

In some embodiments, the compounds provided herein can be used in combination with one or more immune checkpoint inhibitors. Exemplary immune checkpoint inhibitors include inhibitors against immune checkpoint molecules such as CD27, CD28, CD40, CD122, CD96, CD73, CD47, OX40, GITR, CSF1R, JAK, PI3K delta, PI3K gamma, TAM, arginase, CD137 (also known as 4-1BB), ICOS, A2AR, B7-H3, B7-H4, BTLA, CTLA-4, LAG3, TIM3, VISTA, PD-1, PD-L1 and PD-L2. In some embodiments, the immune checkpoint molecule is a stimulatory checkpoint molecule selected from CD27, CD28, CD40, ICOS, OX40, GITR and CD137. In some embodiments, the immune checkpoint molecule is an inhibitory checkpoint molecule selected from A2AR, B7-H3, B7-H4, BTLA, CTLA-4, IDO, KIR, LAG3, PD-1, TIM3, and VISTA. In some embodiments, the compounds provided herein can be used in combination with one or more agents selected from KIR inhibitors, TIGIT inhibitors, LAIR1 inhibitors, CD160 inhibitors, 2B4 inhibitors and TGFR beta inhibitors.

In some embodiments, the inhibitor of an immune checkpoint molecule is anti-PD1 antibody, anti-PD-L1 antibody, or anti-CTLA-4 antibody.

In some embodiments, the inhibitor of an immune checkpoint molecule is an inhibitor of PD-1, e.g., an anti-PD-1 monoclonal antibody. In some embodiments, the anti-PD-1 monoclonal antibody is nivolumab, pembrolizumab (also known as MK-3475), pidilizumab, SHR-1210, PDR001, or AMP-224. In some embodiments, the anti-PD-1 monoclonal antibody is nivolumab or pembrolizumab. In some embodiments, the anti-PD1 antibody is pembrolizumab.

In some embodiments, the inhibitor of an immune checkpoint molecule is an inhibitor of PD-L1, e.g., an anti-PD-L1 monoclonal antibody. In some embodiments, the anti-PD-L1 monoclonal antibody is BMS-935559, MEDI4736, MPDL3280A (also known as RG7446), or MSB0010718C. In some embodiments, the anti-PD-L1 monoclonal antibody is MPDL3280A or MEDI4736.

In some embodiments, the inhibitor of an immune checkpoint molecule is an inhibitor of CTLA-4, e.g., an anti-CTLA-4 antibody. In some embodiments, the anti-CTLA-4 antibody is ipilimumab.

In some embodiments, the inhibitor of an immune checkpoint molecule is an inhibitor of LAG3, e.g., an anti-LAG3 antibody. In some embodiments, the anti-LAG3 antibody is BMS-986016 or LAG525.

In some embodiments, the inhibitor of an immune checkpoint molecule is an inhibitor of GITR, e.g., an anti-GITR antibody. In some embodiments, the anti-GITR antibody is TRX518 or MK-4166.

In some embodiments, the inhibitor of an immune checkpoint molecule is an inhibitor of OX40, e.g., an anti-OX40 antibody or OX40L fusion protein. In some embodiments, the anti-OX40 antibody is MEDI0562. In some embodiments, the OX40L fusion protein is MEDI6383.

Compounds of the present disclosure can be used in combination with one or more agents for the treatment of diseases such as cancer. In some embodiments, the agent is an alkylating agent, a proteasome inhibitor, a corticosteroid, or an immunomodulatory agent. Examples of an alkylating agent include cyclophosphamide (CY), melphalan (MEL), and bendamustine. In some embodiments, the proteasome inhibitor is carfilzomib. In some embodiments, the corticosteroid is dexamethasone (DEX). In some embodiments, the immunomodulatory agent is lenalidomide (LEN) or pomalidomide (POM).

The agents can be combined with the present compound in a single or continuous dosage form, or the agents can be administered simultaneously or sequentially as separate dosage forms.

In some embodiments, a corticosteroid such as dexamethasone is administered to a patient in combination with the compounds provided herein where the dexamethasone is administered intermittently as opposed to continuously.

In some further embodiments, combinations of the compounds provided herein with other therapeutic agents can be administered to a patient prior to, during, and/or after a bone marrow transplant or stem cell transplant.

Pharmaceutical Formulations and Dosage Forms

When employed as pharmaceuticals, the compounds provided herein can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This disclosure also includes pharmaceutical compositions which contain, as the active ingredient, the compound of the disclosure or a pharmaceutically acceptable salt thereof, in combination with one or more pharmaceutically acceptable carriers (excipients). In some embodiments, the composition is suitable for topical administration. In making the compositions of the disclosure, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The compounds provided herein may be milled using known milling procedures such as wet milling to obtain a particle size appropriate for tablet formation and for other formulation types. Finely divided (nanoparticulate) preparations of the compounds of the disclosure can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions provided herein can be formulated so as to provide quick, sustained or delayed release of the active ingredient after administration to the patient by employing procedures known in the art.

The compositions can be formulated in a unit dosage form, each dosage containing from about 5 to about 1000 mg (1 g), more usually about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the compositions of the invention contain from about 5 to about 50 mg of the active ingredient. One having ordinary skill in the art will appreciate that this embodies compositions containing about 5 to about 10, about 10 to about 15, about 15 to about 20, about 20 to about 25, about 25 to about 30, about 30 to about 35, about 35 to about 40, about 40 to about 45, or about 45 to about 50 mg of the active ingredient.

In some embodiments, the compositions of the invention contain from about 50 to about 500 mg of the active ingredient. One having ordinary skill in the art will appreciate that this embodies compositions containing about 50 to about 100, about 100 to about 150, about 150 to about 200, about 200 to about 250, about 250 to about 300, about 350 to about 400, or about 450 to about 500 mg of the active ingredient.

In some embodiments, the compositions of the invention contain from about 500 to about 1000 mg of the active ingredient. One having ordinary skill in the art will appreciate that this embodies compositions containing about 500 to about 550, about 550 to about 600, about 600 to about 650, about 650 to about 700, about 700 to about 750, about 750 to about 800, about 800 to about 850, about 850 to about 900, about 900 to about 950, or about 950 to about 1000 mg of the active ingredient.

Similar dosages may be used of the compounds described herein in the methods and uses of the invention.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present disclosure. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present disclosure.

The tablets or pills of the present disclosure can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present disclosure can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white Vaseline, and the like. Carrier compositions of creams can be based on water in combination with glycerol and one or more other components, e.g. glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like. In some embodiments, topical formulations contain at least about 0.1, at least about 0.25, at least about 0.5, at least about 1, at least about 2, or at least about 5 wt % of the compound of the invention. The topical formulations can be suitably packaged in tubes of, for example, 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds provided herein can be provided in an aqueous physiological buffer solution containing about 0.1 to about 10% w/v of the compound for parenteral administration. Some typical dose ranges are from about 1 Dg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the invention can further include one or more additional pharmaceutical agents such as a chemotherapeutic, steroid, anti-inflammatory compound, or immunosuppressant, examples of which are listed herein.

Labeled Compounds and Assay Methods

Another aspect of the present disclosure relates to labeled compounds of the present disclosure (radio-labeled, fluorescent-labeled, etc.) that would be useful not only in imaging techniques but also in assays, both in vitro and in vivo, for localizing and quantitating PI3K in tissue samples, including human, and for identifying PI3K ligands by inhibition binding of a labeled compound. Accordingly, the present disclosure includes PI3K assays that contain such labeled compounds.

The present disclosure further includes isotopically-labeled compounds of the present disclosure. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present disclosure include but are not limited to $^{2}H$ (also written as D for deuterium), $^{3}H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. The radionuclide that is incorporated in the instant radio-labeled compounds will depend on the specific application of that radio-labeled compound. For example, for in vitro PI3K labeling and competition assays, compounds that incorporate $^3$H, $^{14}$C, $^{82}$Br, $^{125}$I, $^{131}$I, $^{35}$S or will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful.

It is understood that a "radio-labeled" or "labeled compound" is a compound that has incorporated at least one radionuclide. In some embodiments the radionuclide is selected from the group consisting of $^3$H, $^{14}$C, $^{125}$I, $^{35}$S and $^{82}$Br.

The present disclosure can further include synthetic methods for incorporating radio-isotopes into compounds provided herein. Synthetic methods for incorporating radio-isotopes into organic compounds are well known in the art, and an ordinary skill in the art will readily recognize the methods applicable for the compounds of invention.

A labeled compound of the invention can be used in a screening assay to identify/evaluate compounds. For example, a newly synthesized or identified compound (i.e., test compound) which is labeled can be evaluated for its ability to bind a PI3K by monitoring its concentration variation when contacting with the PI3K, through tracking of the labeling. For example, a test compound (labeled) can be evaluated for its ability to reduce binding of another compound which is known to bind to a PI3K (i.e., standard compound). Accordingly, the ability of a test compound to compete with the standard compound for binding to the PI3K directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present disclosure also includes pharmaceutical kits useful, for example, in the treatment or prevention of PI3K-associated diseases or disorders, such as cancer, which include one or more containers containing a pharmaceutical composition comprising a therapeutically effective amount of a compound of the invention. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results. The compounds of the Examples have been found to be PI3Kγ inhibitors according to at least one assay described herein.

EXAMPLES

Preparatory LC-MS purifications of some of the compounds prepared were performed on Waters mass directed fractionation systems. The basic equipment setup, protocols, and control software for the operation of these systems have been described in detail in the literature (see e.g. "Two-Pump At Column Dilution Configuration for Preparative LC-MS", K. Blom, *J. Combi. Chem.*, 4, 295 (2002); "Optimizing Preparative LC-MS Configurations and Methods for Parallel Synthesis Purification", K. Blom, R. Sparks, J. Doughty, G. Everlof, T. Haque, A. Combs, *J. Combi. Chem.*, 5, 670 (2003); and "Preparative LC-MS Purification: Improved Compound Specific Method Optimization", K. Blom, B. Glass, R. Sparks, A. Combs, *J. Combi. Chem.*, 6, 874-883 (2004)). The compounds separated were typically subjected to analytical liquid chromatography mass spectrometry (LCMS) for purity analysis under the following conditions: Instrument; Agilent 1100 series, LC/MSD, Column: Waters Sunfire™ $C_{18}$ 5 µm, 2.1×50 mm, Buffers: mobile phase A: 0.025% TFA in water and mobile phase B: acetonitrile; gradient 2% to 80% of B in 3 minutes with flow rate 2.0 mL/minute.

Some of the compounds prepared were also separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions are as follows:

pH 2 purifications: Waters Sunfire™ $C_{18}$ 5 µm, 19×100 mm column, eluting with mobile phase A: 0.1% TFA (trifluoroacetic acid) in water and mobile phase B: acetonitrile; the flow rate was 30 mL/minute, the separating gradient was optimized for each compound using the Compound Specific Method Optimization protocol as described in the literature (see e.g. "Preparative LCMS Purification: Improved Compound Specific Method Optimization", K. Blom, B. Glass, R. Sparks, A. Combs, *J. Comb. Chem.*, 6, 874-883 (2004)). Typically, the flow rate used with the 30×100 mm column was 60 mL/minute.

pH 10 purifications: Waters XBridge $C_{18}$ 5 µm, 19×100 mm column, eluting with mobile phase A: 0.15% NH$_4$OH in water and mobile phase B: acetonitrile; the flow rate was 30 mL/minute, the separating gradient was optimized for each compound using the Compound Specific Method Optimization protocol as described in the literature (see e.g. "Preparative LCMS Purification: Improved Compound Specific Method Optimization", K. Blom, B. Glass, R. Sparks, A. Combs, *J. Comb. Chem.*, 6, 874-883 (2004)). Typically, the flow rate used with 30×100 mm column was 60 mL/minute.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

Example 1. 4-[1-(4-Chlorobenzyl)-1H-pyrazol-4-yl]-2-(5-phenyl-1H-imidazol-2-yl)pyridine trifluoroacetate salt

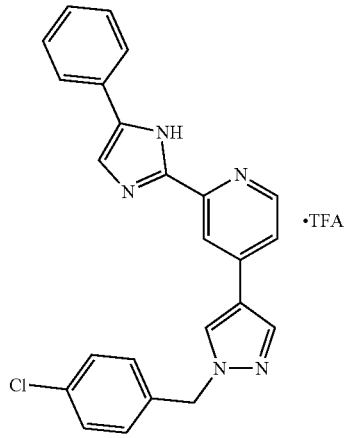 [SMILES: Clc1ccc(Cn2cc(-c3ccnc(-c4ncc(-c5ccccc5)[nH]4)c3)cn2)cc1]

Step 1.
4-Bromo-2-(5-phenyl-1H-imidazol-2-yl)pyridine

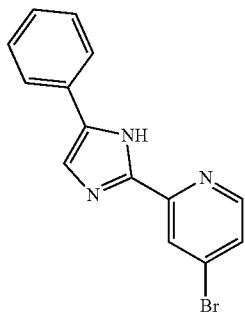 [SMILES: Brc1ccnc(-c2ncc(-c3ccccc3)[nH]2)c1]

4-Bromopyridine-2-carboxylic acid (7.11 g, 35.2 mmol, Combi-Blocks) and 2-bromoacetophenone (7.0 g, 35 mmol, Aldrich) were dissolved in DMF (100. mL), and N,N-diisopropylethylamine (12 mL, 70. mmol) was added. After stirring for 1 hour, the mixture was diluted with water, and the aqueous mixture was extracted with three portions of ethyl acetate (EtOAc). The combined organic extracts were washed sequentially with water and brine, dried over Na$_2$SO$_4$, filtered and concentrated to afford intermediate 2-oxo-2-phenylethyl 4-bromopicolinate. LCMS(M+H)$^+$: 320.0, 322.0. This intermediate was dissolved in AcOH (150 mL), and treated with NH$_4$OAc (41 g, 530 mmol) at 130° C. for 1 hour. The mixture was cooled to room temperature and most of the AcOH was removed in vacuo. The residue was then diluted with an ice-cold solution of NaHCO$_3$ and the aqueous mixture was extracted with three portions of EtOAc. The combined organic extracts were dried over Na$_2$SO$_4$, filtered, and concentrated. The crude product was triturated with DCM and isolated by filtration. Yield: 2.9 g, 27%. LCMS(M+H)$^+$: 300.1, 302.1.

Step 2. 4-Bromo-2-(4-phenyl-1-{[2-(trimethylsilyl)ethoxy]methyl}-1H-imidazol-2-yl)pyridine

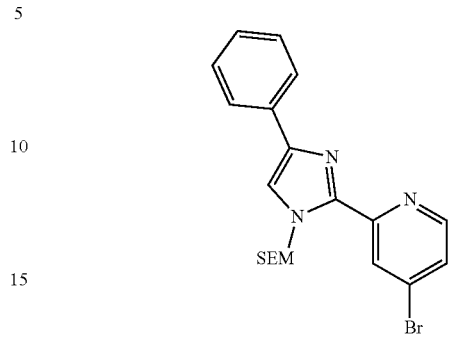

A solution of 4-bromo-2-(5-phenyl-1H-imidazol-2-yl)pyridine (1.4 g, 4.7 mmol, from Step 1) in THF (60 mL) at 0° C. was treated with 1.0 M KO$^t$Bu in THF (6.5 mL, 6.5 mmol) and the reaction was stirred at 0° C. for 30 minutes. The reaction mixture was treated with [β-(trimethylsilyl)ethoxy]methyl chloride (1.2 mL, 6.5 mmol, Aldrich) and stirred at 0° C. for 30 minutes. Aq. NH$_4$Cl solution was poured into the cold reaction mixture and after stirring for 30 minutes, the aqueous mixture was extracted with EtOAc. The extract was washed with water, followed by brine. The solution was dried over sodium sulfate, filtered and concentrated. The product was purified by flash chromatography, eluting with a gradient from 0-10% EtOAc in hexanes. The major isomer, first to elute, was collected. Yield: 1.23 g, 61%. $^1$H NMR (400 MHz, CDCl$_3$) δ 8.68 (br, 1H), 8.42 (d, 1H), 7.96-7.88 (m, 2H), 7.55 (s, 1H), 7.51-7.41 (m, 3H), 7.38-7.29 (m, 1H), 6.08 (s, 2H), 3.66-3.59 (m, 2H), 0.97-0.91 (m, 2H), −0.04 (s, 9H); LCMS (M+H)$^+$: 430.1/432.1.

Step 3. 2-(4-Phenyl-1-{[2-(trimethylsilyl)ethoxy]methyl}-1H-imidazol-2-yl)-4-(1H-pyrazol-4-yl)pyridine

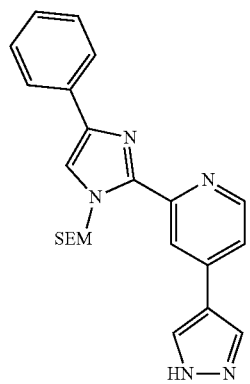 [SMILES: C[Si](C)(C)CCOCn1cc(-c2ccccc2)nc1-c1cc(-c2cn[nH]c2)ccn1]

A degassed mixture of 4-bromo-2-(4-phenyl-1-{[2-(trimethylsilyl)ethoxy]methyl}-1H-imidazol-2-yl)pyridine (0.30 g, 0.70 mmol, from Step 2), 4-(4,4,5,5-tetramethyl-1,3,2-dioxaborolan-2-yl)-1H-pyrazole (190 mg, 0.98 mmol, Aldrich), Na$_2$CO$_3$ (220 mg, 2.1 mmol) and tetrakis(triphenylphosphine)palladium(0) (80 mg, 0.070 mmol) in 1,4-dioxane (10 mL) and water (3.0 mL) was heated to 140° C. in the microwave for 20 min. Upon cooling to room temperature, the reaction mixture was diluted with water and the aqueous mixture was extracted with EtOAc. The combined organic extracts were dried over $Na_2SO_4$, filtered, and concentrated. The product was purified by flash chromatography, eluting with a gradient from 0-50% EtOAc in hexanes. Yield: 0.175 g, 60%. LCMS (M+H)$^+$: 418.3.

Step 4. 4-[1-(4-Chlorobenzyl)-1H-pyrazol-4-yl]-2-(5-phenyl-1H-imidazol-2-yl)pyridine trifluoroacetate salt A mixture of 2-(4-Phenyl-1-{[2-(trimethylsilyl)ethoxy]methyl}-1H-imidazol-2-yl)-4-(1H-pyrazol-4-yl)pyridine (13 mg, 0.031 mmol, from Step 3) in DMF (0.45 mL) was treated with $K_2CO_3$ (26 mg, 0.19 mmol) and 1-(bromomethyl)-4-chlorobenzene (7.7 mg, 0.037 mmol, Aldrich). After 1 hour, the reaction mixture was diluted with water and the aqueous mixture was extracted with EtOAc. The extract was dried over $Na_2SO_4$, filtered, and concentrated. The residue was dissolved in trifluoroacetic acid (TFA, 0.45 mL, 5.9 mmol) and stirred at 40° C. for 20 minutes. The TFA was removed in vacuo and the residue was dissolved in methanol (MeOH) and purified by preparative HPLC (C-18 column eluting with a water:acetonitrile gradient buffered at pH 2 with 0.1% trifluoroacetic acid). Yield: 8.9 mg. $^1$H NMR (400 MHz, $d_6$-DMSO) δ 8.66 (d, J=5.3 Hz, 1H), 8.64 (s, 1H), 8.39 (s, 1H), 8.20 (s, 1H), 8.04 (br, 1H), 7.98-7.90 (m, 2H), 7.74 (d, J=4.7 Hz, 1H), 7.52-7.42 (m, 4H), 7.42-7.29 (m, 3H), 5.45 (s, 2H); LCMS (M+H)$^+$: 412.1.

Examples 5-14, 16-21, 25-26, 30-35, 37, 40-41, and 43 through 60 were synthesized according to the procedure of Example 1 and the data are listed in Table 1. Examples 5-7, 10, 12, 20-21, 26, 30-35, 43 and 56 were prepared via alkylations as described by Example 1 and Scheme 3. Examples 48-51 were prepared via alkylation and subsequent hydrolysis and amide formation. Examples 44-46, and 54 were prepared by sulfonylation as described in Scheme 3. Examples 25, 47 and 60 were prepared via Mitsunobu alkylation as shown in Scheme 3. Aza-Michael addition was used to prepare Examples 52 and 55, as shown in Scheme 3. Aza-Michael addition followed by hydrolysis (to Example 57) and amide formation was used to prepare Examples 53 and 58-59.

TABLE 1

| Ex. No. | Name | R = | MS (M + H)$^+$ | $^1$H NMR |
|---|---|---|---|---|
| 5 | 4-(1-Benzyl-1H-pyrazol-4-yl)-2-(5-phenyl-1H-imidazol-2-yl)pyridine trifluoroacetate salt | | 378.2 | $^1$H NMR (400 MHz, $d_6$-DMSO) δ 8.68 (d, J = 5.3 Hz, 1H), 8.63 (s, 1H), 8.44 (s, 1H), 8.19 (s, 1H), 8.12 (s, 1H), 7.99-7.91 (m, 2H), 7.78 (dd, J = 5.2, 1.4 Hz, 1H), 7.51 (t, J = 7.6 Hz, 2H), 7.43-7.36 (m, 3H), 7.36-7.29 (m, 3H), 5.44 (s, 2H) |
| 6 | 2-((4-(2-(5-Phenyl-1H-imidazol-2-yl)pyridin-4-yl)-1H-pyrazol-1-yl)methyl)benzonitrile trifluoroacetate salt | | 403.2 | $^1$H NMR (400 MHz, $d_6$-DMSO) δ 8.70 (d, J = 5.3 Hz, 1H), 8.67 (s, 1H), 8.44 (s, 1H), 8.23 (s, 1H), 8.10 (s, 1H), 7.97-7.94 (m, 2H), 7.93 (dd, J = 7.8, 1.0 Hz, 1H), 7.79 (dd, J = 5.2, 1.4 Hz, 1H), 7.74 (td, J = 7.7, 1.3 Hz, 1H), 7.57 (td, J = 7.7, 1.0 Hz, 1H), 7.50 (t, J = 7.7 Hz, 2H), 7.43-7.36 (m, 2H), 5.66 (s, 2H) |

TABLE 1-continued

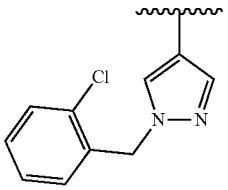 [SMILES: *c1cnn(Cc2ccccc2Cl)c1]

| Ex. No. | Name | R = | MS (M + H)+ | 1H NMR |
|---|---|---|---|---|
| 7 | 4-(1-(2-Chlorobenzyl)-1H-pyrazol-4-yl)-2-(5-phenyl-1H-imidazol-2-yl)pyridine trifluoroacetate salt | 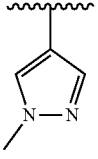 [SMILES: *c1cnn(C)c1] | 412.2 | 1H NMR (400 MHz, d6-DMSO) δ 8.69 (d, J = 5.3 Hz, 1H), 8.62 (s, 1H), 8.44 (s, 1H), 8.23 (s, 1H), 8.10 (s, 1H), 8.00-7.91 (m, 2H), 7.80 (dd, J = 5.2, 1.3 Hz, 1H), 7.56-7.45 (m, 3H), 7.45-7.33 (m, 3H), 7.20 (dd, J = 7.1, 2.2 Hz, 1H), 5.55 (s, 2H) |
| 8 | 4-(1-Methyl-1H-pyrazol-4-yl)-2-(5-phenyl-1H-imidazol-2-yl)pyridine trifluoroacetate salt | 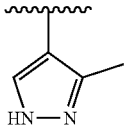 | 302.2 | 1H NMR (400 MHz, d6-DMSO) δ 8.65 (d, J = 5.2 Hz, 1H), 8.48 (s, 1H), 8.41 (s, 1H), 8.12 (s, 1H), 8.06 (s, 1H), 7.98-7.92 (m, 2H), 7.73 (dd, J = 5.2, 1.5 Hz, 1H), 7.52-7.43 (m, 2H), 7.41-7.33 (m, 1H), 3.94 (s, 3H) |
| 9 | 4-(1-Methyl-1H-pyrazol-4-yl)-2-(5-phenyl-1H-imidazol-2-yl)pyridine trifluoroacetate salt | 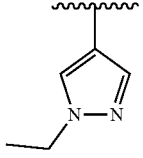 [SMILES: *c1cnn(CC)c1] | 302.2 | 1H NMR (400 MHz, d6-DMSO) δ 8.70 (d, J = 5.3 Hz, 1H), 8.36 (d, J = 0.9 Hz, 1H), 8.13 (s, 1H), 8.12 (s, 1H), 8.00-7.90 (m, 2H), 7.69 (dd, J = 5.3, 1.6 Hz, 1H), 7.54-7.46 (m, 2H), 7.44-7.34 (m, 1H), 2.55 (s, 3H) |
| 10 | 4-(1-Ethyl-1H-pyrazol-4-yl)-2-(5-phenyl-1H-imidazol-2-yl)pyridine trifluoroacetate salt | 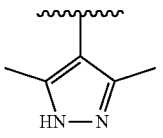 | 316.2 | 1H NMR (400 MHz, d6-DMSO) δ 8.66 (d, J = 5.3 Hz, 1H), 8.54 (s, 1H), 8.43 (d, J = 0.7 Hz, 1H), 8.14 (d, J = 0.5 Hz, 1H), 8.07 (s, 1H), 7.98-7.90 (m, 2H), 7.74 (dd, J = 5.3, 1.6 Hz, 1H), 7.53-7.44 (m, 2H), 7.42-7.31 (m, 1H), 4.22 (q, J = 7.3 Hz, 2H), 1.45 (t, J = 7.3 Hz, 3H) |
| 11 | 4-(3,5-Dimethyl-1H-pyrazol-4-yl)-2-(5-phenyl-1H-imidazol-2-yl)pyridine trifluoroacetate salt | | 316.2 | 1H NMR (400 MHz, d6-DMSO) δ 8.74 (d, J = 5.2 Hz, 1H), 8.20 (d, J = 0.7 Hz, 1H), 8.15 (s, 1H), 7.98-7.86 (m, 2H), 7.54 (dd, J = 5.2, 1.5 Hz, 1H), 7.53-7.46 (m, 2H), 7.43-7.37 (m, 1H), 2.36 (s, 6H) |

TABLE 1-continued

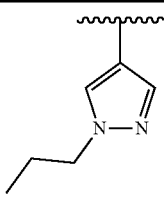

| Ex. No. Name | R = | MS (M + H)+ | 1H NMR |
|---|---|---|---|
| 12 2-(5-Phenyl-1H-imidazol-2-yl)-4-(1-propyl-1H-pyrazol-4-yl)pyridine trifluoroacetate salt | 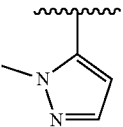 | 330.2 | 1H NMR (400 MHz, d6-DMSO) δ 8.66 (d, J = 5.3 Hz, 1H), 8.53 (s, 1H), 8.42 (s, 1H), 8.14 (s, 1H), 8.07 (s, 1H), 7.99-7.91 (m, 2H), 7.74 (dd, J = 5.2, 1.5 Hz, 1H), 7.52-7.42 (m, 2H), 7.42-7.31 (m, 1H), 4.15 (t, J = 6.9 Hz, 2H), 1.86 (h, J = 7.2 Hz, 2H), 0.87 (t, J = 7.4 Hz, 3H) |
| 13 4-(1-Methyl-1H-pyrazol-5-yl)-2-(5-phenyl-1H-imidazol-2-yl)pyridine trifluoroacetate salt | 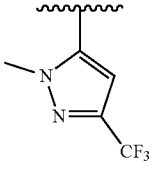 [SMILES: *c1cc(C(F)(F)F)nn1C] | 302.2 | 1H NMR (400 MHz, d6-DMSO) δ 8.85 (d, J = 5.2 Hz, 1H), 8.39 (s, 1H), 8.14 (s, 1H), 7.99-7.86 (m, 2H), 7.78 (dd, J = 5.1, 1.6 Hz, 1H), 7.61 (d, J = 1.9 Hz, 1H), 7.55-7.44 (m, 2H), 7.44-7.33 (m, 1H), 6.75 (d, J = 1.9 Hz, 1H), 4.03 (s, 3H) |
| 14 4-(1-Methyl-3-(trifluoromethyl)-1H-pyrazol-5-yl)-2-(5-phenyl-1H-imidazol-2-yl)pyridine trifluoroacetate salt | 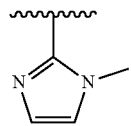 [SMILES: *c1nccn1C] | 370.1 | 1H NMR (400 MHz, d6-DMSO) δ 8.89 (d, J = 5.1 Hz, 1H), 8.41 (s, 1H), 8.09 (s, 1H), 7.99-7.91 (m, 2H), 7.82 (dd, J = 5.1, 1.5 Hz, 1H), 7.52-7.45 (m, 2H), 7.43-7.31 (m, 1H), 7.25 (s, 1H), 4.10 (s, 3H) |
| 16 4-(1-Methyl-1H-imidazol-2-yl)-2-(5-phenyl-1H-imidazol-2-yl)pyridine trifluoroacetate salt | | 302.2 | 1H NMR (400 MHz, CD3CN) δ 12.09 (br s, 3H), 8.90 (d, J = 5.1 Hz, 1H), 8.83 (s, 1H), 7.96-7.89 (m, 2H), 7.83 (dd, J = 5.1, 1.6 Hz, 1H), 7.81 (s, 1H), 7.59 (d, J = 1.8 Hz, 1H), 7.55 (d, J = 1.8 Hz, 1H), 7.53-7.48 (m, 2H), 7.48-7.42 (m, 1H), 3.99 (s, 3H) |

TABLE 1-continued

| Ex. No. | Name | R = | MS (M + H)+ | 1H NMR |
|---|---|---|---|---|
| 17 | N-(2'-(5-Phenyl-1H-imidazol-2-yl)-3,4'-bipyridin-5-yl)acetamide trifluoroacetate salt | 5-acetamido-pyridin-3-yl | 356.1 | 1H NMR (400 MHz, d6-DMSO) δ 10.48 (s, 1H), 8.87 (d, J = 5.1 Hz, 1H), 8.84 (d, J = 2.2 Hz, 1H), 8.80 (d, J = 1.9 Hz, 1H), 8.60 (t, J = 1.9 Hz, 1H), 8.57 (s, 1H), 8.13 (s, 1H), 7.99-7.93 (m, 2H), 7.91 (dd, J = 5.1, 1.3 Hz 1H), 7.51 (t, J = 7.7 Hz, 2H), 7.43-7.32 (m, 1H), 2.15 (s, 3H) |
| 18 | 4-(2'-(5-Phenyl-1H-imidazol-2-yl)-3,4'-bipyridin-5-yl)morpholine trifluoroacetate salt | 5-morpholinopyridin-3-yl | 384.2 | 1H NMR (400 MHz, d6-DMSO) δ 8.85 (d, J = 5.2 Hz, 1H), 8.60 (d, J = 1.5 Hz, 1H), 8.59 (s, 1H), 8.51 (d, J = 2.6 Hz, 1H), 8.08 (s, 1H), 8.01-7.92 (m, 4H), 7.49 (t, J = 7.7 Hz, 2H), 7.42-7.33 (m, 1H), 3.90-3.63 (m, 4H), 3.47-3.19 (m, 4H) |
| 19 | 5-Methoxy-2'-(5-phenyl-1H-imidazol-2-yl)-3,4'-bipyridine trifluoroacetate salt | 5-methoxypyridin-3-yl | 329.1 | 1H NMR (400 MHz, d6-DMSO) δ 8.88 (d, J = 5.2 Hz, 1H), 8.74 (d, J = 1.7 Hz, 1H), 8.65 (s, 1H), 8.50 (d, J = 2.7 Hz, 1H), 8.17 (s, 1H), 8.04 (dd, J = 5.1, 1.4 Hz, 1H), 7.99-7.94 (m, 2H), 7.93-7.87 (m, 1H), 7.52 (t, J = 7.6 Hz, 2H), 7.41 (t, J = 7.4 Hz, 1H), 3.99 (s, 3H) |
| 20 | 3-((4-(2-(5-Phenyl-1H-imidazol-2-yl)pyridin-4-yl)-1H-pyrazol-1-yl)methyl)benzonitrile trifluoroacetate salt | 1-(3-cyanobenzyl)-1H-pyrazol-4-yl | 403.1 | 1H NMR (400 MHz, d6-DMSO) δ 8.71-8.64 (m, 2H), 8.42 (s, 1H), 8.22 (s, 1H), 8.07 (s, 1H), 7.98-7.91 (m, 2H), 7.85-7.78 (m, 2H), 7.76 (dd, J = 5.2, 1.4 Hz, 1H), 7.68-7.58 (m, 2H), 7.52-7.46 (m, 2H), 7.40-7.34 (m, 1H), 5.52 (s, 2H) |

TABLE 1-continued

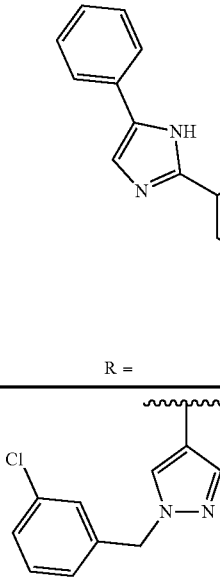

| Ex. No. | Name | R = | MS (M + H)+ | 1H NMR |
|---|---|---|---|---|
| 21 | 4-(1-(3-Chlorobenzyl)-1H-pyrazol-4-yl)-2-(5-phenyl-1H-imidazol-2-yl)pyridine trifluoroacetate salt | | 412.1 | 1H NMR (400 MHz, d6-DMSO) δ 8.68 (d, J = 5.3 Hz, 1H), 8.66 (s, 1H), 8.43 (s, 1H), 8.21 (s, 1H), 8.08 (s, 1H), 7.98-7.93 (m, 2H), 7.77 (dd, J = 5.2, 1.4 Hz, 1H), 7.50 (t, J = 7.7 Hz, 2H), 7.46-7.35 (m, 4H), 7.29 (dt, J = 6.6, 2.0 Hz, 1H), 5.46 (s, 2H) |
| 25 | 2-(5-Phenyl-1H-imidazol-2-y])-4-(1-(piperidin-4-yl)-1H-pyrazol-4-yl)pyridine trifluoroacetate salt | | 371.2 | 1H NMR (400 MHz, d6-DMSO) δ 8.91 (br, d, J = 9.4 Hz, 1H), 8.69 (d, J = 5.2 Hz, 1H), 8.67-8.55 (m, 2H), 8.48 (s, 1H), 8.22 (s, 1H), 8.09 (s, 1H), 8.01-7.92 (m, 2H), 7.80 (dd, J = 5.2, 1.4 Hz, 1H), 7.49 (t, J = 7.6 Hz, 2H), 7.38 (t, J = 7.4 Hz, 1H), 4.60 (tt, J = 10.6, 3.8 Hz, 1H), 3.46 (d, J = 12.6 Hz, 2H), 3.15 (q, J = 11.6 Hz, 2H), 2.36-2.25 (m, 2H), 2.25-2.10 (m, 2H) |
| 26 | 4-(2-(4-(2-(5-Phenyl-1H-imidazol-2-yl)pyridin-4-yl)-1H-pyrazol-1-yl)ethyl)morpholine trifluoroacetate salt | | 401.2 | 1H NMR (400 MHz, d6-DMSO) δ 8.71 (d, J = 5.2 Hz, 1H), 8.63 (s, 1H), 8.50 (s, 1H), 8.26 (s, 1H), 8.12 (s, 1H), 8.00-7.93 (m, 2H), 7.78 (dd, J = 5.2, 1.5 Hz, 1H), 7.50 (t, J = 7.6 Hz, 2H), 7.39 (t, J = 7.4 Hz, 1H), 4.67 (t, J = 6.4 Hz, 2H), 3.84 (br s, 4H), 3.72 (t, J = 6.4 Hz, 2H), 3.32 (br s, 4H) |
| 30 | Methyl 2-((4-(2-(5-phenyl-1H-imidazol-2-yl)pyridin-4-yl)-1H-pyrazol-1-yl)methyl)benzoate trifluoroacetate salt | | 436.2 | 1H NMR (400 MHz, d6-DMSO) δ 8.68 (d, J = 5.2 Hz, 1H), 8.60 (s, 1H), 8.43 (s, 1H), 8.23 (s, 1H), 8.08 (s, 1H), 7.99-7.90 (m, 3H), 7.78 (d, J = 4.5 Hz, 1H), 7.60 (td, J = 7.6, 1.2 Hz, 1H), 7.54-7.42 (m, 3H), 7.38 (t, J = 7.3 Hz, 1H), 6.99 (d, J = 7.8 Hz, 1H), 5.80 (s, 2H), 3.89 (s, 3H) |

TABLE 1-continued

| Ex. No. | Name | R = | MS (M + H)+ | 1H NMR |
|---|---|---|---|---|
| 31 | Methyl 3-((4-(2-(5-phenyl-1H-imidazol-2-yl)pyridin-4-yl)-1H-pyrazol-1-yl)methyl)benzoate trifluoroacetate salt | *pyrazole-CH2-phenyl-3-CO2Me* | 436.2 | 1H NMR (400 MHz, d6-DMSO) δ 8.71-8.63 (m, 2H), 8.42 (s, 1H), 8.22 (s, 1H), 8.06 (s, 1H), 7.99-7.88 (m, 4H), 7.78-7.70 (m, 1H), 7.67-7.60 (m, 1H), 7.55 (t, J = 1.1 Hz, 1H), 7.49 (t, J = 7.7 Hz, 2H), 7.37 (t, J = 7.4 Hz, 1H), 5.53 (s, 2H), 3.86 (s, 3H) |
| 32 | Methyl 4-((4-(2-(5-phenyl-1H-imidazol-2-yl)pyridin-4-yl)-1H-pyrazol-1-yl)methyl)benzoate trifluoroacetate salt | *pyrazole-CH2-phenyl-4-CO2Me* | 436.2 | 1H NMR (400 MHz, d6-DMSO) δ 8.68 (s, 1H), 8.65 (d, J = 5.3 Hz, 1H), 8.39 (s, 1H), 8.22 (s, 1H), 8.02-7.89 (m, 5H), 7.75-7.69 (m, 1H), 7.47 (t, J = 7.6 Hz, 2H), 7.42 (d, J = 8.3 Hz, 2H), 7.34 (t, J = 7.4 Hz, 1H), 5.54 (s, 2H), 3.84 (s, 3H) |
| 33 | 2-((4-(2-(5-Phenyl-1H-imidazol-2-yl)pyridin-4-yl)-1H-pyrazol-1-yl)methyl)benzoic acid trifluoroacetate salt | *pyrazole-CH2-phenyl-2-CO2H* | 422.2 | 1H NMR (400 MHz, d6-DMSO) δ 8.67 (d, J = 5.2 Hz, 1H), 8.60 (s, 1H), 8.42 (s, 1H), 8.23 (s, 1H), 8.06 (s, 1H), 7.99-7.93 (m, 3H), 7.78-7.74 (m, 1H), 7.56 (td, J = 7.6, 1.3 Hz, 1H), 7.51-7.41 (m, 3H), 7.37 (t, J = 7.4 Hz, 1H), 6.92 (d, J = 7.7 Hz, 1H), 5.83 (s, 2H) |
| 34 | 3-((4-(2-(5-Phenyl-1H-imidazol-2-yl)pyridin-4-yl)-1H-pyrazol-1-yl)methyl)benzoic acid trifluoroacetate salt | *pyrazole-CH2-phenyl-3-CO2H* | 422.2 | 1H NMR (400 MHz, d6-DMSO) δ 8.69 (s, 1H), 8.66 (d, J = 5.2 Hz, 1H), 8.41 (s, 1H), 8.22 (s, 1H), 8.03 (s, 1H), 7.98-7.93 (m, 2H), 7.93-7.86 (m, 2H), 7.75 (dd, J = 5.4, 1.2 Hz, 1H), 7.63-7.55 (m, 1H), 7.56-7.42 (m, 3H), 7.36 (t, J = 7.4 Hz, 1H), 5.52 (s, 2H) |

TABLE 1-continued

| Ex. No. | Name | R = | MS (M + H)+ | 1H NMR |
|---|---|---|---|---|
| 35 | 4-((4-(2-(5-Phenyl-1H-imidazol-2-yl)pyridin-4-yl)-1H-pyrazol-1-yl)methyl)benzoic acid trifluoroacetate salt | | 422.2 | 1H NMR (400 MHz, d6-DMSO) δ 8.68 (s, 1H), 8.66 (d, J = 5.3 Hz, 1H), 8.40 (s, 1H), 8.22 (s, 1H), 8.02 (s, 1H), 7.98-7.90 (m, 4H), 7.74 (d, J = 4.8 Hz, 1H), 7.48 (t, J = 7.6 Hz, 2H), 7.41 (d J = 8.2 Hz, 2H), 7.36 (t, J = 7.2 Hz, 1H), 5.53 (s, 2H) |
| 37 | 5-(4-Methylpiperazin-1-yl)-2'-(5-phenyl-1H-imidazol-2-yl)-3,4'-bipyridine trifluoroacetate salt | | 397.2 | 1H NMR (400 MHz, d6-DMSO) δ 10.20 (br s, 1H), 8.80 (d, J = 1.9 Hz, 1H), 8.77 (d, J = 5.2 Hz, 1H), 8.60 (s, 1H), 8.21 (dd, J = 9.0, 2.2 Hz, 1H), 8.17 (s, 1H), 8.00-7.87 (m, 3H), 7.52 (t, J = 7.6 Hz, 2H), 7.42 (t, J = 7.3 Hz, 1H), 7.18 (d, J = 9.0 Hz, 1H), 4.57 (br m, 2H), 3.46 (br m, J = 84.8 Hz, 2H), 3.26 (br m, 2H), 3.12 (br m, 2H), 2.88 (s, 3H) |
| 40 | 5-(Methylsulfonyl)-2'-(5-phenyl-1H-imidazol-2-yl)-3,4'-bipyridine trifluoroacetate salt | | 377.2 | 1H NMR (400 MHz, d6-DMSO) δ 9.45 (d, J = 2.1 Hz, 1H), 9.24 (d, J = 2.0 Hz, 1H), 8.93 (d, J = 5.1 Hz, 1H), 8.80 (t, J = 2.1 Hz, 1H), 8.71 (s, 1H), 8.17 (s, 1H), 8.13 (dd, J = 5.1, 1.4 Hz, 1H), 8.00-7.90 (m, 2H), 7.52 (t, J = 7.6 Hz, 2H), 7.41 (t, J = 7.4 Hz, 1H), 3.47 (s, 3H) |
| 41 | 4-(2'-(5-Phenyl-1H-imidazol-2-yl)-3,4'-bipyridin-6-yl)morpholine trifluoroacetate salt | | 384.2 | 1H NMR (400 MHz, d6-DMSO) δ 8.81-8.74 (m, 2H), 8.63 (s, 1H), 8.25 (s, 1H), 8.15 (dd, J = 9.0, 2.1 Hz, 1H), 8.02-7.90 (m, 3H), 7.54 (t, J = 7.5 Hz, 2H), 7.45 (t, J = 7.3 Hz, 1H), 7.07 (d, J = 9.0 Hz, 1H), 3.77-3.69 (m, 4H), 3.65-3.58 (m, 4H) |

TABLE 1-continued

| Ex. No. | Name | R = | MS (M + H)+ | 1H NMR |
|---|---|---|---|---|
| 43 | 4-((4-(2-(5-Phenyl-1H-imidazol-2-yl)pyridin-4-yl)-1H-pyrazol-1-yl)methyl)benzonitrile trifluoroacetate salt | (pyrazole-N-CH2-phenyl-CN) | 403.2 | 1H NMR (400 MHz, d6-DMSO) δ 8.70-8.66 (m, 2H), 8.42 (s, 1H), 8.23 (s, 1H), 8.06 (s, 1H), 7.98-7.91 (m, 2H), 7.87 (d, J = 8.2 Hz, 2H), 7.79-7.73 (m, 1H), 7.54-7.42 (m, 4H), 7.38 (t, J = 7.3 Hz, 1H), 5.57 (s, 2H) |
| 44 | 4-(1-(Methylsulfonyl)-1H-pyrazol-4-yl)-2-(5-phenyl-1H-imidazol-2-yl)pyridine trifluoroacetate salt | (pyrazole-N-SO2-CH3) | 366.2 | 1H NMR (400 MHz, d6-DMSO) δ 9.14 (s, 1H), 8.71 (s, 1H), 8.66 (d, J = 5.1 Hz, 1H), 8.45 (s, 1H), 7.96-7.92 (m, 2H), 7.86-7.78 (m, 2H), 7.41 (t, J = 7.7 Hz, 2H), 7.27 (t, J = 6.9 Hz, 1H), 3.65 (s, 3H) |
| 45 | 4-(1-(Ethylsulfonyl)-1H-pyrazol-4-yl)-2-(5-phenyl-1H-imidazol-2-yl)pyridine trifluoroacetate salt | (pyrazole-N-SO2-CH2CH3) | 380.1 | 1H NMR (400 MHz, CD3OD) δ 8.88 (s, 1H), 8.76 (br s, 1H), 8.51 (s, 1H), 8.47 (s, 1H), 7.91-7.78 (m, 4H), 7.52 (t, J = 7.5 Hz, 2H), 7.44 (t, J = 7.4 Hz, 1H), 3.69 (q, J = 7.3 Hz, 2H), 1.27 (t, J = 7.3 Hz, 3H) |
| 46 | 4-(1-(Cyclopropylsulfonyl)-1H-pyrazol-4-yl)-2-(5-phenyl-1H-imidazol-2-yl)pyridine trifluoroacetate salt | (pyrazole-N-SO2-cyclopropyl) | 392.1 | 1H NMR (400 MHz, d6-DMSO) δ 9.14 (s, 1H), 8.72 (d, J = 4.8 Hz, 1H), 8.68 (s, 1H), 8.51 (s, 1H), 8.00-7.92 (m, 3H), 7.90 (d, J = 4.5 Hz, 1H), 7.46 (t, J = 7.4 Hz, 2H), 7.33 (t, J = 7.1 Hz, 1H), 3.30-3.16 (m, 1H), 1.39-1.32 (m, 2H), 1.30-1.19 (m, 2H) |

TABLE 1-continued

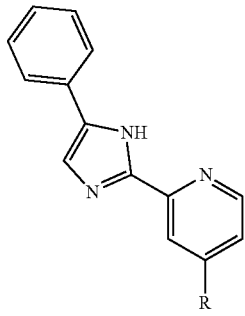

| Ex. No. | Name | R = | MS (M + H)+ | 1H NMR |
|---|---|---|---|---|
| 47 | 2-(5-Phenyl-1H-imidazol-2-yl)-4-(1-(tetrahydro-2H-pyran-4-yl)-1H-pyrazol-4-yl)pyridine trifluoroacetate salt | 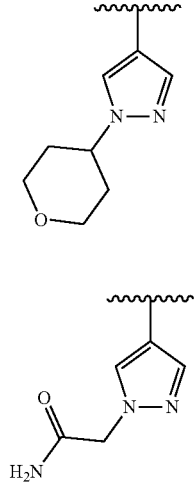 | 372.1 | = 5.3 Hz, 1H), 8.63 (s, 1H), 8.41 (s, 1H), 8.16 (s, 1H), 8.02 (s, 1H), 7.95 (d, J = 7.4 Hz, 2H), 7.74 (d, J = 4.1 Hz, 1H), 7.48 (t, J = 7.5 Hz, 2H), 7.36 (t, J = 7.2 Hz, 1H), 4.60-4.39 (m, 1H), 4.10-3.84 (m, 2H), 3.62-3.32 (m, 2H), 2.12-1.80 (m, 4H) |
| 48 | 2-(4-(2-(5-Phenyl-1H-imidazol-2-yl)pyridin-4-yl)-1H-pyrazol-1-yl)acetamide trifluoroacetate salt | 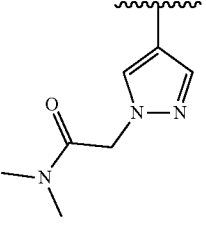 [SMILES: *c1cnn(CC(=O)N(C)C)c1] | 345.2 | 1H NMR (400 MHz, d6-DMSO) δ 8.67 (d, J = 5.1 Hz, 1H), 8.48 (s, 1H), 8.42 (s, 1H), 8.16 (s, 1H), 8.06 (s, 1H), 7.95 (d, J = 7.6 Hz, 2H), 7.76 (d, J = 4.0 Hz, 1H), 7.63 (s, 1H), 7.49 (t, J = 7.5 Hz, 2H), 7.37 (t, , J = 7.2 Hz, 1H), 7.34 (s, 1H), 4.87 (s, 2H) |
| 49 | N,N-Dimethyl-2-(4-(2-(5-phenyl-1H-imidazol-2-yl)pyridin-4-yl)-1H-pyrazol-1-yl)acetamide trifluoroacetate salt | 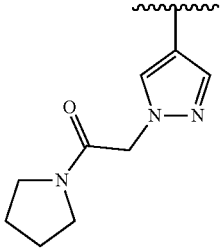 [SMILES: *c1cnn(CC(=O)N2CCCC2)c1] | 373.2 | 1H NMR (400 MHz, d6-DMSO) δ 8.69 (d, J = 5.3 Hz, 1H), 8.46 (s, 1H), 8.42 (s, 1H), 8.15 (s, 1H), 8.13 (s, 1H), 8.00-7.93 (m, 2H), 7.79 (dd, J = 5.2, 1.1 Hz, 1H), 7.51 (t, J = 7.6 Hz, 2H), 7.40 (t, J = 7.3 Hz, 1H), 5.24 (s, 2H), 3.08 (s, 3H), 2.89 (s, 3H) |
| 50 | 2-(4-(2-(5-Phenyl-1H-imidazol-2-yl)pyridin-4-yl)-1H-pyrazol-1-yl)-1-(pyrrolidin-1-yl)ethanone trifluoroacetate salt | | 399.2 | 1H NMR (400 MHz, d6-DMSO) δ 8.69 (d, J = 5.2 Hz, 1H), 8.46 (s, 1H), 8.44 (s, 1H), 8.15 (s, 1H), 8.12 (s, 1H), 7.95 (d, J = 7.4 Hz, 2H), 7.79 (d, J = 5.1 Hz, 1H), 7.50 (t, J = 7.6 Hz, 2H), 7.39 (t, J = 7.3 Hz, 1H), 5.14 (s, 2H), 3.54 (t, J = 6.8 Hz, 2H), 3.34 (t, J = 6.8 Hz, 2H), 1.94 (p, J = 6.8 Hz, 2H), 1.81 (p, J= 6.7 Hz, 2H) |

TABLE 1-continued

| Ex. No. | Name | R = | MS (M + H)+ | 1H NMR |
|---|---|---|---|---|
| 51 | 1-Morpholino-2-(4-(2-(5-phenyl-1H-imidazol-2-yl)pyridin-4-yl)-1H-pyrazol-1-yl)ethanone trifluoroacetate salt | pyrazole-CH2-C(O)-morpholine | 415.2 | 1H NMR (400 MHz, d6-DMSO) δ 8.71 (d, J = 5.1 Hz, 1H), 8.48 (s, 1H), 8.44 (s, 1H), 8.16 (s, 2H), 7.97 (d, J = 7.5 Hz, 2H), 7.81 (d, J = 4.4 Hz, 1H), 7.52 (t, J = 7.5 Hz, 2H), 7.42 (t, J = 7.3 Hz, 1H), 5.29 (s, 2H), 3.69-3.64 (m, 2H), 3.63-3.59 (m, 2H), 3.59-3.53 (m, 2H), 3.52-3.39 (m, 2H) |
| 52 | 3-(4-(2-(5-Phenyl-1H-imidazol-2-yl)pyridin-4-yl)-1H-pyrazol-1-yl)propanenitrile trifluoroacetate salt | pyrazole-CH2CH2-CN | 341.2 | 1H NMR (400 MHz, d6-DMSO) δ 8.69 (d, J = 5.2 Hz, 1H), 8.62 (s, 1H), 8.43 (s, 1H), 8.24 (s, 1H), 8.07 (s, 1H), 7.96 (d, J = 7.4 Hz, 2H), 7.76 (d, J = 4.2 Hz, 1H), 7.50 (t, J = 7.6 Hz, 2H), 7.38 (t, J = 7.2 Hz, 1H), 4.51 (t, J = 6.4 Hz, 2H), 3.17 (t, J = 6.3 Hz, 2H) |
| 53 | 3-(4-(2-(5-Phenyl-1H-imidazol-2-yl)pyridin-4-yl)-1H-pyrazol-1-yl)propanamide | pyrazole-CH2CH2-C(O)NH2 | 359.2 | 1H NMR (400 MHz, d6-DMSO) δ 8.66 (d, J = 5.2 Hz, 1H), 8.46 (s, 1H), 8.41 (s, 1H), 8.16 (s, 1H), 8.08 (s, 1H), 7.96 (d, J = 7.5 Hz, 2H), 7.75 (d, J = 5.0 Hz, 1H), 7.50 (t, J = 7.6 Hz, 2H), 7.43 (s, 1H), 7.39 (t, J = 7.4 Hz, 1H), 6.92 (s, 1H), 4.40 (t, J = 6.7 Hz, 2H), 2.71 (t, J = 6.7 Hz, 2H) |
| 54 | 4-(1-(Cyclopentylsulfonyl)-1H-pyrazol-4-yl)-2-(5-phenyl-1H-imidazol-2-yl)pyridine trifluoroacetate salt | pyrazole-N-SO2-cyclopentyl | 420.2 | 1H NMR (400 MHz, d6-DMSO) δ 9.17 (s, 1H), 8.78 (d, J = 5.1 Hz, 1H), 8.69 (s, 1H), 8.62 (s, 1H), 8.13 (s, 1H), 8.02-7.87 (m, 3H), 7.51 (t, J = 7.6 Hz, 2H), 7.40 (t, J = 7.3 Hz, 1H), 4.29 (ddd, J = 15.4, 8.7, 6.7 Hz, 1H), 2.09-1.87 (m, 4H), 1.67-1.43 (m, 4H) |

TABLE 1-continued

| Ex. No. | Name | R = | MS (M + H)⁺ | ¹H NMR |
|---|---|---|---|---|
| 55 | Ethyl 3-(4-(2-(5-phenyl-1H-imidazol-2-yl)pyridin-4-yl)-1H-pyrazol-1-yl)propanoate trifluoroacetate salt | (pyrazole linked via C4, N1-CH₂CH₂C(O)OEt) | 388.2 | ¹H NMR (400 MHz, d₆-DMSO) δ 8.68 (d, J = 5.3 Hz, 1H), 8.62 (s, 1H), 8.55 (s, 1H), 8.20 (s, 1H), 8.13 (s, 1H), 8.00 (d, J = 7.4 Hz, 2H), 1.11 (d, J = 4.5 Hz, 1H), 7.51 (t, J = 7.6 Hz, 2H), 7.40 (t, J = 7.4 Hz, 1H), 4.45 (t, J = 6.6 Hz, 2H), 4.08 (q, J = 7.1 Hz, 2H), 2.96 (t, J = 6.6 Hz, 2H), 1.17 (t, J = 7.1 Hz, 3H) |
| 56 | 2-(4-(2-(5-Phenyl-1H-imidazol-2-yl)pyridin-4-yl)-1H-pyrazol-1-yl)acetonitrile trifluoroacetate salt | (pyrazole linked via C4, N1-CH₂CN) | 327.1 | ¹H NMR (400 MHz, d₆-DMSO) δ 8.71 (d, J = 5.2 Hz, 1H), 8.64 (s, 1H), 8.55 (s, 1H), 8.34 (s, 1H), 8.10 (s, 1H), 7.98 (d, J = 7.5 Hz, 2H), 7.83-7.75 (m, 1H), 7.50 (t, J = 7.6 Hz, 2H), 7.39 (t, J = 7.3 Hz, 1H), 5.63 (s, 2H) |
| 57 | 3-(4-(2-(5-Phenyl-1H-imidazol-2-yl)pyridin-4-yl)-1H-pyrazol-1-yl)propanoic acid trifluoroacetate salt | (pyrazole linked via C4, N1-CH₂CH₂C(O)OH) | 360.1 | ¹H NMR (400 MHz, d₆-DMSO) δ 8.66 (d, J = 5.2 Hz, 1H), 8.54 (s, 1H), 8.52 (s, 1H), 8.19 (s, 1H), 8.06 (s, 1H), 7.98 (d, J = 7.4 Hz, 2H), 7.74 (d, J = 4.7 Hz, 1H), 7.49 (t, J = 7.6 Hz, 2H), 7.37 (t, J = 7.3 Hz, 1H), 4.41 (t, J = 6.6 Hz, 2H), 2.89 (t, J = 6.7 Hz, 2H) |
| 58 | N-Methyl-3-(4-(2-(5-phenyl-1H-imidazol-2-yl)pyridin-4-yl)-1H-pyrazol-1-yl)propanamide trifluoroacetate salt | (pyrazole linked via C4, N1-CH₂CH₂C(O)NHCH₃) | 373.2 | ¹H NMR (400 MHz, d₆-DMSO) δ 8.63 (d, J = 5.0 Hz, 1H), 8.47 (s, 1H), 8.37 (s, 1H), 8.15 (s, 1H), 8.01-7.92 (m, 3H), 7.93-7.86 (m, 1H), 7.70 (d, J = 4.4 Hz, 1H), 7.47 (t, J = 7.6 Hz, 2H), 7.34 (t, J = 7.4 Hz, 1H), 4.41 (t, J = 6.8 Hz, 2H), 2.71 (t, J = 6.8 Hz, 2H), 2.57 (d, J = 4.6 Hz, 3H) |

TABLE 1-continued

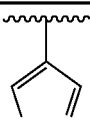

| Ex. No. | Name | R = | MS (M + H)+ | 1H NMR |
|---|---|---|---|---|
| 59 | N-cyclopentyl-3-(4-(2-(5-phenyl-1H-imidazol-2-yl)pyridin-4-yl)-1H-pyrazol-1-yl)propanamide trifluoroacetate salt | 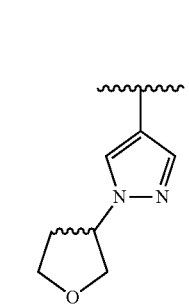 [SMILES: *c1cnn(C2CCOC2)c1] | 427.2 | 1H NMR (400 MHz, d6-DMSO) δ 8.67 (d, J = 5.3 Hz, 1H), 8.51 (s, 1H), 8.45 (s, 1H), 8.18 (s, 1H), 8.09 (s, 1H), 7.98 (d, J = 7.5 Hz, 2H), 7.91 (d, J = 7.3 Hz, 1H), 7.74 (d, J = 4.6 Hz, 1H), 7.50 (t, J = 7.6 Hz, 2H), 7.39 (t, J = 7.2 Hz, 1H), 4.41 (t, J = 6.7 Hz, 2H), 4.03-3.90 (m, 1H), 2.68 (t, J = 6.7 Hz, 2H), 1.80-1.64 (m, 2H), 1.64-1.50 (m, 2H), 1.50-1.36 (m, 2H), 1.37-1.20 (m, 2H) |
| 60 | 2-(5-Phenyl-1H-imidazol-2-yl)-4-(1-(tetrahydrofuran-3-yl)-1H-pyrazol-4-yl)pyridine trifluoroacetate salt, racemic mixture prepared | | 358.1 | 1H NMR (400 MHz, d6-DMSO) δ 8.87 (s, 1H), 8.68 (d, J = 5.2 Hz, 1H), 8.60 (s, 1H), 8.44 (s, 1H), 8.19 (s, 1H), 8.08 (s, 1H), 7.96 (d, J = 7.4 Hz, 2H), 7.81-7.75 (m, 1H), 7.50 (t, J = 7.6 Hz, 2H), 7.38 (t, J = 7.3 Hz, 1H), 5.16-5.07 (m, 1H), 4.09-3.94 (m, 3H), 3.87 (td, J = 8.4, 5.6 Hz, 1H), 2.50-2.40 (m, 1H), 2.40-2.30 (m, 1H) |

Example 61. 5-(5-Methoxy-3,4'-bipyridin-2'-yl)-1H-imidazol-2-amine

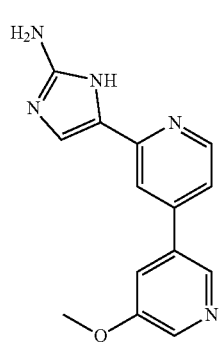 [SMILES: COc1cncc(-c2ccnc(-c3cnc(N)[nH]3)c2)c1]

Step 1. 2-(4-Chloropyridin-2-yl)imidazo[1,2-a]pyrimidine

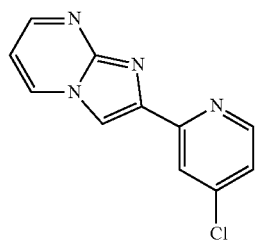 [SMILES: Clc1ccnc(-c2cn3cccnc3n2)c1]

2-Bromo-1-(4-chloropyridin-2-yl)ethanone (0.050 g, 0.21 mmol, J&W Pharmlab), 2-amino-pyrimidine (0.020 g, 0.21 mmol, Aldrich), and 4-dimethylaminopyridine (0.001 g, 0.01 mmol) were combined in CH$_3$CN (1 mL) and heated in a microwave reactor to 100° C. for 30 minutes. Upon cooling, the reaction mixture was diluted with CH$_3$CN and water and purified by preparative HPLC (C-18 column eluting with a water:acetonitrile gradient buffered at pH 10 with 0.15% ammonium hydroxide). Yield: 0.032 g, 65%. LCMS(M+H)$^+$: 231.1.

Step 2. 2'-Imidazo[1,2-a]pyrimidin-2-yl-5-methoxy-3,4'-bipyridine trifluoroacetate salt

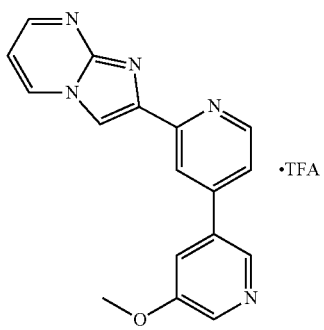 [SMILES: COc1cncc(-c2ccnc(-c3cn4cccnc4n3)c2)c1]

A mixture of 2-(4-chloropyridin-2-yl)imidazo[1,2-a]pyrimidine (0.032 g, 0.14 mmol, from Step 1), 3-methoxy-5-(4,4,5,5-tetramethyl-1,3,2-dioxaborolan-2-yl)pyridine (0.033 g, 0.14 mmol, Aldrich) and CsF (0.063 g, 0.42 mmol) in 1,4-dioxane (1 mL) and water (0.5 mL was degassed by a stream of nitrogen bubbled through the solution subsurface for 10 minutes). 4-(di-tert-Butylphosphino)-N,N-dimethylaniline-dichloropalladium (2:1) (0.015 g, 0.021 mmol, Aldrich) was added and the mixture was sealed and heated to 90° C. for 3 hours. Upon cooling to room temperature, the reaction mixture was diluted with water, CH$_3$CN, and MeOH for purification by preparative HPLC (C-18 column eluting with a water:acetonitrile gradient buffered at pH 2 with 0.1% trifluoroacetic acid). Yield: 43 mg. LCMS (M+H)$^+$: 304.1.

Step 3. 5-(5-Methoxy-3,4'-bipyridin-2'-yl)-1H-imidazol-2-amine

2'-Imidazo[1,2-a]pyrimidin-2-yl-5-methoxy-3,4'-bipyridine trifluoroacetate salt (0.043 g, 0.067 mmol, from Step 2) and hydrazine hydrate (0.023 g, 0.47 mmol) in CH$_3$CN (0.5 mL) was heated to 100° C. in the microwave for 10 minutes. The product was purified by preparative HPLC (C-18 column eluting with a water:acetonitrile gradient buffered at pH 10 with 0.15% ammonium hydroxide). Yield: 5 mg, 30%. $^1$H NMR (400 MHz, CD$_3$OD) δ 8.64 (d, J=5.2 Hz, 1H), 8.57 (d, J=1.8 Hz, 1H), 8.37 (d, J=2.7 Hz, 1H), 8.09-8.03 (m, 1H), 7.80 (dd, J=2.6, 1.9 Hz, 1H), 7.62 (dd, J=5.2, 1.7 Hz, 1H), 7.54 (s, 1H), 4.01 (s, 3H); LCMS(M+H)$^+$: 268.1.

Example 62. N-Ethyl-5-(5-methoxy-3,4'-bipyridin-2'-yl)-1H-imidazol-2-amine trifluoroacetate salt

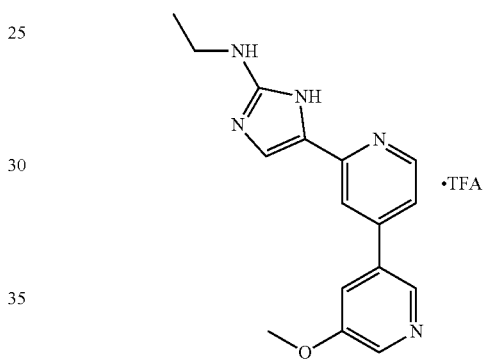

5-(5-Methoxy-3,4'-bipyridin-2'-yl)-1H-imidazol-2-amine (0.030 g, 0.11 mmol, from Example 61) was stirred with acetaldehyde (8 μL, 0.1 mmol) in MeOH (0.20 mL) and NaCNBH$_3$ (0.014 g, 0.22 mmol) and 3 Å molecular sieves were added. The reaction was stirred for 72 h. Additional NaCNBH$_3$ (0.014 g, 0.22 mmol) was added and the reaction was continued for 8 hours. The reaction was quenched by the addition of water and was purified by preparative HPLC (C-18 column eluting with a water:acetonitrile gradient buffered at pH 2 with 0.1% trifluoroacetic acid). Yield: 10 mg. $^1$H NMR (400 MHz, d$_6$-DMSO) δ 12.57 (s, 1H), 8.74 (d, J=1.6 Hz, 1H), 8.70 (d, J=5.2 Hz, 1H), 8.46 (d, J=2.7 Hz, 1H), 8.28 (s, 1H), 7.97 (t, J=5.7 Hz, 1H), 7.90 (s, 1H), 7.89-7.86 (m, 1H), 7.80 (dd, J=5.2, 1.4 Hz, 1H), 3.97 (s, 3H), 3.39 (dq, J=7.0 Hz, 2H), 1.20 (t, J=7.1 Hz, 3H); LCMS (M+H)$^+$: 296.2.

Examples 63 through 65 were synthesized according to the procedure of Example 62 and the data are listed in Table 2.

TABLE 2

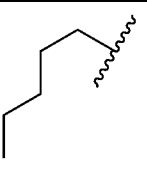

| Ex. No. | Name | R = | MS (M + H)+ | 1H NMR |
|---|---|---|---|---|
| 63 | 5-(5-Methoxy-3,4'-bipyridin-2'-yl)-N-pentyl-1H-imidazol-2-amine trifluoroacetate salt | 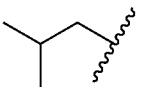 [SMILES: *CC(C)C] | 338.2 | 1H NMR (400 MHz, d6-DMSO) δ 12.45 (s, 1H), 8.73 (d, J = 1.8 Hz, 1H), 8.70 (d, J = 5.3 Hz, 1H), 8.45 (d, J = 2.7 Hz, 1H), 8.28 (s, 1H), 7.94-7.88 (m, 2H), 7.88-7.86 (m, 1H), 7.80 (dd, J = 5.3, 1.6 Hz, 1H), 3.97 (s, 3H), 3.34 (q, J = 6.7 Hz, 2H), 1.67-1.44 (m, 2H), 1.42-1.19 (m, 4H), 1.00-0.67 (m, 3H) |
| 64 | N-Isobutyl-5-(5-methoxy-3,4'-bipyridin-2'-yl)-1H-imidazol-2-amine trifluoroacetate salt |  | 324.2 | 1H NMR (400 MHz, d6-DMSO) δ 12.38 (s, 1H), 8.73 (d, J = 1.6 Hz, 1H), 8.70 (d, J = 5.2 Hz, 1H), 8.45 (d, J = 2.7 Hz, 1H), 8.29-8.26 (m, 1H), 7.94 (t, J = 6.0 Hz, 1H), 7.89 (s, 1H), 7.88-7.85 (m, 1H), 7.81 (dd, J = 5.2, 1.5 Hz, 1H), 3.97 (s, 3H), 3.19 (t, J = 6.7 Hz, 2H), 2.03-1.69 (m, 1H), 0.94 (d, J = 6.6 Hz, 6H) |
| 65 | N-(Cyclobutylmethyl)-5-(5-methoxy-3,4'-bipyridin-2'-yl)-1H-imidazol-2-amine trifluoroacetate salt | | 336.2 | 1H NMR (400 MHz, d6-DMSO) δ 12.47 (s, 1H), 8.73 (d, J = 1.7 Hz, 1H), 8.70 (d, J = 5.3 Hz, 1H), 8.45 (d, J = 2.7 Hz, 1H), 8.29-8.24 (m, 1H), 7.99 (t, J = 5.9 Hz, 1H), 7.88 (s, 1H), 7.88-7.86 (m, 1H), 7.80 (dd, J = 5.3, 1.5 Hz, 1H), 3.97 (s, 3H), 3.41 (t, J = 6.6 Hz, 2H), 2.64-2.53 (m, 1H), 2.11-1.97 (m, 2H), 1.94-1.80 (m, 2H), 1.80-1.66 (m, 2H) |

Example 66. N-Butyl-5-(5-methoxy-3,4'-bipyridin-2'-yl)-4H-1,2,4-triazol-3-amine trifluoroacetate salt

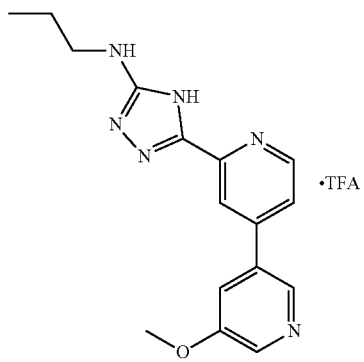 [SMILES: CCCNc1nnc(-c2cc(-c3cncc(OC)c3)ccn2)[nH]1]

Step 1. Methyl 5-methoxy-3,4'-bipyridine-2'-carboxylate

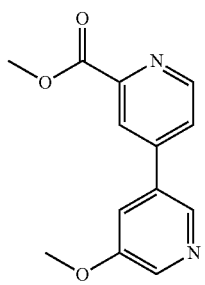 [SMILES: COC(=O)c1cc(-c2cncc(OC)c2)ccn1]

A degassed mixture of methyl 4-bromopyridine-2-carboxylate (2.0 g, 9.2 mmol, Combi-Blocks), 3-methoxy-5-(4,4,5,5-tetramethyl-1,3,2-dioxaborolan-2-yl)pyridine (2.2 g, 9.2 mmol, Aldrich), CsF (4 g, 30 mmol), and 4-(di-tert-butylphosphino)-N,N-dimethylaniline-dichloropalladium (2:1) (0.65 g, 0.92 mmol, Aldrich) in 1,4-dioxane (20 mL) and water (7 mL) was heated to 120° C. for 3.5 hours. The layers were separated and the organic layer was diluted with EtOAc and dried over Na$_2$SO$_4$, filtered, and concentrated. The product was purified by flash chromatography, eluting with a gradient from 0-100% EtOAc in hexanes. Yield: 1.64 g, 73%. $^1$H NMR (400 MHz, CDCl$_3$) δ 8.83 (d, J=5.0 Hz, 1H), 8.54 (d, J=1.8 Hz, 1H), 8.41 (d, J=2.7 Hz, 1H), 8.36 (d, J=1.7 Hz, 1H), 7.69 (dd, J=5.0, 1.8 Hz, 1H), 7.46-7.42 (m, 1H), 4.05 (s, 3H), 3.95 (s, 3H); LCMS(M+H)$^+$: 245.1.

Step 2. 5-Methoxy-3,4'-bipyridine-2'-carbohydrazide

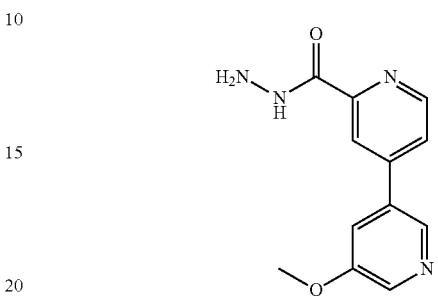

A mixture of methyl 5-methoxy-3,4'-bipyridine-2'-carboxylate (0.250 g, 1.02 mmol, from Step 1) and hydrazine hydrate (0.299 mL, 6.14 mmol) in MeOH (2.5 mL) was heated in an oil bath at 70° C. for 4 hours. Upon cooling to room temperature, the solid product was isolated by filtration, rinsed with a small amount of MeOH, and air dried. Yield: 0.19 g, 76%. $^1$H NMR (400 MHz, d$_6$-DMSO) δ 9.96 (t, J=4.2 Hz, 1H), 8.71 (dd, J=5.1, 0.6 Hz, 1H), 8.63 (d, J=1.8 Hz, 1H), 8.41 (d, J=2.8 Hz, 1H), 8.29 (dd, J=1.8, 0.6 Hz, 1H), 7.98 (dd, J=5.1, 1.9 Hz, 1H), 7.81 (dd, J=2.7, 2.0 Hz, 1H), 4.60 (d, J=4.6 Hz, 2H), 3.95 (s, 3H); LCMS(M+H)$^+$: 245.0.

Step 3. N-Butyl-5-(5-methoxy-3,4'-bipyridin-2'-yl)-4H-1,2,4-triazol-3-amine trifluoroacetate salt To N-butylthiourea (0.019 g, 0.15 mmol) in DCM (0.3 mL) was added MeI (23 μL, 0.37 mmol) and the reaction mixture was heated to 40° C. for 1 hour. The solvent was evaporated under a stream of nitrogen. Acetonitrile (0.6 mL) was added, followed by 5-methoxy-3,4'-bipyridine-2'-carbohydrazide (0.030 g, 0.12 mmol, from Step 2) and 2,6-lutidine (0.057 mL, 0.49 mmol). The reaction mixture was heated in a sealed vial to 90° C. for 14 hours, then at 120° C. for 1 hour. The product was purified by preparative HPLC (C-18 column eluting with a water:acetonitrile gradient buffered at pH 2 with 0.1% trifluoroacetic acid). Yield: 9 mg. $^1$H NMR (400 MHz, d$_6$-DMSO) δ 8.82 (d, J=5.2 Hz, 1H), 8.68 (d, J=1.7 Hz, 1H), 8.46 (d, J=2.7 Hz, 1H), 8.38-8.32 (m, 1H), 8.00 (dd, J=5.2, 1.6 Hz, 1H), 7.91-7.83 (m, 1H), 7.55 (br s, 1H), 6.86 (br s, 1H), 3.97 (s, 3H), 3.30 (t, J=7.2 Hz, 2H), 1.57 (p, J=7.4 Hz, 2H), 1.48-1.19 (m, 2H), 0.95-0.85 (m, 3H); LCMS (M+H)$^+$: 325.2.

Examples 67, 68, and 70 were synthesized according to the procedure of Example 66 and the data are listed in Table 3.

TABLE 3

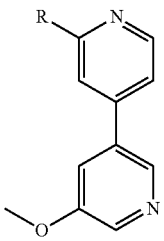

| Ex. No. | Name | R = | MS (M + H)+ | 1H NMR |
|---|---|---|---|---|
| 67 | N-Isopropyl-5-(5-methoxy-3,4'-bipyridin-2'-yl)-4H-1,2,4-triazol-3-amine trifluoroacetate salt | | 311.2 | 1H NMR (400 MHz, $d_6$-DMSO) δ 8.81 (d, J = 5.2 Hz, 1H), 8.67 (d, J = 1.8 Hz, 1H), 8.46 (d, J = 2.7 Hz, 1H), 8.36-8.31 (m, 1H), 7.99 (dd, J = 5.3, 1.6 Hz, 1H), 7.88-7.85 (m, 1H), 3.97 (s, 3H), 3.84 (hept, J = 5.8 Hz, 1H), 1.23 (d, J = 6.4 Hz, 6H) |
| 68 | 5-(5-Methoxy-3,4'-bipyridin-2'-yl)-N-methyl-4H-1,2,4-triazol-3-amine trifluoroacetate salt | | 283.2 | 1H NMR (400 MHz, $d_6$-DMSO) δ 8.83 (d, J = 5.3 Hz, 1H), 8.69 (d, J = 1.7 Hz, 1H), 8.46 (d, J = 2.7 Hz, 1H), 8.40-8.36 (m, 1H), 8.01 (dd, J = 5.2, 1.5 Hz, 1H), 7.90-7.87 (m, 1H), 3.97 (s, 3H), 2.93 (s, 3H) |
| 70 | 5-(5-Methoxy-3,4'-bipyridin-2'-yl)-N-phenyl-4H-1,2,4-triazol-3-amine trifluoroacetate salt | | 345.1 | 1H NMR (400 MHz, $CD_3OD$) δ 8.78 (d, J = 5.2 Hz, 1H), 8.68 (d, J = 1.8 Hz, 1H), 8.55 (d, J = 1.2 Hz, 1H), 8.46 (d, J = 2.7 Hz, 1H), 8.01-7.99 (m, 1H), 7.96 (dd, J = 5.4, 1.8 Hz, 1H), 7.55-7.49 (m, 2H), 7.35-7.28 (m, 2H), 7.02-6.95 (m, 1H), 4.03 (s, 3H) |

Example 71. 5-Methoxy-2'-(5-phenyl-4H-1,2,4-triazol-3-yl)-3,4'-bipyridine

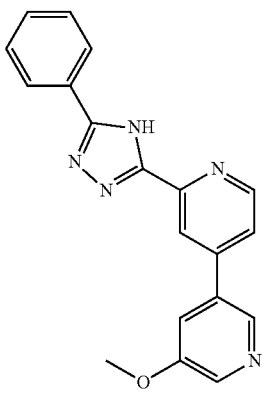 [SMILES: COc1cncc(-c2ccnc(-c3nnc(-c4ccccc4)[nH]3)c2)c1]

Step 1. 5-Methoxy-3,4'-bipyridine-2'-carbonitrile

A degassed mixture of 4-bromopyridine-2-carbonitrile (1.0 g, 5.5 mmol, Synthonix), 3-methoxy-5-(4,4,5,5-tetramethyl-1,3,2-dioxaborolan-2-yl)pyridine (1.3 g, 5.4 mmol, Aldrich), CsF (2 g, 20 mmol), and 4-(di-tert-butylphosphino)-N,N-dimethylaniline-dichloropalladium (2:1) (0.38 g, 0.54 mmol) in 1,4-dioxane (10 mL) and water (3 mL) was heated to 120° C. for 2 hours. Upon cooling, ethyl acetate and water were added into the reaction mixture and the solid product was isolated by filtration and dried under vacuum at 40° C. to afford 0.84 g of product. The filtrate, which contained product, was washed with water, followed by brine, dried over $Na_2SO_4$, filtered, and concentrated to afford crude product which was purified by trituration with DCM overnight and filtered to afford an additional 0.12 g of product. Combined yield: 0.96 g, 84%. LCMS (M+H)+: 212.1.

Step 2. 5-Methoxy-2'-(5-phenyl-4H-1,2,4-triazol-3-yl)-3,4'-bipyridine

A suspension of 5-methoxy-3,4'-bipyridine-2'-carbonitrile (30.0 mg, 0.142 mmol, from Step 1) and sodium methoxide (25 wt % in MeOH, 30.0 µL, 0.13 mmol) in MeOH (1 mL) was stirred for 2 hours. To about ⅓ of the reaction mixture was added benzhydrazide (13 mg, 0.095 mmol, Aldrich) and the mixture was heated to reflux overnight. The product was diluted with MeOH and purified by preparative HPLC (C-18 column eluting with a water:acetonitrile gradient buffered at pH 10 with 0.15% ammonium hydroxide). Yield: 9.5 mg, 60%. ¹H NMR (400 MHz, d₆-DMSO) δ 8.83 (d, J=5.0 Hz, 1H), 8.69 (s, 1H), 8.47 (s, 1H), 8.45 (d, J=2.3 Hz, 1H), 8.15 (d, J=7.3 Hz, 2H), 7.96-7.92 (m, 1H), 7.90-7.83 (m, 1H), 7.52 (t, J=7.3 Hz, 2H), 7.49-7.43 (m, 1H); LCMS (M+H)+: 330.1.

Examples 72 through 73 were synthesized according to the procedure of Example 71 and the data are listed in Table 4.

TABLE 4

| Ex. No. | Name | R = | MS (M + H)+ | ¹H NMR |
|---|---|---|---|---|
| 72 | 5-Methoxy-2'-(4H-1,2,4-triazol-3-yl)3,4'-bipyridine | H | 254.1 | ¹H NMR (400 MHz, d₆-DMSO) δ 8.72 (d, J = 5.2 Hz, 1H), 8.63 (d, J = 1.7 Hz, 1H), 8.42 (d, J = 2.7 Hz, 1H), 8.39-8.35 (m, 1H), 8.15 (s, 1H), 7.82-7.75 (m, 2H), 3.96 (s, 3H) |
| 73 | 5-Methoxy-2'-(5-methyl-4H-1,2,4-triazol-3-yl)-3,4'-bipyridine | CH₃ | 268.1 | ¹H NMR (400 MHz, d₆-DMSO) δ 8.77 (d, J = 5.1 Hz, 1H), 8.64 (d, J = 1.3 Hz, 1H), 8.42 (d, J = 2.7 Hz, 1H), 8.34 (s, 1H), 7.87 (d, J = 4.3 Hz, 1H), 7.84-7.72 (m, 1H), 3.96 (s, 3H), 2.40 (s, 3H) |

Example 74. 5-Methoxy-2'-(2-phenyl-1H-imidazol-5-yl)-3,4'-bipyridine

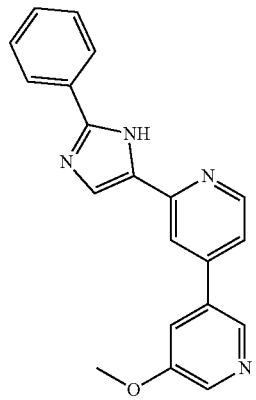 [SMILES: COc1cncc(-c2ccnc(-c3cnc(-c4ccccc4)[nH]3)c2)c1]

Step 1. 2'-Chloro-5-methoxy-3,4'-bipyridine

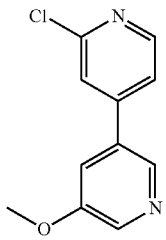

A degassed mixture of 4-bromo-2-chloropyridine (0.74 g, 3.8 mmol, Aldrich), 3-methoxy-5-(4,4,5,5-tetramethyl-1,3,2-dioxaborolan-2-yl)pyridine (0.90 g, 3.8 mmol, Aldrich), CsF (2 g, 10 mmol), and 4-(di-tert-butylphosphino)-N,N-dimethylaniline-dichloropalladium (2:1) (0.27 g, 0.38 mmol, Aldrich) in 1,4-dioxane (10 mL) and $H_2O$ (3 mL) was heated to 90° C. for 2 hours. Upon cooling, ethyl acetate and water were added and a precipitate formed. This mixture was stirred overnight and the solid product was isolated by filtration and dried under vacuum at 40° C. overnight to afford 0.35 g of product. The layers of the filtrate were separated and the organic solution was washed with water, followed by brine, dried over $Na_2SO_4$, filtered, and concentrated. The crude solid was triturated with DCM and isolated by filtration to afford a further 0.17 g of product. Yield: 0.52 g, 62%. ¹H NMR (400 MHz, d₆-DMSO) δ 8.66 (d, J=1.8 Hz, 1H), 8.52 (d, J=5.2 Hz, 1H), 8.42 (d, J=2.8 Hz, 1H), 8.03-8.00 (m, 1H), 7.88 (dd, J=5.2, 1.6 Hz, 1H), 7.85-7.82 (m, 1H); LCMS (M+H)+: 221.1.

Step 2. 5-Methoxy-2'-(2-phenyl-1H-imidazol-5-yl)-3,4'-bipyridine

To a suspension of 4-bromo-2-phenyl-1H-imidazole (0.49 g, 2.2 mmol, Matrix) in DCM (6 mL) was added di-tertbutyldicarbonate (0.53 g, 2.4 mmol) and 4-dimethylaminopyridine (DMAP, 0.026 g, 0.21 mmol). After 20 minutes, solvent was removed in vacuo. The residue was partitioned between EtOAc and water and the organic layer was washed twice with saturated NH$_4$Cl and once with brine. The organic solution was dried over sodium sulfate, filtered, and concentrated. The product was purified by flash chromatography, eluting with a gradient from 0-20% EtOAc in hexanes. Yield: 0.52 g, 73%.

A solution of the Boc-protected bromo-2-phenylimidazole (0.20 g, 0.62 mmol) in THF (4 mL) at 0° C. was treated with $^i$PrMgCl—LiCl complex in THF (1.3 M, 0.71 mL, 0.93 mmol). The reaction mixture was warmed to room temperature over 1 hour and was stirred at room temperature for an additional 2.5 hours. Additional $^i$PrMgCl—LiCl complex in THF (1.3 M, 0.50 mL, 0.65 mmol) was added. After 2 hours, the reaction mixture was cooled to 0° C. and trimethylborate (190 µL, 1.7 mmol) was added. The reaction mixture was stirred overnight with warming to room temperature. The reaction mixture was then quenched with water and extracted with EtOAc. The organic layer was washed with water, followed by brine, dried over sodium sulfate, filtered, and concentrated. The product was purified using preparative HPLC (C-18 column eluting with a water:acetonitrile gradient buffered at pH 2 with 0.1% trifluoroacetic acid) and used in the coupling reaction below.

A degassed mixture of 2'-chloro-5-methoxy-3,4'-bipyridine, potassium acetate (13.0 mg, 0.132 mmol, from Step 1), (2-phenyl-1H-imidazol-4-yl)boronic acid trifluoroacetate (7.8 mg, 0.026 mmol, prepared above) and 4-(di-tert-butylphosphino)-N,N-dimethylaniline-dichloropalladium (2:1) (2.3 mg, 0.0032 mmol, Aldrich) in 1,4-dioxane (0.3 mL) and H$_2$O (0.1 mL) was heated to 120° C. for 2 hours. The product was purified by preparative HPLC (C-18 column eluting with a water:acetonitrile gradient buffered at pH 10 with 0.15% ammonium hydroxide). Yield: 4.4 mg, 52%. $^1$H NMR (400 MHz, d$_6$-DMSO) δ 12.91 (br s, 1H), 8.69-8.60 (m, 2H), 8.43 (d, J=2.5 Hz, 1H), 8.30-8.23 (m, 1H), 8.10 (d, J=7.4 Hz, 2H), 7.91 (s, 1H), 7.83-7.78 (m, 1H), 7.67-7.58 (m, 1H), 7.49 (t, J=7.6 Hz, 2H), 7.43-7.36 (m, 1H), 3.97 (s, 3H); LCMS (M+H)$^+$: 329.1.

Example 75. N-[2-(5-Methoxy-3,4'-bipyridin-2'-yl)-4-methyl-1H-imidazol-5-yl]acetamide

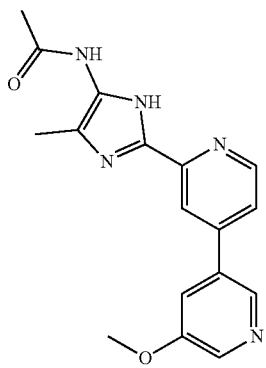 [SMILES: COc1cncc(-c2ccnc(-c3nc(C)c(NC(C)=O)[nH]3)c2)c1]

Step 1.
4-Bromo-2-(4-methyl-1H-imidazol-2-yl)pyridine

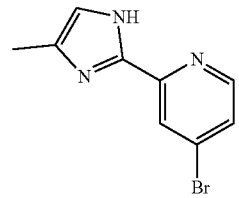

To 4-bromopyridine-2-carbonitrile (0.500 g, 2.73 mmol, Synthonix) in MeOH (3 mL) was added sodium methoxide (25 wt % in MeOH, 0.050 mL, 0.24 mmol, Aldrich) and the reaction mixture was heated at 40° C. for 1 hour. Upon cooling to room temperature, 1,1-diethoxypropan-2-amine (0.40 g, 2.7 mmol, AstaTech) and AcOH (0.3 mL) were added. The reaction mixture was heated in an oil bath held at 100° C. for 30 minutes. The reaction mixture was removed from the bath, MeOH (1.5 mL) and 6 N HCl (1.25 mL, 7.50 mmol) were added, and heating was resumed at 70° C. for 5 hours. Upon cooling to room temperature, solvent was removed via rotary evaporation. Potassium carbonate in water was added to adjust the pH to 10 and the precipitated product was stirred for 1 hour and isolated by filtration and air dried. Yield: 0.57 g, 88%. $^1$H NMR (400 MHz, d$_6$-DMSO) δ 12.65 (br s, 1H), 8.45 (d, J=5.3 Hz, 1H), 8.11 (d, J=1.6 Hz, 1H), 7.58 (dd, J=5.3, 1.9 Hz, 1H), 6.88 (s, 1H), 2.21 (s, 3H); LCMS (M+H)$^+$: 238.0/240.0.

Step 2. 4-Bromo-2-(4-methyl-5-nitro-1H-imidazol-2-yl)pyridine

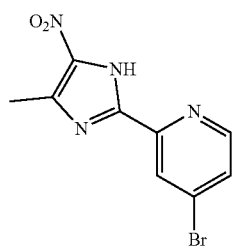 [SMILES: Cc1nc(-c2cc(Br)ccn2)[nH]c1[N+](=O)[O-]]

A solution of 4-bromo-2-(4-methyl-1H-imidazol-2-yl)pyridine (0.300 g, 1.26 mmol, from Step 1) in HNO$_3$ (1 mL) and H$_2$SO$_4$ (1 mL) was stirred at ambient temperature overnight. The reaction mixture was added to a solution of sat'd NaHCO$_3$. The yellow solid formed was isolated by filtration and air dried and used without further purification. Yield: 0.14 g, 39% yield. $^1$H NMR (400 MHz, d$_6$-DMSO) δ 8.54 (d, J=5.3 Hz, 1H), 8.20 (s, 1H), 7.73 (d, J=3.9 Hz, 1H), 2.60 (s, 3H); LCMS (M+H)$^+$: 283.0/285.0.

Step 3. N-[2-(5-Methoxy-3,4'-bipyridin-2'-yl)-4-methyl-1H-imidazol-5-yl]acetamide A mixture of 4-bromo-2-(4-methyl-5-nitro-1H-imidazol-2-yl)pyridine (0.14 g, 0.49 mmol, from Step 2) in AcOH (6 mL) was treated with iron powder (0.2 g, 4 mmol) and the mixture was heated at 60° C. for 2 hours. The reaction mixture was filtered and the acetic acid was removed from the filtrate via rotary evaporation. The residue was dissolved in MeOH, filtered, and purified by preparative HPLC (C-18 column eluting with a water:methanol gradient buffered at pH 2 with 0.1% trifluoroacetic acid). The product as the trifluoroacetate salt (0.120 g) and 3-methoxy-5-(4,4,5,5-tetramethyl-1,3,2-dioxaborolan-2-yl)pyridine (0.19 g, 0.81 mmol, Aldrich) were combined with CsF (0.18 g, 1.2 mmol) in 1,4-dioxane (4 mL) and H$_2$O (1 mL). The mixture was degassed. Dichloro(bis{di-tert-butyl[4-(dimethylamino)phenyl]phosphoranyl})palladium (0.058 g, 0.081 mmol, Aldrich) was added and the reaction mixture was sealed and heated at 90° C. for 5 hours. Upon cooling to room temperature, the reaction mixture was diluted with MeCN, filtered, and purified by preparative HPLC (C-18 column eluting with a water:acetonitrile gradient buffered at pH 2 with 0.1% trifluoroacetic acid), followed by further purification via preparative HPLC (C-18 column eluting with a water:acetonitrile gradient buffered at pH 10 with 0.15% ammonium hydroxide).

$^1$H NMR (400 MHz, CD$_3$OD) δ 8.66 (d, J=5.2 Hz, 1H), 8.56 (s, 1H), 8.33 (d, J=2.5 Hz, 1H), 8.30 (s, 1H), 7.79 (br m, 1H), 7.66-7.60 (m, 1H), 3.98 (s, 3H), 2.21 (s, 3H), 2.15 (s, 3H); LCMS(M+H)$^+$: 324.2.

Example 76. 2'-(4,5-Dimethyl-1H-imidazol-2-yl)-5-methoxy-3,4'-bipyridine

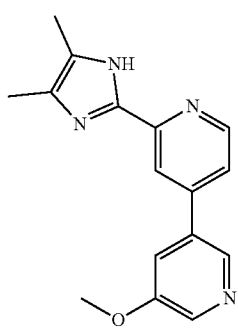 [SMILES: COc1cncc(-c2ccnc(-c3nc(C)c(C)[nH]3)c2)c1]

Step 1. 5-Methoxy-3,4'-bipyridine-2'-carboximidamide

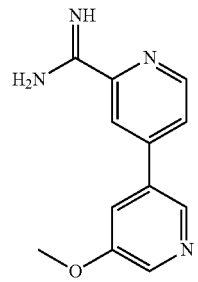

To a suspension of 5-methoxy-3,4'-bipyridine-2'-carbonitrile (0.50 g, 2.4 mmol, prepared as in Example 71, Step 1) in MeOH (4.5 mL) was added sodium methoxide (25 wt % in MeOH, 0.50 mL, 2.2 mmol) and the reaction was stirred for 4.5 hours. Ammonium chloride (0.15 g, 2.8 mmol) was added and the reaction mixture was stirred at room temperature overnight. Methanol (1 mL) was added and the reaction mixture was heated to 60° C. for 4 hours. Additional NH$_4$Cl (35 mg, 0.65 mmol) was added and heating at 60° C. was continued overnight. The methanol was then removed via rotary evaporation. The crude solid was stirred with EtOAc:H$_2$O (1:1, 20 mL) for 5 hours. The solid product was isolated by filtration and dried under vacuum at 40° C. to afford 0.24 g of product. The filtrate was concentrated to dryness via rotary evaporation and the solid was stirred with EtOAc:H$_2$O (2:1, 6 mL) overnight. Additional solid product formed was again isolated by filtration and dried under vacuum at 40° C. to afford 0.27 g of product. Combined yield: 0.51 g, 93%. LCMS (M+H)$^+$: 229.1.

Step 2. 2'-(4,5-Dimethyl-1H-imidazol-2-yl)-5-methoxy-3,4'-bipyridine

To a suspension of 5-methoxy-3,4'-bipyridine-2'-carboximidamide (10.0 mg, 0.044 mmol, from Step 1) in THF (0.3 mL) was added KHCO$_3$ (0.021 g, 0.21 mmol), followed by 3-bromo-2-butanone (5.0 μL, 0.066 mmol) and H$_2$O (75 μL). The reaction mixture was heated in a sealed vial at 100° C. for 2 hours, then at 90° C. overnight. The product was purified via preparative HPLC (C-18 column eluting with a water:acetonitrile gradient buffered at pH 10 with 0.15% ammonium hydroxide). Yield: 3.6 mg, 24%. $^1$H NMR (400 MHz, d$_6$-DMSO) δ 12.40 (s, 1H), 8.64 (d, J=5.1 Hz, 1H), 8.60 (d, J=1.6 Hz, 1H), 8.41 (d, J=2.7 Hz, 1H), 8.22-8.17 (m, 1H), 7.80-7.75 (m, 1H), 7.68 (dd, J=5.2, 1.7 Hz, 1H), 3.96 (s, 3H), 2.19 (s, 3H), 2.12 (s, 3H); LCMS (M+H)$^+$: 281.1.

Examples 77 through 88 were synthesized according to the procedure of Example 76 and the data are listed in Table 5.

TABLE 5

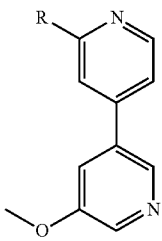

| Ex. No. | Name | R = | MS (M + H)+ | 1H NMR |
|---|---|---|---|---|
| 77 | 5-Methoxy-2'-(5-methyl-1H-imidazol-2-yl)-3,4'-bipyridine | 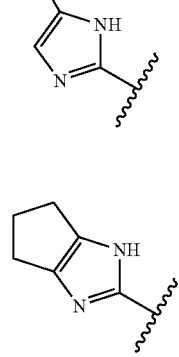 | 267.1 | 1H NMR (400 MHz, CDCl3) δ 8.99 (br s, 1H), 8.62 (d, J = 5.2 Hz, 1H), 8.55 (d, J = 1.8 Hz, 1H), 8.37 (d, J = 2.7 Hz, 1H), 7.91 (s, 1H), 7.62 (dd, J = 5.1, 1.2 Hz, 1H), 7.03 (s, 1H), 4.04 (s, 3H), 2.43 (s, 3H) |
| 78 | 2-(5-Methoxy-3,4'-bipyridin-2'-yl)-1,4,5,6-tetrahydrocyclopenta[d]imidazole | 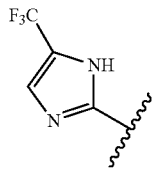 | 293.1 | 1H NMR (400 MHz, d6-DMSO) δ 12.54 (s, 1H), 8.64 (d, J = 5.1 Hz, 1H), 8.61 (s, 1H), 8.43-8.38 (m, 1H), 8.25 (s, 1H), 7.81-7.75 (m, 1H), 7.73-7.66 (m, 1H), 3.96 (s, 3H), 2.74-2.65 (m, 2H), 2.64-2.55 (m, 2H), 2.48-2.36 (m, 2H) |
| 79 | 5-Methoxy-2'-(5-(trifluoromethyl)-1H-imidazol-2-yl)-3,4'-bipyridine trifluoroacetate salt | 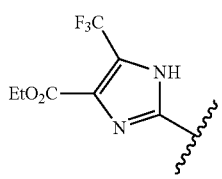 [SMILES: *c1nc(C(=O)OCC)c(C(F)(F)F)[nH]1] | 321.0 | 1H NMR (400 MHz, CD3OD) δ 8.76 (s, 1H), 8.71 (d, J = 5.0 Hz, 1H), 8.62 (s, 1H), 8.49 (s, 1H), 8.15 (s, 1H), 7.70 (d, J = 3.9 Hz, 1H), 7.54 (s, 1H), 4.07 (s, 3H) |
| 80 | Ethyl 2-(5-methoxy-3,4'-bipyridin-2'-yl)-5-(trifluoromethyl)-1H-imidazole-4-carboxylate | 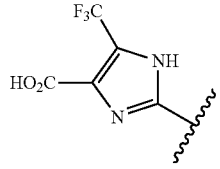 [SMILES: *c1nc(C(=O)O)c(C(F)(F)F)[nH]1] | 393.0 | 1H NMR (400 MHz, CDCl3) δ 8.73 (d, J = 5.1 Hz, 1H), 8.59 (s, 1H), 8.52-8.39 (m, 2H), 7.62 (d, J = 4.4 Hz, 1H), 7.57-7.48 (m, 1H), 4.48 (q, J = 7.0 Hz, 2H), 4.00 (s, 3H), 1.46 (t, J = 7.1 Hz, 3H) |
| 81 | 2-(5-Methoxy-3,4'-bipyridin-2'-yl)-5-(trifluoromethyl)-1H-imidazole-4-carboxylic acid trifluoroacetate salt | 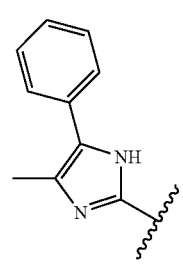 [SMILES: *c1nc(C)c(-c2ccccc2)[nH]1] | 365.0 | 1H NMR (400 MHz, d6-DMSO) δ 13.03 (s, 1H), 11.38 (s, 1H), 8.81 (d, J = 5.1 Hz, 1H), 8.63 (d, J = 1.6 Hz, 1H), 8.45 (d, J = 2.7 Hz, 1H), 8.43-8.39 (m, 1H), 7.99 (dd, J = 5.1, 1.6 Hz, 1H), 7.84-7.81 (m, 1H), 3.95 (s, 3H) |
| 82 | 5-Methoxy-2'-(4-methyl-5-phenyl-1H-imidazol-2-yl)-3,4'-bipyridine trifluoroacetate salt |  | 343.1 | 1H NMR (400 MHz, d6-DMSO) δ 12.85 (br s, 2H), 8.71 (d, J = 5.1 Hz, 1H), 8.65 (s, 1H), 8.43 (d, J = 2.2 Hz, 1H), 8.35 (s, 1H), 7.86-7.68 (m, 4H), 7.43 (t, J = 7.2 Hz, 2H), 7.26 (t, J = 7.6 Hz, 1H), 3.97 (s, 3H), 2.51 (s, 3H) |

TABLE 5-continued

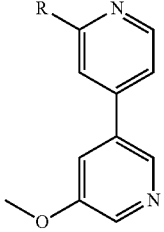

| Ex. No. | Name | R = | MS (M + H)⁺ | ¹H NMR |
|---|---|---|---|---|
| 83 | 4-(2-(5-Methoxy-3,4'-bipyridin-2'-yl)-1H-imidazol-5-yl)-N,N-dimethylbenzene-sulfonamide trifluoroacetate salt | 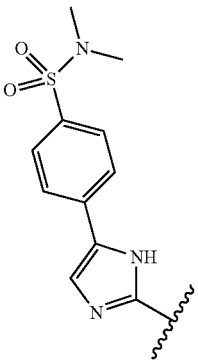 [SMILES: *c1ncc(-c2ccc(S(=O)(=O)N(C)C)cc2)[nH]1] | 436.1 | $^1$H NMR (400 MHz, d$_6$-DMSO) δ 8.80 (d, J = 5.0 Hz, 1H), 8.72 (s, 1H), 8.53-8.40 (m, 2H), 8.20 (d, J = 8.3 Hz, 2H), 8.12 (s, 1H), 7.96-7.86 (m, 2H), 7.79 (d, J = 8.4 Hz, 2H), 3.99 (s, 3H), 2.64 (s, 6H) |
| 84 | 2'-(5-Isopropyl-1H-imidazol-2-yl)-5-methoxy-3,4'-bipyridine trifluoroacetate salt | 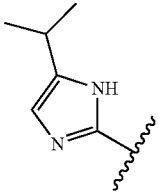 [SMILES: *c1ncc(C(C)C)[nH]1] | 295.1 | $^1$H NMR (400 MHz, d$_6$-DMSO) δ 8.92 (d, J = 5.1 Hz, 1H), 8.75-8.72 (m, 1H), 8.64 (s, 1H), 8.50 (d, J = 2.3 Hz, 1H), 8.12 (d, J = 4.2 Hz, 1H), 7.91-7.87 (m, 1H), 7.68 (s, 1H), 3.98 (s, 3H), 3.12 (hept, J = 7.5 Hz, 1H), 1.34 (d, J = 6.9 Hz, 6H) |
| 85 | 2'-(5-Ethyl-1H-imidazol-2-yl)-5-methoxy-3,4'-bipyridine trifluoroacetate salt | 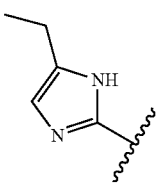 [SMILES: *c1ncc(CC)[nH]1] | 281.1 | $^1$H NMR (400 MHz, CD$_3$OD) δ 8.93-8.91 (m, 1H), 8.68 (d, J = 1.7 Hz, 1H), 8.49 (d, J = 2.7 Hz, 1H), 8.46 (dd, J = 1.5, 0.8 Hz, 1H), 8.00 (dd, J = 5.1, 1.6 Hz, 1H), 7.96 (dd, J = 2.6, 1.9 Hz, 1H), 7.52-7.48 (m, 1H), 4.05 (s, 3H), 2.88 (qd, J = 7.6, 0.7 Hz, 2H), 1.42 (t, J = 7.6 Hz, 3H) |
| 86 | 2'-(5-Cyclopropyl-1H-imidazol-2-yl)-5-methoxy-3,4'-bipyridine | 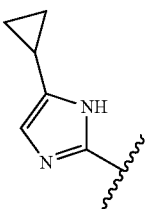 [SMILES: *c1ncc(C2CC2)[nH]1] | 293.1 | $^1$H NMR (400 MHz, d$_6$-DMSO) δ 8.66 (d, J = 5.1 Hz, 1H), 8.61 (br s, 1H), 8.42 (d, J = 2.4 Hz, 1H), 8.23 (s, 1H), 7.80-7.76 (m, 1H), 7.71 (dd, J = 5.0, 1.5 Hz, 1H), 6.97 (br s, 0.65H), 6.68 (br s, 0.35H), 3.96 (s, 3H), 1.98-1.80 (m, 1H), 0.95-0.76 (m, 2H), 0.76-0.62 (m, 2H) |

TABLE 5-continued

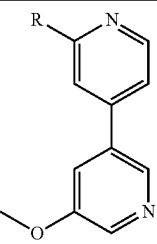

| Ex. No. | Name | R = | MS (M + H)+ | 1H NMR |
|---|---|---|---|---|
| 87 | 5-Methoxy-2'-(5-(pyridin-2-yl)-1H-imidazol-2-yl)-3,4'-bipyridine trifluoroacetate salt | | 330.1 | 1H NMR (400 MHz, CD3OD) δ 8.75 (d, J = 5.2 Hz, 1H), 8.72 (s, 1H), 8.65 (d, J = 5.3 Hz, 1H), 8.60 (d, J = 1.2 Hz, 1H), 8.40-8.30 (m, 3H), 8.22 (t, J = 7.7 Hz, 1H), 7.84 (br m, 1H), 7.67 (dd, J = 5.1, 1.4 Hz, 1H), 7.58 (t, J = 6.5 Hz, 1H), 4.02 (s, 3H) |
| 88 | 2'-(5-tert-Butyl-1H-imidazol-2-yl)-5-methoxy-3,4'-bipyridine trifluoroacetate salt | | 309.1 | 1H NMR (400 MHz, d6-DMSO) δ 8.92 (d, J = 5.1 Hz, 1H), 8.75 (d, J = 1.4 Hz, 1H), 8.68 (s, 1H), 8.50 (d, J = 2.6 Hz, 1H), 8.13 (dd, J = 5.1, 1.2 Hz, 1H), 7.94-7.82 (m, 1H), 7.66 (s, 1H), 3.98 (s, 3H), 1.41 (s, 9H) |

Example 94. 2-[4-(5-Methoxypyridin-3-yl)pyrimidin-2-yl]-1H-benzimidazole trifluoroacetate salt

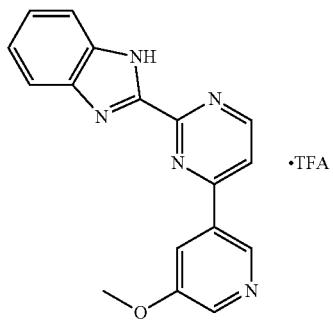 [SMILES: COc1cncc(-c2ccnc(-c3nc4ccccc4[nH]3)n2)c1]

Step 1.
2-Chloro-4-(5-methoxypyridin-3-yl)pyrimidine

A mixture of 2,4-dichloropyrimidine (0.30 g, 2.0 mmol, Aldrich), 3-methoxy-5-(4,4,5,5-tetramethyl-1,3,2-dioxaborolan-2-yl)pyridine (0.47 g, 2.0 mmol, Aldrich) and CsF (0.95 g, 6.2 mmol) in 1,4-dioxane (10 mL) and water (5 mL) was degassed by a stream of nitrogen through the solution for 10 minutes. 4-(di-tert-Butylphosphino)-N,N-dimethylaniline-dichloropalladium (2:1) (0.23 g, 0.32 mmol, Aldrich) was added and the reaction was heated to 90° C. for 3 hours. Upon cooling to room temperature, the reaction was diluted with EtOAc and the organic solution was washed with water. The aqueous layer was extracted with two further portions of EtOAc, which were combined with the original organic layer and dried over Na2SO4, filtered, and concentrated. The product was purified by flash chromatography, eluting with a gradient from 0-80% EtOAc in hexanes. 1H NMR (400 MHz, CDCl3) δ 8.82 (s, 1H), 8.70 (d, J=5.2 Hz, 1H), 8.47 (s, 1H), 7.97 (s, 1H), 7.70 (d, J=5.2 Hz, 1H), 3.97 (s, 3H); LCMS (M+H)+: 222.0/224.0.

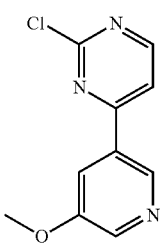

Step 2.
4-(5-Methoxypyridin-3-yl)pyrimidine-2-carbonitrile

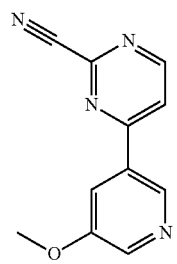 [SMILES: COc1cncc(-c2ccnc(C#N)n2)c1]

To a degassed mixture of 2-chloro-4-(5-methoxypyridin-3-yl)pyrimidine (0.21 g, 0.95 mmol, from Step 1) and zinc cyanide (1.11 g, 9.47 mmol) in DMF (10 mL) was added tetrakis(triphenylphosphine)palladium(0) (0.27 g, 0.24 mmol, Strem) and the reaction mixture was heated to 165° C. in a microwave reactor for 10 minutes. Upon cooling, the reaction mixture was diluted with water and extracted with three portions of EtOAc. The combined organic extracts were dried over $Na_2SO_4$, filtered, and concentrated. The product was purified by flash chromatography, eluting with a gradient from 0-80% EtOAc in hexanes. To remove residual DMF, the purified product was diluted with EtOAc and washed with three portions of water, then with brine, dried over $Na_2SO_4$, filtered, and concentrated. Yield: 80 mg, 40%. $^1$H NMR (400 MHz, $CDCl_3$) δ 8.91 (d, J=5.4 Hz, 1H), 8.87 (s, 1H), 8.50 (s, 1H), 8.01 (s, 1H), 7.98 (d, J=5.4 Hz, 1H), 3.98 (s, 3H). LCMS (M+H)$^+$: 213.1.

Step 3. 2-[4-(5-Methoxypyridin-3-yl)pyrimidin-2-yl]-1H-benzimidazole trifluoroacetate salt To 4-(5-methoxypyridin-3-yl)pyrimidine-2-carbonitrile (0.080 g, 0.38 mmol, from Step 2) in MeOH (2.5 mL) was added sodium methoxide (25 wt % in MeOH, 0.010 mL, 0.045 mmol) and the reaction mixture was heated to 40° C. for 1 hour. Upon cooling to room temperature, 1,2-benzenediamine (0.041 g, 0.38 mmol, Aldrich) and AcOH (0.041 mL) were added. The reaction was heated in a sealed vial in an oil bath at 100° C. for 30 minutes. The reaction vial was removed from the heating bath and after a few minutes, MeOH (1 mL) and 6.0 N HCl (0.17 mL, 1.0 mmol) were added. The reaction was not heated further, as the product had formed. The mixture was diluted with water and the product was purified by preparative HPLC (C-18 column eluting with a water:acetonitrile gradient buffered at pH 2 with 0.1% trifluoroacetic acid). Yield: 89 mg. $^1$H NMR (400 MHz, $d_6$-DMSO) δ 9.48 (d, J=1.2 Hz, 1H), 9.11 (d, J=1.6 Hz, 1H), 8.93 (d, J=1.2 Hz, 1H), 8.53 (d, J=2.8 Hz, 1H), 8.25 (dd, J=2.6, 2.0 Hz, 1H), 7.73 (dd, J=6.0, 3.2 Hz, 2H), 7.35 (dd, J=6.1, 3.2 Hz, 2H), 4.01 (s, 3H); LCMS (M+H)$^+$: 304.0. Example 95 was synthesized according to the procedure of Example 94 and the data are listed in Table 7.

TABLE 7

| Ex. No. | Name | Y | MS (M + H)$^+$ | $^1$H NMR |
|---|---|---|---|---|
| 95 | 2-[6-(5-Methoxypyridin-3-yl)pyrimidin-4-yl]-1H-benzimidazole trifluoroacetate salt | N | 304.0 | $^1$H NMR (400 MHz, $d_6$-DMSO) δ 9.38 (s, 1H), 9.27 (d, J = 5.1 Hz, 1H), 8.63_8.57 (m, 1H), 8.53 (d, J = 5.3 Hz, 1H), 8.45 (s, 1H), 7.89 (dd, J = 5.7, 2.8 Hz, 2H), 7.62 (dd, J = 5.8, 2.8 Hz, 2H), 4.03 (s, 3H) |

Example 97. 2'-(5-Methyl-1H-imidazol-2-yl)-5-morpholin-4-yl-3,4'-bipyridine

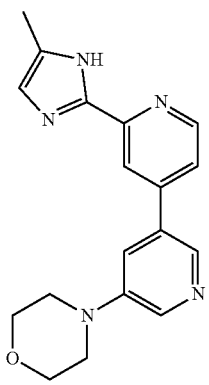 [SMILES: Cc1cnc(-c2cc(-c3cncc(N4CCOCC4)c3)ccn2)[nH]1]

Step 1. 5-Morpholin-4-yl-3,4'-bipyridine-2'-carbonitrile

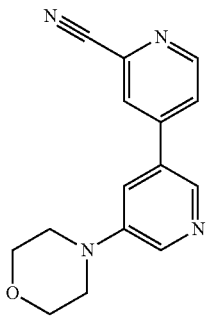 [SMILES: N#Cc1cc(-c2cncc(N3CCOCC3)c2)ccn1]

A degassed mixture of 4-bromopyridine-2-carbonitrile (0.51 g, 2.8 mmol, Synthonix), 4-[5-(4,4,5,5-tetramethyl-1,3,2-dioxaborolan-2-yl)pyridin-3-yl]morpholine (0.80 g, 2.8 mmol, Aldrich), CsF (1 g, 8 mmol), and 4-(di-tert-butylphosphino)-N,N-dimethylaniline-dichloropalladium (2:1) (0.20 g, 0.28 mmol, Aldrich) in 1,4-dioxane (7 mL) and $H_2O$ (2 mL) was heated to 120° C. for 3 hours. Upon cooling, EtOAc and water were added. The organic layer was separated, dried over $Na_2SO_4$, filtered, and concentrated. The product was purified by flash chromatography, eluting with a gradient from 0-100% EtOAc in hexanes. Yield: 0.40 g, 54%. $^1$H NMR (400 MHz, $CDCl_3$) δ 8.91 (d, J=4.4 Hz, 1H), 8.43-8.35 (m, 2H), 7.98 (s, 1H), 7.76-7.71 (m, 2H), 4.01-3.76 (m, 4H), 3.52-3.42 (m, 4H); LCMS (M+H)$^+$: 267.1.

Step 2. 5-Morpholin-4-yl-3,4'-bipyridine-2'-carboximidamide

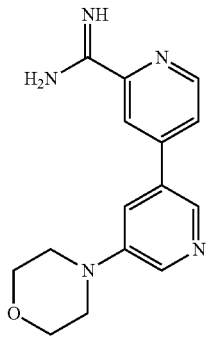 [SMILES: N=C(N)c1cc(-c2cncc(N3CCOCC3)c2)ccn1]

To a suspension of 5-morpholin-4-yl-3,4'-bipyridine-2'-carbonitrile (0.40 g, 1.5 mmol, from Step 1) in MeOH (6.0 mL) was added sodium methoxide (25 wt % in MeOH, 0.36 mL, 1.3 mmol, Aldrich). After stirring for 1.5 hours, ammonium chloride (160 mg, 3.0 mmol) was added, and the reaction was stirred overnight. Solvent was removed in vacuo and the product was triturated in water, isolated by filtration, and dried by azeotropic removal with acetonitrile. Yield: 0.39 g, 92%. $^1$H NMR (400 MHz, d$_6$-DMSO) δ 9.69 (s, 2H), 9.38 (s, 2H), 8.89 (d, J=5.1 Hz, 1H), 8.73 (s, 1H), 8.59 (s, 1H), 8.46 (d, J=2.2 Hz, 1H), 8.22 (d, J=4.1 Hz, 1H), 7.83 (s, 1H), 3.97-3.60 (m, 4H), 3.44-3.09 (m, 4H); LCMS (M+H)$^+$: 284.2.

Step 3. 2'-(5-Methyl-1H-imidazol-2-yl)-5-morpholin-4-yl-3,4'-bipyridine

To a mixture of 5-morpholin-4-yl-3,4'-bipyridine-2'-carboximidamide (15 mg, 0.053 mmol, from Step 2) and chloroacetone (5.0 µL, 0.064 mmol, Aldrich) in EtOH (0.3 mL) was added K$_2$CO$_3$ (29 mg, 0.21 mmol). The sealed reaction vial was heated to 100° C. for 1.5 hours. Additional chloroacetone (5.0 µL, 0.064 mmol) was added and heating at 100° C. was continued overnight. Upon cooling to room temperature, the reaction was diluted with MeOH and CH$_3$CN and the product was purified by preparative HPLC (C-18 column eluting with a water:acetonitrile gradient buffered at pH 2 with 0.1% trifluoroacetic acid), followed by further purification via preparative HPLC (C-18 column eluting with a water:acetonitrile gradient buffered at pH 10 with 0.15% ammonium hydroxide). $^1$H NMR (400 MHz, d$_6$-DMSO, tautomers) δ 12.63 (s, 0.5H), 12.51 (s, 0.5H), 8.64 (d, J=4.9 Hz, 1H), 8.45-8.39 (m, 2H), 8.25-8.21 (m, 1H), 7.71-7.64 (m, 2H), 6.96 (s, 0.5H), 6.79 (s, 0.5H), 3.84-3.74 (m, 4H), 3.36-3.25 (m, 4H), 2.25 (s, 1.5H), 2.20 (s, 1.5H); LCMS(M+H)$^+$: 322.1.

Examples 98 through 105 were synthesized according to the procedure of Example 97 and the data are listed in Table 8.

TABLE 8

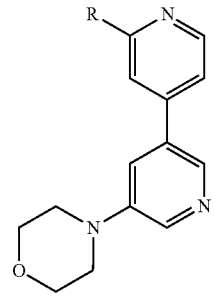

| Ex. No. | Name | R = | MS (M + H)$^+$ | $^1$H NMR |
|---|---|---|---|---|
| 98 | 4-(2'-(4,5-Dimethyl-1H-imidazol-2-yl)-3,4'-bipyridin-5-yl)morpholine trifluoroacetate salt | 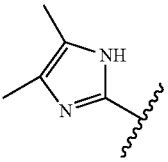 | 336.2 | $^1$H NMR (400 MHz, d$_6$-DMSO) δ 8.88 (d, J = 5.1 Hz, 1H), 8.56-8.52 (m, 2H), 8.50 (d, J = 2.6 Hz, 1H), 8.07 (dd, J = 5.2, 1.4 Hz, 1H), 7.81-7.77 (m, 1H), 3.84-3.76 (m, 4H), 3.38-3.29 (m, 4H), 2.32 (s, 6H);\ |
| 99 | 4-(2'-(5-(Trifluoromethyl)-1H-imidazol-2-yl)-3,4'-bipyridin-5-yl)morpholine trifluoroacetate salt | 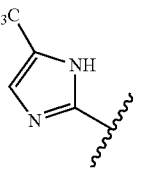 | 376.1 | $^1$H NMR (400 MHz, d$_6$-DMSO) δ 13.59 (br s, 1H), 8.77 (d, J = 5.1 Hz, 1H), 8.54-8.51 (m, 1H), 8.46 (d, J = 2.5 Hz, 1H), 8.36-8.30 (m, 1H), 7.94-7.91 (m, 1H), 7.87 (dd, J = 5.2, 1.7 Hz, 1H), 7.86-7.82 (m, 1H), 3.88-3.70 (m, 4H), 3.45-3.20 (m, 4H) |

TABLE 8-continued

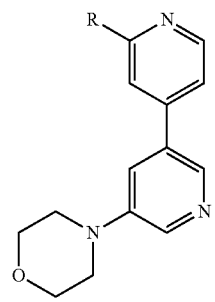

| Ex. No. | Name | R = | MS (M + H)+ | 1H NMR |
|---|---|---|---|---|
| 100 | 4-(2'-(5-Ethyl-1H-imidazol-2-yl)-3,4'-bipyridin-5-yl)morpholine trifluoroacetate salt | | 336.2 | 1H NMR (400 MHz, d6-DMSO) δ 8.88 (d, J = 5.1 Hz, 1H), 8.60 (s, 1H), 8.55 (d, J = 1.5 Hz, 1H), 8.49 (d, J = 2.6 Hz, 1H), 8.07 (dd, J = 5.2, 1.4 Hz, 1H), 7.81-7.75 (m, 1H), 7.61 (s, 1H), 3.84-3.76 (m, 4H), 3.36-3.31 (m, 4H), 2.75 (q, J = 7.5 Hz, 2H), 1.29 (t, J = 7.5 Hz, 3H) |
| 101 | 4-(2'-(5-Isopropyl-1H-imidazol-2-yl)-3,4'-bipyridin-5-yl)morpholine trifluoroacetate salt | | 350.2 | 1H NMR (400 MHz, d6-DMSO) δ 8.89 (d, J = 5.2 Hz, 1H), 8.60 (s, 1H), 8.55 (d, J = 1.6 Hz, 1H), 8.50 (d, J = 2.6 Hz, 1H), 8.09 (dd, J = 5.2, 1.4 Hz, 1H), 7.81-7.75 (m, 1H), 7.65 (s, 1H), 3.84-3.77 (m, 4H), 3.38-3.29 (m, 4H), 3.11 (hept, J = 6.8 Hz, 1H), 1.34 (d, J = 6.9 Hz, 6H) |
| 102 | 4-(2'-(5-Cyclopropyl-1H-imidazol-2-yl)-3,4'-bipyridin-5-yl)morpholine trifluoroacetate salt | | 348.3 | 1H NMR (400 MHz, d6-DMSO) δ 8.88 (d, J = 5.1 Hz, 1H), 8.61-8.57 (m, 1H), 8.56 (d, J = 1.6 Hz, 1H), 8.50 (d, J = 2.7 Hz, 1H), 8.08 (dd, J = 5.2, 1.5 Hz, 1H), 7.87-7.78 (m, 1H), 7.57 (s, 1H), 3.86-3.67 (m, 4H), 3.45-3.08 (m, 4H), 2.13-1.92 (m, 1H), 1.12-0.94 (m, 2H), 0.91-0.78 (m, 2H) |
| 103 | 4-(2'-(5-Cyclobutyl-1H-imidazol-2-yl)-3,4'-bipyridin-5-yl)morpholine trifluoroacetate salt | | 362.2 | 1H NMR (400 MHz, d6-DMSO) δ 8.90 (d, J = 5.1 Hz, 1H), 8.61 (s, 1H), 8.57 (s, 1H), 8.51 (d, J = 2.2 Hz, 1H), 8.10 (d, J = 4.7 Hz, 1H), 7.86 (s, 1H), 7.78 (s, 1H), 3.85-3.76 (m, 4H), 3.67 (p, J = 8.6 Hz, 1H), 3.41-3.27 (m, 4H), 2.44-2.18 (m, 4H), 2.14-1.98 (m, 1H), 1.98-1.83 (m, 1H) |
| 104 | 4-(2'-(5-Cyclopropyl-4-methyl-1H-imidazol-2-yl)-3,4'-bipyridin-5-yl)morpholine trifluoroacetate salt | | 362.2 | 1H NMR (400 MHz, d6-DMSO) δ 8.87 (d, J = 5.0 Hz, 1H), 8.57 (s, 1H), 8.55 (d, J = 1.1 Hz 1H), 8.50 (d, J = 2.2 Hz, 1H), 8.06 (dd, J = 5.1, 1.3 Hz 1H), 7.84-7.79 (m, 1H), 3.88-3.68 (m, 4H), 3.44-3.17 (m, 4H), 2.37 (s, 3H), 2.06-1.93 (m, 1H), 1.10-1.00 (m, 2H), 0.97-0.85 (m, 2H) |

TABLE 8-continued

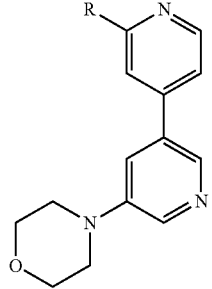

| Ex. No. | Name | R = | MS (M + H)+ | 1H NMR |
|---|---|---|---|---|
| 105 | 4-(2'-(5-Ethyl-4-methyl-1H-imidazol-2-yl)-3,4'-bipyridin-5-yl)morpholine | | 350.2 | 1H NMR (400 MHz, d6-DMSO) δ 12.38 (s, 1H), 8.62 (d, J = 5.1 Hz, 1H), 8.44-8.41 (m, 2H), 8.18 (dd, 1H), 7.67-7.65 (m, 1H), 7.64 (dd, J = 5.1, 1.7 Hz, 1H), 3.90-3.61 (m, 4H), 3.33-3.26 (m, 4H), 2.59 (q, J = 7.5 Hz, 2H), 2.20 (s, 1.5 H), 2.13 (s, 1.5 H), 1.16 (t, J = 7.5 Hz, 3H) |

Example 106. 2'-(5-Cyclohexyl-1H-imidazol-2-yl)-5-(methylsulfonyl)-3,4'-bipyridine trifluoroacetate salt

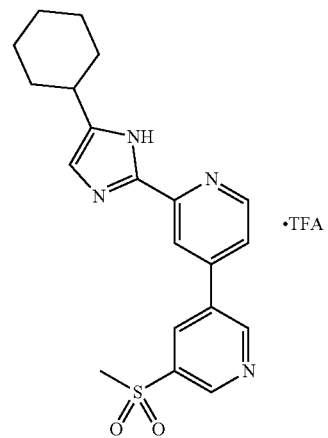 [SMILES: CS(=O)(=O)c1cncc(-c2ccnc(-c3ncc(C4CCCCC4)[nH]3)c2)c1]

Step 1. 5-(Methylsulfonyl)-3,4'-bipyridine-2'-carbonitrile

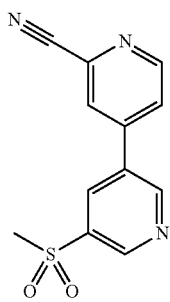 [SMILES: CS(=O)(=O)c1cncc(-c2ccnc(C#N)c2)c1]

A degassed mixture of 4-bromopyridine-2-carbonitrile (1.0 g, 5.5 mmol, Synthonix), 3-(methylsulfonyl)-5-(4,4,5,5-tetramethyl-1,3,2-dioxaborolan-2-yl)pyridine (1.5 g, 5.4 mmol, PepTech Corp.), CsF (2 g, 20 mmol), and 4-(di-tert-butylphosphino)-N,N-dimethylaniline-dichloropalladium (2:1) (0.38 g, 0.54 mmol, Aldrich) in 1,4-dioxane (10 mL) and H₂O (3 mL) was heated to 120° C. for 2 hours. Upon cooling to room temperature, the reaction mixture was diluted with CH₂Cl₂ and H₂O. The layers were shaken and separated and the organic layer was dried over Na₂SO₄, filtered, and concentrated to give a mixture of solids and oil. CH₂Cl₂ was added to this mixture and the solid product was isolated by filtration. The solid was then triturated with Et₂O. Yield: 0.71 g, 50%. ¹H NMR (400 MHz, CDCl₃) δ 9.29 (d, J=1.7 Hz, 1H), 9.16 (d, J=1.8 Hz, 1H), 8.90 (d, J=5.1 Hz, 1H), 8.46 (t, J=2.0 Hz, 1H), 8.00-7.89 (m, 1H), 7.78 (dd, J=5.1, 1.7 Hz, 1H), 3.20 (s, 3H); LCMS (M+H)⁺: 260.1.

Step 2. 5-(Methylsulfonyl)-3,4'-bipyridine-2'-carboximidamide

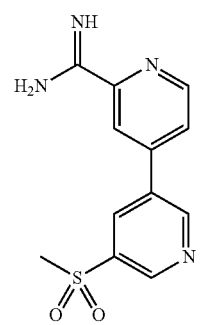 [SMILES: CS(=O)(=O)c1cncc(-c2ccnc(C(=N)N)c2)c1]

To a suspension of 5-(methylsulfonyl)-3,4'-bipyridine-2'-carbonitrile (0.70 g, 2.7 mmol, from Step 1) in MeOH (11 mL) was added sodium methoxide (25 wt % in MeOH, 0.68 mL, 2.4 mmol, Aldrich). The mixture was stirred at room temperature overnight. Ammonium chloride (290 mg, 5.4 mmol) was then added and the reaction mixture was heated to 40° C. overnight. Solvent was removed via rotary evaporation and the product was triturated with water, then isolated by filtration and dried by repeated azeotropic removal of water with acetonitrile. Yield: 0.71 g, 86%. $^1$H NMR (400 MHz, d$_6$-DMSO) δ 9.57 (br s, 3H), 9.50 (s, 1H), 9.24-9.20 (m, 1H), 8.98 (d, J=5.0 Hz, 1H), 8.89 (s, 2H), 8.36 (d, J=4.5 Hz, 1H), 3.45 (s, 3H); LCMS(M+H)$^+$: 277.1.

Step 3. 2'-(5-Cyclohexyl-1H-imidazol-2-yl)-5-(methylsulfonyl)-3,4'-bipyridine trifluoroacetate salt To a mixture of 5-(methylsulfonyl)-3,4'-bipyridine-2'-carboximidamide (16 mg, 0.053 mmol, from Step 2) and 2-bromo-1-cyclohexylethanone (16 mg, 0.079 mmol, Enamine Ltd.) in EtOH (0.3 mL) was added K$_2$CO$_3$ (29 mg, 0.21 mmol). The reaction mixture was heated to 100° C. in a sealed vial for 1.5 hours. Upon cooling to room temperature, the reaction mixture was diluted with MeOH and CH$_3$CN, filtered, and purified by preparative HPLC (C-18 column eluting with a water:acetonitrile gradient buffered at pH 2 with 0.1% trifluoroacetic acid). Yield 4.0 mg. $^1$H NMR (400 MHz, d$_6$-DMSO) δ 9.45 (s, 1H), 9.26 (s, 1H), 8.97 (d, J=5.0 Hz, 1H), 8.78 (s, 1H), 8.68 (s, 1H), 8.21 (d, J=4.5 Hz, 1H), 7.65 (s, 1H), 3.46 (s, 3H), 2.79 (t, J=10.9 Hz, 1H), 2.11-1.98 (m, 2H), 1.88-1.77 (m, 2H), 1.77-1.67 (m, 1H), 1.57-1.14 (m, 5H); LCMS (M+H)$^+$: 383.2.

Examples 107 through 119 were synthesized according to the procedure of Example 106 and the data are listed in Table 9.

TABLE 9

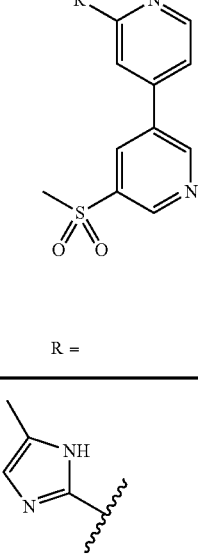

| Ex. No. | Name | R = | MS (M + H)$^+$ | $^1$H NMR |
|---|---|---|---|---|
| 107 | 2'-(5-Methyl-1H-imidazol-2-yl)-5-(methylsulfonyl)-3,4'-bipyridine trifluoroacetate salt | 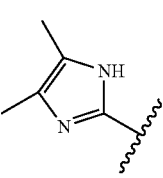 [SMILES: *c1nc(C)c(C)[nH]1] | 315.1 | $^1$H NMR (400 MHz, d$_6$-DMSO) δ 9.44 (d, J = 2.1 Hz, 1H), 9.25 (d, J = 2.0 Hz, 1H), 8.94 (d, J = 5.2 Hz, 1H), 8.77 (t, J = 2.1 Hz, 1H), 8.62 (s, 1H), 8.20-8.10 (m, 1H), 7.52 (s, 1H), 3.46 (s, 3H), 2.38 (s, 3H) |
| 108 | 2'-(4,5-Dimethyl-1H-imidazol-2-yl)-5-(methylsulfonyl)-3,4'-bipyridine trifluoroacetate salt |  | 329.2 | $^1$H NMR (400 MHz, d$_6$-DMSO) δ 9.44 (d, J = 2.1 Hz, 1H), 9.26 (d, J = 2.1 Hz, 1H), 8.95 (d, J = 5.1 Hz, 1H), 8.76 (t, J = 2.1 Hz, 1H), 8.61-8.56 (m, 1H), 8.20 (dd, J = 5.1, 1.6 Hz, 1H), 3.45 (s, 3H), 2.33 (s, 6H) |
| 109 | 5-(Methylsulfonyl)-2'-(5-(trifluoromethyl)-1H-imidazol-2-yl)-3,4'-bipyridine trifluoroacetate salt | 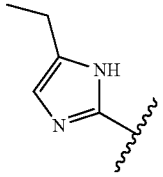 [SMILES: *c1ncc(CC)[nH]1] | 369.1 | $^1$H NMR (400 MHz, d$_6$-DMSO) δ 9.41 (d, J = 1.9 Hz, 1H), 9.17 (d, J = 1.9 Hz, 1H), 8.82 (d, J = 5.1 Hz, 1H), 8.78 (t, J = 1.9 Hz, 1H), 8.49-8.45 (m, 1H), 7.99 (dd, J = 5.2, 1.6 Hz, 1H), 7.95-7.88 (m, 1H), 3.45 (s, 3H) |
| 110 | 2'-(5-Ethyl-1H-imidazol-2-yl)-5-(methylsulfonyl)-3,4'-bipyridine trifluoroacetate salt | | 329.1 | $^1$H NMR (400 MHz, d$_6$-DMSO) δ 9.47-9.43 (m, 1H), 9.28-9.25 (m, 1H), 8.97 (d, J = 5.1 Hz, 1H), 8.79-8.77 (m, 1H), 8.69 (s, 1H), 8.25-8.19 (m, 1H), 7.68 (s, 1H), 3.46 (s, 3H), 2.77 (q, J = 7.4 Hz, 2H), 1.30 (t, J = 7.5 Hz, 3H) |

TABLE 9-continued

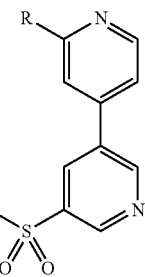

| Ex. No. | Name | R = | MS (M + H)+ | 1H NMR |
|---|---|---|---|---|
| 111 | 2'-(5-Isopropyl-1H-imidazol-2-yl)-5-(methylsulfonyl)-3,4'-bipyridine trifluoroacetate salt | | 343.2 | 1H NMR (400 MHz, d6-DMSO) δ 9.45 (d, J = 2.1 Hz, 1H), 9.26 (d, J = 2.0 Hz, 1H), 8.97 (d, J = 5.1 Hz, 1H), 8.78 (t, J = 2.1 Hz, 1H), 8.70 (s, 1H), 8.22 (dd, J = 5.2, 1.5 Hz, 1H), 7.67 (s, 1H), 3.46 (s, 3H), 3.12 (hept, J = 7.2 Hz, 1H), 1.34 (d, J = 6.9 Hz, 6H) |
| 112 | 2'-(5-Cyclopropyl-1H-imidazol-2-yl)-5-(methylsulfonyl)-3,4'-bipyridine trifluoroacetate salt | | 341.1 | 1H NMR (400 MHz, d6-DMSO) δ 9.44 (d, J = 2.1 Hz, 1H), 9.25 (d, J = 2.0 Hz, 1H), 8.94 (d, J = 5.1 Hz, 1H), 8.77 (t, J = 2.1 Hz, 1H), 8.63 (s, 1H), 8.20-8.15 (m, 1H), 7.53 (s, 1H), 3.46 (s, 3H), 2.08-1.95 (m, 1H), 1.10-0.96 (m, 2H), 0.92-0.81 (m, 2H) |
| 113 | 2'-(5-Cyclobutyl-1H-imidazol-2-yl)-5-(methylsulfonyl)-3,4'-bipyridine trifluoroacetate salt | | 355.1 | 1H NMR (400 MHz, d6-DMSO) δ 9.44 (d, J = 1.9 Hz, 1H), 9.25 (d, J = 1.8 Hz, 1H), 8.96 (d, J = 5.1 Hz, 1H), 8.79-8.75 (m, 1H), 8.68 (s, 1H), 8.21 (dd, J = 5.0, 1.0 Hz, 1H), 7.77 (s, 1H), 3.67 (p, J = 8.4 Hz, 1H), 3.45 (s, 3H), 2.43-2.19 (m, 4H), 2.12-1.97 (m, 1H), 1.97-1.83 (m, 1H) |
| 114 | 2'-(5-Cyclopentyl-1H-imidazol-2-yl)-5-(methylsulfonyl)-3,4'-bipyridine trifluoroacetate salt | | 369.1 | 1H NMR (400 MHz, d6-DMSO) δ 9.45 (d, J = 2.1 Hz, 1H), 9.26 (d, J = 2.0 Hz, 1H), 8.97 (d, J = 5.2 Hz, 1H), 8.78 (t, J = 2.1 Hz, 1H), 8.68 (s, 1H), 8.22 (dd, J = 5.2, 1.5 Hz, 1H), 7.71 (s, 1H), 3.46 (s, 3H), 3.22 (p, J = 7.5, 7.0 Hz, 1H), 2.18-2.00 (m, 2H), 1.83-1.58 (m, 6H) |
| 115 | 2'-(5-Benzyl-1H-imidazol-2-yl)-5-(methylsulfonyl)-3,4'-bipyridine trifluoroacetate salt | | 391.1 | 1H NMR (400 MHz, CD3OD) δ 9.31 (d, J = 2.1 Hz, 1H), 9.24 (d, J = 2.0 Hz, 1H), 8.93 (d, J = 5.1 Hz, 1H), 8.76 (t, J = 2.1 Hz, 1H), 8.48 (s, 1H), 8.04 (dd, J = 5.1, 1.5 Hz, 1H), 7.44 (s, 1H), 7.41-7.20 (m, 5H), 4.19 (s, 2H), 3.33 (s, 3H) |

TABLE 9-continued

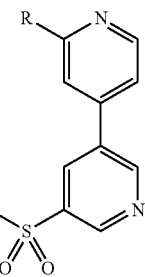

| Ex. No. | Name | R = | MS (M + H)+ | 1H NMR |
|---|---|---|---|---|
| 116 | 2'-(5-Cyclopropyl-4-methyl-1H-imidazol-2-yl)-5-(methylsulfonyl)-3,4'-bipyridine trifluoroacetate salt | | 355.1 | 1H NMR (400 MHz, d6-DMSO) δ 9.43 (d, J = 2.1 Hz, 1H), 9.25 (d, J = 2.0 Hz, 1H), 8.93 (d, J = 5.2 Hz, 1H), 8.76 (t, J = 2.1 Hz, 1H), 8.62 (s, 1H), 8.17 (dd, J = 5.1, 1.3 Hz, 1H), 3.45 (s, 3H), 2.37 (s, 3H), 2.05-1.95 (m, 1H), 1.07-1.00 (m, 2H), 0.96-0.89 (m, 2H) |
| 117 | 2'-(5-Ethyl-4-methyl-1H-imidazol-2-yl)-5-(methylsulfonyl)-3,4'-bipyridine | | 343.1 | 1H NMR (400 MHz, d6-DMSO) δ 12.45 (br s, 1H), 9.40-9.35 (m, 1H), 9.19-9.14 (m, 1H), 8.75-8.71 (m, 1H), 8.70 (d, J = 5.1 Hz, 1H), 8.33 (d, J = 10.1 Hz, 1H), 7.85-7.69 (m, 1H), 3.45 (s, 3H), 2.59 (q, J = 7.4 Hz, 2H), 2.21 (s, 1.5 H), 2.15 (s, 1.5 H), 1.17 (t, J = 7.5 Hz, 3H) |
| 118 | 5-(Methylsulfonyl)-2'-(5-(pyridin-2-yl)-1H-imidazol-2-yl)-,4'-bipyridine | | 378.1 | 1H NMR (400 MHz, d6-DMSO) δ 13.15 (br s, 1H), 9.43 (d, J = 2.0 Hz, 1H), 9.19 (d, J = 1.9 Hz, 1H), 8.80 (d, J = 5.2 Hz, 1H), 8.78 (t, J = 2.0 Hz, 1H), 8.60-8.45 (m, 2H), 8.06 (d, J = 7.7 Hz, 1H), 7.93 (dd, J = 5.1, 1.4 Hz, 1H), 7.86-7.80 (m, 2H), 7.28-7.21 (m, 1H), 3.46 (s, 3H) |
| 119 | 5-Methyl-2-(5-(methylsulfonyl)-3,4'-bipyridin-2'-yl)-1H-imidazole-4-carboxylic acid trifluoroacetate salt | | 359.1 | 1H NMR (400 MHz, d6-DMSO) δ 9.43 (d, J = 2.1 Hz, 1H), 9.21 (d, J = 2.1 Hz, 1H), 8.85 (d, J = 5.2 Hz, 1H), 8.77 (t, J = 2.1 Hz, 1H), 8.57 (s, 1H), 8.03 (dd, J = 5.2, 1.6 Hz, 1H), 3.46 (s, 3H), 2.55 (s, 3H) |

Example 120. 4-Cyclohexyl-2-[5-(methylsulfonyl)-3,4'-bipyridin-2'-yl]-1H-imidazol-5-amine trifluoroacetate salt

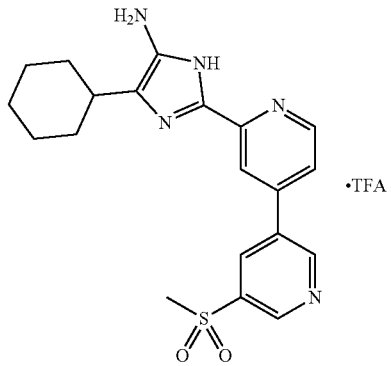 [SMILES: CS(=O)(=O)c1cncc(-c2ccnc(-c3nc(C4CCCCC4)c(N)[nH]3)c2)c1]

Step 1. 2'-(4-Cyclohexyl-5-nitro-1H-imidazol-2-yl)-5-(methylsulfonyl)-3,4'-bipyridine

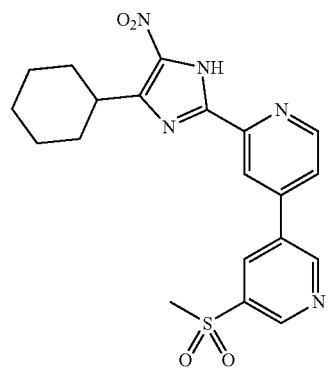 [SMILES: CS(=O)(=O)c1cncc(-c2ccnc(-c3nc(C4CCCCC4)c([N+](=O)[O-])[nH]3)c2)c1]

A solution of 2'-(5-cyclohexyl-1H-imidazol-2-yl)-5-(methylsulfonyl)-3,4'-bipyridine trifluoroacetate salt (0.040 g, 0.10 mmol, from Example 106) in HNO₃ (0.09 mL) and H₂SO₄ (0.2 mL) was stirred at room temperature for 1 hour. The reaction mixture was added into saturated NaHCO₃ and stirred for 30 minutes. The aqueous solution was extracted with three portions of EtOAc. The combined organic extracts were dried over Na₂SO₄, filtered, and concentrated. The product was used without further purification in Step 2. LCMS (M+H)⁺: 428.1.

Step 2. 4-Cyclohexyl-2-[5-(methylsulfonyl)-3,4'-bipyridin-2'-yl]-1H-imidazol-5-amine trifluoroacetate salt 2'-(4-Cyclohexyl-5-nitro-1H-imidazol-2-yl)-5-(methylsulfonyl)-3,4'-bipyridine (0.014 g, 0.033 mmol, from Step 1) in EtOH (6 mL) and H₂O (2 mL) was treated with iron (0.013 g, 0.23 mmol) and concentrated HCl (0.019 mL, 0.23 mmol) and heated to 70° C. for 2.5 hours. The reaction mixture was diluted with water and DMF and was filtered and purified by preparative HPLC (C-18 column eluting with a water:acetonitrile gradient buffered at pH 2 with 0.1% trifluoroacetic acid). Yield: 2 mg. ¹H NMR (400 MHz, CD₃OD) δ 9.31 (d, J=2.1 Hz, 1H), 9.24 (d, J=2.0 Hz, 1H), 8.84 (d, J=5.0 Hz, 1H), 8.76 (t, J=2.1 Hz, 1H), 8.43-8.39 (m, 1H), 7.92 (dd, J=5.1, 1.7 Hz, 1H), 2.91-2.78 (m, 1H), 1.95-1.83 (m, 4H), 1.83-1.74 (m, 1H), 1.74-1.56 (m, 2H), 1.56-1.24 (m, 3H); LCMS (M+H)⁺: 398.1.

Example 121. 2'-[4-(Difluoromethyl)-5-methyl-1H-imidazol-2-yl]-5-(methylsulfonyl)-3,4'-bipyridine trifluoroacetate salt

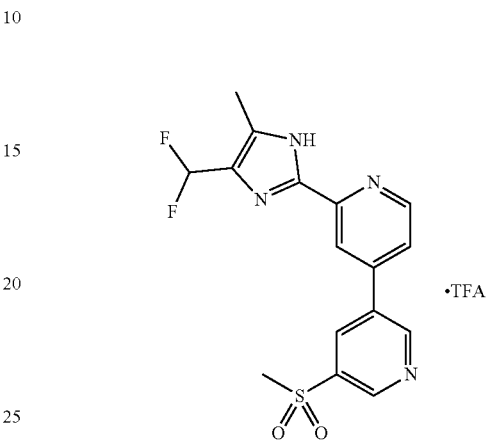

Carbon monoxide was introduced into a degassed mixture of 2'-(4-iodo-5-methyl-1-{[2-(trimethylsilyl)ethoxy]methyl}-1H-imidazol-2-yl)-5-(methylsulfonyl)-3,4'-bipyridine (0.22 g, 0.38 mmol, Peak 1 from Example 243, Step 3), Na₂CO₃ (82 mg, 0.77 mmol), [1,1'-bis(diphenylphosphino)ferrocene]dichloropalladium(II), complex with dichloromethane (1:1) (31 mg, 0.038 mmol, Aldrich) and triethylsilane (180 μL, 1.2 mmol, Aldrich) in DMF (5.5 mL) by bubbling through the reaction mixture subsurface for 3 minutes. The reaction vessel was sealed and heated to 65° C. for 2.5 hours. Upon cooling to room temperature, water was added and the mixture was extracted with EtOAc. The organic layer was washed twice with water and once with saturated NaCl solution, dried over Na₂SO₄, filtered, and concentrated. The aldehyde product was purified by flash chromatography, eluting with a gradient from 0-100% EtOAc in hexanes. Yield: 0.14 g, 77%. LCMS (M+H)+: 473.1.

To a solution of the aldehyde (10. mg, 0.021 mmol) in DCM (0.50 mL) was added Deoxofluor® (7.8 μL, 0.042 mmol) dropwise, followed by ethanol (0.25 μL, 0.0042 mmol, as a solution of 0.25 μL of EtOH in 0.10 ml DCM). The mixture was stirred overnight and then heated to 35° C. for 30 minutes. Additional Deoxofluor® (3.9 μL, 0.021 mmol) was added and the reaction was heated to 40° C. for 30 minutes. Upon cooling to room temperature, TFA (0.50 mL) was added and the reaction mixture was stirred for 1.5 hours. TFA was removed in vacuo and the product was purified by preparative HPLC (C-18 column eluting with a gradient from 8.6-26.6% acetonitrile in water containing 0.1% trifluoroacetic acid over 12 minutes). Yield: 2.1 mg. ¹H NMR (400 MHz, CD3OD) δ 9.33 (d, J=1.4 Hz, 1H), 9.22 (d, J=1.4 Hz, 1H), 8.87 (d, J=5.1 Hz, 1H), 8.80-8.72 (m, 1H), 8.54 (s, 1H), 7.97 (d, J=4.5 Hz, 1H), 7.02 (t, J=53.5 Hz, 1H), 3.30 (s, 3H), 2.50 (s, 3H); LCMS (M+H)⁺: 365.1.

Example 122. [5-Methyl-2-(5-morpholin-4-yl-3,4'-bipyridin-2'-yl)-1H-imidazol-4-yl]methanol

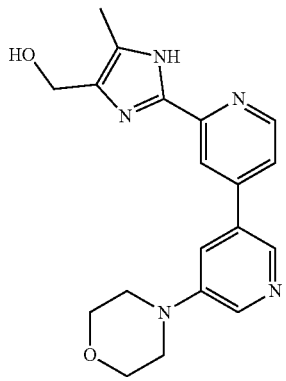 [SMILES: Cc1[nH]c(-c2cc(-c3cncc(N4CCOCC4)c3)ccn2)nc1CO]

Step 1. 2'-(5-Methyl-1H-imidazol-2-yl)-5-morpholin-4-yl-3,4'-bipyridine

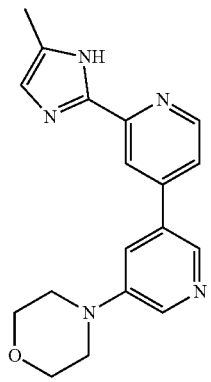

To 5-morpholin-4-yl-3,4'-bipyridine-2'-carbonitrile (0.75 g, 2.8 mmol, prepared as in Example 97, Step 1) in MeOH (11 mL) was added sodium methoxide (25 wt % in MeOH, 0.05 mL, 0.24 mmol) and the solution was stirred overnight. 1,1-Diethoxypropan-2-amine (0.41 g, 2.8 mmol, AstaTech) and acetic acid (0.32 mL) were added dropwise. The reaction was heated in a sealed vial immersed in an oil bath to 100° C. for 1 hour. The mixture was cooled to room temperature and concentrated HCl (0.60 mL, 7.2 mmol) was added. The mixture was then heated in an oil bath at 85° C. for 5.5 hours. The mixture was cooled and solvent was removed via rotary evaporation. A solution of K$_2$CO$_3$ in water was added to adjust to pH 10. The precipitated product was isolated by filtration. Yield: 0.70 g, 70%. LCMS (M+H)$^+$: 322.2.

Step 2. 2'-(4-Iodo-5-methyl-1H-imidazol-2-yl)-5-morpholin-4-yl-3,4'-bipyridine

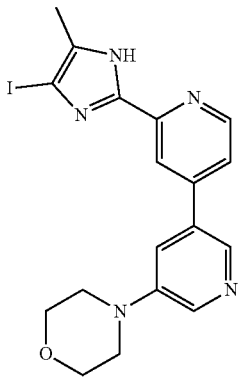 [SMILES: Cc1[nH]c(-c2cc(-c3cncc(N4CCOCC4)c3)ccn2)nc1I]

N-Iodosuccinimide (0.463 g, 2.06 mmol, Aldrich) was added to a solution of 2'-(5-methyl-1H-imidazol-2-yl)-5-morpholin-4-yl-3,4'-bipyridine (0.70 g, 2.0 mmol, from Step 1) in DMF (6.2 mL). After stirring for 20 minutes, water (50 mL) and saturated NaHCO$_3$ solution (20 mL) were added. The precipitated product was isolated by filtration and dried by repeated azeotropic removal of water by evaporation with acetonitrile. Yield: 0.86 g, 98%. LCMS (M+H)$^+$: 448.0.

Step 3. 5-Methyl-2-(5-morpholin-4-yl-3,4'-bipyridin-2'-yl)-1H-imidazole-4-carbaldehyde

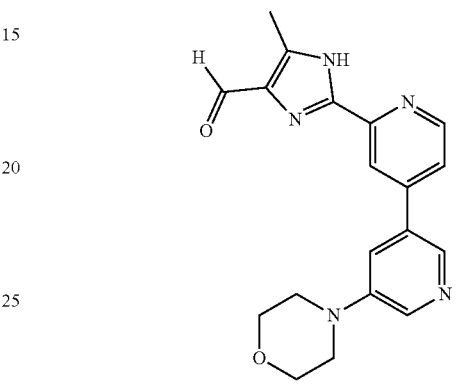

Carbon monoxide was introduced to a degassed mixture of 2'-(4-iodo-5-methyl-1H-imidazol-2-yl)-5-morpholin-4-yl-3,4'-bipyridine (0.50 g, 1.1 mmol, from Step 2), Na$_2$CO$_3$ (0.24 g, 2.2 mmol), [1,1'-bis(diphenylphosphino)ferrocene]dichloropalladium(II), complex with dichloromethane (1:1) (91 mg, 0.11 mmol, Aldrich) and triethylsilane (0.54 mL, 3.4 mmol, Aldrich) in DMF (12 mL) by bubbling the CO through the reaction mixture subsurface for 5 minutes. The reaction vessel was then sealed and heated to 65° C. for 2.5 hours. Upon cooling to room temperature, water (60 mL) was added and the aqueous mixture was saturated with NaCl to afford a precipitate that was isolated by filtration. The aqueous mixture was then extracted with three portions of DCM. The combined organic extracts were dried over Na$_2$SO$_4$, filtered, and concentrated. This material was combined with the solid isolated by the initial filtration. The product was purified by flash chromatography, eluting with a gradient from 0-5% MeOH in DCM. Yield: 0.14 g, 36%. LCMS (M+H)$^+$: 350.2.

Step 4. [5-Methyl-2-(5-morpholin-4-yl-3,4'-bipyridin-2'-yl)-1H-imidazol-4-yl]methanol 5-Methyl-2-(5-morpholin-4-yl-3,4'-bipyridin-2'-yl)-1H-imidazole-4-carbaldehyde (10. mg, 0.029 mmol, from Step 3) in EtOH (0.50 mL) was treated with NaBH$_4$ (2.2 mg, 0.057 mmol). After stirring for 1 hour at room temperature, additional NaBH$_4$ (1.1 mg, 0.029 mmol) was added. The reaction was quenched by the addition of water. The product was initially purified by preparative HPLC (C-18 column eluting with 7.3% to 27.3% MeCN in water containing 0.1% TFA over 5 minutes) and the second peak with mass M+H=352 (retention time: 6.6 min) was collected. The product was further purified by preparative HPLC (C-18 column eluting with a water:acetonitrile gradient buffered at pH 10 with 0.15% ammonium hydroxide). Yield: 2.1 mg, 21%. $^1$H NMR (400 MHz, CD$_3$OD) δ 8.85 (d, J=5.1 Hz, 1H), 8.45 (d, J=1.5 Hz, 1H), 8.43 (s, 1H), 8.41 (d, J=2.6 Hz, 1H), 7.92 (dd, J=5.1, 1.5 Hz, 1H), 7.83-7.79 (m, 1H), 4.69 (s, 2H), 3.93-3.82 (m, 4H), 3.40-3.33 (m, 4H), 2.44 (s, 3H); LCMS (M+H)⁺: 352.2.

Example 123. 2-[5-Methyl-2-(5-morpholin-4-yl-3,4'-bipyridin-2'-yl)-1H-imidazol-4-yl]ethanol

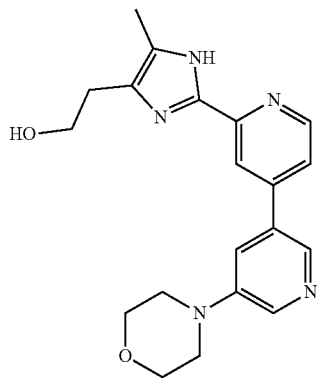 [SMILES: Cc1[nH]c(-c2cc(-c3cncc(N4CCOCC4)c3)ccn2)nc1CCO]

Step 1. 2'-{4-[(E)-2-Methoxyvinyl]-5-methyl-1H-imidazol-2-yl}-5-morpholin-4-yl-3,4'-bipyridine and 2'-{4-[(Z)-2-methoxyvinyl]-5-methyl-1H-imidazol-2-yl}-5-morpholin-4-yl-3,4'-bipyridine (Mixture of Isomers)

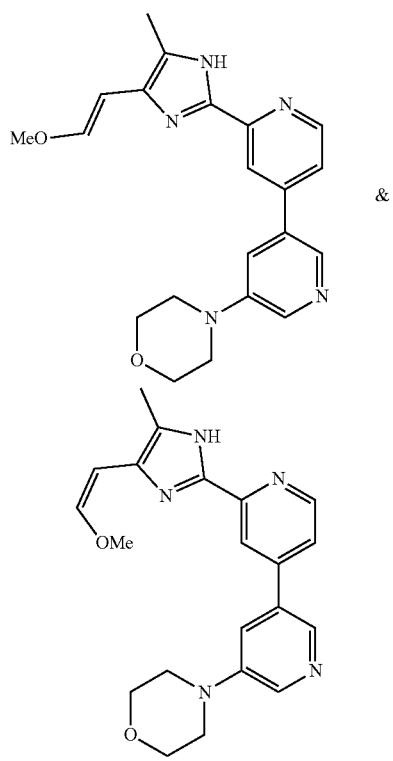

To (methoxymethyl)(triphenyl)phosphonium chloride (0.22 g, 0.64 mmol, Aldrich) in THF (6.8 mL) at 0° C. was added 1.0 M KO'Bu in THF (0.64 mL, 0.64 mmol, Aldrich). After stirring for 30 minutes at 0° C., a slurry of 5-methyl-2-(5-morpholin-4-yl-3,4'-bipyridin-2'-yl)-1H-imidazole-4-carbaldehyde (50. mg, 0.14 mmol, from Example 122, Step 3) in THF (3.4 mL) was added. The reaction mixture was stirred at 0° C. for 1.5 hours, then at room temperature for 30 minutes. Most of the THF was then removed in vacuo and the mixture was diluted with MeCN and MeOH and filtered. The product was purified by preparative HPLC (C-18 column eluting with a water:acetonitrile gradient buffered at pH 10 with 0.15% ammonium hydroxide). Yield: 33 mg, 61%. LCMS (M+H)⁺: 378.2.

Step 2. [5-Methyl-2-(5-morpholin-4-yl-3,4'-bipyridin-2'-yl)-1H-imidazol-4-yl]acetaldehyde

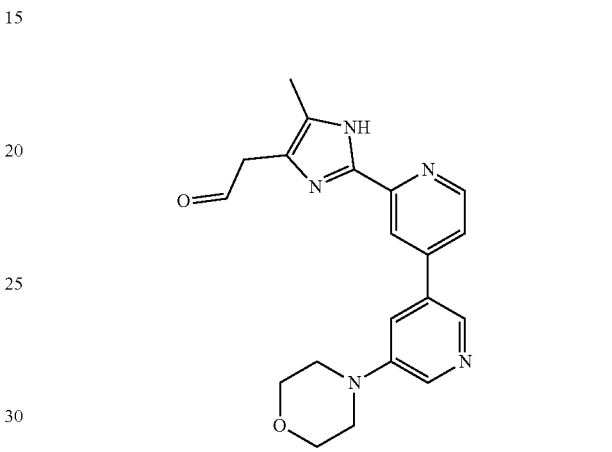

A mixture of 2'-{4-[(E)-2-methoxyvinyl]-5-methyl-1H-imidazol-2-yl}-5-morpholin-4-yl-3,4'-bipyridine and 2'-{4-[(Z)-2-methoxyvinyl]-5-methyl-1H-imidazol-2-yl}-5-morpholin-4-yl-3,4'-bipyridine (33 mg, 0.087 mmol, from Step 1) in MeCN (1.9 mL) was treated with NaI (26 mg, 0.17 mmol) and TMSCl (22 µL, 0.17 mmol). The reaction was stirred at room temperature for 3 hours, at which time additional NaI (13 mg, 0.087 mmol) and TMSCl (11 µL, 0.087 mmol) were added. After stirring for an additional 1.5 hours, the reaction was quenched by the addition of water (0.20 mL). The mixture was diluted with MeCN/MeOH (1:1, 20 mL). The mixture was filtered and solvent was removed from the filtrate in vacuo. The product was used without further purification in Step 3.

Step 3. 2-[5-Methyl-2-(5-morpholin-4-yl-3,4'-bipyridin-2'-yl)-1H-imidazol-4-yl]ethanol

[5-Methyl-2-(5-morpholin-4-yl-3,4'-bipyridin-2'-yl)-1H-imidazol-4-yl]acetaldehyde (9.0 mg, 0.025 mmol) in EtOH (0.50 mL) was treated with NaBH₄ (2.2 mg, 0.057 mmol). After stirring at room temperature for one hour, the reaction was quenched by the addition of 1.0 N HCl. The product was purified by preparative HPLC (C-18 column eluting with a water:acetonitrile gradient buffered at pH 10 with 0.15% ammonium hydroxide). Yield: 2.7 mg, 30%. ¹H NMR (400 MHz, CD₃OD) δ 8.62 (d, J=5.2 Hz, 1H), 8.41 (d, J=1.7 Hz, 1H), 8.34-8.31 (m, 2H), 7.75-7.70 (m, 1H), 7.61 (dd, J=5.2, 1.7 Hz, 1H), 3.91-3.83 (m, 4H), 3.78 (t, J=6.9 Hz, 2H), 3.36-3.31 (m, 4H), 2.82 (t, J=5.7 Hz, 2H), 2.27 (s, 3H); LCMS (M+H)⁺: 366.2.

Example 124. 1-[5-Methyl-2-(5-morpholin-4-yl-3,4'-bipyridin-2'-yl)-1H-imidazol-4-yl]ethanol (Racemic Mixture)

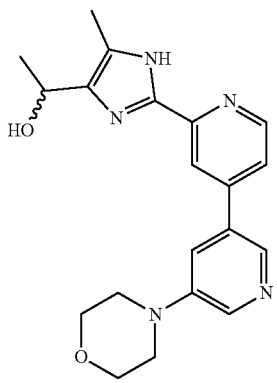 [SMILES: Cc1[nH]c(-c2cc(-c3cncc(N4CCOCC4)c3)ccn2)nc1C(C)O]

5-Methyl-2-(5-morpholin-4-yl-3,4'-bipyridin-2'-yl)-1H-imidazole-4-carbaldehyde (10. mg, 0.029 mmol) in THF (0.50 mL) at 0° C. was treated with 1.0 M methyl magnesium bromide in THF (57 µL, 0.057 mmol, Aldrich). After stirring for 20 minutes at 0° C., the reaction was quenched with 0.10 mL 1.0 N HCl. The mixture was diluted with MeOH/MeCN, filtered and purified by preparative HPLC (C-18 column eluting with a water:acetonitrile gradient buffered at pH 10 with 0.15% ammonium hydroxide). Yield: 7.2 mg, 69%. $^1$H NMR (500 MHz, d$_6$-DMSO, tautomers) δ 12.44 (s, 0.7H), 12.22 (s, 0.3H), 8.66-8.59 (m, 1H), 8.46-8.36 (m, 2H), 8.20 (s, 0.3H), 8.16 (s, 0.7H), 7.69-7.61 (m, 2H), 4.96 (br m, 0.3H), 4.86 (br m, 0.3H), 4.75 (br m, 0.7H), 4.69 (br m, 0.7H), 3.81-3.75 (m, 4H), 3.31-3.26 (m, 4H), 2.27 (s, 2H), 2.19 (s, 1H), 1.44-1.35 (m, 3H); LCMS (M+H)$^+$: 366.2.

Example 125. Methyl 5-methyl-2-(5-morpholin-4-yl-3,4'-bipyridin-2'-yl)-1H-imidazole-4-carboxylate

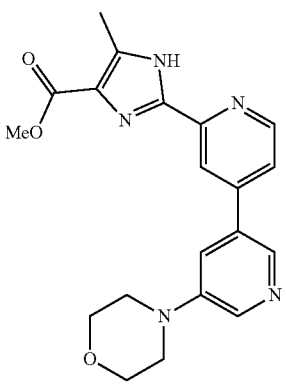 [SMILES: COC(=O)c1nc(-c2cc(-c3cncc(N4CCOCC4)c3)ccn2)[nH]c1C]

2'-(4-Iodo-5-methyl-1H-imidazol-2-yl)-5-morpholin-4-yl-3,4'-bipyridine (0.98 g, 2.2 mmol, from Example 122, Step 2) in MeOH (24 mL) containing triethylamine (0.76 mL, 5.5 mmol) was degassed by bubbling nitrogen through the solution, and [1,1'-bis(diphenylphosphino)ferrocene] dichloropalladium (II) (0.16 g, 0.22 mmol, Aldrich) was added. The slurry was then saturated with carbon monoxide by bubbling the CO gas through the reaction mixture sub- surface for 3 minutes. The reaction vessel was sealed and heated to 60° C. overnight. Additional triethylamine (0.49 mL, 3.5 mmol) and [1,1'-bis(diphenylphosphino)ferrocene] dichloropalladium(II), complex with dichloromethane (1:1) (0.14 g, 0.18 mmol) were added, and the slurry was again saturated with CO. The sealed reaction vessel was heated to about 60-65° C. for an additional 24 hours. Upon cooling to room temperature, water (50 mL) was added to the reaction mixture. The suspension was stirred for 15 minutes, and the solid product was isolated by filtration. The product was purified by flash chromatography, eluting with a gradient from 0-10% MeOH in DCM. Theoretical yield obtained. A portion was subsequently purified via preparative HPLC (C-18 column eluting with a water:acetonitrile gradient buffered at pH 2 with 0.1% TFA). $^1$H NMR (400 MHz, d$_6$-DMSO) δ 8.77 (d, J=5.1 Hz, 1H), 8.61 (d, J=1.2 Hz, 1H), 8.49 (d, J=2.6 Hz, 1H), 8.39-8.34 (m, 1H), 8.05 (s, 1H), 7.87 (dd, J=5.2, 1.7 Hz, 1H), 3.83-3.74 (m, 4H), 3.80 (s, 3H), 3.47-3.33 (m, 4H), 2.54 (s, 3H); LCMS (M+H)$^+$: 380.1.

Example 126. tert-Butyl [2'-(5-phenyl-1H-imidazol-2-yl)-3,4'-bipyridin-5-yl]carbamate

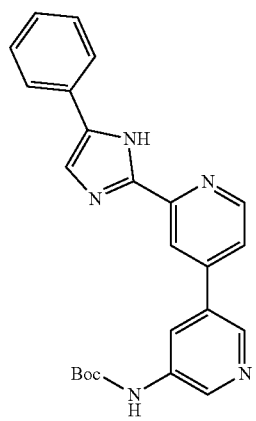 [SMILES: CC(C)(C)OC(=O)Nc1cncc(-c2ccnc(-c3ncc(-c4ccccc4)[nH]3)c2)c1]

Step 1. tert-Butyl (2'-cyano-3,4'-bipyridin-5-yl)carbamate

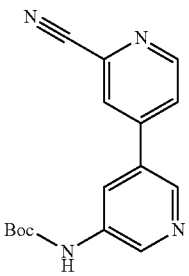 [SMILES: CC(C)(C)OC(=O)Nc1cncc(-c2ccnc(C#N)c2)c1]

A degassed mixture of 4-bromopyridine-2-carbonitrile (1.0 g, 5.5 mmol, Synthonix), tert-butyl [5-(4,4,5,5-tetramethyl-1,3,2-dioxaborolan-2-yl)pyridin-3-yl]carbamate (1.7 g, 5.4 mmol, Small Molecules, Inc.), CsF (2 g, 20 mmol, Aldrich), and 4-(di-tert-butylphosphino)-N,N-dimethylaniline-dichloropalladium (2:1) (0.38 g, 0.54 mmol) in 1,4-dioxane (10 mL) and water (3 mL) was heated to 120° C. for 70 minutes. Upon cooling to room temperature, EtOAc and water were added. The layers were shaken and separated, and the organic layer was washed twice with water, once with brine, dried over $Na_2SO_4$, filtered, and concentrated. The product was purified by flash chromatography, eluting with a gradient from 0-80% EtOAc in hexanes. Yield: 1.1 g, 68%. $^1$H NMR (400 MHz, $CDCl_3$) δ 8.81 (d, J=5.1 Hz, 1H), 8.63-8.59 (m, 2H), 8.53 (s, 1H), 7.94 (s, 1H), 7.76 (dd, J=5.0, 1.4 Hz, 1H), 7.23 (s, 1H), 1.55 (s, 9H); LCMS $(M+H)^+$: 297.2.

Step 2. tert-Butyl {2'-[amino(imino)methyl]-3,4'-bipyridin-5-yl}carbamate

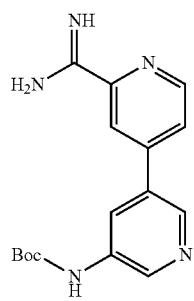 [SMILES: CC(C)(C)OC(=O)Nc1cncc(-c2ccnc(C(=N)N)c2)c1]

To a suspension of tert-butyl (2'-cyano-3,4'-bipyridin-5-yl)carbamate (1.1 g, 3.7 mmol, from Step 1) in MeOH (15 mL) was added sodium methoxide (25 wt % in MeOH, 0.93 mL, 3.3 mmol). The mixture was stirred at room temperature for 1.5 hours. Ammonium chloride (0.40 g, 7.4 mmol) was then added and the reaction was stirred overnight. Solvent was removed in vacuo and the solid was triturated with a mixture of water and ether and isolated by filtration. The aqueous layer of the filtrate was then extracted with $CHCl_3$ (3 times) to wash out a small impurity. The volume of the aqueous mixture was reduced via rotary evaporation and solid NaCl was added to precipitate additional solid product, which was isolated by filtration. Combined yield: 1.0 g, yield 86%. $^1$H NMR (400 MHz, $d_6$-DMSO) δ 9.85 (s, 1H), 9.69 (br s, 2H), 9.48 (br s, 2H), 8.91 (d, J=5.1 Hz, 1H), 8.78-8.72 (m, 1H), 8.72-8.62 (m, 2H), 8.42 (s, 1H), 8.13-8.00 (m, 1H), 1.51 (s, 9H); LCMS $(M+H)^+$: 314.2.

Step 3. tert-Butyl [2'-(5-phenyl-1H-imidazol-2-yl)-3,4'-bipyridin-5-yl]carbamate To a mixture of tert-butyl {2'-[amino(imino)methyl]-3,4'-bipyridin-5-yl}carbamate (0.30 g, 0.96 mmol, from Step 2) and 2-bromoacetophenone (0.28 g, 1.4 mmol, Aldrich) in EtOH (5.0 mL) was added $K_2CO_3$ (0.53 g, 3.8 mmol). The mixture was sealed and heated in a sealed vessel to 80° C. for 1 hour. Additional 2-bromoacetophenone (95 mg, 0.48 mmol) was added and heating was continued for 40 minutes. Upon cooling to room temperature, the reaction mixture was diluted with $CH_2Cl_2$, filtered, and concentrated. The product was purified by flash chromatography, eluting with a gradient of 0-5% MeOH in $CH_2Cl_2$. The product so obtained was further purified by trituration with $Et_2O$. Yield: 0.12 g, 29%. $^1$H NMR (400 MHz, $d_6$-DMSO) δ 13.04 (s, 1H), 9.79 (s, 1H), 8.77 (s, 1H), 8.72 (d, J=5.1 Hz, 1H), 8.68 (d, J=1.9 Hz, 1H), 8.35-8.30 (m, 1H), 7.92 (d, J=7.6 Hz, 2H), 7.80 (d, J=1.9 Hz, 1H), 7.73-7.70 (m, 1H), 7.43-7.35 (m, 2H), 7.27-7.17 (m, 1H), 1.52 (s, 9H); LCMS $(M+H)^+$: 414.2.

Example 127. 2'-(5-Phenyl-1H-imidazol-2-yl)-3,4'-bipyridin-5-amine trifluoroacetate salt

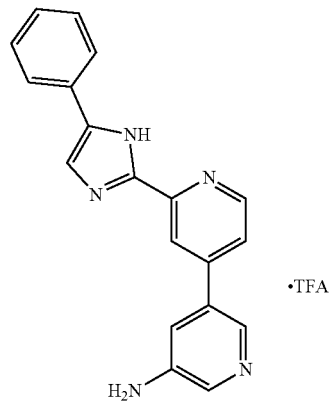 [SMILES: Nc1cncc(-c2ccnc(-c3ncc(-c4ccccc4)[nH]3)c2)c1]

A solution of tert-butyl [2'-(5-phenyl-1H-imidazol-2-yl)-3,4'-bipyridin-5-yl]carbamate (80. mg, 0.19 mmol, from Example 126) in $CH_2Cl_2$ (5 mL) was treated with 4.0 M HCl in dioxane (0.97 mL, 3.9 mmol) overnight. Volatiles were removed in vacuo and the mixture was neutralized by the addition of aqueous $NH_4OH$. The product was purified by purified by preparative HPLC (C-18 column eluting with a water:acetonitrile gradient buffered at pH 2 with 0.1% trifluoroacetic acid). Yield: 56 mg. $^1$H NMR (400 MHz, $d_6$-DMSO) δ 8.84 (d, J=5.2 Hz, 1H), 8.49 (s, 2H), 8.14 (d, J=2.3 Hz, 1H), 8.00-7.92 (m, 3H), 7.88 (br m, 1H), 7.83 (dd, J=5.1, 1.4 Hz, 1H), 7.46 (t, J=7.7 Hz, 2H), 7.33 (t, J=7.4 Hz, 1H); LCMS$(M+H)^+$: 314.1.

Examples 128 through 129 were synthesized according to the procedure of Example 126 and 127, and the data are listed in Table 10.

TABLE 10

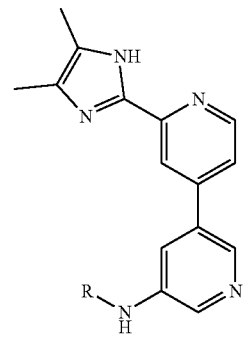

| Ex. No. | Name | R = | MS $(M + H)^+$ | $^1$H NMR |
|---|---|---|---|---|
| 128 | tert-Butyl [2'-(4,5-dimethyl-1H-imidazol-2-yl)-3,4'-bipyridin-5-yl]carbamate | Boc | 365.9 | $^1$H NMR (400 MHz, $CDCl_3$) δ 10.04 (s, 1H), 8.62 (d, J = 1.8 Hz, 1H), 8.54 (d, J = 5.1 Hz, 1H), 8.50 (d, J = 2.4 Hz, 1H), 8.31 (s, 1H), 8.30-8.26 (m, 1H), 7.40 (dd, J = 5.1, 1.6 Hz, 1H), 6.72 (s, 1H), 2.26 (s, 6H), 1.55 (s, 9H) |

TABLE 10-continued

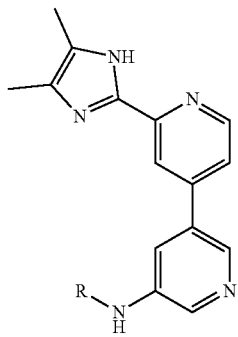

| Ex. No. | Name | R = | MS (M + H)+ | 1H NMR |
|---|---|---|---|---|
| 129 | 2'-(4,5-Dimethyl-1H-imidazol-2-yl)-3,4'-bipyridin-5-amine | H | 266.1 | 1H NMR (400 MHz, d6-DMSO, tautomers) δ 12.38 (s, 1H), 8.59 (d, J = 5.1 Hz, 1H), 8.18 (d, J = 1.9 Hz, 1H), 8.14-8.08 (m, 1H), 8.04 (d, J = 2.5 Hz, 1H), 7.56 (dd, J = 5.2, 1.8 Hz, 1H), 7.36 (t, J = 2.2 Hz, 1H), 2.18 (s, 3H), 2.11 (s, 3H) |

Example 130. N-[2'-(5-Phenyl-1H-imidazol-2-yl)-3,4'-bipyridin-5-yl]ethanesulfonamide trifluoroacetate salt

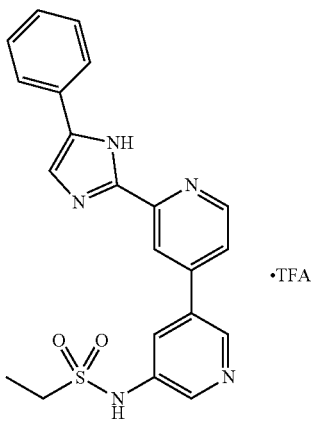 [SMILES: CCS(=O)(=O)Nc1cncc(-c2ccnc(-c3ncc(-c4ccccc4)[nH]3)c2)c1]

2'-(5-Phenyl-1H-imidazol-2-yl)-3,4'-bipyridin-5-amine trifluoroacetate salt (10. mg, 0.015 mmol, from Example 127) in CH$_2$Cl$_2$ (1.0 mL) was treated with N,N-diisopropylethylamine (16 µL, 0.092 mmol), and ethanesulfonyl chloride (2.9 µL, 0.030 mmol, Aldrich). After 70 minutes, solvent was removed under reduced pressure and the residue was treated with aqueous NH$_4$OH (0.2 mL) in MeOH (1 mL) for 30 minutes. Volatiles were removed in vacuo and the product was purified by preparative HPLC (C-18 column eluting with a water:acetonitrile gradient buffered at pH 2 with 0.1% trifluoroacetic acid). 1H NMR (400 MHz, d$_6$-DMSO) δ 10.34 (s, 1H), 8.87 (d, J=5.1 Hz, 1H), 8.84 (s, 1H), 8.60 (s, 1H), 8.54 (s, 1H), 8.11 (s, 1H), 8.05 (br m, 1H), 7.96 (d, J=7.6 Hz, 2H), 7.91 (d, J=4.6 Hz, 1H), 7.50 (t, J=7.4 Hz, 2H), 7.39 (t, J=7.2 Hz, 1H), 3.29 (q, J=7.0 Hz, 2H), 1.27 (t, J=7.2 Hz, 3H); LCMS (M+H)+: 406.1.

Example 131. 2-Methoxy-N-[2'-(5-phenyl-1H-imidazol-2-yl)-3,4'-bipyridin-5-yl]acetamide trifluoroacetate salt

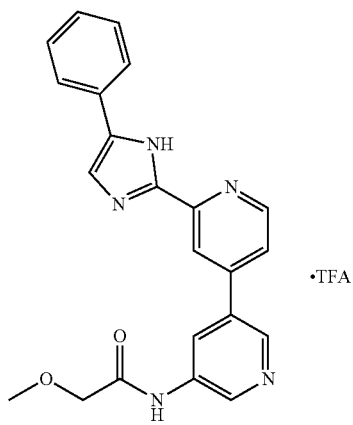 [SMILES: COCC(=O)Nc1cncc(-c2ccnc(-c3ncc(-c4ccccc4)[nH]3)c2)c1]

2'-(5-Phenyl-1H-imidazol-2-yl)-3,4'-bipyridin-5-amine trifluoroacetate salt (13 mg, 0.020 mmol, from Example 127) in CH$_2$Cl$_2$ (1.3 mL, 20. mmol) was treated with N,N-diisopropylethylamine (34.5 µL, 0.198 mmol) and methoxyacetyl chloride (7.2 µL, 0.079 mmol, Aldrich) for 30 minutes. The solvent was removed in vacuo and the residue was reconstituted in MeOH and treated with NH$_4$OH (0.10 mL) for 30 minutes. Volatiles were removed in vacuo and the product was purified by preparative HPLC (C-18 column eluting with a water:acetonitrile gradient buffered at pH 2 with 0.1% trifluoroacetic acid). Yield: 6.3 mg. 1H NMR (400 MHz, d$_6$-DMSO) δ 10.29 (s, 1H), 9.01 (d, J=2.1 Hz, 1H), 8.88 (d, J=5.1 Hz, 1H), 8.85 (d, J=1.9 Hz, 1H), 8.67 (t, J=2.0 Hz, 1H), 8.59 (s, 1H), 8.14 (s, 1H), 7.96 (d, J=7.4 Hz, 2H), 7.93 (dd, J=5.1, 1.2 Hz, 1H), 7.51 (t, J=7.6 Hz, 2H), 7.40 (t, J=7.3 Hz, 1H), 4.12 (s, 2H), 3.44 (s, 3H); LCMS (M+H)+: 386.2.

Examples 132 through 138 were synthesized according to the procedure of Example 131 and the data are listed in Table 11.

TABLE 11

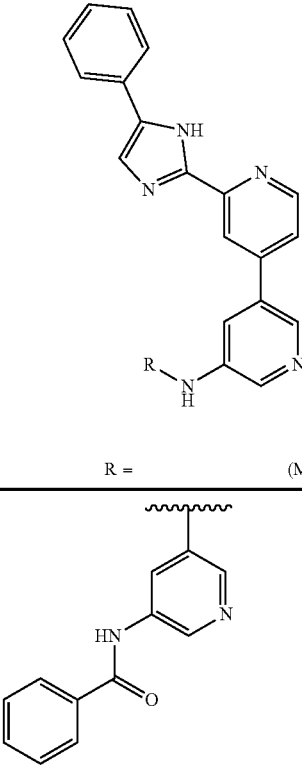

| Ex. No. | Name | R = | MS (M + H)+ | 1H NMR |
|---|---|---|---|---|
| 132 | N-(2'-(5-Phenyl-1H-imidazol-2-yl)-3,4'-bipyridin-5-yl)benzamide | 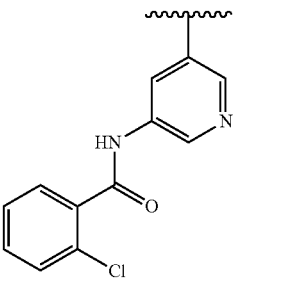 [SMILES: *c1cncc(NC(=O)c2ccccc2Cl)c1] | 418.1 | 1H NMR (400 MHz, d6-DMSO) δ 10.72 (s, 1H), 9.11 (d, J = 1.7 Hz, 1H), 8.90-8.84 (m, 2H), 8.81-8.72 (m, 1H), 8.59 (s, 1H), 8.14-8.00 (m, 3H), 7.98-7.87 (m, 3H), 7.70-7.64 (m, 1H), 7.64-7.55 (m, 2H), 7.50 (t, J = 7.6 Hz, 2H), 7.38 (t, J = 7.3 Hz, 1H) |
| 133 | 2-Chloro-N-(2'-(5-phenyl-1H-imidazol-2-yl)-3,4'-bipyridin-5-yl)benzamide | 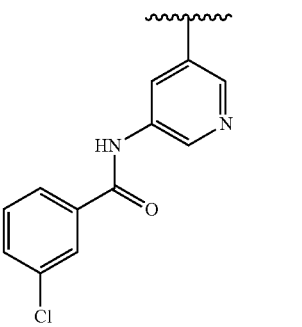 [SMILES: *c1cncc(NC(=O)c2cccc(Cl)c2)c1] | 452.2 | 1H NMR (400 MHz, d6-DMSO) δ 11.02 (s, 1H), 8.98 (d, J = 1.5 Hz, 1H), 8.91-8.82 (m, 2H), 8.79-8.67 (m, 1H), 8.56 (s, 1H), 8.07 (s, 1H), 7.99-7.84 (m, 3H), 7.72-7.67 (m, 1H), 7.64 (d, J = 7.7 Hz, 1H), 7.61-7.55 (m, 1H), 7.55-7.44 (m, 3H), 7.37 (t, J = 7.2 Hz, 1H) |
| 134 | 3-Chloro-N-(2'-(5-phenyl-1H-imidazol-2-yl)-3,4'-bipyridin-5-yl)benzamide | 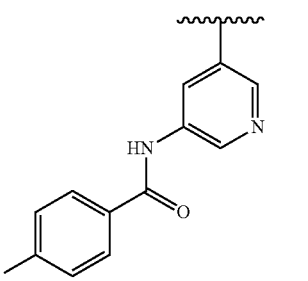 | 452.2 | 1H NMR (400 MHz, d6-DMSO) δ 10.81 (s, 1H), 9.12 (d, J = 1.9 Hz, 1H), 8.89 (d, J = 1.7 Hz, 1H), 8.85 (d, J = 5.1 Hz, 1H), 8.77-8.67 (m, 1H), 8.54 (s, 1H), 8.18-8.07 (m, 1H), 8.04-7.98 (m, 2H), 7.95 (d, J = 7.5 Hz, 2H), 7.90 (d, J = 5.0 Hz, 1H), 7.77-7.68 (m, 1H), 7.64 (t, J = 7.9 Hz, 1H), 7.47 (t, J = 7.6 Hz, 2H), 7.34 (t, J = 7.4 Hz, 1H) |
| 135 | 4-Chloro-N-(2'-(5-phenyl-1H-imidazol-2-yl)-3,4'-bipyridin-5-yl)benzamide | | 452.2 | 1H NMR (400 MHz, d6-DMSO) δ 10.77 (s, 1H), 9.11 (d, J = 2.1 Hz, 1H), 8.88 (d, J = 1.9 Hz, 1H), 8.84 (d, J = 5.1 Hz, 1H), 8.72 (t, J = 2.1 Hz, 1H), 8.54 (s, 1H), 8.11-8.02 (m, 2H), 8.00 (s, 1H), 7.98-7.92 (m, 2H), 7.90 (dd, J = 5.1, 1.2 Hz, 1H), 7.72-7.66 (m, 2H), 7.47 (t, J = 7.6 Hz, 2H), 7.34 (t, J = 7.2 Hz, 1H) |

TABLE 11-continued

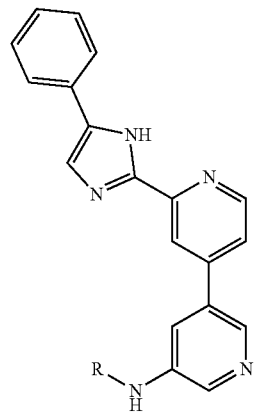

| Ex. No. | Name | R = | MS (M + H)+ | 1H NMR |
|---|---|---|---|---|
| 136 | 3-Cyano-N-(2'-(5-phenyl-1H-imidazol-2-yl)-3,4'-bipyridin-5-yl)benzamide | | 443.2 | 1H NMR (400 MHz, d6-DMSO) δ 10.88 (s, 1H), 9.10 (d, J = 2.0 Hz, 1H), 8.91 (d, J = 1.8 Hz, 1H), 8.86 (d, J = 5.0 Hz, 1H), 8.73 (t, J = 1.9 Hz, 1H), 8.56 (s, 1H), 8.52-8.44 (m, 1H), 8.39-8.28 (m, 1H), 8.18-8.10 (m, 1H), 8.04 (s, 1H), 7.98-7.94 (m, 2H), 7.94-7.90 (m, 1H), 7.83 (t, J = 7.8 Hz, 1H), 7.48 (t, J = 7.7 Hz, 2H), 7.36 (t, J = 7.4 Hz, 1H) |
| 137 | 4-Cyano-N-(2'-(5-phenyl-1H-imidazol-2-yl)-3,4'-bipyridin-5-yl)benzamide | | 443.1 | 1H NMR (400 MHz, d6-DMSO) δ 10.92 (s, 1H), 9.11 (d, J = 1.9 Hz, 1H), 8.90 (d, J = 1.8 Hz, 1H), 8.84 (d, J = 5.1 Hz, 1H), 8.78-8.67 (m, 1H), 8.52 (s, 1H), 8.20 (d, J = 8.4 Hz, 2H), 8.10 (d, J = 8.3 Hz, 2H), 8.01-7.91 (m, 3H), 7.91-7.86 (m, 1H), 7.46 (t, J = 7.5 Hz, 2H), 7.33 (t, J = 7.2 Hz, 1H) |
| 138 | N-(2'-(5-Phenyl-1H-imidazol-2-yl)-3,4'-bipyridin-5-yl)cyclopentanecarboxamide | | 410.2 | 1H NMR (400 MHz, d6-DMSO) δ 10.40 (s, 1H), 8.91-8.85 (m, 2H), 8.80 (s, 1H), 8.66 (s, 1H), 8.58 (s, 1H), 8.14 (s, 1H), 7.96 (d, J = 7.8 Hz, 2H), 7.93 (d, J = 4.1 Hz, 1H), 7.52 (t, J = 7.4 Hz, 2H), 7.41 (t, J = 7.2 Hz, 1H), 2.88 (p, J = 8.1 Hz, 1H), 1.99-1.85 (m, 2H), 1.85-1.45 (m, 6H) |

Example 139. N-Ethyl-N'-[2'-(5-phenyl-1H-imidazol-2-yl)-3,4'-bipyridin-5-yl]urea trifluoroacetate salt

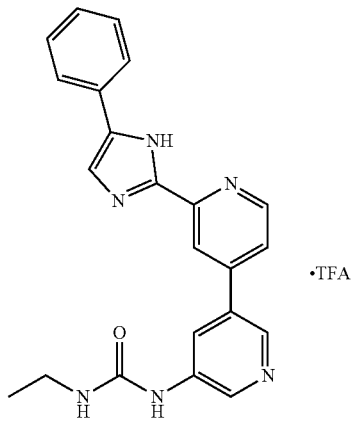 [SMILES: CCNC(=O)Nc1cncc(-c2ccnc(-c3ncc(-c4ccccc4)[nH]3)c2)c1]

2'-(5-phenyl-1H-imidazol-2-yl)-3,4'-bipyridin-5-amine trifluoroacetate salt (15 mg, 0.023 mmol, from Example 127) in $CH_2Cl_2$ (1.0 mL) was treated with triethylamine (16 μL, 0.11 mmol) and ethyl isocyanate (3 μL, 0.04 mmol) overnight. Additional ethyl isocyanate (8 μL, 0.1 mmol) was added and the reaction was stirred for 72 hours. The product was purified by preparative HPLC (C-18 column eluting with a water:acetonitrile gradient buffered at pH 2 with 0.1% trifluoroacetic acid). Yield: 10. mg. $^1$H NMR (400 MHz, $d_6$-DMSO) δ 9.10 (s, 1H), 8.88 (d, J=5.1 Hz, 1H), 8.72-8.68 (m, 2H), 8.58 (s, 1H), 8.54 (t, J=2.0 Hz, 1H), 8.14 (s, 1H), 8.00-7.94 (m, 2H), 7.91 (dd, J=5.1, 1.3 Hz, 1H), 7.52 (t, J=7.6 Hz, 2H), 7.41 (t, J=7.4 Hz, 1H), 6.59 (t, J=5.1 Hz, 1H), 3.23-3.09 (m, 2H), 1.10 (t, J=7.2 Hz, 3H); LCMS (M+H)$^+$: 385.1.

Example 140. Ethyl 2'-(5-phenyl-1H-imidazol-2-yl)-3,4'-bipyridin-5-ylcarbamate trifluoroacetate salt

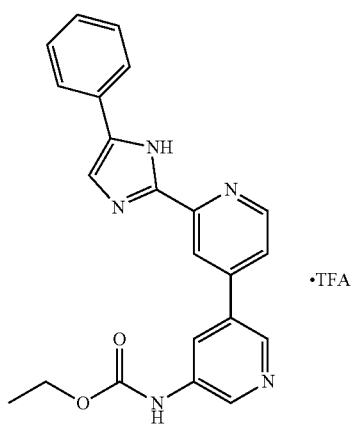 [SMILES: CCOC(=O)Nc1cncc(-c2ccnc(-c3ncc(-c4ccccc4)[nH]3)c2)c1]

2'-(5-Phenyl-1H-imidazol-2-yl)-3,4'-bipyridin-5-amine trifluoroacetate salt (10.6 mg, 0.016 mmol, from Example 127) in $CH_2Cl_2$ (1.0 mL) was treated with pyridine (13 μL, 0.16 mmol) and ethyl chloroformate (3 uL, 0.03 mmol). After 10 minutes, volatiles were removed in vacuo and the residue was dissolved in MeOH (1.0 mL) and treated with $NH_4OH$ (0.10 mL) for 15 minutes. Volatiles were again removed in vacuo and the residue was reconstituted and the product was purified by preparative HPLC (C-18 column eluting with a water:acetonitrile gradient buffered at pH 2 with 0.1% trifluoroacetic acid). Yield: 7.0 mg. $^1$H NMR (400 MHz, $d_6$-DMSO) δ 10.14 (s, 1H), 8.86 (d, J=5.2 Hz, 1H), 8.78-8.72 (m, 2H), 8.55 (s, 1H), 8.45-8.40 (m, 1H), 8.12 (s, 1H), 7.98-7.92 (m, 2H), 7.92-7.85 (m, 1H), 7.50 (t, J=7.6 Hz, 2H), 7.39 (t, J=7.4 Hz, 1H), 4.20 (q, J=7.1 Hz, 2H), 1.29 (t, J=7.1 Hz, 3H); LCMS (M+H)$^+$: 386.1.

Example 141. 2'-(5-Phenyl-1H-imidazol-2-yl)-N-(tetrahydro-2H-pyran-4-ylmethyl)-3,4'-bipyridin-5-amine trifluoroacetate salt

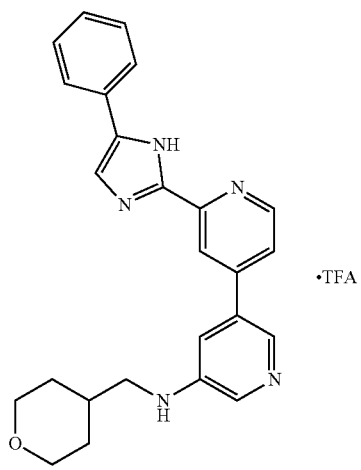 [SMILES: c1ccc(-c2cnc(-c3cc(-c4cncc(NCC5CCOCC5)c4)ccn3)[nH]2)cc1]

2'-(5-Phenyl-1H-imidazol-2-yl)-3,4'-bipyridin-5-amine trifluoroacetate salt (15 mg, 0.023 mmol, from Example 127) and tetrahydro-2H-pyran-4-carbaldehyde (13 mg, 0.11 mmol, PharmaCore) were combined in 1,2-dichloroethane (1.0 mL), and N,N-diisopropylethylamine (20 μL, 0.11 mmol) was added. After stirring for 1 hour, AcOH (0.50 mL) and $Na(OAc)_3BH$ (39 mg, 0.18 mmol) were added. After 1 hour, the solvent was removed via rotary evaporation and the product was purified by preparative HPLC (C-18 column eluting with a water:acetonitrile gradient buffered at pH 2 with 0.1% trifluoroacetic acid). Yield: 7.2 mg. $^1$H NMR (400 MHz, $d_6$-DMSO) δ 8.87 (d, J=5.0 Hz, 1H), 8.54 (s, 1H), 8.47 (s, 1H), 8.23 (s, 1H), 8.04 (s, 1H), 7.96 (d, J=7.5 Hz, 2H), 7.93-7.86 (m, 2H), 7.48 (t, J=7.6 Hz, 2H), 7.35 (t, J=7.3 Hz, 1H), 3.97-3.77 (m, 2H), 3.33 (t, J=11.3 Hz, 2H), 3.21-3.03 (m, 2H), 1.94-1.79 (m, 1H), 1.72 (d, J=12.9 Hz, 2H), 1.31 (ddt, J=16.0, 12.5, 5.0 Hz, 2H); LCMS (M+H)$^+$: 412.3.

Examples 142 through 144 were synthesized according to the procedure of Example 141 and the data are listed in Table 12.

TABLE 12

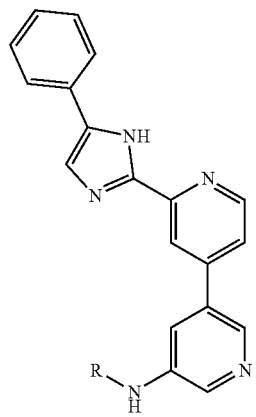

| Ex. No. | Name | R = | MS (M + H)+ | 1H NMR |
|---|---|---|---|---|
| 142 | 2'-(5-Phenyl-1H-imidazol-2-yl)-N-(tetrahydro-2H-pyran-4-yl)-3,4'-bipyridin-5-amine trifluoroacetate salt | | 398.2 | 1H NMR (400 MHz, $d_6$-DMSO) δ 8.86 (d, J = 5.1 Hz, 1H), 8.51 (s, 1H), 8.46 (s, 1H), 8.23 (d, J = 2.2 Hz, 1H), 8.01 (s, 1H), 7.98-7.93 (m, 2H), 7.91-7.82 (m, 2H), 7.47 (t, J = 7.6 Hz, 2H), 7.35 (t, J = 7.3 Hz, 1H), 3.92 (dt, J = 11.7, 3.0 Hz, 2H), 3.78 (tt, J = 9.9, 4.1 Hz, 1H), 3.48 (td, J = 11.4, 1.6 Hz, 2H), 2.03-1.91 (m, 2H), 1.53-1.34 (m, 2H) |
| 143 | N-(1-Methylpiperidin-4-yl)-2'-(5-phenyl-1H-imidazol-2-yl)-3,4'-bipyridin-5-amine trifluoroacetate salt | | 411.2 | 1H NMR (400 MHz, $d_6$-DMSO) δ 9.48 (br s, 1H), 8.80 (d, J = 5.1 Hz, 1H), 8.45 (s, 1H), 8.40 (s, 1H), 8.19 (d, J = 2.4 Hz, 1H), 7.98-7.88 (m, 3H), 7.83-7.74 (m, 1H), 7.63 (s, 1H), 7.45 (t, J = 7.6 Hz, 2H), 7.31 (t, J = 7.3 Hz, 1H), 3.79-3.63 (m, 1H), 3.59-3.45 (m, 2H), 3.17-3.00 (m, 2H), 2.82 (d, J = 4.4 Hz, 3H), 2.27-2.16 (m, 2H), 1.69-1.53 (m, 2H) |
| 144 | N-((1-Methylpiperidin-4-yl)methyl)-2'-(5-phenyl-1H-imidazol-2-yl)-3,4'-bipyridin-5-amine trifluoroacetate salt | | 425.3 | 1H NMR (400 MHz, $d_6$-DMSO) δ 9.37 (br s, 1H), 8.83 (d, J = 5.1 Hz, 1H), 8.49 (s, 1H), 8.44 (s, 1H), 8.21 (d, J = 2.4 Hz, 1H), 7.99-7.90 (m, 3H), 7.86 (dd, J = 5.1, 1.5 Hz, 1H), 7.76 (s, 1H), 7.46 (t, J = 7.7 Hz, 2H), 7.33 (t, J = 7.4 Hz, 1H), 3.52-3.41 (m, 2H), 3.22-3.13 (m, 2H), 3.01-2.87 (m, 2H), 2.77 (d, J = 4.6 Hz, 3H), 2.07-1.96 (m, 2H), 1.94-1.76 (m, 1H), 1.50-1.32 (m, 2H) |

Examples 145-145C was synthesized according to the procedure of Example 141 and the data are listed in Table 13. Example 145C was prepared with the modification that the imine was formed first with heating at 190-200° C. prior to reduction with sodium cyanoborohydride.

TABLE 13

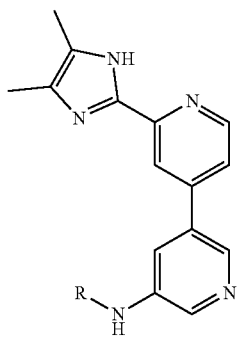

| Ex. No. | Name | R = | MS (M + H)+ | 1H NMR |
|---|---|---|---|---|
| 145 | 2'-(4,5-Dimethyl-1H-imidazol-2-yl)-N-(tetrahydro-2H-pyran-4-ylmethyl)-3,4'-bipyridin-5-amine | | 364.2 | 1H NMR (400 MHz, d6-DMSO) δ 12.38 (s, 1H), 8.60 (d, J = 5.1 Hz, 1H), 8.16 (s, 1H), 8.13 (s, 1H), 8.08 (d, J = 2.1 Hz, 1H), 7.62-7.53 (m, 1H), 7.36-7.23 (m, 1H), 6.14 (t, J = 5.5 Hz, 1H), 3.88 (dd, J = 11.0, 2.8 Hz, 2H), 3.32-3.25 (m, 2H), 3.05 (t, J = 6.0 Hz, 2H), 2.18 (s, 3H), 2.11 (s, 3H), 1.92-1.77 (m, 1H), 1.72 (d, J = 13.0 Hz, 2H), 1.27 (qd, J = 12.4, 4.0 Hz, 2H) |
| 145B | 2'-(4,5-Dimethyl-1H-imidazol-2-yl)-N-(tetrahydrofuran-3-ylmethyl)-3,4'-bipyridin-5-amine (racemic mixture prepared) | | 350.1 | 1H NMR (400 MHz, CDCl3) δ 10.22 (br s, 1H), 8.55 (d, J = 5.1 Hz, 1H), 8.30 (s, 2H), 8.10 (d, J = 2.6 Hz, 1H), 7.40 (dd, J = 5.1, 1.5 Hz, 1H), 7.19 (s, 1H), 4.06-3.88 (m, 3H), 3.86-3.77 (m, 1H), 372-3.66 (m, 1H), 3.30-3.20 (m, 2H), 2.71-2.55 (m, 1H), 2.28 (s, 6H), 2.23-2.09 (m, 1H), 1.80-1.70 (m, 1H) |
| 145C | 2'-(4,5-Dimethyl-1H-imidazol-2-yl)-N-(1-phenylethyl)-3,4'-bipyridin-5-amine trifluoroacetate salt (racemic mixture prepared) | | 370.1 | 1H NMR (400 MHz, DMSO) δ 8.85 (d, J = 5.1 Hz, 1H), 8.44 (s, 1H), 8.24 (d, J = 1.7 Hz, 1H), 8.08 (d, J = 2.5 Hz, 1H), 7.80 (dd, J = 5.1, 1.4 Hz, 1H), 7.49-7.41 (m, 2H), 7.41-7.28 (m, 3H), 7.28-7.15 (m, 1H), 7.01 (br s, 1H), 4.79-4.64 (m, 1H), 2.31 (s, 6H), 1.50 (d, J =6.7 Hz, 3H) |

Example 146. (S)-(2'-(4,5-Dimethyl-1H-imidazol-2-yl)-3,4'-bipyridin-5-yl)(3-hydroxypyrrolidin-1-yl)methanone

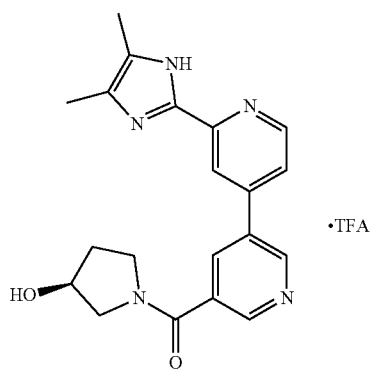 [SMILES: Cc1nc(-c2cc(-c3cncc(C(=O)N4CC[C@H](O)C4)c3)ccn2)[nH]c1C]

Step 1. Ethyl 2'-cyano-3,4'-bipyridine-5-carboxylate

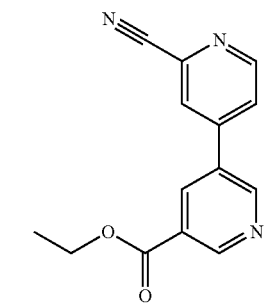 [SMILES: CCOC(=O)c1cncc(-c2ccnc(C#N)c2)c1]

A degassed mixture of 4-bromopyridine-2-carbonitrile (1.0 g, 5.5 mmol, Synthonix), ethyl 5-(4,4,5,5-tetramethyl- 1,3,2-dioxaborolan-2-yl)nicotinate (1.5 g, 5.4 mmol, Frontier Scientific), CsF (2 g, 20 mmol), and 4-(di-tert-butylphosphino)-N,N-dimethylaniline-dichloropalladium (2:1) (0.38 g, 0.54 mmol, Aldrich) in 1,4-dioxane (10 mL) and water (3 mL) was heated to 120° C. for 2 hours. Upon cooling to room temperature, EtOAc and $H_2O$ were added. The biphasic mixture was filtered. The organic layer was washed with $H_2O$, followed by brine, dried over $Na_2SO_4$, filtered and concentrated. The product was purified by flash chromatography, eluting with a gradient from 0-100% EtOAc/hexanes. The eluent was evaporated and the solid was dried at 40° C. overnight. Yield: 0.9 g, 66%. LCMS $(M+H)^+$: 254.1.

Step 2. Methyl 2'-[amino(imino)methyl]-3,4'-bipyridine-5-carboxylate

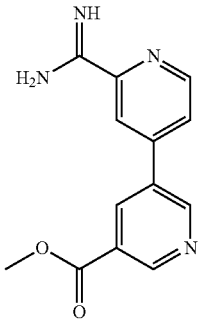 [SMILES: COC(=O)c1cncc(-c2ccnc(C(=N)N)c2)c1]

A solution of ethyl 2'-cyano-3,4'-bipyridine-5-carboxylate (0.40 g, 1.6 mmol, from Step 1) in THF (4 mL) and methanol (4 mL) was treated with NaOMe in methanol (25 wt % in MeOH, 0.030 mL, 0.13 mmol). After heating to reflux for 2.5 hours, the reaction mixture was cooled to room temperature and $NH_4Cl$ (0.125 g, 2.34 mmol) was added. After stirring for 4 days, the solid product was isolated by filtration. The product was triturated with EtOAc and isolated by filtration. The solid was washed with EtOAc and dried under vacuum at 40° C. overnight. Yield: 0.18 g, 44%. LCMS $(M+H)^+$: 257.0.

Step 3. Methyl 2'-(4,5-dimethyl-1H-imidazol-2-yl)-3,4'-bipyridine-5-carboxylate

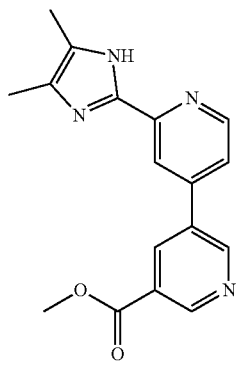 [SMILES: COC(=O)c1cncc(-c2ccnc(-c3nc(C)c(C)[nH]3)c2)c1]

To a suspension of methyl 2'-[amino(imino)methyl]-3,4'-bipyridine-5-carboxylate (0.25 g, 0.78 mmol, from Step 2) in DMF (3 mL) was added $K_2CO_3$ (0.16 g, 1.2 mmol), followed by 3-bromo-2-butanone (0.088 mL, 1.2 mmol, Alfa Aesar). The reaction mixture was stirred for 4 days. Water (10 mL) and EtOAc (10 mL) were added and the mixture was stirred for 30 minutes. The precipitated solid was isolated by filtration and washed with both water and EtOAc. The solid was dried under vacuum at 40° C. for 1.5 hours. The filtrate contained some product and the mixture was washed with water, followed by saturated NaCl. The organic layer was dried over sodium sulfate, filtered, and concentrated. The residue was triturated with DCM (2 mL) and additional solid product was isolated by filtration. Yield: 0.18 g, 75%. $^1$H NMR (400 MHz, $d_6$-DMSO) δ 12.44 (br s, 1H), 9.30 (d, J=2.2 Hz, 1H), 9.19 (d, J=1.9 Hz, 1H), 8.67 (d, J=5.1 Hz, 1H), 8.62 (t, J=2.1 Hz, 1H), 8.29-8.15 (m, 1H), 7.76 (dd, J=5.2, 1.7 Hz, 1H), 3.96 (s, 3H), 2.19 (s, 3H), 2.12 (s, 3H); LCMS $(M+H)^+$: 309.0.

Step 4. 2'-(4,5-Dimethyl-1H-imidazol-2-yl)-3,4'-bipyridine-5-carboxylic acid HCl salt

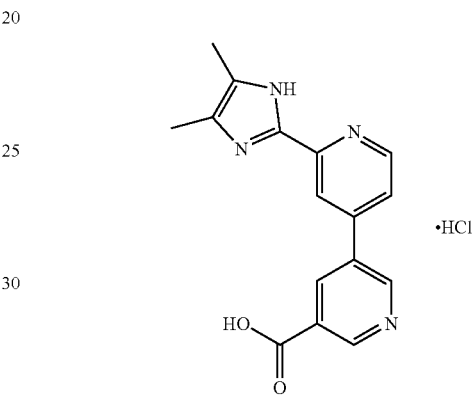

To a suspension of methyl 2'-(4,5-dimethyl-1H-imidazol-2-yl)-3,4'-bipyridine-5-carboxylate (0.18 g, 0.58 mmol, from Step 3) in THF (6 mL) and MeOH (6 mL) was added 1.0 N NaOH (1.2 mL, 1.2 mmol). The reaction mixture was stirred for 5 hours. 1.0 N HCl (1.0 mL, 1.0 mmol) was then added. After stirring for 3 hours, the volume of solution was reduced to about 3 mL via rotary evaporation. THF (1 mL) and MeOH (1 mL) were added. The solid product was isolated by filtration and dried under vacuum at 40° C. overnight. Yield: 142 mg, 83%. $^1$H NMR (400 MHz, $d_6$-DMSO) δ 13.75 (br s, 1H), 9.30 (d, J=2.3 Hz, 1H), 9.18 (d, J=1.9 Hz, 1H), 8.75 (d, J=5.2 Hz, 1H), 8.65 (t, J=2.1 Hz, 1H), 8.43 (s, 1H), 7.90 (dd, J=5.0, 1.1 Hz, 1H), 2.21 (s, 6H); LCMS $(M+H)^+$: 295.1.

Step 5. (3S)-1-{[2'-(4,5-Dimethyl-1H-imidazol-2-yl)-3,4'-bipyridin-5-yl]carbonyl}pyrrolidin-3-ol trifluoroacetate salt To a suspension of 2'-(4,5-dimethyl-1H-imidazol-2-yl)-3,4'-bipyridine-5-carboxylic acid (7.0 mg, 0.024 mmol, from Step 4) and HATU (0.014 g, 0.036 mmol) in DMF (1 mL, 10 mmol) was added N,N-diisopropylethylamine (0.015 mL, 0.086 mmol). After 1 hour, (3S)-pyrrolidin-3-ol (13.0 mg, 0.149 mmol) was added. The product was purified by preparative HPLC (C-18 column eluting with a water:acetonitrile gradient buffered at pH 2 with 0.1% trifluoroacetic acid). Yield: 5.6 mg. $^1$H NMR (400 MHz, $CD_3OD$) δ 9.11 (d, J=2.2 Hz, 1H), 8.91-8.85 (m, 2H), 8.43-8.38 (m, 1H), 8.38-8.34 (m, 1H), 7.95 (dd, J=5.1, 1.5 Hz, 1H), 4.58-4.53 (m, 0.5H, rotamers), 4.48-4.43 (m, 0.5H, rotamers), 3.95-3.34 (m, 4H), 2.38 (s, 6H), 2.24-1.89 (m, 2H); LCMS $(M+H)^+$: 364.2.

Examples 147 through 212B were synthesized according to the procedure of Example 146 and the data are listed in Table 14.

TABLE 14

| Ex. No. | Name | R = | MS (M + H)⁺ | ¹H NMR |
|---|---|---|---|---|
| 147 | (2'-(4,5-Dimethyl-1H-imidazol-2-yl)-3,4'-bipyridin-5-yl)(4-methylpiperazin-1-yl)methanone | 4-methylpiperazin-1-yl | 377.1 | ¹H NMR (400 MHz, d₆-DMSO) δ 12.40 (br s, 1H), 9.10 (s, 1H), 8.70 (s, 1H), 8.66 (d, J = 5.1 Hz, 1H), 8.28 (s, 1H), 8.24 (s, 1H), 7.72 (d, J = 3.9 Hz, 1H), 3.68 (br m, 2H), 3.39 (br m, 2H), 2.36 (br m, J = 40.0 Hz, 4H), 2.22 (s, 3H), 2.18 (s, 3H), 2.13 (s, 3H) |
| 148 | (2'-(4,5-Dimethyl-1H-imidazol-2-yl)-3,4'-bipyridin-5-yl)(morpholino)methanone | morpholino | 364.1 | ¹H NMR (400 MHz, d₆-DMSO) δ 12.40 (br s, 1H), 9.11 (d, J = 2.1 Hz, 1H), 8.73 (d, J = 1.8 Hz, 1H), 8.66 (d, J = 5.2 Hz, 1H), 8.31 (t, J = 2.0 Hz, 1H), 8.24 (s, 1H), 7.72 (dd, J = 5.2, 1.7 Hz, 1H), 3.69 (br m, 4H), 3.60 (br m, 2H), 3.41 (br m, 2H), 2.19 (s, 3H), 2.13 (s, 3H) |
| 149 | 2'-(4,5-Dimethyl-1H-imidazol-2-yl)-N-(3-(dimethylamino)propyl)-3,4'-bipyridine-5-carboxamide | 3-(dimethylamino)propylamino | 379.2 | ¹H NMR (400 MHz, DMSO) δ 12.40 (br s, 1H), 9.16 (d, J = 1.9 Hz, 1H), 9.08 (d, J = 1.7 Hz, 1H), 8.93 (t, J = 4.9 Hz, 1H), 8.67 (d, J = 5.2 Hz, 1H), 8.63-8.58 (m, 1H), 8.30 (s, 1H), 7.74 (dd, J = 5.1, 1.6 Hz, 1H), 3.35 (q, J = 6.2 Hz, 2H), 2.29 (t, J = 7.0 Hz, 2H), 2.19 (s, 3H), 2.15 (s, 6H), 2.13 (s, 3H), 1.71 (p, J = 7.1 Hz, 2H) |
| 150 | 4-(2'-(4,5-Dimethyl-1H-imidazol-2-yl)-3,4'-bipyridine-5-carbonyl)piperazine-1-carboxamide | 4-carbamoylpiperazin-1-yl | 406.1 | ¹H NMR (400 MHz, d₆-DMSO) δ 12.37 (br s, 1H), 9.16-9.07 (m, 1H), 8.73 (s, 1H), 8.66 (d, J = 5.1 Hz, 1H), 8.34-8.28 (m, 1H), 8.25 (s, 1H), 7.75-7.69 (m, 1H), 6.08 (s, 2H), 3.64 (br m, 2H), 3.43 (br m, 2H), 3.35 (br m, 4H), 2.19 (s, 3H), 2.12 (s, 3H) |

TABLE 14-continued

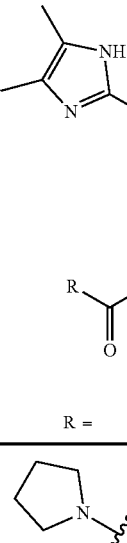

| Ex. No. | Name | R = | MS (M + H)+ | 1H NMR |
|---|---|---|---|---|
| 151 | (2'-(4,5-Dimethyl-1H-imidazol-2-yl)-3,4'-bipyridin-5-yl)(pyrrolidin-1-yl)methanone | 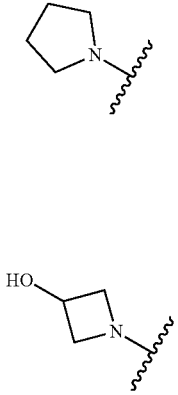 | 348.1 | 1H NMR (400 MHz, d6-DMSO) δ 12.41 (br s, 1H), 9.10 (d, J = 2.2 Hz, 1H), 8.81 (d, J = 1.9 Hz, 1H), 8.65 (d, J = 5.2 Hz, 1H), 8.35 (t, J = 2.1 Hz, 1H), 8.24-8.22 (m, 1H), 7.72 (dd, J = 5.2, 1.8 Hz, 1H), 3.53 (t, J = 6.7 Hz, 2H), 3.48 (t, J = 6.4 Hz, 2H), 2.19 (s, 3H), 2.12 (s, 3H), 1.96-1.81 (m, 4H) |
| 152 | (2'-(4,5-Dimethyl-1H-imidazol-2-yl)-3,4'-bipyridin-5-yl)(3-hydroxyazetidin-1-yl)methanone trifluoroacetate salt | 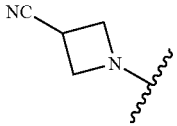 [SMILES: *N1CC(C#N)C1] | 350.2 | 1H NMR (400 MHz, d6-DMSO) δ 9.25 (d, J = 2.2 Hz, 1H), 8.96 (d, J = 1.8 Hz, 1H), 8.92 (d, J = 5.1 Hz, 1H), 8.58 (s, 1H), 8.48 (t, J = 2.0 Hz, 1H), 8.15 (dd, J = 5.2, 1.4 Hz, 1H), 4.62-4.43 (m, 2H), 4.39-4.23 (m, 1H), 4.23-4.04 (m, 1H), 3.97-3.76 (m, 1H), 2.33 (s, 6H) |
| 153 | 1-(2'-(4,5-Dimethyl-1H-imidazol-2-yl)-3,4'-bipyridine-5-carbonyl)azetidine-3-carbonitrile trifluoroacetate salt | 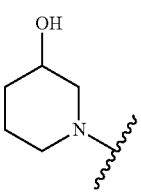 [SMILES: *N1CCCC(O)C1] | 359.2 | 1H NMR (400 MHz, d6-DMSO) δ 9.26 (d, J = 2.2 Hz, 1H), 8.96 (d, J = 1.8 Hz, 1H), 8.92 (d, J = 5.2 Hz, 1H), 8.57 (s, 1H), 8.48 (t, J = 2.0 Hz, 1H), 8.14 (dd, J = 5.2, 1.4 Hz, 1H), 4.77-4.67 (m, 1H), 4.67-4.57 (m, 1H), 4.47-4.36 (m, 1H), 4.33-4.20 (m, 1H), 3.91 (tt, J = 9.1, 6.4 Hz, 1H), 2.33 (s, 6H) |
| 154 | (2'-(4,5-Dimethyl-1H-imidazol-2-yl)-3,4'-bipyridin-5-yl)(3-hydroxypiperidin-1-yl)methanone (racemic mixture prepared) | 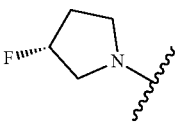 [SMILES: *N1CC[C@@H](F)C1] | 378.2 | 1H NMR (400 MHz, CD3OD) δ 9.09 (s, 1H), 8.88 (d, J = 5.1 Hz, 1H), 8.78 (d, J = 12.1 Hz, 1H), 8.42-8.28 (m, 2H), 7.94 (dd, J = 5.1, 1.6 Hz, 1H), 4.18-3.31 (m, 5H), 2.38 (s, 6H), 2.09-1.41 (m, 4H) |
| 155 | (R)-(2'-(4,5-Dimethyl-1H-imidazol-2-yl)-3,4'-bipyridin-5-yl)(3-fluoropyrrolidin-1-yl)methanone trifluoroacetate salt |  | 366.2 | 1H NMR (400 MHz, d6-DMSO) δ 9.24 (d, J = 2.1 Hz, 1H), 8.97-8.85 (m, 2H), 8.60 (s, 1H), 8.50-8.43 (m, 1H), 8.21-8.12 (m, 1H), 5.40 (dd, J = 52.7, 35.8 Hz, 1H), 4.00-3.52 (m, 4H), 2.33 (s, 6H), 2.30-2.00 (m, 2H) |

TABLE 14-continued

| Ex. No. | Name | R = | MS (M + H)+ | 1H NMR |
|---|---|---|---|---|
| 156 | (2'-(4,5-Dimethyl-1H-imidazol-2-yl)-3,4'-bipyridin-5-yl)(3-oxa-9-azaspiro[5.5]undecan-9-yl)methanone trifluoroacetate salt | (3-oxa-9-azaspiro[5.5]undecan-9-yl) | 432.2 | 1H NMR (400 MHz, d6-DMSO) δ 9.19 (d, J = 2.2 Hz, 1H), 8.91 (d, J = 5.2 Hz, 1H), 8.77 (d, J = 1.9 Hz, 1H), 8.58 (s, 1H), 8.33 (t, J = 2.1 Hz, 1H), 8.13 (dd, J = 5.2, 1.5 Hz, 1H), 3.73-3.62 (m, 2H), 3.56 (q, J = 5.5 Hz, 4H), 3.41-3.22 (m, 2H), 2.32 (s, 6H), 1.62-1.54 (m, 2H), 1.54-1.41 (m, 6H) |
| 157 | 2'-(4,5-Dimethyl-1H-imidazol-2-yl)-N-isopropyl-3,4'-bipyridine-5-carboxamide trifluoroacetate salt | isopropylamino | 336.2 | 1H NMR (400 MHz, d6-DMSO) δ 9.24 (d, J = 2.2 Hz, 1H), 9.16 (d, J = 1.9 Hz, 1H), 8.93 (d, J = 5.1 Hz, 1H), 8.66 (t, J = 2.1 Hz, 1H), 8.63 (d, J = 7.6 Hz, 1H), 8.60 (s, 1H), 8.14 (dd, J = 5.1, 1.4 Hz, 1H), 4.24-4.07 (m, 1H), 2.33 (s, 6H), 1.23 (d, J = 6.6 Hz, 6H) |
| 158 | (2'-(4,5-Dimethyl-1H-imidazol-2-yl)-3,4'-bipyridin-5-yl)(4-(1-methylpiperidin-4-yl)piperazin-1-yl)methanone | 4-(1-methylpiperidin-4-yl)piperazin-1-yl | 460.3 | 1H NMR (400 MHz, CD3OD) δ 9.07 (d, J = 2.2 Hz, 1H), 8.70 (d, J = 1.9 Hz, 1H), 8.66 (d, J = 5.2 Hz, 1H), 8.33-8.29 (m, 1H), 8.28 (t, J = 2.0 Hz, 1H), 7.64 (dd, J = 5.2, 1.7 Hz, 1H), 4.70 (br d, J = 11.3 Hz, 1H), 3.79 (br d, J = 13.1 Hz, 1H), 2.95 (br t, J = 13.0 Hz, 1H), 2.81-2.35 (m, 9H), 2.27 (s, 3H), 2.23 (s, 6H), 2.10-1.99 (m, 1H), 1.96-1.84 (m, 1H), 1.66-1.40 (m, 2H) |
| 159 | 1-(4-(2'-(4,5-Dimethyl-1H-imidazol-2-yl)-3,4'-bipyridine-5-carbonyl)piperazin-1-yl)ethanone trifluoroacetate salt | 4-acetylpiperazin-1-yl | 405.2 | 1H NMR (400 MHz, d6-DMSO, tautomers) δ 12.40 (br s, 1H), 9.12-9.06 (m, 1H), 8.72-8.68 (m, 1H), 8.66 (d, J = 5.1 Hz, 1H), 8.32-8.26 (m, 1H), 8.24 (s, 1H), 7.75-7.67 (m, 1H), 3.79-3.59 (br m, 2H), 3.44-3.35 (br m, 2H), 2.45-2.37 (br m, 2H), 2.37-2.26 (br m, 2H), 2.22 (s, 3H), 2.18 (br s, 3H), 2.13 (br s, 3H) |

TABLE 14-continued

| Ex. No. | Name | R = | MS (M + H)+ | 1H NMR |
|---|---|---|---|---|
| 160 | 2'-(4,5-Dimethyl-1H-imidazol-2-yl)-N-(tetrahydro-2H-pyran-4-yl)-3,4'-bipyridine-5-carboxamide trifluoroacetate salt | | 378.2 | 1H NMR (400 MHz, d6-DMSO) δ 9.23 (d, J = 2.2 Hz, 1H), 9.15 (d, J = 1.9 Hz, 1H), 8.91 (d, J = 5.2 Hz, 1H), 8.70 (d, J = 7.6 Hz, 1H), 8.65 (t, J = 2.1 Hz, 1H), 8.57 (s, 1H), 8.20-7.97 (m, 1H), 4.15-3.99 (m, 1H), 3.99-3.83 (m, 2H), 3.67-3.06 (m, 2H), 2.31 (s, 6H), 1.89-1.74 (m, 2H), 1.61 (qd, J = 12.1, 4.4 Hz, 2H) |
| 161 | (R)-(2'-(4,5-Dimethyl-1H-imidazol-2-yl)-3,4'-bipyridin-5-yl)(3-(dimethylamino)pyrrolidin-1-yl)methanone trifluoroacetate salt | | 391.2 | 1H NMR (400 MHz, CD3OD, rotamers) δ 9.13 (d, J = 2.0 Hz, 1H), 8.90-8.84 (m, 2H), 8.43 (t, J = 2.1 Hz, 1H), 8.40 (s, 1H), 7.94 (d, J = 4.0 Hz, 1H), 4.20-3.67 (m, 5H), 3.00 (s, 3.8H), 2.91 (s, 2.2H), 2.62-2.41 (m, 1H), 2.38 (s, 6H), 2.33-2.16 (m, 1H) |
| 162 | 2'-(4,5-Dimethyl-1H-imidazol-2-yl)-N-((tetrahydro-2H-pyran-4-yl)methyl)-3,4'-bipyridine-5-carboxamide trifluoroacetate salt | | 392.2 | 1H NMR (400 MHz, d6-DMSO) δ 9.25 (d, J = 2.2 Hz, 1H), 9.16 (d, J = 1.9 Hz, 1H), 8.93 (d, J = 5.2 Hz, 1H), 8.88 (t, J = 5.6 Hz, 1H), 8.68 (t, J = 2.0 Hz, 1H), 8.60 (s, 1H), 8.13 (dd, J = 5.1, 1.3 Hz, 1H), 3.93-3.80 (m, 2H), 3.33-3.22 (m, 4H), 2.33 (s, 6H), 1.92-1.76 (m, 1H), 1.71-1.57 (m, 2H), 1.25 (qd, J = 12.4, 4.3 Hz, 2H) |
| 163 | (R)-(2'-(4,5-Dimethyl-1H-imidazol-2-yl)-3,4'-bipyridin-5-yl)(3-hydroxypyrrolidin-1-yl)methanone trifluoroacetate salt | | 364.1 | 1H NMR (400 MHz, CD3OD, rotamers) δ 9.11 (d, J = 2.2 Hz, 1H), 8.90-8.85 (m, 2H), 8.43-8.39 (m, 1H), 8.39-8.35 (m, 1H), 7.95 (dd, J = 5.1, 1.5 Hz, 1H), 4.55-4.50 (m, 0.5H), 4.45-4.39 (m, 0.5H), 3.90-3.36 (m, 4H), 2.38 (s, 6H), 2.24-1.87 (m, 2H) |

TABLE 14-continued

| Ex. No. | Name | R = | MS (M + H)+ | 1H NMR |
|---|---|---|---|---|
| 164 | 2'-(4,5-Dimethyl-1H-imidazol-2-yl)-N-(2-(tetrahydro-2H-pyran-4-yl)ethyl)-3,4'-bipyridine-5-carboxamide trifluoroacetate salt | 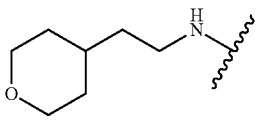 [SMILES: *NCCC1CCOCC1] | 406.2 | 1H NMR (400 MHz, d6-DMSO) δ 9.25 (d, J = 2.2 Hz, 1H), 9.15 (d, J = 1.8 Hz, 1H), 8.93 (d, J = 5.2 Hz, 1H), 8.84 (t, J = 5.5 Hz, 1H), 8.67 (t, J = 2.0 Hz, 1H), 8.60 (s, 1H), 8.14 (dd, J = 5.1, 1.4 Hz, 1H), 3.85 (dd, J = 11.1, 3.5 Hz, 2H), 3.39 (q, J = 6.7 Hz, 2H), 3.28 (td, J = 11.8, 1.4 Hz, 2H), 2.33 (s, 6H), 1.70-1.43 (m, 5H), 1.28-1.11 (m, 2H) |
| 165 | (2'-(4,5-Dimethyl-1H-imidazol-2-yl)-3,4'-bipyridin-5-yl)(2-oxa-7-azaspiro[3.5]nonan-7-yl)methanone trifluoroacetate salt | 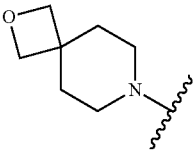 [SMILES: *N1CCC2(CC1)COC2] | 404.1 | 1H NMR (400 MHz, d6-DMSO) δ 9.21 (d, J = 2.2 Hz, 1H), 8.91 (d, J = 5.2 Hz, 1H), 8.77 (d, J = 1.8 Hz, 1H), 8.59 (s, 1H), 8.33 (t, J = 2.0 Hz, 1H), 8.13 (dd, J = 5.2, 1.5 Hz, 1H), 4.36 (br m, 4H), 3.61 (br m, 2H), 3.32 (br m, 2H), 2.33 (s, 6H), 1.86 (br m, 4H) |
| 166 | 2'-(4,5-Dimethyl-1H-imidazol-2-yl)-N-(2-methoxyethyl)-3,4'-bipyridine-5-carboxamide trifluoroacetate salt | 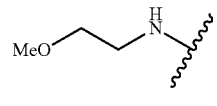 [SMILES: *NCCOC] | 352.2 | 1H NMR (400 MHz, d6-DMSO) δ 9.25 (d, J = 2.1 Hz, 1H), 9.17 (d, J = 1.9 Hz, 1H), 8.99-8.94 (m, 1H), 8.93 (d, J = 5.2 Hz, 1H), 8.69 (t, J = 2.0 Hz, 1H), 8.60 (s, 1H), 8.14 (dd, J = 5.1, 1.4 Hz, 1H), 3.55-3.48 (m, 4H), 3.30 (s, 3H), 2.33 (s, 6H) |
| 167 | 2'-(4,5-Dimethyl-1H-imidazol-2-yl)-N-((tetrahydrofuran-2-yl)methyl)-3,4'-bipyridine-5-carboxamide trifluoroacetate salt (racemic mixture prepared) | 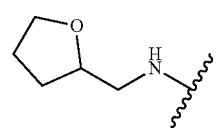 | 378.2 | 1H NMR (400 MHz, d6-DMSO) δ 9.25 (d, J = 2.2 Hz, 1H), 9.17 (d, J = 1.9 Hz, 1H), 8.98 (t, J = 5.7 Hz, 1H), 8.93 (d, J = 5.1 Hz, 1H), 8.70 (t, J = 2.1 Hz, 1H), 8.61 (s, 1H), 8.14 (dd, J = 5.2, 1.5 Hz, 1H), 4.03 (p, J = 6.3 Hz, 1H), 3.81 (q, J = 7.0 Hz, 1H), 3.66 (q, J = 7.5 Hz, 1H), 3.41 (t, J = 5.8 Hz, 2H), 2.33 (s, 6H), 2.02-1.72 (m, 3H), 1.69-1.52 (m, 1H) |
| 168 | 1-(2'-(4,5-Dimethyl-1H-imidazol-2-yl)-3,4'-bipyridine-5-carbonyl)pyrrolidin-3-one trifluoroacetate salt | 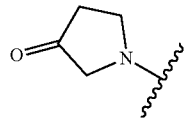 [SMILES: *N1CCC(=O)C1] | 362.1 | |

TABLE 14-continued

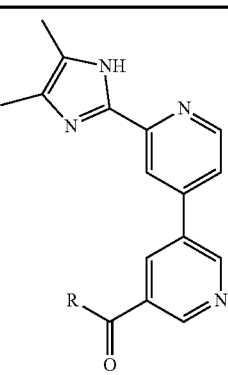

| Ex. No. | Name | R = | MS (M + H)+ | 1H NMR |
|---|---|---|---|---|
| 169 | (2'-(4,5-Dimethyl-1H-imidazol-2-yl)-3,4'-bipyridin-5-yl)(3-(2-hydroxyethyl)pyrrolidin-1-yl)methanone (racemic mixture prepared) | 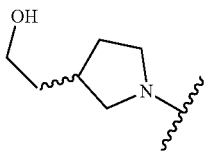 [SMILES: *N1CCC(CCO)C1] | 392.2 | 1H NMR (400 MHz, d6-DMSO, rotamers) δ 9.24-9.18 (m, 1H), 8.94-8.86 (m, 2H), 8.62-8.57 (m, 1H), 8.44-8.38 (m, 1H), 8.17-8.06 (m, 1H), 3.77 (dd, J = 12.0, 7.4 Hz, 0.5H), 3.71-3.24 (m, 4.5H), 3.20 (t, J = 9.6 Hz, 0.5H), 3.12 (dd, J = 11.9, 9.0 Hz, 0.5H), 2.33 (s, 6H), 2.28-1.94 (m, 2H), 1.69-1.39 (m, 3H) |
| 170 | (2'-(4,5-Dimethyl-1H-imidazol-2-yl)-3,4'-bipyridin-5-yl)(3-(pyridin-2-yl)pyrrolidin-1-yl)methanone trifluoroacetate salt (racemic mixture prepared) | 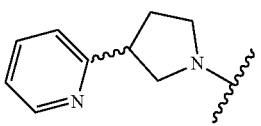 [SMILES: *N1CCC(c2ccccn2)C1] | 425.2 | 1H NMR (400 MHz, d6-DMSO, rotamers) δ 9.26-9.17 (m, 1H), 8.98-8.86 (m, 2H), 8.63-8.58 (m, 1.5H), 8.54-8.50 (m, 0.5H), 8.49-8.42 (m, 1H), 8.19-8.10 (m, 1H), 7.89 (td, J = 8.0, 1.6 Hz, 0.5H), 7.81 (td, J = 7.7, 1.5 Hz, 0.5H), 7.52 (d, J = 7.9 Hz, 0.5H), 7.44-7.36 (m, 1H), 7.32 (dd, J = 7.1, 5.4 Hz, 0.5H), 4.05 (dd, J = 11.1, 7.2 Hz, 0.5H), 3.89 1(dd, J = 9.8, 7.8 Hz, 0.5H), 3.84-3.53 (m, 4H), 2.45-2.07 (m, 2H), 2.335 (s, 3H), 2.330 (s, 3H) |
| 171 | 2-(2'-(4,5-Dimethyl-1H-imidazol-2-yl)-3,4'-bipyridine-5-carbonyl)-6-methyl-2,6-diazaspiro[3.4]octan-5-one trifluoroacetate salt | 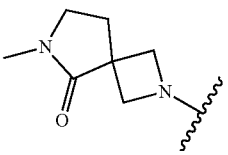 [SMILES: *N1CC2(CCN(C)C2=O)C1] | 417.2 | 1H NMR (400 MHz, d6-DMSO) δ 9.25 (d, J = 2.2 Hz, 1H), 8.98 (d, J = 1.9 Hz, 1H), 8.91 (d, J = 5.2 Hz, 1H), 8.59 (s, 1H), 8.49 (t, J = 2.1 Hz, 1H), 8.15 (dd, J = 5.2, 1.5 Hz, 1H), 4.41 (s, 2H), 4.21 (d, J = 9.9 Hz, 1H), 4.03 (d, J = 10.0 Hz, 1H), 3.33-3.24 (m, 2H), 2.76 (s, 3H), 2.36 (t, J = 6.9 Hz, 2H), 2.33 (s, 6H) |
| 172 | ((3R,4R)-1-{[2'-(4,5-Dimethyl-1H-imidazol-2-yl)-3,4'-bipyridin-5-yl]carbonyl}-4-methylpyrrolidin-3-yl)methanol trifluoroacetate salt | 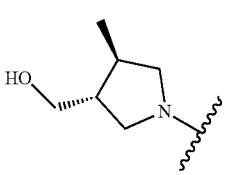 [SMILES: *N1C[C@H](CO)[C@@H](C)C1] | 392.2 | 1H NMR (400 MHz, d6-DMSO, rotamers) δ 9.24-9.18 (m, 1H), 8.94-8.86 (m, 2H), 8.60 (s, 1H), 8.44-8.36 (m, 1H), 8.15 (d, J = 5.1 Hz, 1H), 3.83 (dd, J = 12.0, 7.8 Hz, 0.5H), 3.73 (dd, J = 12.4, 7.8 Hz, 0.5H), 3.68-3.55 (m, 1.5H), 3.55-3.27 (m, 2.5H), 3.20 (t, J = 9.6 Hz, 0.5H), 3.10 (dd, J = 12.0, 9.0 Hz, 0.5H), 2.33 (s, 6H), 2.12-1.84 (m, 2H), 1.08 (d, J = 6.5 Hz, 1.5H), 0.97 (d, J = 6.4 Hz, 1.5H) |

TABLE 14-continued

| Ex. No. | Name | R = | MS (M + H)+ | 1H NMR |
|---|---|---|---|---|
| 173 | 5-[(3,3-Difluoropyrrolidin-1-yl)carbonyl]-2'-(4,5-dimethyl-1H-imidazol-2-yl)-3,4'-bipyridine trifluoroacetate salt | (3,3-difluoropyrrolidin-1-yl) | 384.1 | 1H NMR (400 MHz, d6-DMSO, rotamers) δ 9.24 (s, 1H), 8.94-8.92 (m, 1H), 8.91 (d, J = 5.2 Hz, 1H), 8.63-8.56 (m, 1H), 8.49-8.39 (m, 1H), 8.14 (dd, J = 5.2, 1.4 Hz, 1H), 4.05 (t, J = 12.5 Hz, 0.9H), 3.98 (t, J = 13.3 Hz, 1.1H), 3.80 (t, J = 7.4 Hz, 2H), 2.58-2.41 (m, 2H), 2.33 (s, 6H) |
| 174 | 2'-(4,5-Dimethyl-1H-imidazol-2-yl)-5-[(3-methoxypyrrolidin-1-yl)carbonyl]-3,4'-bipyridine trifluoroacetate salt (racemic mixture prepared) | (3-methoxypyrrolidin-1-yl) | 378.2 | 1H NMR (400 MHz, CD3OD, rotamers) δ 9.16-9.12 (m, 1H), 8.93-8.89 (m, 2H), 8.45-8.42 (m, 1H), 8.42-8.39 (m, 1H), 8.00-7.95 (m, 1H), 4.19-4.11 (m, 0.5H), 4.11-3.98 (m, 0.5H), 3.88-3.66 (m, 3H), 3.66-3.57 (m, 0.5H), 3.57-3.50 (m, 0.5H), 3.41 (s, 1.5H), 3.31 (s, 1.5H), 2.41 (s, 6H), 2.29-1.99 (m, 2H) |
| 175 | Methyl 1-{[2'-(4,5-dimethyl-1H-imidazol-2-yl)-3,4'-bipyridin-5-yl]carbonyl}pyrrolidine-3-carboxylate trifluoroacetate salt (racemic mixture prepared) | (methyl pyrrolidine-3-carboxylate) | 406.1 | 1H NMR (400 MHz, d6-DMSO, rotamers) δ 9.26-9.18 (m, 1H), 8.95-8.86 (m, 2H), 8.60 (s, 1H), 8.46-8.35 (m, 1H), 8.17-8.10 (m, 1H), 3.69 (s, 1.5H), 3.88-3.46 (m, 4H), 3.61 (s, 1.5H), 3.34-3.15 (m, 1H), 2.33 (s, 6H), 2.29-1.93 (m, 2H) |
| 176 | 2'-(4,5-Dimethyl-1H-imidazol-2-yl)-N-[(3R)-tetrahydrofuran-3-yl]-3,4'-bipyridine-5-carboxamide trifluoroacetate salt | ((3R)-tetrahydrofuran-3-ylamino) | 364.1 | 1H NMR (400 MHz, d6-DMSO δ 9.25 (d, J = 2.2 Hz, 1H), 9.17 (d, J = 1.9 Hz, 1H), 8.98-8.89 (m, 2H), 8.68 (t, J = 2.1 Hz, 1H), 8.60 (s, 1H), 8.14 (dd, J = 5.2, 1.5 Hz, 1H), 4.60-4.45 (m, 1H), 3.97-3.82 (m, 2H), 3.75 (td, J = 8.1, 5.9 Hz, 1H), 3.67 (dd, J = 9.0, 4.0 Hz, 1H), 2.33 (s, 6H), 2.23 (dq, J = 13.0, 7.9 Hz, 1H), 2.03-1.86 (m, 1H) |

TABLE 14-continued

| Ex. No. | Name | R = | MS (M + H)+ | 1H NMR |
|---|---|---|---|---|
| 177 | 1-{[2'-(4,5-Dimethyl-1H-imidazol-2-yl)-3,4'-bipyridin-5-yl]carbonyl}piperidin-4-ol | HO-piperidin-4-yl | 378.1 | 1H NMR (400 MHz, d6-DMSO) δ 9.20 (d, J = 2.2 Hz, 1H), 8.91 (d, J = 5.1 Hz, 1H), 8.77 (d, J = 1.8 Hz, 1H), 8.60 (s, 1H), 8.33 (t, J = 2.0 Hz, 1H), 8.13 (dd, J = 5.2, 1.4 Hz, 1H), 4.12-3.89 (m, 1H), 3.79 (tt, J = 7.7, 3.4 Hz, 1H), 3.63-3.43 (m, 1H), 3.43-3.28 (m, 1H), 3.28-3.13 (m, 1H), 2.33 (s, 6H), 1.92-1.78 (m, 1H), 1.79-1.63 (m, 1H), 1.55-1.31 (m, 2H) |
| 178 | 2'-(4,5-Dimethyl-1H-imidazol-2-yl)-5-{[3-(trifluoromethyl)pyrrolidin-1-yl]carbonyl}-3,4'-bipyridine trifluoroacetate salt (racemic mixture prepared) | F3C-pyrrolidin-1-yl | 416.2 | 1H NMR (400 MHz, d6-DMSO) δ 9.26-9.21 (m, 1H), 8.96-8.85 (m, 2H), 8.60 (s, 1H), 8.48-8.35 (m, 1H), 8.15 (dd, J = 5.2, 1.4 Hz, 1H), 3.92-3.78 (m, 1H), 3.78-3.52 (m, 3H), 3.47-3.15 (m, 1H), 2.33 (s, 6H), 2.29-2.13 (m, 1H), 2.13-1.85 (m, 1H) |
| 179 | 5-(7-Azabicyclo[2.2.1]hept-7-ylcarbonyl)-2'-(4,5-dimethyl-1H-imidazol-2-yl)-3,4'-bipyridine trifluoroacetate salt | 7-azabicyclo[2.2.1]hept-7-yl | 374.2 | 1H NMR (400 MHz, d6-DMSO) δ 9.25 (d, J = 2.2 Hz, 1H), 8.91 (d, J = 5.2 Hz, 1H), 8.89 (d, J = 1.8 Hz, 1H), 8.60 (s, 1H), 8.41 (t, J = 2.1 Hz, 1H), 8.16 (dd, J = 5.2, 1.5 Hz, 1H), 4.62 (s, 1H), 4.13 (s, 1H), 2.33 (s, 6H), 1.93-1.68 (m, 4H), 1.68-1.37 (m, 4H) |
| 180 | 1-{[2'-(4,5-Dimethyl-1H-imidazol-2-yl)-3,4'-bipyridin-5-yl]carbonyl}-3-methylpyrrolidin-3-ol trifluoroacetate salt (racemic mixture prepared) | HO,Me-pyrrolidin-1-yl | 378.2 | 1H NMR (400 MHz, d6-DMSO, rotamers) δ 9.24-9.20 (m, 1H), 8.94-8.84 (m, 2H), 8.60 (s, 1H), 8.44-8.38 (m, 1H), 8.15 (dd, J = 5.2, 1.2 Hz, 1H), 3.78-3.57 (m, 1.5H), 3.57-3.44 (m, 1.5H), 3.37 (d, J = 12.4 Hz, 0.5H), 3.26 (d, J = 10.4 Hz, 0.5H), 2.33 (s, 6H), 1.96-1.69 (m, 2H), 1.37 (s, 1.5H), 1.26 (s, 1.5H) |

TABLE 14-continued

| Ex. No. | Name | R = | MS (M + H)+ | 1H NMR |
|---|---|---|---|---|
| 181 | 2'-(4,5-Dimethyl-1H-imidazol-2-yl)-5-[(3-phenylpyrrolidin-1-yl)carbonyl]-3,4'-bipyridine trifluoroacetate salt (racemic mixture prepared) | | 424.2 | 1H NMR (400 MHz, d6-DMSO, rotamers) δ 9.24 (d, J = 2.1 Hz, 0.4H), 9.21 (d, J = 2.1 Hz, 0.6H), 8.98-8.84 (m, 2H), 8.62 (s, 0.4H), 8.60 (s, 0.6H), 8.49-8.43 (m, 1H), 8.16 (dd, J = 5.1, 1.2 Hz, 0.4H), 8.13 (dd, J = 5.1, 1.2 Hz, 0.6H), 7.41-7.19 (m, 5H), 4.12-3.31 (m, 5H), 2.42-2.24 (m, 1H), 2.335 (s, 2.4H), 2.330 (s, 3.6H), 2.16-1.95 (m, 1H) |
| 182 | 2'-(4,5-Dimethyl-1H-imidazol-2-yl)-5-[(3-pyridin-4-ylpyrrolidin-1-yl)carbonyl]-3,4'-bipyridine (racemic mixture prepared) | | 425.2 | 1H NMR (400 MHz, d6-DMSO, rotamers) δ 9.13 (d, J = 2.1 Hz, 0.5H), 9.11 (d, J = 2.1 Hz, 0.5H), 8.86-8.84 (m, 1H), 8.68-8.62 (m, 1H), 8.56-8.52 (m, 1H), 8.49-8.46 (m, 1H), 8.39 (t, J = 2.0 Hz, 0.5H), 8.38 (t, J = 2.0 Hz, 0.5H), 8.25 (s, 0.5H), 8.23 (s, 0.5H), 7.74 (dd, J = 5.2, 1.6 Hz, 0.5H), 7.71 (dd, J = 5.2, 1.6 Hz, 0.5H), 7.40 (d, J = 5.9 Hz, 1H), 7.32 (d, J = 5.9 Hz, 1H), 4.14-3.41 (m, 5H), 2.43-2.26 (m, 1H), 2.19 (s, 3H), 2.12 (s, 3H), 2.10-1.95 (m, 1H) |
| 183 | 1-{[2'-(4,5-Dimethyl-1H-imidazol-2-yl)-3,4'-bipyridin-5-yl]carbonyl}pyrrolidine-3-carbonitrile trifluoroacetate salt (racemic mixture prepared) | | 373.1 | 1H NMR (400 MHz, CD3OD) δ 9.18 (d, J = 2.1 Hz, 1H), 8.99-8.96 (m, 1H), 8.92 (d, J = 5.1 Hz, 1H), 8.50 (t, J = 2.1 Hz, 1H), 8.44-8.35 (m, 1H), 8.00 (dd, J = 5.1, 1.6 Hz, 1H), 4.99 (dd, J = 7.5, 5.0 Hz, 1H), 3.87-3.75 (m, 1H), 3.75-3.61 (m, 1H), 2.41 (s, 6H), 2.57-2.30 (m, 2H), 2.30-2.00 (m, 2H) |
| 184 | 2'-(4,5-Dimethyl-1H-imidazol-2-yl)-5-{[2-(trifluoromethyl)azetidin-1-yl]carbonyl}-3,4'-bipyridine trifluoroacetate salt (racemic mixture prepared) | | 402.1 | 1H NMR (400 MHz, d6-DMSO) δ 9.27 (d, J = 2.2 Hz, 1H), 9.00 (d, J = 1.9 Hz, 1H), 8.91 (d, J = 5.1 Hz, 1H), 8.58 (s, 1H), 8.50 (t, J = 2.0 Hz, 1H), 8.14 (dd, J = 5.2, 1.4 Hz, 1H), 4.68 (t, J = 9.1 Hz, 1H), 4.53 (dd, J = 8.6, 5.2 Hz, 1H), 4.38 (t, J = 9.9 Hz, 1H), 4.13 (dd, J = 10.5, 5.3 Hz, 1H), 3.82-3.67 (m, 1H), 2.33 (s, 6H) |

TABLE 14-continued

| Ex. No. | Name | R = | MS (M + H)+ | 1H NMR |
|---|---|---|---|---|
| 185 | 5-[(3,3-Dimethylazetidin-1-yl)carbonyl]-2'-(4,5-dimethyl-1H-imidazol-2-yl)-3,4'-bipyridine trifluoroacetate salt | | 362.2 | 1H NMR (400 MHz, d6-DMSO) δ 9.23 (d, J = 2.2 Hz, 1H), 8.97 (d, J = 1.9 Hz, 1H), 8.91 (d, J = 5.1 Hz, 1H), 8.59 (s, 1H), 8.48 (t, J = 2.1 Hz, 1H), 8.13 (dd, J = 5.2, 1.5 Hz, 1H), 4.10 (s, 2H), 3.81 (s, 2H), 2.33 (s, 6H), 1.28 (s, 6H) |
| 186 | 2'-(4,5-Dimethyl-1H-imidazol-2-yl)-5-[(4-phenylpiperidin-1-yl)carbonyl]-3,4'-bipyridine trifluoroacetate salt | | 438.2 | 1H NMR (400 MHz, d6-DMSO) δ 9.22 (d, J = 2.2 Hz, 1H), 8.92 (d, J = 5.1 Hz, 1H), 8.85 (d, J = 1.8 Hz, 1H), 8.61 (s, 1H), 8.39 (t, J = 2.0 Hz, 1H), 8.14 (dd, J = 5.2, 1.5 Hz, 1H), 7.36-7.18 (m, 5H), 4.78-4.64 (br m, 1H), 3.76-3.62 (br m, 1H), 3.39-3.17 (br m, 1H), 3.06-2.80 (br m, 2H), 2.33 (s, 6H), 1.99-1.85 (br m, 1H), 1.82-1.57 (br m, 3H) |
| 187 | 2'-(4,5-Dimethyl-1H-imidazol-2-yl)-5-[(4aR,8aS)-octahydroisoquinolin-2(1H)-ylcarbonyl]-3,4'-bipyridine trifluoroacetate salt | | 416.2 | 1H NMR (400 MHz, d6-DMSO) δ 9.21 (d, J = 1.3 Hz, 1H), 8.91 (d, J = 5.1 Hz, 1H), 8.77 (d, J = 1.8 Hz, 1H), 8.59 (s, 1H), 8.34-8.26 (m, 1H), 8.14 (dd, J = 5.2, 1.4 Hz, 1H), 4.72-2.38 (m, 4H), 2.33 (s, 6H), 1.83-0.75 (m, 12H) |
| 188 | 2'-(4,5-Dimethyl-1H-imidazol-2-yl)-5-[(3-phenylpiperidin-1-yl)carbonyl]-3,4'-bipyridine trifluoroacetate salt (racemic mixture prepared) | | 438.2 | 1H NMR (400 MHz, d6-DMSO, rotamers) δ 9.26-9.13 (m, 1H), 8.96-8.87 (m, 1H), 8.83 (s, 1H), 8.65-8.53 (m, 1H), 8.42-8.31 (m, 1H), 8.19-8.05 (m, 1H), 7.48-6.99 (m, 5H), 4.71-2.73 (m, 5H), 2.33 (s, 6H), 2.05-1.56 (m, 4H) |
| 189 | 5-[(4-Benzylpiperidin-1-yl)carbonyl]-2'-(4,5-dimethyl-1H-imidazol-2-yl)-3,4'-bipyridine trifluoroacetate salt | | 452.1 | 1H NMR (400 MHz, d6-DMSO) δ 9.20 (d, J = 2.2 Hz, 1H), 8.91 (d, J = 5.2 Hz, 1H), 8.76 (d, J = 1.8 Hz, 1H), 8.59 (s, 1H), 8.32 (t, J = 2.0 Hz, 1H), 8.13 (dd, J = 5.2, 1.4 Hz, 1H), 7.32-7.24 (m, 2H), 7.23-7.14 (m, 3H), 4.60-2.72 (m, 4H), 2.56 (d, J = 7.0 Hz, 2H), 2.33 (s, 6H), 1.92-1.47 (m, 3H), 1.32-1.12 (m, 2H) |

TABLE 14-continued

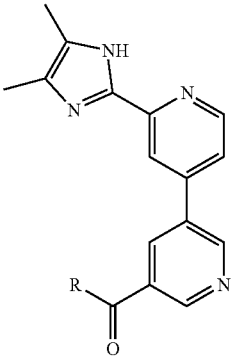

| Ex. No. | Name | R = | MS (M + H)+ | 1H NMR |
|---|---|---|---|---|
| 190 | 2'-(4,5-Dimethyl-1H-imidazol-2-yl)-5-[(2-methylpiperidin-1-yl)carbonyl]-3,4'-bipyridine trifluoroacetate salt (racemic mixture prepared) | 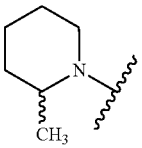 | 376.2 | 1H NMR (400 MHz, d6-DMSO) δ 9.20 (d, J = 2.1 Hz, 1H), 8.91 (d, J = 5.2 Hz, 1H), 8.75 (d, J = 1.4 Hz, 1H), 8.60 (s, 1H), 8.34-8.27 (m, 1H), 8.14 (dd, J = 5.2, 1.5 Hz, 1H), 5.00-2.69 (m, 3H), 2.33 (s, 6H), 1.84-1.33 (m, 6H), 1.25 (d, J = 6.9 Hz, 3H) |
| 191 | 5-(Azetidin-1-ylcarbonyl)-2'-(4,5-dimethyl-1H-imidazol-2-yl)-3,4'-bipyridine trifluoroacetate salt | 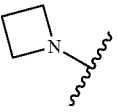 [SMILES: *N1CCC1] | 334.1 | 1H NMR (400 MHz, CD3OD) δ 9.15 (d, J = 2.2 Hz, 1H), 8.97 (d, J = 1.9 Hz, 1H), 8.92 (d, J = 5.1 Hz, 1H), 8.51 (t, J = 2.1 Hz, 1H), 8.42-8.38 (m, 1H), 7.98 (dd, J = 5.1, 1.6 Hz, 1H), 4.52 (t, J = 7.7 Hz, 2H), 4.30 (t, J = 7.8 Hz, 2H), 2.46 (pent, J = 15.8, 7.9 Hz, 2H), 2.41 (s, 6H) |
| 192 | N-Benzyl-2'-(4,5-dimethyl-1H-imidazol-2-yl)-3,4'-bipyridine-5-carboxamide trifluoroacetate salt | 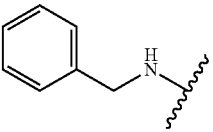 [SMILES: *NCc1ccccc1] | 384.1 | 1H NMR (400 MHz, d6-DMSO) δ 9.44 (t, J = 5.9 Hz, 1H), 9.27 (d, J = 2.2 Hz, 1H), 9.22 (d, J = 2.0 Hz, 1H), 8.93 (d, J = 5.1 Hz, 1H), 8.74 (t, J = 2.1 Hz, 1H), 8.61 (s, 1H), 8.15 (dd, J = 5.2, 1.6 Hz, 1H), 7.43-7.23 (m, 5H), 4.58 (d, J = 5.9 Hz, 2H), 2.33 (s, 6H) |
| 193 | N-Benzyl-2'-(4,5-dimethyl-1H-imidazol-2-yl)-N-methyl-3,4'-bipyridine-5-carboxamide trifluoroacetate salt | 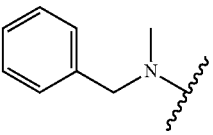 [SMILES: *N(C)Cc1ccccc1] | 398.1 | 1H NMR (400 MHz, d6-DMSO, rotamers) δ 9.24-9.16 (m, 1H), 8.96-8.74 (m, 2H), 8.62-8.53 (m, 1H), 8.47-8.34 (m, 1H), 8.21-8.10 (m, 0.6H), 8.09-7.97 (m, 0.4H), 7.48-7.14 (m, 5H), 4.75 (s, 1.2H), 4.56 (s, 0.8H), 3.01 (s, 1.2H), 2.95 (s, 1.8H), 2.33 (s, 6H) |
| 194 | 2'-(4,5-Dimethyl-1H-imidazol-2-yl)-N-methyl-N-phenyl-3,4'-bipyridine-5-carboxamide trfluoroacetate salt | 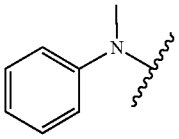 [SMILES: *N(C)c1ccccc1] | 384.2 | 1H NMR (400 MHz, d6-DMSO) δ 8.99 (d, J = 1.9 Hz, 1H), 8.88 (d, J = 5.1 Hz, 1H), 8.52 (s, 1H), 8.46 (br, 1H), 8.31-8.26 (m, 1H), 7.95-7.90 (m, 1H), 7.35-7.26 (m, 4H), 7.25-7.17 (m, 1H), 3.46 (s, 3H), 2.33 (s, 6H) |

TABLE 14-continued

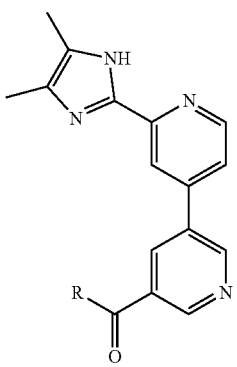

| Ex. No. | Name | R = | MS (M + H)+ | 1H NMR |
|---|---|---|---|---|
| 195 | 2'-(4,5-Dimethyl-1H-imidazol-2-yl)-N-[(1S)-1-phenylethyl]-3,4'-bipyridine-5-carboxamide trifluoroacetate salt | | 398.1 | 1H NMR (400 MHz, d6-DMSO) δ 9.26 (d, J = 2.3 Hz, 1H), 9.23-9.18 (m, 2H), 8.93 (d, J = 5.3 Hz, 1H), 8.69 (t, J = 2.1 Hz, 1H), 8.62-8.53 (m, 1H), 8.15 (dd, J = 5.2, 1.7 Hz, 1H), 7.48-7.41 (m, 2H), 7.41-7.32 (m, 2H), 7.30-7.21 (m, 1H), 5.24 (p, J = 7.2 Hz, 1H), 2.33 (s, 6H), 1.54 (d, J = 7.1 Hz, 3H) |
| 196 | 4-Benzyl-1-{[2'-(4,5-dimethyl-1H-imidazol-2-yl)-3,4'-bipyridin-5-yl]carbonyl}piperidin-4-ol trifluoroacetate salt | | 468.2 | 1H NMR (400 MHz, d6-DMSO) δ 9.20 (d, J = 2.3 Hz, 1H), 8.91 (d, J = 5.2 Hz, 1H), 8.76 (d, J = 1.9 Hz, 1H), 8.59-8.55 (m, 1H), 8.32 (t, J = 2.1 Hz, 1H), 8.13 (dd, J = 5.2, 1.6 Hz, 1H), 7.30-7.15 (m, 5H), 4.36-4.17 (br m, 1H), 3.48-3.32 (br m, 2H), 3.23-3.04 (br m, 1H), 2.73 (s, 2H), 2.33 (s, 6H), 1.60-1.22 (m, 4H) |
| 197 | 2'-(4,5-Dimethyl-1H-imidazol-2-yl)-5-[(3-pyrazin-2-ylpyrrolidin-1-yl)carbonyl]-3,4'-bipyridine trifluoroacetate salt | | 426.2 | 1H NMR (400 MHz, d6-DMSO, rotamers) δ 9.25-9.21 (m, 1H), 8.96-8.86 (m, 2H), 8.76-8.50 (m, 4H), 8.48-8.44 (m, 1H), 8.18-8.11 (m, 1H), 4.12-3.61 (m, 5H), 2.33 (s, 3H), 2.33 (s, 3H), 2.47-2.10 (m, 2H) |
| 198 | 2'-(4,5-Dimethyl-1H-imidazol-2-yl)-N-ethyl-N-methyl-3,4'-bipyridine-5-carboxamide trifluoroacetate salt | | 336.1 | 1H NMR (400 MHz, d6-DMSO, rotamers) δ 9.21 (br s, 1H), 8.91 (d, J = 5.2 Hz, 1H), 8.79 (d, J = 9.1 Hz, 1H), 8.59 (s, 1H), 8.37-8.29 (m, 1H), 8.15 (dd, J = 5.2, 1.6 Hz, 1H), 3.54 (q, J = 6.5 Hz, 1H), 3.28 (q, J = 6.5 Hz, 1H), 3.03 (s, 1.5H), 2.97 (s, 1.5H), 2.33 (s, 6H), 1.20 (t, J = 7.1 Hz, 1.5H), 1.11 (t, J = 6.9 Hz, 1.5H) |

TABLE 14-continued

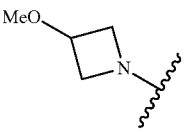 [SMILES: *N1CC(OC)C1]

| Ex. No. | Name | R = | MS (M + H)+ | 1H NMR |
|---|---|---|---|---|
| 199 | 2'-(4,5-Dimethyl-1H-imidazol-2-yl)-5-[(3-methoxyazetidin-1-yl)carbonyl]-3,4'-bipyridine | 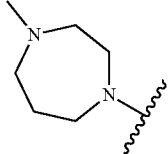 | 364.1 | 1H NMR (400 MHz, d6-DMSO) δ 12.43 (br s, 1H), 9.15 (d, J = 2.2 Hz, 1H), 8.90 (d, J = 1.9 Hz, 1H), 8.66 (d, J = 5.1 Hz, 1H), 8.38 (t, J = 2.1 Hz, 1H), 8.29-8.14 (m, 1H), 7.73 (dd, J = 5.2, 1.8 Hz, 1H), 4.60-4.41 (m, 1H), 4.36-4.21 (m, 3H), 3.99-3.84 (m, 1H), 3.24 (s, 3H), 2.19 (s, 3H), 2.12 (s, 3H) |
| 200 | 2'-(4,5-Dimethyl-1H-imidazol-2-yl)-5-[(4-methyl-1,4-diazepan-1-yl)carbonyl]-3,4'-bipyridine | 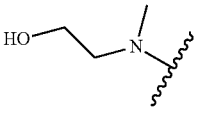 | 391.2 | 1H NMR (400 MHz, d6-DMSO, rotamers) δ 12.42 (s, 1H), 9.09 (d, J = 2.2 Hz, 1H), 8.71-8.68 (m, 1H), 8.65 (d, J = 5.2 Hz, 1H), 8.31-8.25 (m, 1H), 8.24 (s, 1H), 7.72 (d, J = 5.0 Hz, 1H), 3.73-3.62 (m, 2H), 3.51-3.39 (m, 2H), 2.72-2.63 (m, 1H), 2.63-2.49 (m, 3H), 2.30 (s, 1.5H), 2.26 (s, 1.5H,), 2.19 (s, 3H), 2.12 (s, 3H), 1.94-1.83 (m, 1H), 1.83-1.70 (m, 1H) |
| 201 | 2'-(4,5-Dimethyl-1H-imidazol-2-yl)-N-(2-hydroxyethyl)-N-methyl-3,4'-bipyridine-5-carboxamide trifluoroacetate salt | 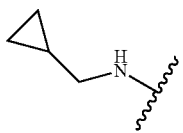 [SMILES: *NCC1CC1] | 352.1 | 1H NMR (400 MHz,d6-DMSO, rotamers) δ 9.21-9.16 (m, 1H), 8.91 (d, J = 5.1 Hz, 1H), 8.83-8.79 (m, 1H), 8.59 (s, 1H), 8.38-8.32 (m, 1H), 8.16-8.05 (m, 1H), 3.71-3.64 (m, 0.8H), 3.61-3.56 (m, 0.8H), 3.56-3.49 (m, 1.2H), 3.38-3.29 (m, 1.2H), 3.06 (s, 1.8H), 3.04 (s, 1.2H), 2.33 (s, 6H) |
| 202 | N-(Cyclopropyl-methyl)-2'-(4,5-dimethyl-1H-imidazol-2-yl)-3,4'-bipyridine-5-carboxamide trifluoroacetate salt | | 348.2 | 1H NMR (400 MHz, d6-DMSO) δ 9.25 (d, J = 2.2 Hz, 1H), 9.17 (d, J = 1.9 Hz, 1H), 8.99 (t, J = 5.5 Hz, 1H), 8.93 (d, J = 5.1 Hz, 1H), 8.69 (t, J = 2.1 Hz, 1H), 8.61 (s, 1H), 8.14 (dd, J = 5.2, 1.5 Hz, 1H), 3.23 (t, J = 6.2 Hz, 2H), 2.33 (s, 6H), 1.13-0.99 (m, 1H), 0.53-0.43 (m, 2H), 0.33-0.20 (m, 2H) |

TABLE 14-continued

| Ex. No. | Name | R = | MS (M + H)+ | ¹H NMR |
|---|---|---|---|---|
| 203 | N-(Cyanomethyl)-2'-(4,5-dimethyl-1H-imidazol-2-yl)-N-methyl-3,4'-bipyridine-5-carboxamide | | 347.1 | ¹H NMR (400 MHz, d₆-DMSO) δ 12.42 (s, 1H), 9.16 (d, J = 2.2 Hz, 1H), 8.78 (s, 1H), 8.66 (d, J = 5.2 Hz, 1H), 8.40 (s, 1H), 8.29-8.17 (m, 1H), 7.74 (dd, J = 5.2, 1.6 Hz, 1H), 4.62 (s, 2H), 3.10 (s, 3H), 2.19 (s, 3H), 2.12 (s, 3H) |
| 204 | 2'-(4,5-Dimethyl-1H-imidazol-2-yl)-N-(2-methoxyethyl)-N-methyl-3,4'-bipyridine-5-carboxamide trifluoroacetate salt | | 366.2 | ¹H NMR (400 MHz, d₆-DMSO, rotamers) δ 9.20 (s, 1H), 8.91 (d, J = 5.2 Hz, 1H), 8.82-8.72 (m, 1H), 8.59 (s, 1H), 8.37-8.29 (m, 1H), 8.19-8.04 (m, 1H), 3.72-3.66 (m, 1H), 3.66-3.58 (m, 1H), 3.46 (br s, 2H), 3.33 (s, 1.4H), 3.20 (s, 1.6H), 3.06 (s, 1.6H), 3.03 (s, 1.4H), 2.33 (s, 6H) |
| 205 | 2'-(4,5-Dimethyl-1H-imidazol-2-yl)-N-{[1-(hydroxymethyl)cyclopropyl]methyl}-N-methyl-3,4'-bipyridine-5-carboxamide trifluoroacetate salt | | 392.2 | ¹H NMR (400 MHz, d₆-DMSO) δ 9.22-9.06 (m, 1H), 8.94-8.84 (m, 1H), 8.82-8.73 (m, 1H), 8.58 (s, 1H), 8.35 (s, 1H), 8.16-8.08 (m, 1H), 3.57 (s, 1H), 3.38 (s, 1H), 3.28 (s, 1H), 3.16 (s, 1H), 3.07 (s, 1.6H), 3.03 (s, 1.4H), 2.33 (s, 6H), 0.56-0.30 (m, 4H) |
| 206 | N-(Cyclobutylmethyl)-2'-(4,5-dimethyl-1H-imidazol-2-yl)-3,4'-bipyridine-5-carboxamide trifluoroacetate salt | | 362.1 | ¹H NMR (400 MHz, d₆-DMSO) δ 9.24 (d, J = 2.2 Hz, 1H), 9.15 (d, J = 1.9 Hz, 1H), 8.93 (d, J = 5.1 Hz, 1H), 8.85 (t, J = 5.6 Hz, 1H), 8.67 (t, J = 2.1 Hz, 1H), 8.61 (s, 1H), 8.14 (dd, J = 5.2, 1.5 Hz, 1H), 3.44-3.33 (m, 2H), 2.63-2.53 (m, 1H), 2.33 (s, 6H), 2.11-1.95 (m, 2H), 1.94-1.81 (m, 2H), 1.81-1.68 (m, 2H) |
| 207 | N-(Cyclopentylmethyl)-2'-(4,5-dimethyl-1H-imidazol-2-yl)-3,4'-bipyridine-5-carboxamide trifluoroacetate salt | | 376.2 | ¹H NMR (400 MHz, d₆-DMSO) δ 9.24 (d, J = 2.2 Hz, 1H), 9.15 (d, J = 1.9 Hz, 1H), 8.93 (d, J = 5.1 Hz, 1H), 8.88 (t, J = 5.6 Hz, 1H), 8.67 (t, J = 2.1 Hz, 1H), 8.61 (s, 1H), 8.14 (dd, J = 5.2, 1.5 Hz, 1H), 3.32-3.22 (m, 2H), 2.33 (s, 6H), 2.19 (hept, J = 7.4 Hz, 1H), 1.79-1.43 (m, 6H), 1.37-1.17 (m, 2H) |

TABLE 14-continued

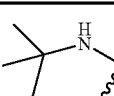

| Ex. No. | Name | R = | MS (M + H)+ | 1H NMR |
|---|---|---|---|---|
| 208 | N-(tert-Butyl)-2'-(4,5-dimethyl-1H-imidazol-2-yl)-3,4'-bipyridine-5-carboxamide trifluoroacetate salt | 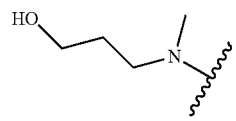 [SMILES: *N(C)CCCO] | 350.2 | 1H NMR (400 MHz, d6-DMSO) δ 9.22 (d, J = 2.2 Hz, 1H), 9.11 (d, J = 1.9 Hz, 1H), 8.92 (d, J = 5.2 Hz, 1H), 8.64-8.57 (m, 2H), 8.23 (s, 1H), 8.15 (dd, J = 5.1, 1.4 Hz, 1H), 2.33 (s, 6H), 1.44 (s, 9H) |
| 209 | 2'-(4,5-Dimethyl-1H-imidazol-2-yl)-N-(3-hydroxypropyl)-N-methyl-3,4'-bipyridine-5-carboxamide | 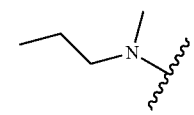 [SMILES: *N(C)CCC] | 366.2 | 1H NMR (400 MHz, d6-DMSO, rotamers) δ 12.43 (s, 1H), 9.09 (d, J = 2.2 Hz, 1H), 8.70 (d, J = 4.3 Hz, 1H), 8.65 (d, J = 5.2 Hz, 1H), 8.33 -8.15 (m, 2H), 7.73 (d, J = 4.8 Hz, 1H), 4.68 (s, 0.5H), 4.53 (s, 0.5H), 3.61-3.43 (m, 2H), 3.39-3.22 (m, 2H), 3.02 (s, 1.5H), 2.97 (s, 1.5H), 2.19 (s, 3H), 2.12 (s, 3H), 1.84-1.68 (m, 2H) |
| 210 | 2'-(4,5-Dimethyl-1H-imidazol-2-yl)-N-methyl-N-propyl-3,4'-bipyridine-5-carboxamide | 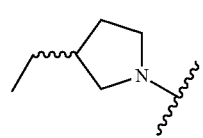 [SMILES: *N1CCC(CC)C1] | 350.1 | 1H NMR (400 MHz, CD3OD, rotamers) δ 9.10 (s, 1H), 8.75-8.65 (m, 2H), 8.35 (s, 1H), 8.33-8.24 (m, 1H), 7.72-7.62 (m, 1H), 3.60 (t, J = 7.4 Hz, 1H), 3.37 (t, J = 7.4 Hz, 1H), 3.16 (s, 1.5H), 3.10 (s, 1.5H), 2.26 (s, 6H), 1.79 (h, J = 7.2 Hz, 1H), 1.68 (h, J = 7.0 Hz, 1H), 1.05 (t, J = 7.3 Hz, 1.5H), 0.83 (t, J = 7.4 Hz, 1.5H) |
| 211 | 2'-(4,5-Dimethyl-1H-imidazol-2-yl)-5-[(3-ethylpyrrolidin-1-yl)carbonyl]-3,4'-bipyridine trifluoroacetate salt | | 376.2 | 1H NMR (400 MHz, d6-DMSO, rotamers) δ 9.23-9.18 (m, 1H), 8.93-8.86 (m, 2H), 8.60 (s, 1H), 8.43-8.39 (m, 1H), 8.17-8.10 (m, 1H), 3.80-3.40 (m, 3H), 3.23-3.04 (m, 1H), 2.33 (s, 6H), 2.18-1.95 (m, 2H), 1.63-1.17 (m, 3H), 0.95 (t, J = 7.4 Hz, 1.5H), 0.85 (t, J = 7.4 Hz, 1.5H) |

TABLE 14-continued

| Ex. No. | Name | R = | MS (M + H)+ | 1H NMR |
|---|---|---|---|---|
| 212 | 5-(5-Azaspiro[2.4]hept-5-ylcarbonyl)-2'-(4,5-dimethyl-1H-imidazol-2-yl)-3,4'-bipyridine trifluoroacetate salt | | 374.2 | 1H NMR (400 MHz, d6-DMSO, rotamers) δ 9.25-9.18 (m, 1H), 8.96-8.87 (m, 2H), 8.62-8.55 (m, 1H), 8.46 (t, J = 2.0 Hz, 0.5H), 8.43 (t, J = 2.0 Hz, 0.5H), 8.19-8.10 (m, 1H), 3.74-3.63 (m, 2H), 3.47 (s, 1H), 3.43 (s, 1H), 2.33 (s, 6H), 1.88 (t, J = 7.0 Hz, 1H), 1.83 (t, J = 6.7 Hz, 1H), 0.72-0.67 (m, 1H), 0.67-0.61 (m, 1H), 0.57 (s, 2H) |
| 212B | 2'-(4,5-Dimethyl-1H-imidazol-2-yl)-5-{[(3S)-3-methoxypyrrolidin-1-yl]carbonyl}-3,4'-bipyridine trifluoroacetate salt | | 378.1 | 1H NMR (400 MHz, d6-DMSO, rotamers) δ 9.24-9.19 (m, 1H), 8.93-8.85 (m, 2H), 8.62-8.56 (m, 1H), 8.45-8.39 (m, 1H), 8.17-8.12 (m, 1H), 4.10-4.03 (m, 0.5H), 4.02-3.95 (m, 0.5H), 3.79-3.38 (m, 4H), 3.30 (s, 1.5H), 3.19 (s, 1.5H), 2.33 (s, 6H), 2.13-1.89 (m, 2H) |

Example 214. 2'-(4,5-Dimethyl-1H-imidazol-2-yl)-1-(phenylsulfonyl)-1,2,5,6-tetrahydro-3,4'-bipyridine trifluoroacetate salt

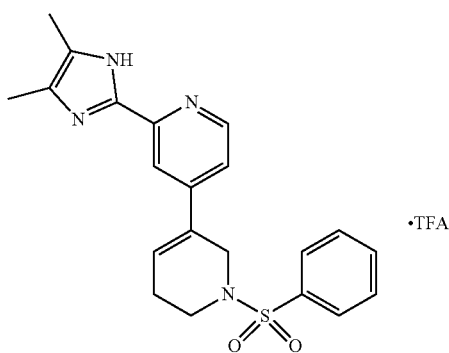 [SMILES: Cc1nc(-c2cc(C3=CCCN(S(=O)(=O)c4ccccc4)C3)ccn2)[nH]c1C ; "·TFA"]

To 2'-(4,5-dimethyl-1H-imidazol-2-yl)-1,2,5,6-tetrahydro-3,4'-bipyridine (0.015 g, 0.059 mmol, from Step 3) in DCM (0.3 mL) was added Et₃N (0.025 mL, 0.18 mmol), followed by benzenesulfonyl chloride (0.007 mL, 0.05 mmol). After stirring overnight, the reaction mixture was diluted with MeOH and water. The product was purified by preparative HPLC (C-18 column eluting with a water:acetonitrile gradient buffered at pH 2 with 0.1% trifluoroacetic acid). Yield: 8 mg. 1H NMR (400 MHz, CD₃OD) δ 8.69 (d, J=5.0 Hz, 1H), 8.01-7.98 (m, 1H), 7.92-7.87 (m, 2H), 7.72-7.66 (m, 1H), 7.66-7.59 (m, 2H), 7.55 (dd, J=5.2, 1.6 Hz, 1H), 6.68-6.61 (m, 1H), 4.18-3.92 (m, 2H), 3.34-3.31 (m, 2H), 2.51-2.42 (m, 2H), 2.36 (s, 6H); LCMS (M+H)+: 395.1.

Example 215. 2-(4,5-Dimethyl-1H-imidazol-2-yl)-4-[1-(phenylsulfonyl)piperidin-3-yl]pyridine trifluoroacetate salt, Racemic Mixture Prepared

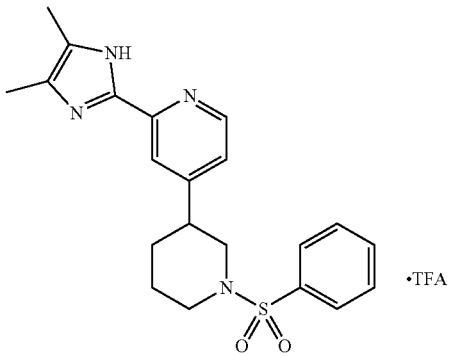 [SMILES: Cc1nc(-c2cc(C3CCCN(S(=O)(=O)c4ccccc4)C3)ccn2)[nH]c1C ; "·TFA"]

A mixture of 2'-(4,5-dimethyl-1H-imidazol-2-yl)-1-(phenylsulfonyl)-1,2,5,6-tetrahydro-3,4'-bipyridine trifluoroacetate salt (0.049 g, 0.079 mmol, from Step 4), Na$_2$CO$_3$ (0.025 g, 0.24 mmol), and palladium (10% on carbon, 0.025 g, 0.024 mmol) in MeOH (10 mL) was degassed and shaken under 40 psi H$_2$ for 2 hours. The reaction mixture was filtered and the MeOH was removed in vacuo. The product was purified by preparative HPLC (C-18 column eluting with a water:acetonitrile gradient buffered at pH 2 with 0.1% trifluoroacetic acid). Yield: 4 mg. $^1$H NMR (400 MHz, CD$_3$OD) δ 8.67 (d, J=5.1 Hz, 1H), 7.87 (s, 1H), 7.82-7.74 (m, 2H), 7.71-7.64 (m, 1H), 7.64-7.54 (m, 2H), 7.48 (dd, J=5.1, 1.4 Hz, 1H), 3.91-3.82 (m, 1H), 3.81-3.69 (m, 1H), 3.08-2.96 (m, 1H), 2.57-2.40 (m, 2H), 2.34 (s, 6H), 2.05-1.95 (m, 1H), 1.95-1.85 (m, 1H), 1.85-1.66 (m, 1H), 1.59 (qd, J=12.0, 3.6 Hz, 1H); LCMS (M+H)$^+$: 397.2.

Examples 217 and 219 through 230 were synthesized by the methods of Examples 213-215 and the data are listed in Table 15. Examples 217, 219, 222 and 226 were prepared via the procedure of Example 214, using acyl chlorides instead of sulfonyl chlorides, as outlined in Scheme 15. Examples 223-225 and 228-230 were prepared by reductive aminations as described in Scheme 15.

TABLE 15

| Ex. No. | Name | R = | MS (M + H)$^+$ | $^1$H NMR |
|---|---|---|---|---|
| 217 | 1-(4-(2-(4,5-Dimethyl-1H-imidazol-2-yl)pyridin-4-yl)-5,6-dihydropyridin-1(2H)-yl)ethanone trifluoroacetate salt | | 297.2 | $^1$H NMR (400 MHz, CD$_3$OD, rotamers) δ 8.73 (d, J = 5.2 Hz, 1H), 8.11-8.09 (m, 0.6H), 8.09-8.06 (m, 0.4H), 7.68-7.64 (m, 0.4H), 7.64-7.61 (m, 0.6H), 6.65-6.58 (m, 1H), 4.37-4.25 (m, 2H), 3.87 (t, J = 5.7 Hz, 0.8H), 3.82 (t, J = 5.7 Hz, 1.2H), 2.76-2.68 (m, 1.2H), 2.68-2.60 (m, 0.8H), 2.38 (s, 6H), 2.22 (s, 1.8H), 2.18 (s, 1.2H) |
| 219 | 1-(3-(2-(4,5-Dimethyl-1H-imidazol-2-yl)pyridin-4-yl)-5,6-dihydropyridin-1(2H)-yl)ethanone trifluoroacetate salt | | 297.1 | $^1$H NMR (400 MHz, CD$_3$OD, rotamers) δ 8.72-8.67 (m, 2H, major and minor rotamers), 8.10-8.06 (m, 1H, minor rotamer), 8.06-8.00 (m, 1H, major rotamer), 7.65-7.57 (m, 2H, major and minor rotamer), 6.83-6.80 (m, 1H, minor rotamer), 6.80-6.75 (m, 1H, major rotamer), 4.52-4.49 (m, 2H, major rotamer), 4.49-4.45 (m, 2H, minor rotamer), 3.75 (t, J = 5.9 Hz, 2H, minor rotamer), 3.71 (t, J = 5.8 Hz, 2H, major rotamer), 2.56-2.46 (m, 2H, major rotamer), 2.45-2.38 (m, 2H, minor rotamer), 2.36 (s, 6H, minor rotamer), 2.35 (s, 6H, major rotamer), 2.22 (s, 3H, minor rotamer), 2.20 (s, 3H, major rotamer) |
| 220 | 2-(4,5-Dimethyl-1H-imidazol-2-yl)-4-(1-(methylsulfonyl)-1,2,5,6-tetrahydropyridin-3-yl)pyridine trifluoroacetate salt | | 333.0 | $^1$H NMR (400 MHz, CD$_3$OD) δ 8.71 (d, J = 5.2 Hz, 1H), 8.09-7.97 (m, 1H), 7.62 (dd, J = 5.2, 1.6 Hz, 1H), 6.82-6.74 (m, 1H), 4.31-4.13 (m, 2H), 3.46 (t, J = 5.8 Hz, 2H), 2.97 (s, 3H), 2.69-2.46 (m, 2H), 2.36 (s, 6H) |

TABLE 15-continued

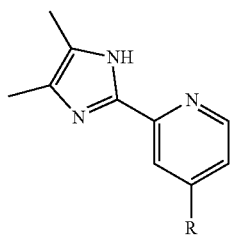

| Ex. No. | Name | R = | MS (M + H)+ | 1H NMR |
|---|---|---|---|---|
| 221 | 4-(1-(4-Chlorophenylsulfonyl)-1,2,5,6-tetrahydropyridin-3-yl)-2-(4,5-dimethyl-1H-imidazol-2-yl)pyridine trifluoroacetate salt | | 429.1 | 1H NMR (400 MHz, CD3OD) δ 8.69 (d, J = 5.2 Hz, 1H), 8.01-7.97 (m, 1H), 7.88 (d, J = 8.6 Hz, 2H), 7.64 (d, J = 8.6 Hz, 2H), 7.56 (dd, J = 5.2, 1.6 Hz, 1H), 6.68-6.63 (m, 1H), 4.13-4.02 (m, 2H), 3.33 (t, J = 5.8 Hz, 2H), 2.52-2.41 (m, 2H), 2.37 (s, 6H) |
| 222 | (3-(2-(4,5-Dimethyl-1H-imidazol-2-yl)pyridin-4-yl)-5,6-dihydropyridin-1(2H)-yl)(phenyl)methanone trifluoroacetate salt | | 359.1 | |
| 223 | 4-(1-Benzyl-1,2,5,6-tetrahydropyridin-3-yl)-2-(4,5-dimethyl-1H-imidazol-2-yl)pyridine trifluoroacetate salt | | 345.2 | 1H NMR (400 MHz, CD3OD) δ 8.74 (d, J = 5.2 Hz, 1H), 8.14 (s, 1H), 7.64-7.56 (m, 2H), 7.56-7.46 (m, 4H), 6.84-6.73 (m, 1H), 4.55 (s, 2H), 4.27 (s, 2H), 3.65-3.38 (m, 2H), 2.81-2.53 (m, 2H), 2.37 (s, 6H) |
| 224 | 4-(1-(4-Chlorobenzyl)-1,2,5,6-tetrahydropyridin-3-yl)-2-(4,5-dimethyl-1H-imidazol-2-yl)pyridine trifluoroacetate salt | | 379.1 | 1H NMR (400 MHz, CD3OD) δ 8.74 (d, J = 5.2 Hz, 1H), 8.16-8.08 (m, 1H), 7.60 (d, J = 8.5 Hz, 2H), 7.56-7.49 (m, 3H), 6.95-6.68 (m, 1H), 4.54 (s, 2H), 4.27 (s, 2H), 3.67-3.35 (m, 2H), 2.83-2.53 (m, 2H), 2.37 (s, 6H) |

TABLE 15-continued

| Ex. No. | Name | R = | MS (M + H)+ | 1H NMR |
|---|---|---|---|---|
| 225 | 2-(4,5-Dimethyl-1H-imidazol-2-yl)-4-(1-((tetrahydro-2H-pyran-4-yl)methyl)-1,2,5,6-tetrahydropyridin-3-yl)pyridine trifluoroacetate salt | (1-((tetrahydro-2H-pyran-4-yl)methyl)-1,2,5,6-tetrahydropyridin-3-yl) | 353.2 | 1H NMR (400 MHz, CD3OD) δ 8.76 (d, J = 5.2 Hz, 1H), 8.21-8.09 (m, 1H), 7.60 (dd, J = 5.2, 1.6 Hz, 1H), 6.91-6.68 (m, 1H), 4.05-3.93 (m, 2H), 3.50 (td, J = 11.8, 1.8 Hz, 2H), 3.26 (d, J = 7.1 Hz, 2H), 2.37 (s, 6H), 2.34-2.21 (m, 1H), 1.83-1.71 (m, 2H), 1.43 (qd, J = 12.2, 4.5 Hz, 2H) |
| 226 | 1-(3-(2-(4,5-Dimethyl-1H-imidazol-2-yl)pyridin-4-yl)-2,5-dihydro-1H-pyrrol-1-yl)ethanone trifluoroacetate salt | (1-acetyl-2,5-dihydro-1H-pyrrol-3-yl) | 283.1 | 1H NMR (400 MHz, CD3OD, rotamers) δ 8.77-8.72 (m, 1H), 8.11 (s, 0.4H), 8.05 (s, 0.6H), 7.68 (dd, J = 5.1, 1.4 Hz, 0.6H), 7.63 (d, J = 3.8 Hz, 0.4H), 6.83-6.75 (m, 1H), 4.83-4.75 (m, 1H), 4.67-4.56 (m, 2H), 4.48-4.41 (m, 1H), 2.37 (s, 6H), 2.20 (s, 1.2H), 2.15 (s, 1.8H) |
| 227 | 2-(4,5-Dimethyl-1H-imidazol-2-yl)-4-(1-(methylsulfonyl)-2,5-dihydro-1H-pyrrol-3-yl)pyridine trifluoroacetate salt | (1-(methylsulfonyl)-2,5-dihydro-1H-pyrrol-3-yl) | 319.0 | 1H NMR (400 MHz, CD3OD) δ 8.74 (d, J = 5.2 Hz, 1H), 8.06 (s, 1H), 7.63 (dd, J = 5.2, 1.4 Hz, 1H), 6.77-6.72 (m, 1H), 4.72-4.54 (m, 2H), 4.50-4.26 (m, 2H), 2.98 (s, 3H), 2.37 (s, 6H) |
| 228 | 4-(1-Benzyl-2,5-dihydro-1H-pyrrol-3-yl)-2-(4,5-dimethyl-1H-imidazol-2-yl)pyridine trifluoroacetate salt | (1-benzyl-2,5-dihydro-1H-pyrrol-3-yl) | 331.1 | 1H NMR (400 MHz, CD3OD) δ 8.78 (d, J = 5.1 Hz, 1H), 8.09 (s, 1H), 7.64-7.56 (m, 3H), 7.56-7.49 (m, 3H), 6.89-6.16 (m, 1H), 4.65 (s, 2H), 4.63-4.59 (m, 2H), 4.49-4.42 (m, 2H), 2.36 (s, 6H) |
| 229 | 4-(1-(4-Chlorobenzyl)-2,5-dihydro-1H-pyrrol-3-yl)-2-(4,5-dimethyl-1H-imidazol-2-yl)pyridine trifluoroacetate salt | (1-(4-chlorobenzyl)-2,5-dihydro-1H-pyrrol-3-yl) | 365.1 | 1H NMR (400 MHz, CD3OD) δ 8.77 (d, J = 5.1 Hz, 1H), 8.10 (s, 1H), 7.64-7.57 (m, 3H), 7.57-7.51 (m, 2H), 6.96-6.68 (m, 1H), 4.64 (s, 2H), 4.63-4.57 (m, 2H), 4.49-4.40 (m, 2H), 2.36 (s, 6H) |

TABLE 15-continued

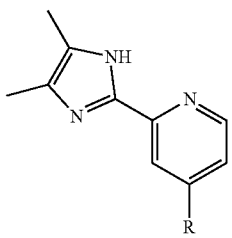

| Ex. No. | Name | R = | MS (M + H)+ | 1H NMR |
|---|---|---|---|---|
| 230 | 2-(4,5-Dimethyl-1H-imidazol-2-yl)-4-(1-((tetrahydro-2H-pyran-4-yl)methyl)-2,5-dihydro-1H-pyrrol-3-yl)pyridine trifluoroacetate salt | | 339.2 | 1H NMR (400 MHz, CD3OD) δ 8.80 (d, J = 5.1 Hz, 1H), 8.18 (s, 1H), 7.63 (dd, J = 5.1, 1.4 Hz, 1H), 6.83-6.78 (m, 1H), 4.06-3.92 (m, 2H), 3.50 (td, J = 11.8, 1.7 Hz, 2H), 3.40 (d, J = 7.1 Hz, 2H), 2.37 (s, 6H), 2.25-2.09 (m, 1H), 1.83-1.72 (m, 2H), 1.44 (qd, J = 12.3, 4.6 Hz, 2H) |

Example 231. (3R)-1-[2'-(4,5-Dimethyl-1H-imidazol-2-yl)-3,4'-bipyridin-5-yl]pyrrolidin-3-ol

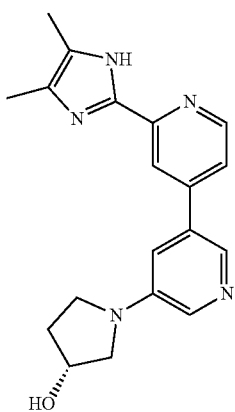 [SMILES: Cc1nc(-c2cc(-c3cncc(N4CC[C@@H](O)C4)c3)ccn2)[nH]c1C]

Step 1.
4-Bromo-2-(4,5-dimethyl-1H-imidazol-2-yl)pyridine

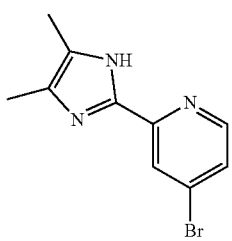

4-Bromopyridine-2-carbonitrile (1.0 g, 5.5 mmol, Synthonix) in MeOH (10 mL) was treated with sodium methoxide (25 wt % in MeOH, 0.095 mL, 0.47 mmol) and the reaction was stirred for 1 hour. Ammonium chloride (0.37 g, 6.9 mmol) was added and the reaction was stirred for 4 days. Solvent was then removed in vacuo. Water (4 mL) and EtOAc (6 mL) were added, the mixture was saturated with solid NaCl, and the mixture was stirred overnight. The solid product was isolated by filtration and dried at 40° C. under vacuum overnight. The product was used below without further purification.

To 4-bromopyridine-2-carboximidamide (0.50 g, 2.5 mmol) in DMF (5 mL) was added $K_2CO_3$ (0.52 g, 3.7 mmol) and 3-bromo-2-butanone (0.24 mL, 3.2 mmol). The reaction was stirred for 4 days. The reaction mixture was partitioned between EtOAc and $H_2O$. The aqueous layer was extracted with two further portions of EtOAc. The combined organic extracts were washed sequentially with water and saturated NaCl solution. The organic solution was dried over $Na_2SO_4$, filtered, and concentrated. The crude product was triturated with methyl tert-butyl ether (MTBE, 2 mL) and the solid product was isolated by filtration and dried under vacuum at 40° C. for 3 hours. Yield: 372 mg, 59%. LCMS (M+H)+: 252.0/254.0.

Step 2. 4-Bromo-2-(4,5-dimethyl-1-{[2-(trimethylsilyl)ethoxy]methyl}-1H-imidazol-2-yl)pyridine To a solution of 4-bromo-2-(4,5-dimethyl-1H-imidazol-2-yl)pyridine (0.31 g, 1.2 mmol, from Step 1) in DMF (3 mL) was added $Cs_2CO_3$ (0.60 g, 1.8 mmol) and [β-(trimethylsilyl)ethoxy]methyl chloride (0.33 mL, 1.8 mmol, Aldrich). The reaction mixture was stirred overnight. Water was then added. After the mixture was stirred for 15 minutes, it was extracted with EtOAc. The organic layer was washed with water, followed by saturated NaCl, dried over $Na_2SO_4$, filtered, and concentrated. The product was purified by flash chromatography, eluting with a gradient from 0-100% EtOAc in hexanes. Yield: 0.35 g, 76%. LCMS $(M+H)^+$: 382.1/384.1.

Step 3. 5-Chloro-2'-(4,5-dimethyl-1-{[2-(trimethylsilyl)ethoxy]methyl}-1H-imidazol-2-yl)-3,4'-bipyridine

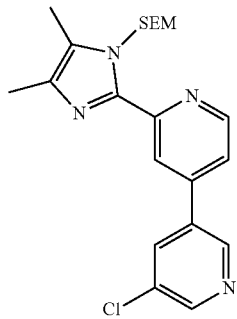 [SMILES: Cc1nc(-c2cc(-c3cncc(Cl)c3)ccn2)n(COCC[Si](C)(C)C)c1C]

A degassed mixture of (5-chloropyridin-3-yl)boronic acid (0.15 g, 0.96 mmol, Aldrich), CsF (0.42 g, 2.7 mmol), 4-bromo-2-(4,5-dimethyl-1-{[2-(trimethylsilyl)ethoxy]methyl}-1H-imidazol-2-yl)pyridine (0.35 g, 0.92 mmol, from Step 2) and 4-(di-tert-butylphosphino)-N,N-dimethylaniline-dichloropalladium (2:1) (65 mg, 0.092 mmol, Aldrich) in 1,4-dioxane (4 mL) and $H_2O$ (1 mL) was heated to 90° C. for 2.5 hours. Upon cooling, the reaction mixture was filtered. The filtrate was diluted with water and extracted with EtOAc. The organic extract was washed with water, followed by brine, dried over $Na_2SO_4$, filtered, and concentrated. The product was used without further purification in coupling reactions as in Step 4. LCMS $(M+H)^+$: 415.1.

Step 4. (3R)-1-[2'-(4,5-Dimethyl-1H-imidazol-2-yl)-3,4'-bipyridin-5-yl]pyrrolidin-3-ol A degassed mixture of 5-chloro-2'-(4,5-dimethyl-1-{[2-(trimethylsilyl)ethoxy]methyl}-1H-imidazol-2-yl)-3,4'-bipyridine (0.020 g, 0.048 mmol, from Step 3), (3R)-pyrrolidin-3-ol (12.0 μL, 0.144 mmol, Aldrich), $Cs_2CO_3$ (47 mg, 0.14 mmol) and tBuBrettPhos Pd G3 (4.1 mg, 0.0048 mmol, Aldrich) in toluene (0.3 mL) and 1,4-dioxane (30 μL) was heated to 100° C. overnight. Upon cooling, the reaction mixture was diluted with water and EtOAc and filtered. The organic layer of the filtrate was removed via rotary evaporation. The product was purified by preparative HPLC (C-18 column eluting with a water:acetonitrile gradient buffered at pH 10 with 0.15% ammonium hydroxide). (3R)-1-[2'-(4,5-dimethyl-1-{[2-(trimethylsilyl)ethoxy]methyl}-1H-imidazol-2-yl)-3,4'-bipyridin-5-yl]pyrrolidin-3-ol (3.2 mg, 0.0069 mmol) was stirred in TFA (2.0 mL) for 5 hours. The TFA was removed via rotary evaporation and the residue was reconstituted in DCM and MeOH and again removed via rotary evaporation. The residue was reconstituted in a mixture of THF, MeOH, and DMF for purification by preparative HPLC (C-18 column eluting with a water:acetonitrile gradient buffered at pH 10 with 0.15% ammonium hydroxide). Yield: 1.2 mg, 52%. $^1$H NMR (400 MHz, $CD_3OD$) δ 8.61 (d, J=5.1 Hz, 1H), 8.30 (s, 1H), 8.21 (s, 1H), 7.96 (d, J=2.0 Hz, 1H), 7.62-7.52 (m, 1H), 7.36-7.29 (m, 1H), 4.64-4.53 (m, 1H), 3.64-3.54 (m, 2H), 3.50 (td, J=8.8, 3.1 Hz, 1H), 3.35 (d, J=10.4 Hz, 1H), 2.30-2.00 (m, 2H), 2.23 (s, 6H); LCMS $(M+H)^+$: 336.1.

Examples 232 through 234 were synthesized according to the procedure of Example 231 and the data are listed in Table 16.

TABLE 16

| Ex. No. | Name | R = | MS $(M + H)^+$ | $^1$H NMR |
|---|---|---|---|---|
| 232 | (3S)-1-[2'-(4,5-Dimethyl-1H-imidazol-2-yl)-3,4'-bipyridin-5-yl]pyrrolidin-3-ol | pyrrolidin-3-ol with HO | 336.2 | $^1$H NMR (400 MHz, $d_6$-DMSO) δ 8.63 (d, J = 5.1 Hz, 1H), 8.22 (d, J = 1.5 Hz, 1H), 8.19 (s, 1H), 8.03 (d, J = 2.6 Hz, 1H), 7.68 (dd, J = 5.1, 1.5 Hz, 1H), 7.19-7.13 (m, 1H), 5.02 (d, J = 3.4 Hz, 1H), 4.52-4.39 (m, 1H), 3.53 (dd, J = 10.3, 4.8 Hz, 1H), 3.48-3.40 (m, 2H), 3.23 (d, J = 10.9 Hz, 1H), 2.17 (s, 6H), 2.12-1.99 (m, 1H), 1.99-1.87 (m, 1H) |

TABLE 16-continued

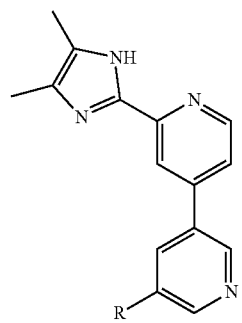

| Ex. No. | Name | R = | MS (M + H)+ | 1H NMR |
|---|---|---|---|---|
| 233 | 2'-(4,5-Dimethyl-1H-imidazol-2-yl)-N-phenyl-3,4'-bipyridin-5-amine | | 342.2 | 1H NMR (400 MHz, CD3OD) δ 8.62 (d, J = 5.1 Hz, 1H), 8.35 (s, 2H), 8.22 (s, 1H), 7.82 (t, J = 2.1 Hz, 1H), 7.53 (dd, J = 5.1, 1.4 Hz, 1H), 7.33 (t, J = 7.9 Hz, 2H), 7.21 (d, J = 7.6 Hz, 2H), 7.00 (t, J = 7.4 Hz, 1H), 2.22 (s, 6H) |
| 234 | 5-Chloro-2'-(4,5-dimethyl-1H-imidazol-2-yl)-3,4'-bipyridine | Cl | 285.0 | 1H NMR (400 MHz, CD3OD) δ 8.85 (d, J = 1.9 Hz, 1H), 8.64 (d, J = 5.2 Hz, 1H), 8.62 (d, J = 2.2 Hz, 1H), 8.32-8.25 (m, 1H), 8.19 (t, J = 2.1 Hz, 1H), 7.52 (dd, J = 5.2, 1.7 Hz, 1H), 2.25 (s, 6H) |

Example 235. tert-Butyl 3-[2'-(4,5-dimethyl-1H-imidazol-2-yl)-3,4'-bipyridin-5-yl]-2,5-dihydro-1H-pyrrole-1-carboxylate

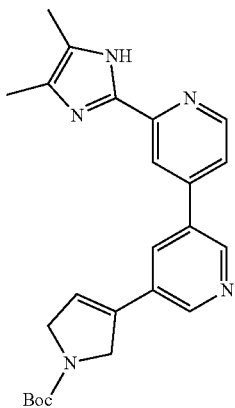 [SMILES: Cc1nc(-c2cc(-c3cncc(C4=CCN(C(=O)OC(C)(C)C)C4)c3)ccn2)[nH]c1C]

Step 1. 5-Chloro-3,4'-bipyridine-2'-carbonitrile

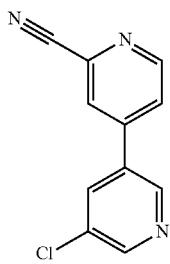

A degassed mixture of 4-bromopyridine-2-carbonitrile (0.99 g, 5.4 mmol, Synthonix), (5-chloropyridin-3-yl)boronic acid (0.847 g, 5.38 mmol, Aldrich), CsF (2.4 g, 16 mmol), and 4-(di-tert-butylphosphino)-N,N-dimethylaniline-dichloropalladium (2:1) (0.38 g, 0.54 mmol, Aldrich) in 1,4-dioxane (10 mL) and water (3 mL) was heated to 90-105° C. for 2.5 hours. The reaction mixture was filtered and the volume was reduced via rotary evaporation. The mixture was diluted with water and extracted with EtOAc. The combined organic extracts were washed sequentially with water and brine, dried over sodium sulfate, filtered, and concentrated. The resulting solid was triturated with MTBE (5 mL). The solid product was isolated by filtration and air dried. Yield: 0.95 g, 82%. LCMS (M+H)+: 216.0/218.0.

Step 2. tert-Butyl 3-(2'-cyano-3,4'-bipyridin-5-yl)-2,5-dihydro-1H-pyrrole-1-carboxylate

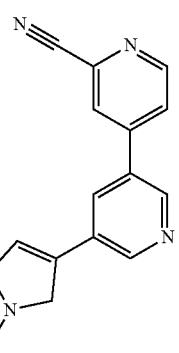

A degassed mixture of 5-chloro-3,4'-bipyridine-2'-carbonitrile (0.65 g, 3.0 mmol, from Step 1), tert-butyl 3-(4,4,5, 5-tetramethyl-1,3,2-dioxaborolan-2-yl)-2,5-dihydro-1H-pyrrole-1-carboxylate (0.83 g, 3.1 mmol, Synthonix), K₃PO₄ (1.9 g, 9.2 mmol) and bis(triphenylphosphine)palladium(II) chloride (0.21 g, 0.31 mmol, Aldrich) in 1,4-dioxane (7 mL) and water (2 mL) was refluxed at 120° C. for 2 hours. Upon cooling, the reaction mixture was filtered and the filtrate was partitioned between water and EtOAc. The organic layer was washed with brine, dried over Na₂SO₄, filtered, and concentrated. The product was purified by flash chromatography, eluting with a gradient from 0-100% EtOAc in hexanes. Yield: 0.39 g, 45%. LCMS (M+H)⁺: 349.1.

Step 3. tert-Butyl 3-{2'-[amino(imino)methyl]-3,4'-bipyridin-5-yl}-2,5-dihydro-1H-pyrrole-1-carboxylate

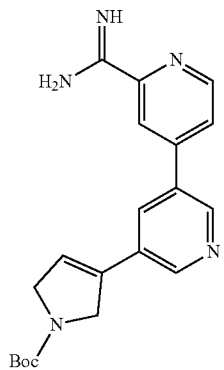 [SMILES: CC(C)(C)OC(=O)N1CC=C(c2cncc(-c3ccnc(C(=N)N)c3)c2)C1]

A mixture of tert-butyl 3-(2'-cyano-3,4'-bipyridin-5-yl)-2,5-dihydro-1H-pyrrole-1-carboxylate (0.45 g, 1.3 mmol, from Step 2) in MeOH (6 mL) and THF (3 mL) was treated with sodium methoxide (25 wt %, 24 µL, 0.11 mmol, Aldrich). After 24 hours, NH₄Cl (95.0 mg, 1.78 mmol) was added and the reaction was stirred overnight. The reaction was cooled in an ice bath and the precipitate formed was isolated by filtration and washed with THF and MeOH. The product was dried under vacuum at 50° C. for 2 hours. Yield: 0.33 g, 70%. LCMS (M+H)⁺: 366.1.

Step 4. tert-Butyl 3-[2'-(4,5-dimethyl-1H-imidazol-2-yl)-3,4'-bipyridin-5-yl]-2,5-dihydro-1H-pyrrole-1-carboxylate A suspension of tert-butyl 3-{2'-[amino(imino)methyl]-3,4'-bipyridin-5-yl}-2,5-dihydro-1H-pyrrole-1-carboxylate (0.33 g, 0.90 mmol, from Step 3) in DMF (4 mL) was treated with 3-bromo-2-butanone (0.10 mL, 1.4 mmol) and K₂CO₃ (0.25 g, 1.8 mmol). The reaction was stirred over three nights. The reaction was diluted with EtOAc (13 mL) and water (13 mL) and a precipitate was formed, which was isolated by filtration and then dried under vacuum at 40° C. overnight. Yield: 0.26 g, 69%. ¹H NMR (400 MHz, d₆-DMSO, rotamers) δ 12.39 (s, 1H), 8.95-8.89 (m, 1H), 8.84-8.78 (m, 1H), 8.64 (d, J=5.1 Hz, 1H), 8.30-8.26 (m, 1H), 8.24 (d, J=7.3 Hz, 1H), 7.76-7.67 (m, 1H), 6.78-6.68 (m, 1H), 4.64-4.45 (m, 2H), 4.35-4.08 (m, 2H), 2.18 (s, 3H), 2.11 (s, 3H), 1.47 (s, 4H), 1.46 (s, 5H); LCMS (M+H)⁺: 418.2.

Example 236. 5-(2,5-Dihydro-1H-pyrrol-3-yl)-2'-(4,5-dimethyl-1H-imidazol-2-yl)-3,4'-bipyridine

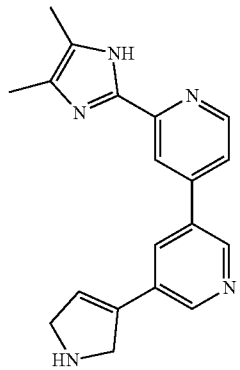 [SMILES: Cc1nc(-c2cc(-c3cncc(C4=CCNC4)c3)ccn2)[nH]c1C]

tert-Butyl 3-[2'-(4,5-dimethyl-1H-imidazol-2-yl)-3,4'-bipyridin-5-yl]-2,5-dihydro-1H-pyrrole-1-carboxylate (0.10 g, 0.24 mmol, from Example 235) was stirred in TFA (2.0 mL) for 1 hour and 45 minutes. The TFA was removed in vacuo and the residue was redissolved in MeOH and rotary evaporated to remove TFA. Acetonitrile (1 mL) and 1.0 N NaOH (1.5 mL, 1.5 mmol) were added. After the mixture was stirred for 2 hours, the fine powder that formed was isolated by filtration, washed with MeCN and water. The solid was dried at 50° C. under vacuum for 1 hour. Yield: 59 mg, 77%. ¹H NMR (400 MHz, d₆-DMSO) δ 12.41 (br s, 1H), 8.90 (d, J=2.0 Hz, 1H), 8.78 (d, J=1.9 Hz, 1H), 8.65 (d, J=5.1 Hz, 1H), 8.24 (t, J=2.0 Hz, 1H), 8.23-8.21 (m, 1H), 7.70 (dd, J=5.2, 1.8 Hz, 1H), 6.89-6.42 (m, 1H), 4.19-4.12 (m, 2H), 3.94-3.87 (m, 2H), 2.14 (br, 9H); LCMS (M+H)⁺: 318.1.

Example 237. 2'-(4,5-Dimethyl-1H-imidazol-2-yl)-5-[1-(methylsulfonyl)-2,5-dihydro-1H-pyrrol-3-yl]-3,4'-bipyridine

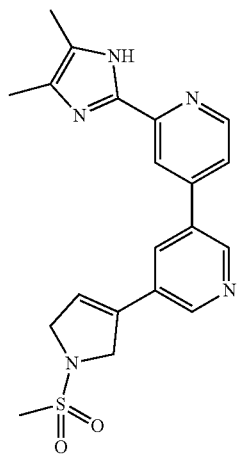 [SMILES: Cc1nc(-c2cc(-c3cncc(C4=CCN(S(C)(=O)=O)C4)c3)ccn2)[nH]c1C]

To a suspension of 5-(2,5-dihydro-1H-pyrrol-3-yl)-2'-(4,5-dimethyl-1H-imidazol-2-yl)-3,4'-bipyridine (7.0 mg, 0.022 mmol, from Example 235) in DMF (1 mL) was added N,N-diisopropylethylamine (15 µL, 0.088 mmol) and methanesulfonyl chloride (MsCl, 2.6 µL, 0.033 mmol). After stirring overnight, additional MsCl was added in sufficient quantity to drive the reaction to completion as determined by LCMS. The product was purified by preparative HPLC (C-18 column eluting with a water:acetonitrile gradient buffered at pH 10 with 0.15% ammonium hydroxide). Yield: 3.8 mg, 43%. $^1$H NMR (400 MHz, d$_6$-DMSO) δ 12.41 (s, 1H), 8.95 (d, J=1.4 Hz, 1H), 8.87 (d, J=1.4 Hz, 1H), 8.65 (d, J=5.0 Hz, 1H), 8.31-8.28 (m, 1H), 8.26 (s, 1H), 7.79-7.61 (m, 1H), 6.79-6.67 (m, 1H), 4.80-4.56 (m, 2H), 4.49-4.20 (m, 2H), 3.01 (s, 3H), 2.19 (s, 3H), 2.12 (s, 3H); LCMS (M+H)$^+$: 396.1.

Examples 238 through 239 were synthesized according to the procedure of Example 237, using acetyl chloride and methyl chloroformate, respectively, in place of methane sulfonyl chloride. The data are listed in Table 17.

TABLE 17

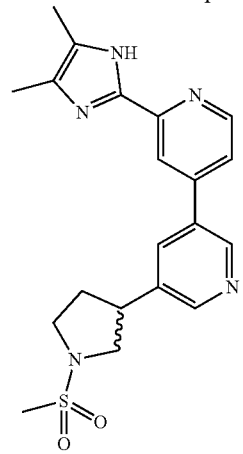

| Ex. No. | Name | R= | MS (M + H)$^+$ | $^1$H NMR |
|---|---|---|---|---|
| 238 | 1-(3-(2'-(4,5-Dimethyl-1H-imidazol-2-yl)-3,4'-bipyridin-5-yl)-2,5-dihydro-1H-pyrrol-1-yl)ethanone | COMe | 360.2 | $^1$H NMR (400 MHz, CD$_3$OD) δ 8.90 (d, J = 2.0 Hz, 1H), 8.77 (t, J = 1.7 Hz, 1H), 8.66 (d, J = 5.2 Hz, 1H), 8.34-8.32 (m, 1H), 8.30 (q, J = 1.8 Hz, 1H), 7.67 (dd, J = 5.2, 1.7 Hz, 1H), 6.70-6.63 (m, 1H), 4.71-4.63 (m, 1H), 4.60-4.52 (m, 1H), 4.46-4.36 (m, 1H), 2.24 (s, 6H), 2.21 (s, 1.5H, rotamers), 2.14 (s, 1.5H, rotamers) |
| 239 | Methyl 3-(2'-(4,5-dimethyl-1H-imidazol-2-yl)-3,4'-bipyridin-5-yl)-2,5-dihydro-1H-pyrrole-1-carboxylate | CO$_2$Me | 376.1 | $^1$H NMR (400 MHz, d$_6$-DMSO, rotamer) δ 9.04-9.01 (m, 1H), 8.97-8.89 (m, 2H), 8.57 (s, 1H), 8.37-8.34 (m, 1H), 8.17-8.13 (m, 1H), 6.81-6.72 (m, 1H), 4.66-4.60 (m, 2H), 4.41-4.29 (m, 2H), 3.69 (s, 1.5H), 3.68 (s, 1.5H), 2.33 (s, 6H) |

Example 240. 2'-(4,5-Dimethyl-1H-imidazol-2-yl)-5-[1-(methylsulfonyl)pyrrolidin-3-yl]-3,4'-bipyridine Racemic Mixture Prepared

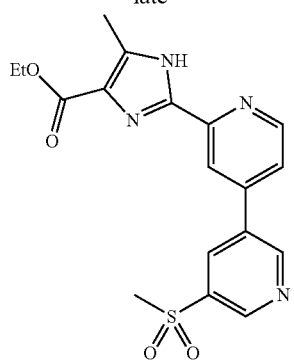

To a solution of 2'-(4,5-dimethyl-1H-imidazol-2-yl)-5-[1-(methylsulfonyl)-2,5-dihydro-1H-pyrrol-3-yl]-3,4'-bipyridine (5.5 mg, 0.014 mmol, prepared as in Example 237) in MeOH (1 mL) and THF (1 mL) was added palladium (10% on carbon, 4.1 mg, 0.0038 mmol). The mixture was degassed and stirred under 1 atm H$_2$ overnight. The reaction mixture was filtered and the product was purified by preparative HPLC (C-18 column eluting with 14.6-32.6% acetonitrile in water containing 0.15% ammonium hydroxide over 12 minutes). Yield: 2.9 mg, 53%. $^1$H NMR (400 MHz, d$_6$-DMSO) δ 12.40 (s, 1H), 8.91 (d, J=2.1 Hz, 1H), 8.68 (d, J=1.9 Hz, 1H), 8.64 (d, J=5.2 Hz, 1H), 8.26-8.16 (m, 2H), 7.69 (dd, J=5.2, 1.7 Hz, 1H), 3.82 (dd, J=9.4, 7.7 Hz, 1H), 3.63-3.49 (m, 2H), 3.40 (td, J=9.9, 6.9 Hz, 1H), 3.36-3.29 (m, 1H), 3.01 (s, 3H), 2.44-2.30 (m, 1H), 2.24-2.13 (m, 1H), 2.19 (s, 3H), 2.12 (s, 3H); LCMS (M+H)$^+$: 398.1.

Example 241. Ethyl 5-methyl-2-[5-(methylsulfonyl)-3,4'-bipyridin-2'-yl]-1H-imidazole-4-carboxylate

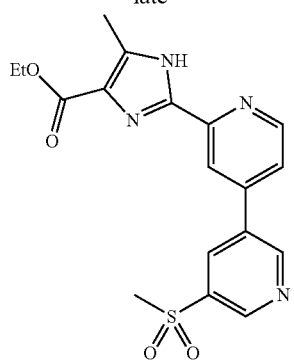

Step 1. Methyl 5-(methylsulfonyl)-3,4'-bipyridine-2'-carboxylate

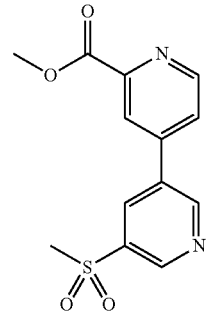 [SMILES: COC(=O)c1cc(-c2cncc(S(C)(=O)=O)c2)ccn1]

A degassed mixture of methyl 4-bromopyridine-2-carboxylate (1.5 g, 6.9 mmol, Combi-Blocks), 3-(methylsulfonyl)-5-(4,4,5,5-tetramethyl-1,3,2-dioxaborolan-2-yl)pyridine (2.2 g, 7.6 mmol, Aldrich), CsF (3 g, 20 mmol), and 4-(di-tert-butylphosphino)-N,N-dimethylaniline-dichloropalladium (2:1) (0.49 g, 0.69 mmol, Aldrich) in 1,4-dioxane (20 mL) and H$_2$O (5 mL) was heated to 105° C. for 1.5 hours. Upon cooling to room temperature, the reaction mixture was diluted with EtOAc and washed with water. The water layer was extracted with two portions of EtOAc. The combined organic extracts were dried over Na$_2$SO$_4$, filtered, and concentrated. The product was purified by flash chromatography, eluting with a gradient from 0-100% EtOAc in hexanes. Yield: 1.84 g, 77%. $^1$H NMR (400 MHz, d$_6$-DMSO) δ 9.41 (d, J=1.8 Hz, 1H), 9.18 (d, J=1.8 Hz, 1H), 8.89 (d, J=5.0 Hz, 1H), 8.78-8.75 (m, 1H), 8.54-8.49 (m, 1H), 8.23-8.13 (m, 1H), 3.95 (s, 3H), 3.44 (s, 3H); LCMS (M+H)$^+$: 293.0.

Step 2. Lithium 5-(methylsulfonyl)-3,4'-bipyridine-2'-carboxylate

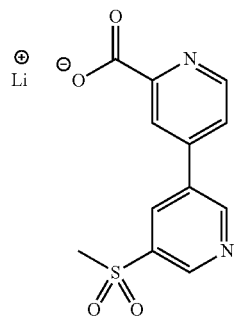 [SMILES: [Li+] ; CS(=O)(=O)c1cncc(-c2ccnc(C(=O)[O-])c2)c1]

A solution of methyl 5-(methylsulfonyl)-3,4'-bipyridine-2'-carboxylate (1.84 g, 6.3 mmol, from Step 1) in THF (50 mL) and H$_2$O (12 mL) was treated with LiOH—H$_2$O (1.1 g, 26 mmol) for 2 hours. The reaction mixture was filtered to afford a white solid, 1.7 g (95%). $^1$H NMR (400 MHz, d$_6$-DMSO) δ 9.34 (d, J=1.7 Hz, 1H), 9.14 (d, J=1.7 Hz, 1H), 8.71-8.65 (m, 1H), 8.61 (d, J=5.0 Hz, 1H), 8.35 (s, 1H), 7.91-7.85 (m, 1H), 3.44 (s, 3H); LCMS calculated for C$_{12}$H$_{11}$N$_2$O$_4$S (M+H)$^+$: m/z=279.0; found 279.1.

Step 3. Ethyl 5-methyl-2-[5-(methylsulfonyl)-3,4'-bipyridin-2'-yl]-1H-imidazole-4-carboxylate Lithium 5-(methylsulfonyl)-3,4'-bipyridine-2'-carboxylate (0.22 g, 0.76 mmol, from Step 2) in DMF (5.4 mL) was treated with HATU (0.32 g, 0.84 mmol) for 35 minutes, at which time a solution of ethyl 2-amino-3-oxobutanoate hydrochloride (0.14 g, 0.80 mmol, AstaTech) and N,N-diisopropylethylamine (0.26 mL, 1.5 mmol) in DMF (1.1 mL, 14 mmol) was added. After stirring overnight, additional HATU (0.29 g, 0.76 mmol) was added. Fifteen minutes later, additional ethyl 2-amino-3-oxobutanoate hydrochloride (0.16 g, 0.91 mmol) and N,N-diisopropylethylamine (0.16 mL, 0.91 mmol) in DMF (2.0 mL) were added. After a reaction time of 5 minutes, the solution was diluted with EtOAc and washed sequentially with water, saturated NaHCO$_3$ solution, water, and brine. The organic solution was then dried over Na$_2$SO$_4$, filtered and concentrated. The product was purified by flash chromatography, eluting with a gradient from 0-90% EtOAc in hexanes to afford 89 mg of product. LCMS (M+H)$^+$: 406.1.

The product was then dissolved in acetic acid (1.0 mL). Ammonium acetate (85 mg, 1.1 mmol) was added, and the reaction was heated to about 120-130° C. in a sealed vial overnight. Upon cooling to room temperature, AcOH was removed in vacuo and the product was purified by preparative HPLC (C-18 column eluting with a water:acetonitrile gradient buffered at pH 10 with 0.15% ammonium hydroxide). Yield: 19 mg, 6.5%. $^1$H NMR (400 MHz, d$_6$-DMSO) δ 13.34 (s, 1H), 9.42 (s, 1H), 9.18 (s, 1H), 8.83-8.74 (m, 2H), 8.43 (s, 1H), 7.97-7.89 (m, 1H), 4.27 (q, J=7.7, 6.4 Hz, 2H), 3.46 (s, 3H), 2.54 (s, 3H), 1.31 (t, J=6.5 Hz, 3H); LCMS (M+H)$^+$: 387.1.

Example 242. 5-Methyl-2-[5-(methylsulfonyl)-3,4'-bipyridin-2'-yl]-1H-imidazole-4-carboxylic acid trifluoroacetate salt

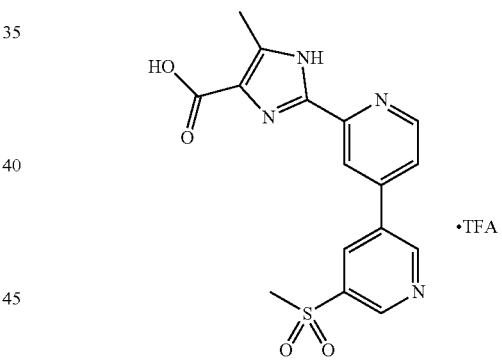

Ethyl 5-methyl-2-[5-(methylsulfonyl)-3,4'-bipyridin-2'-yl]-1H-imidazole-4-carboxylate (16 mg, 0.041 mmol, from Example 241) was treated with LiOH—H$_2$O (7.0 mg, 0.16 mmol) in THF (2 mL) and H$_2$O (0.2 mL) for 35 minutes. 1.0 M aq. NaOH (0.50 mL, 0.50 mmol) was added and the reaction mixture was stirred overnight. 1.0 M aq. KOH (0.20 mL, 0.20 mmol) was added and the mixture was heated to 60° C. for 24 hours and then to 70° C. for 4 hours. Upon cooling to room temperature, TFA was added and the solvent was removed in vacuo. The product was dissolved in CH$_3$CN and MeOH and purified by preparative HPLC (C-18 column eluting with a water:acetonitrile gradient buffered at pH 2 with 0.1% trifluoroacetic acid). Yield: 13 mg. $^1$H NMR (400 MHz, d$_6$-DMSO) δ 9.43 (d, J=2.1 Hz, 1H), 9.21 (d, J=2.1 Hz, 1H), 8.85 (d, J=5.2 Hz, 1H), 8.77 (t, J=2.1 Hz, 1H), 8.57 (s, 1H), 8.03 (dd, J=5.2, 1.6 Hz, 1H), 3.46 (s, 3H), 2.55 (s, 3H); LCMS (M+H)$^+$: 359.1.

Example 243. N-Cyclopentyl-5-methyl-2-[5-(methylsulfonyl)-3,4'-bipyridin-2'-yl]-1H-imidazole-4-carboxamide

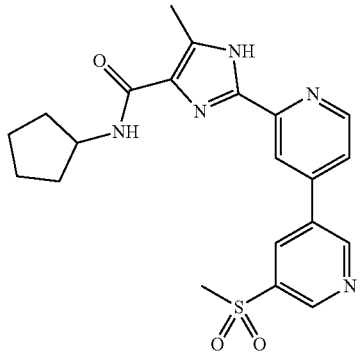 [SMILES: Cc1[nH]c(-c2cc(-c3cncc(S(C)(=O)=O)c3)ccn2)nc1C(=O)NC1CCCC1]

Step 1. 2'-(5-Methyl-1H-imidazol-2-yl)-5-(methylsulfonyl)-3,4'-bipyridine

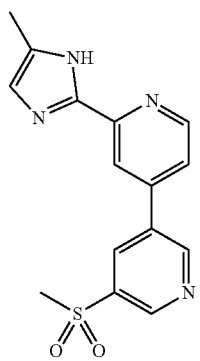 [SMILES: Cc1cnc(-c2cc(-c3cncc(S(C)(=O)=O)c3)ccn2)[nH]1]

To 5-(methylsulfonyl)-3,4'-bipyridine-2'-carbonitrile (1.15 g, 4.44 mmol, from Example 106, Step 1) in MeOH (17 mL) was added sodium methoxide (25 wt % in MeOH, 0.08 mL, 0.35 mmol, Aldrich) and the reaction mixture was heated to 45° C. for 3 hours. Additional sodium methoxide (25 wt % in MeOH, 0.48 mL, 2.0 mmol) was added and the mixture was heated for 30 minutes. 1,1-Diethoxypropan-2-amine (0.65 g, 4.4 mmol, AstaTech) and AcOH (0.76 mL) were added dropwise. The reaction was heated in a sealed vial immersed in an oil bath at 100° C. for 1 hour. The reaction was cooled to room temperature and 6.0 N HCl (3.6 mL, 21 mmol) was added and the reaction vial was then heated in an oil bath held at 75° C. for one hour and 85° C. for three hours. The solvent was then removed via rotary evaporation. An aqueous solution of $K_2CO_3$ was added to adjust to pH 10. The isolated solid was triturated with water, filtered, and air dried to afford a yellow solid. Yield: 1.12 g, 80%. LCMS (M+H)$^+$: 315.1.

Step 2. 2'-(4-Iodo-5-methyl-1H-imidazol-2-yl)-5-(methylsulfonyl)-3,4'-bipyridine

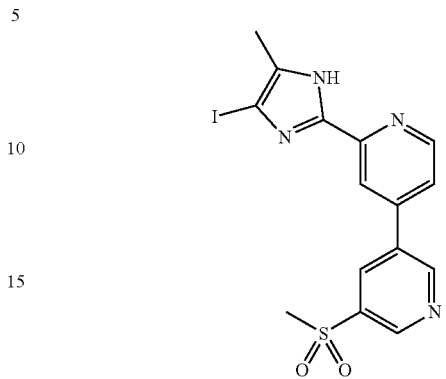

N-Iodosuccinimide (0.800 g, 3.55 mmol) was added to a solution of 2'-(5-methyl-1H-imidazol-2-yl)-5-(methylsulfonyl)-3,4'-bipyridine (1.12 g, 3.38 mmol, from Step 1) in DMF (11 mL). The reaction was stirred at room temperature for 20 minutes. Water (60 mL) was added, followed by saturated NaHCO$_3$ solution (30 mL). The solid product was isolated by filtration, washed with water and air dried. Yield: 1.27 g 85%. LCMS (M+H)$^+$: 441.0.

Step 3. 2'-(4-Iodo-5-methyl-1-{[2-(trimethylsilyl)ethoxy]methyl}-1H-imidazol-2-yl)-5-(methylsulfonyl)-3,4'-bipyridine (Peak 1) and 2'-(5-Iodo-4-methyl-1-{[2-(trimethylsilyl)ethoxy]methyl}-1H-imidazol-2-yl)-5-(methylsulfonyl)-3,4'-bipyridine (Peak 2) (Isomers Separated)

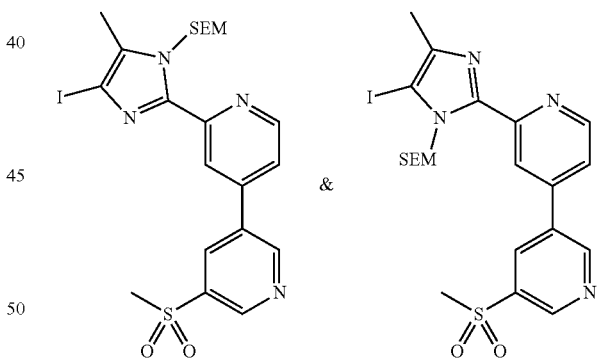

2'-(4-Iodo-5-methyl-1H-imidazol-2-yl)-5-(methylsulfonyl)-3,4'-bipyridine (1.27 g, 2.88 mmol, from Step 2) and NaH (60% in mineral oil, 0.23 g, 5.8 mmol, Aldrich) were combined under nitrogen and the flask was immersed in a dry-ice acetone bath. DMF (28 mL) was introduced, and the cooling bath was removed and the mixture was warmed to room temperature and stirred for 15 minutes. The reaction mixture was then cooled to 0° C. and [β-(trimethylsilyl)ethoxy]methyl chloride (0.76 mL, 4.3 mmol, Aldrich) was added. The reaction was allowed to proceed at 0° C. for 20 minutes. The reaction was then quenched by the addition of water, followed by saturated NaHCO$_3$, and the mixture was extracted with EtOAc. The combined organic extracts were washed sequentially with water and brine, dried over Na₂SO₄, filtered, and concentrated. The product was purified by flash chromatography, eluting with a gradient from 0-80% EtOAc in hexanes and the first isomer to elute (Peak 1) was the major product and the second isomer to elute (Peak 2) was the minor product. The major product (Peak 1), 2'-(4-iodo-5-methyl-1-{[2-(trimethylsilyl)ethoxy]methyl}-1H-imidazol-2-yl)-5-(methylsulfonyl)-3,4'-bipyridine) was used in Step 4. Yield (Peak 1): 0.70 g, 43%. Yield (Peak 2): 0.47 g, 29%. Peak 1 LCMS(M+H)⁺: 571.1. Peak 2 LCMS (M+H)⁺: 571.1.

Step 4. N-Cyclopentyl-5-methyl-2-[5-(methylsulfonyl)-3,4'-bipyridin-2'-yl]-1H-imidazole-4-carboxamide To a degassed mixture of 2'-(4-iodo-5-methyl-1-{[2-(trimethylsilyl)ethoxy]methyl}-1H-imidazol-2-yl)-5-(methylsulfonyl)-3,4'-bipyridine (0.36 g, 0.63 mmol, Peak 1 from Step 3) in MeOH (5 mL) and triethylamine (0.22 mL, 1.6 mmol) was added [1,1'-bis(diphenylphosphino)ferrocene]dichloropalladium(II), complex with dichloromethane (1:1)] (52 mg, 0.063 mmol, Aldrich) and the solution was saturated with CO by bubbling the gas through the reaction subsurface for 3 minutes. The reaction vessel was sealed and heated to 60° C. for 2 hours. Upon cooling to room temperature, the reaction mixture was diluted with water and the precipitated product was isolated by filtration and air dried. The methyl ester intermediate was further purified by flash chromatography, eluting with a gradient from 0-100% EtOAc in hexanes. Yield: 0.30 g, 94%. LCMS (M+H)⁺: 503.1.

The ester was hydrolyzed to the acid intermediate by treating a solution of the ester in THF (10 mL) and MeOH (1 mL) with 2 N NaOH (2.8 mL, 5.7 mmol). The reaction mixture was stirred overnight with gentle warming (33° C.). Upon cooling, the pH of the reaction mixture was adjusted to pH 5 by the addition of 1.0 N HCl. The aqueous mixture was saturated with NaCl and was extracted with three portions of EtOAc. The combined organic extracts were dried over Na₂SO₄, filtered, and concentrated to afford the crude carboxylic acid. Yield: 0.26 g, 89%. LCMS (M+H)⁺: 489.1.

To a portion of the carboxylic acid (15 mg, 0.031 mmol) in DCM (0.5 mL) was added N,N-diisopropylethylamine (16 µL, 0.092 mmol), HATU (15 mg, 0.040 mmol), and cyclopentylamine (6.0 uL, 0.061 mmol) and the reaction mixture was stirred for 1 hour. Trifluoroacetic acid (0.50 mL) was added and the reaction mixture was stirred at 35° C. for 1 hour. Solvent and TFA were then removed in vacuo and the residue was reconstituted in MeCN and MeOH. The product was purified by preparative HPLC (C-18 column eluting with a water:acetonitrile gradient buffered at pH 2 with 0.1% trifluoroacetic acid). Yield: 14. mg, 71%. ¹H NMR (400 MHz, d₆-DMSO) δ 9.41 (d, J=1.9 Hz, 1H), 9.20 (d, J=1.9 Hz, 1H), 8.81 (d, J=5.1 Hz, 1H), 8.76 (t, J=1.8 Hz, 1H), 8.55 (s, 1H), 7.98 (dd, J=5.1, 1.4 Hz, 1H), 7.79 (d, J=7.6 Hz, 1H), 4.21 (h, J=6.8, 6.3 Hz, 1H), 3.45 (s, 3H), 2.54 (s, 3H), 1.97-1.81 (m, 2H), 1.78-1.64 (m, 2H), 1.64-1.37 (in, 4H). LCMS(M+H)⁺: 426.1.

Examples 244 through 256 were synthesized according to the procedure of Example 243 and the data are listed in Table 18.

TABLE 18

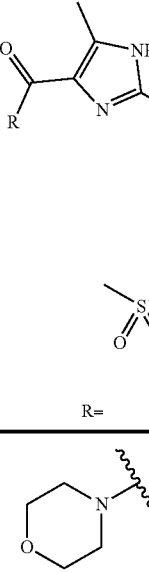

| Ex. No. | Example | R= | MS (M + H)⁺ | ¹H NMR |
|---|---|---|---|---|
| 244 | 2'-[5-Methyl-4-(morpholin-4-ylcarbonyl)-1H-imidazol-2-yl]-5-(methylsulfonyl)-3,4'-bipyridine | 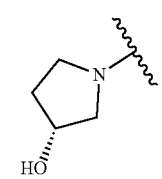 | 428.1 | ¹H NMR (400 MHz, d₆-DMSO) δ 13.16 (s, 1H), 9.39 (d, J = 2.2 Hz, 1H), 9.18 (d, J = 2.1 Hz, 1H), 8.78 (d, J = 5.1 Hz, 1H), 8.72 (t, J = 2.1 Hz, 1H), 8.37-8.30 (m, 1H), 7.89 (dd, J = 5.2, 1.9 Hz, 1H), 3.45 (s, 3H), 3.41-3.27 (m, 4H), 3.65-3.60 (m, 4H), 2.43 (s, 3H) |
| 245 | (3R)-1-({5-Methyl-2-[5-(methylsulfonyl)-3,4'-bipyridin-2'-yl]-1H-imidazol-4-yl}carbonyl)pyrrolidin-3-ol | | 428.1 | ¹H NMR (400 MHz, d₆-DMSO, rotamers) δ 13.09 (br s, 0.5H), 9.41-9.34 (m, 1H), 9.22-9.14 (m, 1H), 8.77 (d, J = 5.2 Hz, 1H), 8.74-8.65 (m, 1H), 8.40-8.37 (m, 0.5H), 8.37-8.35 (m, 0.5H), |

TABLE 18-continued

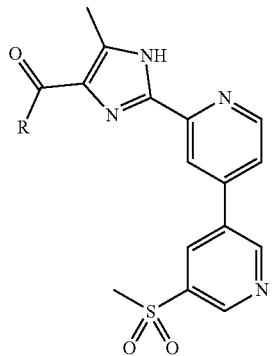

| Ex. No. | Example | R= | MS (M + H)+ | 1H NMR |
|---|---|---|---|---|
| | | | | 7.87 (dd, J = 5.2, 1.7 Hz, 2H), 4.93 (d, J = 3.0 Hz, 0.5H), 4.88 (d, J = 3.0 Hz, 0.5H), 4.35-4.19 (m, 1H), 4.15-4.07 (m, 0.5H), 4.07-3.97 (m, 1H), 3.91-3.85 (m, 0.5H), 3.58-3.41 (m, 2H), 3.44 (s, 3H), 2.47 (s, 1.5H, tautomers), 2.47 (s, 1.5H, tautomers), 2.02-1.50 (m, 2H) |
| 246 | (3S)-1-({5-Methyl-2-[5-(methylsulfonyl)-3,4'-bipyridin-2'-yl]-1H-imidazol-4-yl}carbonyl)pyrrolidin-3-ol | | 428.2 | 1H NMR (400 MHz, d6-DMSO, rotamers) δ 13.11 (br s, 0.5H), 9.41-9.34 (m, 1H), 9.20-9.16 (m, 1H), 8.77 (d, J = 5.1 Hz, 1H), 8.73-8.67 (m, 1H), 8.40-8.37 (m, 0.5H), 8.37-8.33 (m, 0.5H), 7.88 (dd, J = 5.2, 1.8 Hz, 1H), 4.92 (d, J = 3.3 Hz, 0.5H), 4.87 (d, J = 3.4 Hz, 0.5H), 4.36-4.24 (m, 1H), 4.18-3.97 (m, 1.5H), 3.91-3.84 (m, 0.5H), 3.58-3.39 (m, 2H), 3.44 (s, 3H), 2.47 (s, 1.5H, tautomers), 2.47 (s, 1.5H, tautomers), 2.04-1.66 (m, 2H) |
| 247 | 1-({5-Methyl-2-[5-(methylsulfonyl)-3,4'-bipyridin-2'-yl]-1H-imidazol-4-yl}carbonyl)azetidin-3-ol | | 414.1 | 1H NMR (400 MHz, d6-DMSO) δ 13.10 (s, 1H), 9.38 (d, J = 2.1 Hz, 1H), 9.19 (d, J = 2.1 Hz, 1H), 8.77 (d, J = 5.2 Hz, 1H), 8.71 (t, J = 2.1 Hz, 1H), 8.39-8.33 (m, 1H), 7.88 (dd, J = 5.2, 1.8 Hz, 1H), 5.64 (d, J = 6.3 Hz, 1H), 4.85 (dd, J = 10.0, 7.0 Hz, 1H), 4.54-4.44 (m, 1H), 4.32 (dd, J = 10.6, 3.6 Hz, 1H), 4.17 (dd, J = 9.5, 7.1 Hz, 1H), 3.72 (dd, J = 9.7, 3.6 Hz, 1H), 3.45 (s, 3H), 2.50 (s, 3H) |
| 248 | 1-({5-Methyl-2-[5-(methylsulfonyl)-3,4'-bipyridin-2'-yl]-1H-imidazol-4-yl}carbonyl)azetidine-3-carbonitrile | | 423.1 | 1H NMR (400 MHz, d6-DMSO) δ 9.40 (d, J = 2.1 Hz, 1H), 9.19 (d, J = 2.1 Hz, 1H), 8.78 (d, J = 5.2 Hz, 1H), 8.72 (t, J = 2.1 Hz, 1H), 8.43-8.37 (m, 1H), 7.89 (dd, J = 5.2, 1.8 Hz, 1H), 4.99-4.88 (m, 1H), 4.88-4.76 (m, 1H), |

TABLE 18-continued

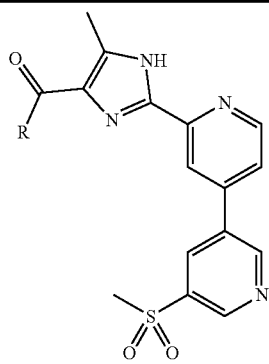

| Ex. No. | Example | R= | MS (M + H)+ | 1H NMR |
|---|---|---|---|---|
| | | | | 4.34-4.23 (m, 1H), 4.19-4.02 (m, 1H), 3.83 (tt, J = 8.9, 5.9 Hz, 1H), 3.45 (s, 3H), 2.51 (s, 3H) |
| 249 | 5-Methyl-2-[5-(methylsulfonyl)-3,4'-bipyridin-2'-yl]-1H-imidazole-4-carboxamide trifluoroacetate salt | H₂N– | 358.1 | 1H NMR (400 MHz, d₆-DMSO) δ 9.41 (d, J = 2.1 Hz, 1H), 9.20 (d, J = 2.1 Hz, 1H), 8.80 (d, J = 5.1 Hz, 1H), 8.75 (t, J = 2.1 Hz, 1H), 8.55-8.48 (m, 1H), 7.95 (dd, J = 5.1, 1.6 Hz, 1H), 7.41 (br s, 1H), 7.14 (br s, 1H), 3.45 (s, 3H), 2.53 (s, 3H) |
| 250 | N,5-Dimethyl-2-[5-(methylsulfonyl)-3,4'-bipyridin-2'-yl]-1H-imidazole-4-carboxamide trifluoroacetate salt | MeNH– | 372.1 | 1H NMR (400 MHz, d₆-DMSO) δ 9.40 (d, J = 2.1 Hz, 1H), 9.21 (d, J = 2.1 Hz, 1H), 8.81 (d, J = 5.1 Hz, 1H), 8.74 (t, J = 2.1 Hz, 1H), 8.54-8.46 (m, 1H), 7.97 (dd, J = 5.2, 1.7 Hz, 1H), 7.95 (s, 1H), 3.46 (s, 3H), 2.79 (d, J = 4.4 Hz, 3H), 2.54 (s, 3H) |
| 251 | N,N,5-Trimethyl-2-[5-(methylsulfonyl)-3,4'-bipyridin-2'-yl]-1H-imidazole-4-carboxamide trifluoroacetate salt | Me₂N– | 386.1 | 1H NMR (400 MHz, d₆-DMSO) δ 9.41 (d, J = 2.1 Hz, 1H), 9.21 (d, J = 2.0 Hz, 1H), 8.86 (d, J = 5.2 Hz, 1H), 8.75 (t, J = 2.1 Hz, 1H), 8.53 (s, 1H), 8.03 (dd, J = 5.1, 1.5 Hz, 1H), 3.45 (s, 3H), 3.25 (s, 3H), 3.00 (s, 3H), 2.40 (s, 3H) |
| 252 | N-Ethyl-5-methyl-2-[5-(methylsulfonyl)-3,4'-bipyridin-2'-yl]-1H-imidazole-4-carboxamide trifluoroacetate salt | EtNH– | 386.1 | 1H NMR (400 MHz, d₆-DMSO) δ 9.41 (d, J = 2.1 Hz, 1H), 9.21 (d, J = 2.1 Hz, 1H), 8.81 (d, J = 5.2 Hz, 1H), 8.75 (t, J = 2.1 Hz, 1H), 8.57-8.44 (m, 1H), 8.00 (t, J = 6.1 Hz, 1H), 7.97 (dd, J = 5.2, 1.7 Hz, 1H), 3.46 (s, 3H), 3.30 (p, J = 7.1 Hz, 2H), 2.54 (s, 3H), 1.13 (t, J = 7.2 Hz, 3H) |
| 253 | N-Isopropyl-5-methyl-2-[5-(methylsulfonyl)-3,4'-bipyridin-2'-yl]-1H-imidazole-4-carboxamide trifluoroacetate salt | iPrNH– | 400.1 | 1H NMR (400 MHz, d₆-DMSO) δ 9.42 (d, J = 2.1 Hz, 1H), 9.20 (d, J = 2.1 Hz, 1H), 8.81 (d, J = 5.2 Hz, 1H), 8.76 (t, J = 2.1 Hz, 1H), 8.57-8.50 (m, 1H), 7.96 (dd, J = 5.2, 1.7 Hz, 1H), 7.67 (d, J = 8.2 Hz, 1H), 4.14-4.04 (m, |

TABLE 18-continued

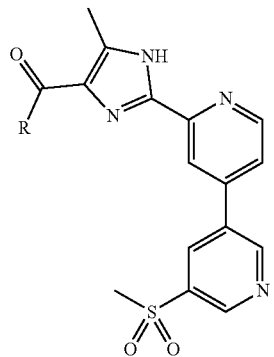

| Ex. No. | Example | R= | MS (M + H)⁺ | ¹H NMR |
|---|---|---|---|---|
| | | | | 1H), 3.46 (s, 3H), 2.54 (s, 3H), 1.19 (d, J = 6.6 Hz, 6H) |
| 254 | 5-Methyl-2-[5-(methylsulfonyl)-3,4'-bipyridin-2'-yl]-N-(tetrahydro-2H-pyran-4-yl)-1H-imidazole-4-carboxamide trifluoroacetate salt | | 442.1 | $^{1}$H NMR (400 MHz, $d_6$-DMSO) δ 9.42 (d, J = 2.1 Hz, 1H), 9.21 (d, J = 2.1 Hz, 1H), 8.81 (d, J = 5.2 Hz, 1H), 8.76 (t, J = 2.1 Hz, 1H), 8.55-8.49 (m, 1H), 7.96 (dd, J = 5.2, 1.7 Hz, 1H), 7.82 (d, J = 8.2 Hz, 1H), 4.05-3.93 (m, 1H), 3.92-3.85 (m, 2H), 3.46 (s, 3H), 3.40 (td, J = 11.7, 1.9 Hz, 2H), 2.54 (s, 3H), 1.80-1.70 (m, 2H), 1.64 (qd, J = 12.1, 4.5 Hz, 2H) |
| 255 | 5-Methyl-2-[5-(methylsulfonyl)-3,4'-bipyridin-2'-yl]-N-[(3S)-tetrahydrofuran-3-yl]-1H-imidazole-4-carboxamide trifluoroacetate salt | | 428.1 | $^{1}$H NMR (400 MHz, $d_6$-DMSO) δ 9.42 (d, J = 2.1 Hz, 1H), 9.21 (d, J = 2.0 Hz, 1H), 8.82 (d, J = 5.2 Hz, 1H), 8.77 (t, J = 2.1 Hz, 1H), 8.57-8.49 (m, 1H), 8.01-7.95 (m, 2H), 4.52-4.41 (m, 1H), 3.89 (q, J = 8.0 Hz, 1H), 3.84 (dd, J = 8.9, 6.3 Hz, 1H), 3.73 (td, J = 8.1, 6.2 Hz, 1H), 3.61 (dd, J = 8.8, 4.4 Hz, 1H), 3.46 (s, 3H), 2.54 (s, 3H), 2.19 (dq, J = 14.4, 7.8 Hz, 1H), 1.94 (dq, J = 12.5, 5.9 Hz, 1H) |
| 256 | 5-Methyl-2-[5-(methylsulfonly)-3,4'-bipyridin-2'-yl]-N-[(3R)-tetrahydrofuran-3-yl]-1H-imidazole-4-carboxamide trifluoroacetate salt | | 428.1 | $^{1}$H NMR (400 MHz, $d_6$-DMSO) δ 9.42 (d, J = 2.1 Hz, 1H), 9.20 (d, J = 2.0 Hz, 1H), 8.80 (d, J = 5.1 Hz, 1H), 8.77 (t, J = 2.1 Hz, 1H), 8.57-8.42 (m, 1H), 7.95 (dd, J = 5.0, 1.5 Hz, 1H), 7.95-7.93 (br, 1H), 4.52-4.39 (m, 1H), 3.89 (q, J = 8.0 Hz, 1H), 3.84 (dd, J = 8.8, 6.3 Hz, 1H), 3.73 (td, J = 8.1, 6.2 Hz, 1H), 3.60 (dd, J = 8.8, 4.5 Hz, 1H), 3.46 (s, 3H), 2.54 (s, 3H), 2.26-2.11 (m, 1H), 1.95 (dq, J = 12.7, 5.9 Hz, 1H) |

Example 257. 5-Methyl-2-(5-morpholin-4-yl-3,4'-bipyridin-2'-yl)-1H-imidazole-4-carboxylic acid trifluoroacetate salt

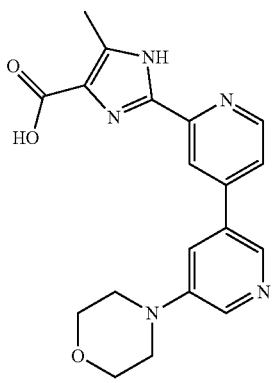 [SMILES: Cc1[nH]c(-c2cc(-c3cncc(N4CCOCC4)c3)ccn2)nc1C(=O)O]

Step 1. 2'-(5-Methyl-1H-imidazol-2-yl)-5-morpholin-4-yl-3,4'-bipyridine

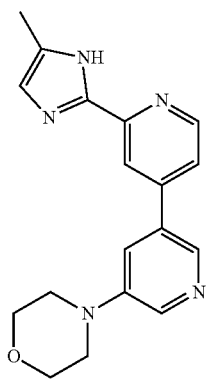 [SMILES: Cc1cnc(-c2cc(-c3cncc(N4CCOCC4)c3)ccn2)[nH]1]

5-Morpholin-4-yl-3,4'-bipyridine-2'-carbonitrile (0.75 g, 2.8 mmol, from Example 97, Step 1) in MeOH (11 mL) was treated with sodium methoxide (25 wt % in MeOH, check calculation, 0.05 mL, 0.3 mmol) overnight. 1,1-Diethoxypropan-2-amine (0.41 g, 2.8 mmol) and AcOH (0.32 mL) were added and the reaction mixture was heated in a sealed vial in an oil bath held at 100° C. for 1 hour. The reaction mixture was cooled and concentrated HCl (0.60 mL, 7.2 mmol) was added and the mixture was heated in the sealed vial in an oil bath held at 85° C. for 5.5 hours. The solvent was then removed via rotary evaporation. A solution of $K_2CO_3$ was added to adjust to pH 10 and the solid product was isolated by filtration. Yield: 0.70 g, 70%. LCMS (M+H)$^+$: 322.2.

Step 2. 2'-(4-Iodo-5-methyl-1H-imidazol-2-yl)-5-morpholin-4-yl-3,4'-bipyridine

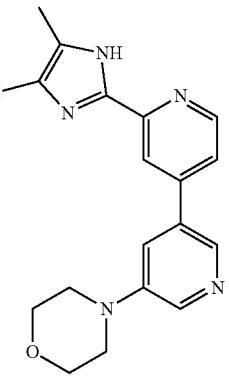

N-Iodosuccinimide (0.463 g, 2.06 mmol, Aldrich) was added to a solution of 2'-(5-methyl-1H-imidazol-2-yl)-5-morpholin-4-yl-3,4'-bipyridine (0.70 g, 2.0 mmol, from Step 1) in DMF (6.2 mL). After stirring for 20 minutes, water (50 mL) and sat'd $NaHCO_3$ solution (20 mL) were added. The solid product was isolated by filtration, washed with water and dried by azeotropic removal of water with acetonitrile in vacuo. Yield: 0.86 g, 98%. LCMS (M+H)$^+$: 448.0.

Step 3. Methyl 5-methyl-2-(5-morpholin-4-yl-3,4'-bipyridin-2'-yl)-1H-imidazole-4-carboxylate

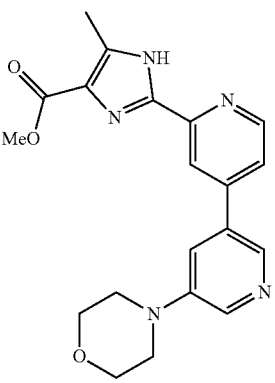 [SMILES: COC(=O)c1nc(-c2cc(-c3cncc(N4CCOCC4)c3)ccn2)[nH]c1C]

A mixture of 2'-(4-iodo-5-methyl-1H-imidazol-2-yl)-5-morpholin-4-yl-3,4'-bipyridine (1.0 g, 2.2 mmol, prepared as in Step 2), MeOH (25 mL) and triethylamine (0.78 mL, 5.6 mmol) was degassed with a stream of nitrogen and [1,1'-bis(diphenylphosphino)ferrocene]dichloropalladium (II), complex with dichloromethane (1:1) (180 mg, 0.22 mmol) was added. The slurry was saturated with CO by bubbling the gas through the reaction subsurface for 3 minutes. The vessel was sealed and was heated to 60° C. overnight. Upon cooling, the reaction mixture was diluted with water (50 mL) and stirred for 15 minutes. The solid product was isolated by filtration. Yield: 0.85 g, 99%. LCMS (M+H)$^+$: 380.2.

Step 4. 5-Methyl-2-(5-morpholin-4-yl-3,4'-bipyridin-2'-yl)-1H-imidazole-4-carboxylic acid trifluoroacetate salt Methyl 5-methyl-2-(5-morpholin-4-yl-3,4'-bipyridin-2'-yl)-1H-imidazole-4-carboxylate (0.85 g, 2.2 mmol, from Step 3) in THF (17 mL) and water (4.2 mL) was treated with lithium hydroxide hydrate (0.38 g, 9.0 mmol). 2.0 N NaOH (11 mL, 22 mmol) and MeOH (2.0 mL) were subsequently added and the mixture was heated in a sealed vial to 60° C. overnight. The organic solvents were then evaporated. The basic aqueous mixture was washed once with DCM and filtered. The aqueous filtrate was acidified to pH 5 by the addition of concentrated HCl and the solution was then saturated with NaCl. The resulting solid product was isolated by filtration and was then mixed with a mixture of $CH_3CN$ (20 mL) and $CHCl_3$ containing 20% $^iPrOH$ (300 mL) and filtered to remove salts. The filtrate was concentrated to give the desired acid, which was used without further purification in Example 258. A small portion was purified by preparative HPLC (C-18 column eluting with a water:acetonitrile gradient buffered at pH 2 with 0.1% trifluoroacetic acid). $^1$H NMR (400 MHz, $d_6$-DMSO) δ 8.80 (d, J=5.2 Hz, 1H), 8.60 (d, J=1.4 Hz, 1H), 8.52-8.43 (m, 2H), 8.03-7.96 (m, 1H), 7.93 (dd, J=5.2, 1.6 Hz, 1H), 3.84-3.73 (m, 4H), 3.46-3.36 (m, 4H), 2.54 (s, 3H); LCMS (M+H)$^+$: 366.1.

Example 258. N-Cyclopentyl-5-methyl-2-(5-morpholin-4-yl-3,4'-bipyridin-2'-yl)-1H-imidazole-4-carboxamide

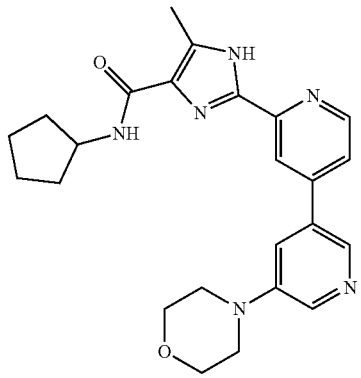 [SMILES: Cc1[nH]c(-c2cc(-c3cncc(N4CCOCC4)c3)ccn2)nc1C(=O)NC1CCCC1]

To 5-methyl-2-(5-morpholin-4-yl-3,4'-bipyridin-2'-yl)-1H-imidazole-4-carboxylic acid (15 mg, 0.033 mmol, from Example 257) in DMF (0.50 mL) was added N,N-diisopropylethylamine (17 µL, 0.098 mmol) and HATU (16 mg, 0.043 mmol), followed by cyclopentanamine (6.5 µL, 0.066 mmol, Aldrich). After stirring for 30 minutes, the product was purified by preparative HPLC (C-18 column eluting with a water:acetonitrile gradient buffered at pH 10 with 0.15% ammonium hydroxide). $^1$H NMR (400 MHz, $CD_3OD$) δ 8.72 (d, J=5.1 Hz, 1H), 8.43 (s, 1H), 8.40-8.30 (m, 2H), 7.78-7.72 (m, 1H), 7.70 (dd, J=5.1, 1.6 Hz, 1H), 4.33 (p, J=6.5 Hz, 1H), 3.99-3.81 (m, 4H), 3.38-3.35 (m, 4H), 2.63 (s, 3H), 2.12-1.99 (m, 2H), 1.88-1.75 (m, 2H), 1.75-1.54 (m, 4H); LCMS (M+H)$^+$: 433.2.

Examples 259 through 282 were synthesized according to the procedure of Example 258 and the data are listed in Table 19.

TABLE 19

| Ex. No. | Name | R= | MS (M + H)$^+$ | $^1$H NMR |
|---|---|---|---|---|
| 259 | N-Isopropyl-N,5-dimethyl-2-(5-morpholin-4-yl-3,4'-bipyridin-2'-yl)-1H-imidazole-4-carboxamide | isopropyl(methyl)amino | 421.2 | $^1$H NMR (400 MHz, $CD_3OD$) δ 8.71 (d, J = 5.3 Hz, 1H), 8.47-8.30 (m, 3H), 7.76 (br m, 1H), 7.73-7.65 (m, 1H), 4.52 (br m, 1H), 3.96-3.85 (m, 4H), 3.38-3.34 (m, 4H), 3.04 (br s, 3H), 2.43 (s, 3H), 1.29 (d, J = 6.7 Hz, 6H) |

TABLE 19-continued

| Ex. No. | Name | R= | MS (M + H)+ | 1H NMR |
|---|---|---|---|---|
| 260 | N-Ethyl-N,5-dimethyl-2-(5-morpholin-4-yl-3,4'-bipyridin-2'-yl)-1H-imidazole-4-carboxamide | (ethyl-methyl-amino) | 407.2 | 1H NMR (400 MHz, CD3OD) δ 8.71 (d, J = 4.9 Hz, 1H), 8.46-8.32 (m, 3H), 7.78-7.73 (m, 1H), 7.72-7.66 (m, 1H), 3.96-3.85 (m, 4H), 3.80-3.05 (br m, 2H), 3.39-3.34 (m, 4H), 2.97 (s, 3H), 2.44 (s, 3H), 1.33-1.22 (m, 3H) |
| 261 | N,5-Dimethyl-2-(5-morpholin-4-yl-3,4'-bipyridin-2'-yl)-N-(tetrahydrofuran-3-yl)-1H-imidazole-4-carboxamide (racemic mixture prepared) | (tetrahydrofuran-3-yl-methyl-amino) | 449.2 | 1H NMR (400 MHz, CD3OD) δ 8.71 (d, J = 5.2 Hz, 1H), 8.46-8.31 (m, 3H), 7.78-7.73 (m, 1H), 7.70 (dd, J = 5.0, 1.4 Hz, 1H), 5.29 (br, 1H), 4.10 (td, J = 8.6, 4.7 Hz, 1H), 3.97 (dd, J = 9.8, 3.8 Hz, 1H), 3.94-3.84 (m, 1H), 3.93-3.89 (m, 4H), 3.81-3.63 (m, 1H), 3.39-3.34 (m, 4H), 3.13 (br s, 3H), 2.45 (s, 3H), 2.40-2.26 (m, 1H), 2.18-2.08 (m, 1H) |
| 262 | 2'-(5-Methyl-4-{[3-(trifluoromethyl)azetidin-1-yl]carbonyl}-1H-imidazol-2-yl)-5-morpholin-4-yl-3,4'-bipyridine | (3-trifluoromethyl-azetidin-1-yl) | 473.2 | |
| 263 | 2'-{4-[(3-Methoxyazetidin-1-yl)carbonyl]-5-methyl-1H-imidazol-2-yl}-5-morpholin-4-yl-3,4'-bipyridine | (3-methoxy-azetidin-1-yl) | 435.2 | 1H NMR (400 MHz, CD3OD) δ 8.70 (d, J = 5.2 Hz, 1H), 8.43-8.34 (m, 2H), 8.32 (s, 1H), 7.75-7.70 (m, 1H), 7.70-7.62 (m, 1H), 4.58-4.46 (m, 1H), 4.38-4.29 (m, 2H), 4.98-4.79 (m, 1H), 4.04-3.94 (m, 1H), 3.94-3.85 (m, 4H), 3.38-3.34 (m, 7H), 2.59 (s, 3H) |

TABLE 19-continued

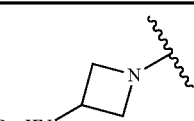

| Ex. No. | Name | R= | MS (M + H)+ | 1H NMR |
|---|---|---|---|---|
| 264 | tert-Butyl (1-{[5-methyl-2-(5-morpholin-4-yl-3,4'-bipyridin-2'-yl)-1H-imidazol-4-yl]carbonyl} azetidin-3-yl) carbamate | 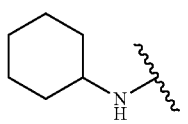 [SMILES: *NC1CCCCC1] | 520.2 | |
| 265 | N-Cyclohexyl-5-methyl-2-(5-morpholin-4-yl-3,4'-bipyridin-2'-yl)-1H-imidazole-4-carboxamide | 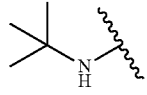 | 447.2 | 1H NMR (400 MHz, CD3OD) δ 8.72 (d, J = 5.1 Hz, 1H), 8.43 (s, 1H), 8.41-8.35 (m, 2H), 7.78-7.72 (m, 1H), 7.72-7.64 (m, 1H), 3.94-3.89 (m, 5H), 3.40-3.35 (m, 4H), 2.62 (s, 3H), 2.04-1.20 (m, 10H) |
| 266 | N-(tert-Butyl)-5-methyl-2-(5-morpholin-4-yl-3,4'-bipyridin-2'-yl)-1H-imidazole-4-carboxamide | | 421.2 | 1H NMR (400 MHz, CD3OD) δ 8.72 (d, J = 5.0 Hz, 1H), 8.43 (s, 1H), 8.38 (s, 0H), 8.35 (s, 1H), 7.78-7.73 (m, 1H), 7.70 (dd, J = 5.0, 1.4 Hz, 1H), 3.95-3.87 (m, 4H), 3.40-3.34 (m, 4H), 2.61 (s, 3H), 1.51 (s, 9H) |
| 267 | 2'-{4-[(3,3-Dimethylazetidin-1-yl)carbonyl]-5-methyl-1H-imidazol-2-yl}-5-morpholin-4-yl-3,4'-bipyridine | 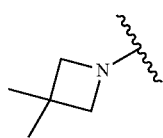 [SMILES: *N1CC(C)(C)C1] | 433.2 | 1H NMR (400 MHz, CD3OD) δ 8.70 (d, J = 5.1 Hz, 1H), 8.40 (s, 1H), 8.39-8.34 (m, 1H), 8.33-8.28 (m, 1H), 7.76-7.69 (m, 1H), 7.66 (dd, J = 5.1, 1.5 Hz, 1H), 3.93-3.87 (m, 4H), 3.38-3.35 (m, 4H), 2.97 (s, 4H), 2.59 (s, 3H), 1.36 (s, 6H) |
| 268 | N-Isopropyl-5-methyl-2-(5-morpholin-4-yl-3,4'-bipyridin-2'-yl)-1H-imidazole-4-carboxamide trifluoroacetate salt | 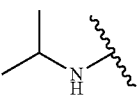 | 407.2 | 1H NMR (400 MHz, d6-DMSO) δ 8.79 (d, J = 5.2 Hz, 1H), 8.65 (s, 1H), 8.53 (d, J = 2.5 Hz, 1H), 8.47 (s, 1H), 8.19-8.12 (m, 1H), 7.89 (dd, J = 5.2, 1.6 Hz, 1H), 7.61 (d, J = 8.2 Hz, 1H), 4.14-4.04 (m, 1H), 3.86-3.76 (m, 4H), 3.50-3.39 (m, 4H), 2.54 (s, 3H), 1.19 (d, J = 6.6 Hz, 6H) |

TABLE 19-continued

| Ex. No. | Name | R= | MS (M + H)+ | 1H NMR |
|---|---|---|---|---|
| 269 | 5-Methyl-2-(5-morpholin-4-yl-3,4'-bipyridin-2'-yl)-N-(tetrahydro-2H-pyran-4-yl)-1H-imidazole-4-carboxamide trifluoroacetate salt | (tetrahydro-2H-pyran-4-yl-NH-) | 449.2 | 1H NMR (400 MHz, d6-DMSO) δ 8.80 (d, J = 5.2 Hz, 1H), 8.68-8.64 (m, 1H), 8.53 (d, J = 2.5 Hz, 1H), 8.50-8.46 (m, 1H), 8.23-8.14 (m, 1H), 7.90 (dd, J = 5.2, 1.7 Hz, 1H), 7.75 (d, J = 8.3 Hz, 1H), 3.99 (tdt, J = 12.3, 8.6, 4.5 Hz, 1H), 3.93-3.85 (m, 2H), 3.84-3.77 (m, 4H), 3.50-3.43 (m, 4H), 3.44-3.33 (m, 2H), 2.54 (s, 3H), 1.84-1.70 (m, 2H), 1.61 (qd, J = 12.1, 4.4 Hz, 2H) |
| 270 | 5-Methyl-2-(5-morpholin-4-yl-3,4'-bipyridin-2'-yl)-N-[(3R)-tetrahydrofuran-3-yl]-1H-imidazole-4-carboxamide trifluoroacetate salt | ((3R)-tetrahydrofuran-3-yl-NH-) | 435.2 | 1H NMR (400 MHz, d6-DMSO) δ 8.78 (d, J = 5.2 Hz, 1H), 8.67-8.62 (m, 1H), 8.52 (d, J = 2.6 Hz, 1H), 8.50-8.46 (m, 1H), 8.16 (s, 1H), 7.92-7.84 (m, 2H), 4.53-4.41 (m, 1H), 3.89 (q, J = 7.9 Hz, 1H), 3.84 (dd, J = 8.9, 6.2 Hz, 1H), 3.82-3.79 (m, 4H), 3.73 (td, J = 8.2, 6.2 Hz, 1H), 3.60 (dd, J = 8.9, 4.3 Hz, 1H), 3.48-3.42 (m, 4H), 2.54 (s, 3H), 2.25-2.13 (m, 1H), 1.97-1.87 (m, 1H) |
| 271 | 5-Methyl-2-(5-morpholin-4-yl-3,4'-bipyridin-2'-yl)-N-[(3S)-tetrahydrofuran-3-yl]-1H-imidazole-4-carboxamide trifluoroacetate salt | ((3S)-tetrahydrofuran-3-yl-NH-) | 435.2 | 1H NMR (400 MHz, d6-DMSO) δ 8.77 (d, J = 5.1 Hz, 1H), 8.63 (d, J = 1.2 Hz, 1H), 8.51 (d, J = 2.6 Hz, 1H), 8.49-8.46 (m, 1H), 8.12-8.06 (m, 1H), 7.92-7.82 (m, 2H), 4.51-4.40 (m, 1H), 3.89 (q, J = 8.0 Hz, 1H), 3.84 (dd, J = 8.9, 6.3 Hz, 1H), 3.82-3.79 (m, 4H), 3.73 (td, J = 8.1, 6.1 Hz, 1H), 3.60 (dd, J = 8.8, 4.3 Hz, 1H), 3.46-3.42 (m, 4H), 2.53 (s, 3H), 2.24-2.12 (m, 1H), 2.00-1.86 (m, 1H) |

TABLE 19-continued

| Ex. No. | Name | R= | MS (M + H)+ | 1H NMR |
|---|---|---|---|---|
| 272 | N-Benzyl-5-methyl-2-(5-morpholin-4-yl-3,4'-bipyridin-2'-yl)-1H-imidazole-4-carboxamide trifluoroacetate salt | | 455.2 | 1H NMR (400 MHz, d6-DMSO) δ 8.77 (d, J = 5.1 Hz, 1H), 8.63-8.54 (m, 1H), 8.50 (d, J = 2.5 Hz, 1H), 8.46-8.39 (m, 2H), 8.10-8.04 (m, 1H), 7.86 (dd, J = 5.2, 1.7 Hz, 1H), 7.42-7.20 (m, 5H), 4.47 (d, J = 6.3 Hz, 2H), 3.83-3.73 (m, 4H), 3.47-3.37 (m, 4H), 2.55 (s, 3H) |
| 273 | 5-Methyl-2-(5-morpholin-4-yl-3,4'-bipyridin-2'-yl)-N-[(1S)-1-phenylethyl]-1H-imidazole-4-carboxamide trifluoroacetate salt | | 469.2 | 1H NMR (400 MHz, d6-DMSO) δ 8.78 (d, J = 5.2 Hz, 1H), 8.66-8.60 (m, 1H), 8.52 (d, J = 2.5 Hz, 1H), 8.50-8.42 (m, 1H), 8.15-8.08 (m, 2H), 7.88 (dd, J = 5.2, 1.6 Hz, 1H), 7.42 (d, J = 7.5 Hz, 2H), 7.34 (t, J = 7.6 Hz, 2H), 7.24 (t, J = 7.2 Hz, 1H), 5.17 (p, J = 7.0 Hz, 1H), 3.85-3.72 (m, 4H), 3.48-3.39 (m, 4H), 2.52 (s, 3H), 1.52 (d, J = 7.0 Hz, 3H) |
| 274 | 5-Methyl-2-(5-morpholin-4-yl-3,4'-bipyridin-2'-yl)-N-[(1R)-1-phenylethyl]-1H-imidazole-4-carboxamide trifluoroacetate salt | | 469.1 | 1H NMR (400 MHz, d6-DMSO) δ 8.77 (d, J = 5.2 Hz, 1H), 8.67-8.58 (m, 1H), 8.51 (d, J = 2.6 Hz, 1H), 8.49-8.44 (m, 1H), 8.12 (d, J = 8.5 Hz, 1H), 8.10-8.05 (m, 1H), 7.87 (dd, J = 5.2, 1.7 Hz, 1H), 7.42 (d, J = 7.4 Hz, 2H), 7.34 (t, J = 7.5 Hz, 2H), 7.24 (t, J = 7.3 Hz, 1H), 5.17 (p, J = 6.9 Hz, 1H), 3.84-3.75 (m, 4H), 3.47-3.39 (m, 4H), 2.52 (s, 3H), 1.52 (d, J = 7.0 Hz, 3H) |
| 275 | N-[(1R)-2-Methoxy-1-phenylethyl]-5-methyl-2-(5-morpholin-4-yl-3,4'-bipyridin-2'-yl)-1H-imidazole-4-carboxamide trifluoroacetate salt | | 499.2 | 1H NMR (400 MHz, d6-DMSO) δ 8.77 (d, J = 5.1 Hz, 1H), 8.65-8.57 (m, 1H), 8.51 (d, J = 2.6 Hz, 1H), 8.47-8.43 (m, 1H), 8.18 (d, J = 8.6 Hz, 1H), 8.12-8.01 (m, 1H), 7.86 (dd, J = 5.2, 1.7 Hz, 1H), |

TABLE 19-continued

| Ex. No. | Name | R= | MS (M + H)+ | 1H NMR |
|---|---|---|---|---|
| | | | | 7.43 (d, J = 7.4 Hz, 2H), 7.34 (t, J = 7.5 Hz, 2H), 7.26 (t, J = 7.3 Hz, 1H), 5.31-5.17 (m, 1H), 3.82-3.79 (m, 4H), 3.77 (dd, J = 10.0, 7.2 Hz, 1H), 3.65 (dd, J = 10.0, 5.2 Hz, 1H), 3.46-3.37 (m, 4H), 3.31 (s, 3H), 2.52 (s, 3H) |
| 276 | N-[(1S)-2-Methoxy-1-phenylethyl]-5-methyl-2-(5-morpholin-4-yl-3,4'-bipyridin-2'-yl)-1H-imidazole-4-carboxamide trifluoroacetate salt | | 499.2 | 1H NMR (400 MHz, d6-DMSO) δ 8.78 (d, J = 5.1 Hz, 1H), 8.65-8.56 (m, 1H), 8.52 (d, J = 2.5 Hz, 1H), 8.49-8.41 (m, 1H), 8.18 (d, J = 8.6 Hz, 1H), 8.14-8.05 (m, 1H), 7.87 (dd, J = 5.2, 1.7 Hz, 1H), 7.43 (d, J = 7.3 Hz, 2H), 7.34 (t, J = 7.5 Hz, 2H), 7.26 (t, J = 7.2 Hz, 1H), 5.30-5.19 (m, 1H), 3.83-3.78 (m, 4H), 3.77 (dd, J = 10.0, 7.2 Hz, 1H), 3.65 (dd, J = 10.0, 5.1 Hz, 1H), 3.47-3.40 (m, 4H), 3.30 (s, 3H), 2.52 (s, 3H) |
| 277 | N-[1-(3-Fluorophenyl)ethyl]-5-methyl-2-(5-morpholin-4-yl-3,4'-bipyridin-2'-yl)-1H-imidazole-4-carboxamide trifluoroacetate salt (racemic mixture prepared) | | 487.1 | 1H NMR (400 MHz, d6-DMSO) δ 8.77 (d, J = 5.2 Hz, 1H), 8.61 (d, J = 1.3 Hz, 1H), 8.51 (d, J = 2.6 Hz, 1H), 8.49-8.44 (m, 1H), 8.21 (d, J = 8.4 Hz, 1H), 8.09-7.97 (m, 1H), 7.86 (dd, J = 5.2, 1.7 Hz, 1H), 7.42-6.97 (m, 4H), 5.17 (p, J = 7.2 Hz, 1H), 3.84-3.73 (m, 4H), 3.48-3.33 (m, 4H), 2.51 (s, 3H), 1.52 (d, J = 7.0 Hz, 3H) |
| 278 | N-2-Adamantyl-5-methyl-2-(5-morpholin-4-yl-3,4'-bipyridin-2'-yl)-1H-imidazole-4-carboxamide trifluoroacetate salt | | 499.3 | 1H NMR (400 MHz, d6-DMSO) δ 8.76 (d, J = 5.2 Hz, 1H), 8.63 (s, 1H), 8.51-8.47 (m, 1H), 8.46 (s, 1H), 8.08-7.96 (m, 1H), 7.87 (dd, J = 5.2, 1.5 Hz, 1H), 7.70 (d, J = 7.8 Hz, 1H), 4.05 (d, J = |

TABLE 19-continued

| Ex. No. | Name | R= | MS (M + H)+ | 1H NMR |
|---|---|---|---|---|
| | | | | 7.8 Hz, 1H), 3.83-3.74 (m, 4H), 3.46-3.30 (m, 4H), 2.54 (s, 3H), 2.02-1.56 (m, 14H) |
| 279 | N-[(3S)-1-Benzylpyrrolidin-3-yl]-5-methyl-2-(5-morpholin-4-yl-3,4'-bipyridin-2'-yl)-1H-imidazole-4-carboxamide trifluoroacetate salt | | 524.3 | 1H NMR (400 MHz, d6-DMSO, interconverting cis and trans salts) δ 10.59-10.32 (2 br s, together 1H), 8.76-8.68 (m, 2H), 8.50 (br, 1H), 8.47 (br, 1H), 8.43 (s, 1H), 8.37-8.31 (m, 1H), 7.86-7.79 (m, 2H), 7.63-7.53 (m, 2H), 7.52-7.42 (m, 3H), 4.80-4.52 (m, 1H), 4.47-4.35 (m, 2H), 3.84-3.72 (m, 4H), 3.72-3.53 (m, 1H), 3.53-3.29 (m, 6H), 3.27-3.12 (m, 1H), 2.64-1.94 (m, 5H) |
| 280 | N-[(3R)-1-Benzylpyrrolidin-3-yl]-5-methyl-2-(5-morpholin-4-yl-3,4'-bipyridin-2'-yl)-1H-imidazole-4-carboxamide trifluoroacetate salt | | 524.3 | 1H NMR (600 MHz, d6-DMSO, interconverting cis and trans salts) δ 10.02 (s, 1H), 8.78-8.72 (m, 1H), 8.57-8.48 (m, 2H), 8.42 (s, 0.4H), 8.36 (s, 0.6H), 8.33 (d, J = 7.4 Hz, 0.4H), 8.17 (d, J = 7.4 Hz, 0.6H), 7.92 (d, J = 14.1 Hz, 1H), 7.87-7.82 (m, 1H), 7.59-7.41 (m, 3H), 4.73-4.66 (m, 0.6H), 4.61-4.53 (m, 0.4H), 4.47-4.35 (m, 2H), 3.82-3.76 (m, 4H), 3.71-3.59 (m, 1H), 3.54-3.44 (m, 1H), 3.44-3.30 (m, 5H), 3.28-3.17 (m, 1H), 2.56-2.53 (m, 0.4H), 2.52 (2 singlets, together 3H), 2.33-2.13 (m, 1H), 2.06-1.96 (m, 0.6H) |
| 281 | 5-Methyl-2-(5-morpholin-4-yl-3,4'-bipyridin-2'-yl)-N-(tetrahydro-2H-thiopyran-4-yl)-1H-imidazole-4- | | 465.2 | 1H NMR (400 MHz, d6-DMSO) δ 8.77 (d, J = 5.2 Hz, 1H), 8.64-8.59 (m, 1H), 8.51 (d, J = 2.6 Hz, 1H), 8.48-8.43 (m, 1H), 8.11- |

TABLE 19-continued

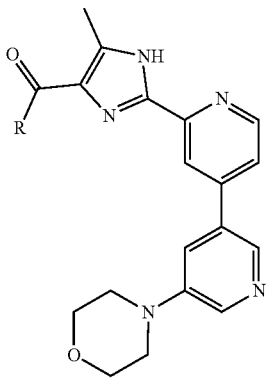

| Ex. No. | Name | R= | MS (M + H)+ | 1H NMR |
|---|---|---|---|---|
| | carboxamide trifluoroacetate salt | | | 8.04 (m, 1H), 7.87 (dd, J = 5.2, 1.7 Hz, 1H), 7.78 (d, J = 8.4 Hz, 1H), 3.86-3.74 (m, 5H), 3.53-3.31 (m, 4H), 2.79-2.60 (m, 4H), 2.53 (s, 3H), 2.15-2.01 (m, 2H), 1.71 (qd, J = 11.7, 3.3 Hz, 2H) |
| 282 | N-(2,3-Dihydro-1H-inden-2-yl)-5-methyl-2-(5-morpholin-4-yl-3,4'-bipyridin-2'-yl)-1H-imidazole-4-carboxamide trifluoroacetate salt | | 481.2 | 1H NMR (400 MHz, d6-DMSO) δ 8.75 (d, J = 5.1 Hz, 1H), 8.59 (d, J = 1.3 Hz, 1H), 8.49 (d, J = 2.6 Hz, 1H), 8.44-8.38 (m, 1H), 8.07-8.02 (m, 1H), 8.01 (d, J = 7.7 Hz, 1H), 7.85 (dd, J = 5.2, 1.7 Hz, 1H), 7.28-7.22 (m, 2H), 7.20-7.14 (m, 2H), 4.71 (h, J = 7.2 Hz, 1H), 3.85-3.75 (m, 4H), 3.46-3.34 (m, 4H), 3.23 (dd, J = 15.9, 7.7 Hz, 2H), 2.99 (dd, J = 15.8, 6.7 Hz, 2H), 2.55 (s, 3H) |

Example 283. N-{[5-Methyl-2-(5-morpholin-4-yl-3,4'-bipyridin-2'-yl)-1H-imidazol-4-yl]methyl}tetrahydro-2H-pyran-4-amine Step 1. 5-Methyl-2-(5-morpholin-4-yl-3,4'-bipyridin-2'-yl)-1H-imidazole-4-carbaldehyde

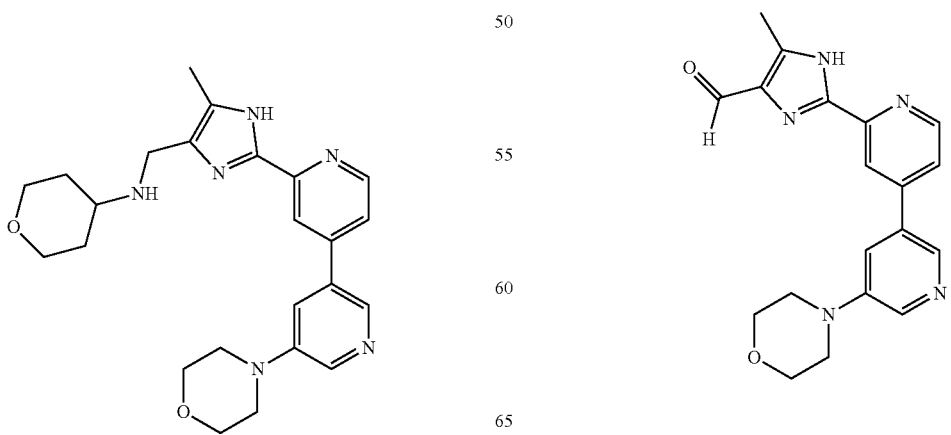

2'-(4-Iodo-5-methyl-1H-imidazol-2-yl)-5-morpholin-4-yl-3,4'-bipyridine (0.70 g, 1.6 mmol, prepared as in Example 257, Step 2) was dissolved in DMF (17 mL), and Na₂CO₃ (0.33 g, 3.1 mmol), [1,1'-bis(diphenylphosphino)ferrocene]dichloropalladium (II) (110 mg, 0.16 mmol, Aldrich) and triethylsilane (0.75 mL, 4.7 mmol, Aldrich) were added. The mixture was degassed with a stream of nitrogen first, and then the solution was saturated with carbon monoxide by bubbling CO gas through the reaction subsurface for 5 minutes. The reaction vessel was then sealed and heated to 60° C. for 3 hours. Upon cooling to room temperature, the reaction mixture was diluted with DCM, filtered, and concentrated. The product was purified by flash chromatography, eluting with a gradient from 0-10% MeOH in DCM containing 1% ammonium hydroxide. Yield: 0.22 g, 40%. LCMS(M+H)⁺: 350.2.

Step 2. N-{[5-Methyl-2-(5-morpholin-4-yl-3,4'-bipyridin-2'-yl)-1H-imidazol-4-yl]methyl}tetrahydro-2H-pyran-4-amine To a mixture of 5-methyl-2-(5-morpholin-4-yl-3,4'-bipyridin-2'-yl)-1H-imidazole-4-carbaldehyde (10. mg, 0.029 mmol, from Step 1) and tetrahydro-2H-pyran-4-amine (4.4 µL, 0.043 mmol, Combi-Blocks) in 1,2-dichloroethane (0.20 mL) was added a drop of acetic acid and the mixture was stirred for 15 minutes. Sodium triacetoxyborohydride (12 mg, 0.057 mmol) was then added and the reaction was stirred overnight. The reaction was quenched by the addition of a small amount of water, and the product was purified by preparative HPLC (C-18 column eluting with 21.6-39.6% acetonitrile in water containing 0.15% ammonium hydroxide over 12 minutes). Yield: 3.6 mg, 29%. ¹H NMR (400 MHz, d₆-DMSO, tautomers) δ 8.63 (d, J=5.2 Hz, 1H), 8.46-8.40 (m, 2H), 8.20 (s, 1H), 7.71-7.62 (m, 2H), 3.88-3.75 (m, 6H), 3.70 (br s, 1H), 3.63 (br s, 1H), 3.40-3.20 (m, 3H), 2.23 (br s, 1.5H), 2.17 (br s, 1.5H), 1.86-1.67 (m, 2H), 1.35-1.18 (m, 2H); LCMS (M+H)⁺: 435.3.

Examples 284 through 292 were synthesized according to the procedure of Example 283 and the data are listed in Table 20.

TABLE 20

| Ex. No. | Name | R= | MS (M + H)⁺ | ¹H NMR |
|---|---|---|---|---|
| 284 | N-{[5-Methyl-2-(5-morpholin-4-yl-3,4'-bipyridin-2'-yl)-1H-imidazol-4-yl]methyl}cyclopentanamine | cyclopentyl-NH | 419.2 | ¹H NMR (400 MHz, d₆-DMSO, tautomers) δ 12.47 (br s, 0.5H), 12.34 (br s, 0.5H), 8.65-8.61 (m, 1H), 8.45-8.39 (m, 2H), 8.22-8.17 (m, 1H), 7.70-7.64 (m, 2H), 3.82-3.73 (m, 4H), 3.64 (s, 1H), 3.56 (s, 1H), 3.37-3.28 (m, 4H), 3.06 (p, J = 6.4 Hz, 0.5H), 2.93 (p, J = 5.9 Hz, 0.5H), 2.24 (s, 1.5H), 2.16 (s, 1.5H), 1.79-1.54 (m, 4H), 1.54-1.41 (m, 2H), 1.41-1.26 (m, 2H) |
| 285 | N-{[5-Methyl-2-(5-morpholin-4-yl-3,4'-bipyridin-2'-yl)-1H-imidazol-4-yl]methyl}propan-2-amine | isopropyl-NH | 393.2 | ¹H NMR (400 MHz, d₆-DMSO, tautomers) δ 12.47 (s, 0.5H), 12.35 (s, 0.5H), 8.66-8.59 (m, 1H), 8.45-8.38 (m, 2H), 8.23-8.17 (m, 1H), 7.71-7.63 (m, 2H), 3.84-3.73 (m, 4H), 3.66 (s, 1H), 3.58 (s, 1H), 3.34-3.29 (m, 4H), 2.77 (p, J = 6.2 Hz, 0.5H), 2.63 (p, J = 6.3 Hz, 0.5H), 2.24 (s, 1.5H), 2.16 (s, 1.5H), 1.02 (d, J = 6.2 Hz, 3H), 0.97 (d, J = 6.2 Hz, 3H) |

TABLE 20-continued

| Ex. No. | Name | R= | MS (M + H)⁺ | ¹H NMR |
|---|---|---|---|---|
| 286 | (3S)-N-{[5-Methyl-2-(5-morpholin-4-yl-3,4'-bipyridin-2'-yl)-1H-imidazol-4-yl]methyl}tetrahydrofuran-3-amine | | 421.2 | ¹H NMR (400 MHz, d₆-CD₃OD) δ 8.68 (d, J = 5.1 Hz, 1H), 8.44 (d, J = 1.5 Hz, 1H), 8.37 (d, J = 2.6 Hz, 1H), 8.35 (s, 1H), 7.79-7.73 (m, 1H), 7.66 (dd, J = 5.1, 1.6 Hz, 1H), 3.99-3.93 (m, 1H), 3.93-3.89 (m, 4H), 3.86 (dd, J = 8.8, 6.2 Hz, 1H), 3.82-3.71 (m, 3H), 3.63 (dd, J = 8.9, 4.3 Hz, 1H), 3.51-3.42 (m, 1H), 3.39-3.35 (m, 4H), 2.34 (s, 3H), 2.23-2.09 (m, 1H), 1.89-1.78 (m, 1H) |
| 287 | (3R)-N-{[5-Methyl-2-(5-morpholin-4-yl-3,4'-bipyridin-2'-yl)-1H-imidazol-4-yl]methyl}tetrahydrofuran-3-amine | | 421.2 | ¹H NMR (400 MHz, d₆-DMSO, tautomers) δ 12.49 (br s, 0.5H), 12.38 (br s, 0.5H), 8.67-8.56 (m, 1H), 8.46-8.37 (m, 2H), 8.23-8.13 (m, 1H), 7.70-7.62 (m, 2H), 3.82-3.76 (m, 4H), 3.76-3.52 (m, 5H), 3.47-3.38 (m, 1H), 3.36-3.28 (m, 4H), 3.25-3.17 (m, 0.5H), 2.24 (s, 1.5H), 2.17 (s, 1.5H), 2.02-1.59 (m, 2H) |
| 288 | N-Methyl-1-[5-methyl-2-(5-morpholin-4-yl-3,4'-bipyridin-2'-yl)-1H-imidazol-4-yl]methanamine | | 365.2 | ¹H NMR (400 MHz, d₆-DMSO, tautomers) δ 8.63 (d, J = 5.2 Hz, 1H), 8.48-8.37 (m, 2H), 8.20 (d, J = 4.6 Hz, 1H), 7.75-7.61 (m, 2H), 3.84-3.75 (m, 4H), 3.62 (s, 1H), 3.54 (s, 1H), 3.34-3.29 (m, 4H), 2.30 (s, 1.5H), 2.24 (s, 1.5H), 2.21 (s, 1.5H), 2.17 (s, 1.5H) |
| 289 | N,N-Dimethyl-1-[5-methyl-2-(5-morpholin-4-yl-3,4'-bipyridin-2'-yl)-1H-imidazol-4-yl]methanamine | | 379.3 | ¹H NMR (400 MHz, d₆-DMSO, tautomers) δ 12.52 (s, 0.6H), 12.43 (s, 0.4H), 8.67-8.57 (m, 1H), 8.46-8.35 (m, 2H), 8.24-8.21 (m, 0.4H), 8.21-8.13 (m, 0.6H), 7.71-7.61 (m, 2H), 3.83-3.72 (m, 4H), 3.43 (s, 0.8H), 3.35-3.30 (m, 4H), 3.29 (s, 1.2H), 2.24 (s, 1.8H), 2.17 (s, 1.2H), 2.14 (s, H) |
| 290 | 2-Methoxy-N-{[5-methyl-2-(5-morpholin-4-yl-3,4'-bipyridin-2'-yl)-1H- | | 409.2 | ¹H NMR (400 MHz, d₆-DMSO, tautomers) δ 12.48 (s, 0.5H), 12.39 (s, 0.5H), 8.66-8.58 (m, 1H), 8.46-8.38 (m, 2H), 8.22-8.18 (m, 1H), 7.70-7.65 (m, 2H), |

TABLE 20-continued

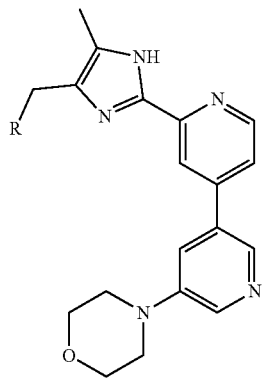

| Ex. No. | Name | R= | MS (M + H)+ | 1H NMR |
|---|---|---|---|---|
|  | imidazol-4-yl]methyl} ethanamine |  |  | 3.84-3.73 (m, 4H), 3.68 (s, 1H), 3.59 (s, 1H), 3.44-3.35 (m, 2H), 3.35-3.28 (m, 4H), 3.24 (s, 1.5H), 3.22 (s, 1.5H), 2.69 (t, J = 5.6 Hz, 1H), 2.59 (t, J = 5.6 Hz, 1H), 2.24 (s, 1.5H), 2.16 (s, 1.5H) |
| 291 | 3-Methoxy-N-{[5-methyl-2-(5-morpholin-4-yl-3,4'-bipyridin-2'-yl)-1H-imidazol-4-yl]methyl}propan-1-amine |  | 423.3 | 1H NMR (400 MHz, d6-DMSO, tautomers) δ 12.47 (s, 0.5H), 12.34 (s, 0.5H), 8.66-8.58 (m, 1H), 8.47-8.36 (m, 2H), 8.23-8.15 (m, 1H), 7.71-7.63 (m, 2H), 3.83-3.75 (m, 4H), 3.65 (s, 1H), 3.57 (s, 1H), 3.37 (q, J = 6.2 Hz, 2H), 3.33-3.28 (m, 4H), 3.21 (s, 1.5H), 3.20 (s, 1.5H), 2.57 (t, J = 6.9 Hz, 1H), 2.47 (t, J = 7.0 Hz, 1H), 2.24 (s, 1.5H), 2.16 (s, 1.5H), 1.70-1.57 (m, 2H) |
| 292 | 2'-[5-Methyl-4-(morpholin-4-ylmethyl)-1H-imidazol-2-yl]-5-morpholin-4-yl-3,4'-bipyridine |  | 421.2 | 1H NMR (400 MHz, d6-DMSO, tautomers) δ 8.64 (d, J = 5.1 Hz, 1H), 8.48-8.38 (m, 2H), 8.24-8.15 (m, 1H), 7.72-7.62 (m, 2H), 3.83-3.71 (m, 4H), 3.59-3.53 (m, 4H), 3.63-3.25 (m, 6H), 2.44-2.30 (m, 4H), 2.25 (s, 2H), 2.19 (s, 1H) |

Example 293. 2'-(4,5-Dimethyl-1H-imidazol-2-yl)-3,4'-bipyridin-5-yl]methanol

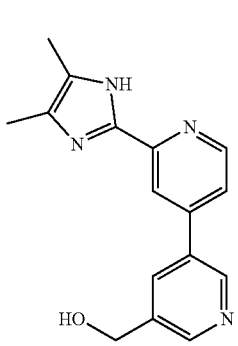 [SMILES: Cc1nc(-c2cc(-c3cncc(CO)c3)ccn2)[nH]c1C]

Step 1.
4-Bromo-2-(4,5-dimethyl-1H-imidazol-2-yl)pyridine

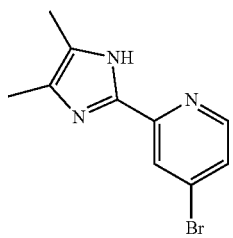

4-Bromopyridine-2-carbonitrile (1.37 g, 7.51 mmol) (Synthonix) was treated according to the procedure of Example 75, Step 1, using 3,3-dimethoxybutan-2-amine (prepared as in *J. Med Chem.* 2005, 48(14), 4618-4627). When complete, the reaction was evaporated to dryness. 1.0

N NaOH was added and the solid product was isolated by filtration and washed with water. The solid was dried by azeotropic removal of water by repeated evaporation from toluene via rotary evaporation. Yield: 1.32 g, 70%. LCMS (M+H)+: 251.9, 254.0.

Step 2. 4-Bromo-2-(4,5-dimethyl-1-{[2-(trimethylsilyl)ethoxy]methyl}-1H-imidazol-2-yl)pyridine

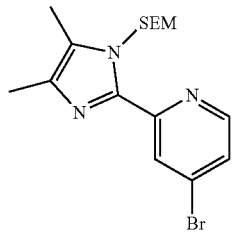 [SMILES: Cc1nc(-c2cc(Br)ccn2)n(COCC[Si](C)(C)C)c1C]

To 4-bromo-2-(4,5-dimethyl-1H-imidazol-2-yl)pyridine (1.32 g, 5.24 mmol, from Step 1) in DMF (30 mL) at 0° C. was added NaH (60% in mineral oil, 0.42 g, 10. mmol) and the reaction mixture was stirred for 20 minutes. [β-(Trimethylsilyl)ethoxy]methyl chloride (1.1 mL, 6.3 mmol, Aldrich) was then added. The reaction was continued for 45 minutes. Water was then added and the reaction mixture was extracted with EtOAc. The combined organic extracts were washed with water and brine, dried over $Na_2SO_4$, filtered, and concentrated. The product was purified by flash chromatography, eluting with a gradient from 0-50% EtOAc in hexanes. Yield: 1.46 g, 76%. LCMS (M+H)+: 382.0

Step 3. Ethyl 2'-(4,5-dimethyl-1-{[2-(trimethylsilyl)ethoxy]methyl}-1H-imidazol-2-yl)-3,4'-bipyridine-5-carboxylate

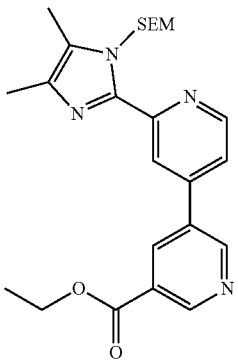 [SMILES: CCOC(=O)c1cncc(-c2ccnc(-c3nc(C)c(C)n3COCC[Si](C)(C)C)c2)c1]

To a degassed mixture of ethyl 5-(4,4,5,5-tetramethyl-1,3,2-dioxaborolan-2-yl)nicotinate (0.72 g, 2.6 mmol) (Fronteir Scientific), 4-bromo-2-(4,5-dimethyl-1-{[2-(trimethylsilyl)ethoxy]methyl}-1H-imidazol-2-yl)pyridine (1.00 g, 2.62 mmol, from Step 2), and CsF (1 g, 8 mmol) in 1,4-dioxane (7 mL) and water (1 mL) was added 4-(di-tert-butylphosphino)-N,N-dimethylaniline-dichloropalladium (2:1) (0.18 g, 0.26 mmol, Aldrich), and the mixture was heated to 60° C. for 2 hours. Additional ethyl 5-(4,4,5,5-tetramethyl-1,3,2-dioxaborolan-2-yl)nicotinate (0.35 g, 1.3 mmol) was added and heating was resumed for 4 hours at 60° C. Water was then added to the reaction mixture and the aqueous mixture was extracted with EtOAc three times. The combined organic extracts were dried over $Na_2SO_4$, filtered, and concentrated. The product was purified by flash chromatography, eluting with a gradient from 0-50% EtOAc in hexanes. Yield: 0.92 g, 78%. LCMS (M+H)+: 453.2.

Step 4. (2'-(4,5-Dimethyl-1-((2-(trimethylsilyl)ethoxy)methyl)-1H-imidazol-2-yl)-3,4'-bipyridin-5-yl)methanol

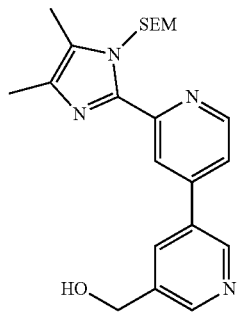 [SMILES: Cc1nc(-c2cc(-c3cncc(CO)c3)ccn2)n(COCC[Si](C)(C)C)c1C]

To a −75° C. solution of ethyl 2'-(4,5-dimethyl-1-{[2-(trimethylsilyl)ethoxy]methyl}-1H-imidazol-2-yl)-3,4'-bipyridine-5-carboxylate (0.40 g, 0.88 mmol, from Step 3) in toluene (4 mL) was added 1.0 M diisobutylaluminum hydride in toluene (1.1 mL, 1.1 mmol). The reaction was slowly warmed to 0° C. over 2 hours. The mixture was re-cooled to −75° C. and additional 1.0 M diisobutylaluminum hydride in toluene (0.77 mL, 0.77 mmol) was added. After gradually warming to −55° C. over 30 minutes, the reaction was quenched by the addition of Rochelle's salt solution. Ethyl acetate was added and the reaction mixture was allowed to stir overnight, and the mixture was then filtered. The organic layer of the filtrate was washed with saturated NaCl, dried over sodium sulfate, filtered, and concentrated. The product was purified by flash chromatography, eluting with a gradient from 50-100% EtOAc containing 10% $^i$PrOH in hexanes, followed by a gradient from 5-10% MeOH in DCM containing 0.5-1% $NH_4OH$. Yield: 0.083 g, 23%. $^1$H NMR (400 MHz, $CDCl_3$) δ 8.74 (d, J=2.1 Hz, 1H), 8.59 (d, J=5.1 Hz, 1H), 8.53 (d, J=1.6 Hz, 1H), 8.31-8.26 (m, 1H), 8.05 (t, J=1.9 Hz, 1H), 7.37 (dd, J=5.1, 1.7 Hz, 1H), 6.03 (s, 2H), 4.75 (s, 2H), 3.60-3.24 (m, 2H), 2.28 (s, 3H), 2.24 (s, 3H), 0.90-0.64 (m, 2H), −0.13 (s, 9H); LCMS (M+H)+: 411.1.

Step 5. 2'-(4,5-Dimethyl-1H-imidazol-2-yl)-3,4'-bipyridin-5-yl]methanol (2'-(4,5-Dimethyl-1-((2-(trimethylsilyl)ethoxy)methyl)-1H-imidazol-2-yl)-3,4'-bipyridin-5-yl)methanol from Step 4 was stirred in TFA solution for 1 hour. The solvent was then removed in vacuo. The product was purified by preparative HPLC (C-18 column eluting with a water:acetonitrile gradient buffered at pH 10 with 0.15% ammonium hydroxide). $^1$H NMR (400 MHz, $d_6$-DMSO) δ 12.42 (br s, 1H), 8.92 (d, J=2.0 Hz, 1H), 8.67-8.54 (m, 2H), 8.23-8.20 (m, 1H), 8.20-8.13 (m, 1H), 7.68 (dd, J=5.2, 1.7 Hz, 1H), 5.46 (t, J=5.8 Hz, 1H), 4.67 (d, J=5.6 Hz, 2H), 2.19 (s, 3H), 2.12 (s, 3H); LCMS (M+H)+: 281.1.

Example 294. 4-(1-(4-Chlorobenzyl)-1H-pyrazol-4-yl)-2-(4,5-dimethyl-1H-imidazol-2-yl)pyridine trifluoroacetate salt

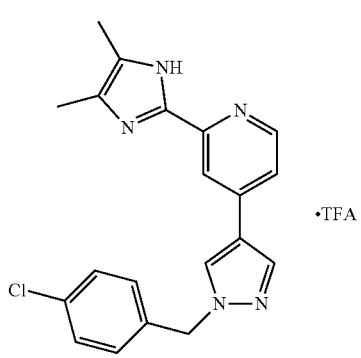 [SMILES: Cc1nc(-c2cc(-c3cnn(Cc4ccc(Cl)cc4)c3)ccn2)[nH]c1C]

Step 1. 4-[1-(4-Chlorobenzyl)-1H-pyrazol-4-yl]pyridine-2-carbonitrile

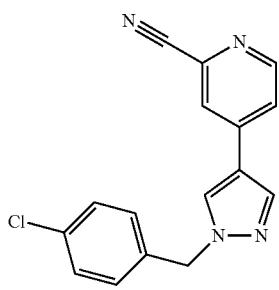 [SMILES: N#Cc1cc(-c2cnn(Cc3ccc(Cl)cc3)c2)ccn1]

4-(4,4,5,5-Tetramethyl-1,3,2-dioxaborolan-2-yl)-1H-pyrazole (0.60 g, 3.1 mmol, Aldrich) in DMF (16 mL) was treated with 1-(bromomethyl)-4-chlorobenzene (0.70 g, 3.4 mmol, Aldrich) and $K_2CO_3$ (1.3 g, 9.3 mmol). After stirring for 2 hours, the mixture was partitioned between water and EtOAc. The organic layer was washed with water, followed by brine, dried over $Na_2SO_4$, filtered, and concentrated. The crude product (0.90 g, 2.8 mmol) was combined with 4-bromopyridine-2-carbonitrile (0.45 g, 2.4 mmol, Synthonix), CsF (1 g, 6 mmol), and 4-(di-tert-butylphosphino)-N,N-dimethylaniline-dichloropalladium (2:1) (0.15 g, 0.22 mmol, Aldrich) in 1,4-dioxane (6 mL, 70 mmol) and water (1 mL, 70 mmol). The mixture was degassed and heated to 100° C. for 10 minutes. Upon cooling to room temperature, the mixture was partitioned between water and EtOAc. The organic layer was washed with brine, dried over $Na_2SO_4$, filtered, and concentrated. The product was purified by flash chromatography, eluting with a gradient from 0-70% EtOAc in hexanes. Yield: 0.38 g, 44%. LCMS (M+H)$^+$: 295.0.

Step 2. 4-[1-(4-Chlorobenzyl)-1H-pyrazol-4-yl]pyridine-2-carboximidamide

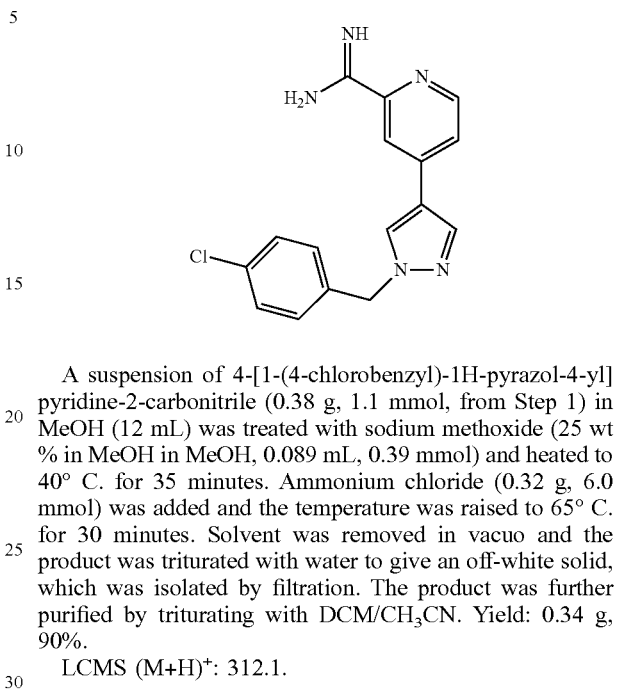

A suspension of 4-[1-(4-chlorobenzyl)-1H-pyrazol-4-yl]pyridine-2-carbonitrile (0.38 g, 1.1 mmol, from Step 1) in MeOH (12 mL) was treated with sodium methoxide (25 wt % in MeOH in MeOH, 0.089 mL, 0.39 mmol) and heated to 40° C. for 35 minutes. Ammonium chloride (0.32 g, 6.0 mmol) was added and the temperature was raised to 65° C. for 30 minutes. Solvent was removed in vacuo and the product was triturated with water to give an off-white solid, which was isolated by filtration. The product was further purified by triturating with DCM/CH$_3$CN. Yield: 0.34 g, 90%.

LCMS (M+H)$^+$: 312.1.

Step 3. 4-[1-(4-Chlorobenzyl)-1H-pyrazol-4-yl]-2-(4,5-dimethyl-1H-imidazol-2-yl)pyridine trifluoroacetate salt 4-[1-(4-Chlorobenzyl)-1H-pyrazol-4-yl]pyridine-2-carboximidamide (100. mg, 0.289 mmol) in DMF (2.0 mL) was treated with 3-bromo-2-butanone (24 μL, 0.32 mmol) and $K_2CO_3$ (60. mg, 0.43 mmol) at 80° C. for 1.5 hours. After cooling to room temperature, the mixture was diluted with CH$_3$CN/MeOH, filtered, and purified by preparative HPLC (C-18 column eluting with a water:acetonitrile gradient buffered at pH 2 with 0.1% trifluoroacetic acid). Yield: 100 mg. $^1$H NMR (400 MHz, d$_6$-DMSO) δ 8.71 (d, J=5.2 Hz, 1H), 8.52 (s, 1H), 8.31 (s, 1H), 8.14 (s, 1H), 7.81 (dd, J=5.2, 1.3 Hz, 1H), 7.49-7.42 (m, 2H), 7.37-7.28 (m, 2H), 5.46 (s, 2H), 2.31 (s, 6H); LCMS(M+H)$^+$: 364.1.

Example 295. (2-{4-[1-(4-Chlorobenzyl)-1H-pyrazol-4-yl]pyridin-2-yl}-5-methyl-N-[(3S)-tetrahydrofuran-3-yl]-1H-imidazole-4-carboxamide

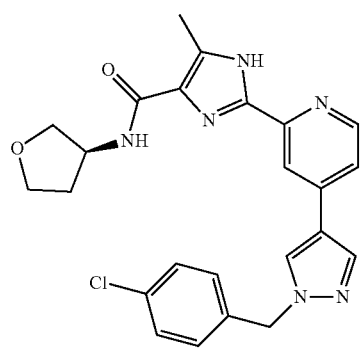 [SMILES: Cc1[nH]c(-c2cc(-c3cnn(Cc4ccc(Cl)cc4)c3)ccn2)nc1C(=O)N[C@H]1CCOC1]

Step 1. 4-(1H-Pyrazol-4-yl)pyridine-2-carbonitrile

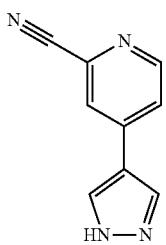 [SMILES: N#Cc1cc(-c2cn[nH]c2)ccn1]

A degassed mixture of 4-bromopyridine-2-carbonitrile (3.3 g, 18 mmol, Synthonix), 1H-pyrazol-4-ylboronic acid (2.00 g, 17.9 mmol, Aldrich), CsF (8 g, 50 mmol), and 4-(di-tert-butylphosphino)-N,N-dimethylaniline-dichloropalladium (2:1) (1.3 g, 1.8 mmol, Aldrich) in 1,4-dioxane (50 mL) and water (10 mL) was heated to 120° C. for 2 h 40 minutes, then cooled to room temperature. The organic layer was separated, and the aqueous layer was extracted with two further portions of EtOAc. The combined organic extracts were washed with water and brine, dried over Na$_2$SO$_4$, filtered, and concentrated. The product was purified by flash chromatography, eluting with a gradient from 0-10% MeOH/DCM. Yield: 1.16 g, 38%. LCMS (M+H)$^+$: 171.0.

Step 2. 4-(1-Benzyl-1H-pyrazol-4-yl)pyridine-2-carbonitrile

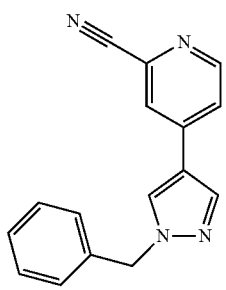 [SMILES: N#Cc1cc(-c2cnn(Cc3ccccc3)c2)ccn1]

4-(1H-Pyrazol-4-yl)pyridine-2-carbonitrile (0.635 g, 3.73 mmol, from Step 1) in DMF (10 mL, 200 mmol) was treated with benzyl bromide (BnBr, 0.38 mL, 3.2 mmol) and K$_2$CO$_3$ (1.55 g, 11.2 mmol). After stirring for 1 hour, water was added and the reaction mixture was extracted with three portions of EtOAc. The combined organic extracts were washed with water twice, then dried over Na$_2$SO$_4$, filtered, and concentrated. The product was purified by flash chromatography, eluting with a gradient from 0-40% EtOAc in hexanes. Yield: 496 mg, 51%. LCMS (M+H)$^+$: 261.0.

Step 3. 4-(1-Benzyl-1H-pyrazol-4-yl)-2-(5-methyl-1H-imidazol-2-yl)pyridine 4-(1-Benzyl-1H-pyrazol-4-yl)pyridine-2-carbonitrile (0.495 g, 1.90 mmol, from Step 2) in MeOH (10 mL) was treated with sodium methoxide (25 wt % in MeOH, 0.03 mL, 0.16 mmol) and the reaction mixture was heated to 45° C. for 2 hours. Upon cooling to room temperature, 1,1-diethoxypropan-2-amine (0.31 g, 2.1 mmol, AstaTech) and acetic acid (0.21 mL) were added and the reaction was heated in a sealed vial to 100° C. for 30 minutes. The mixture was cooled to room temperature and 6.0 N HCl (0.870 mL, 5.22 mmol) was added and the sealed reaction vessel was then heated in an oil bath held at 70° C. overnight, then at 90° C. for 2 hours. The solvent was then removed in vacuo and the resulting residue was treated with 1.0 N NaOH. The solid product was isolated by filtration, washed with a small amount of water, transferred to a round bottom flask and azeotroped twice with toluene. The filtrate was extracted with EtOAc three times. The combined organic extracts were dried over Na$_2$SO$_4$, filtered, concentrated, and combined with the original isolated solid. Yield: 0.46 g, 77%. LCMS (M+H)$^+$: 316.1.

Step 4. 4-(1-Benzyl-1H-pyrazol-4-yl)-2-(5-methyl-1-{[2-(trimethylsilyl)ethoxy]methyl}-1H-imidazol-2-yl)pyridine and 4-(1-Benzyl-1H-pyrazol-4-yl)-2-(4-methyl-1-{[2-(trimethylsilyl)ethoxy]methyl}-1H-imidazol-2-yl)pyridine (a Mixture of Isomers Prepared)

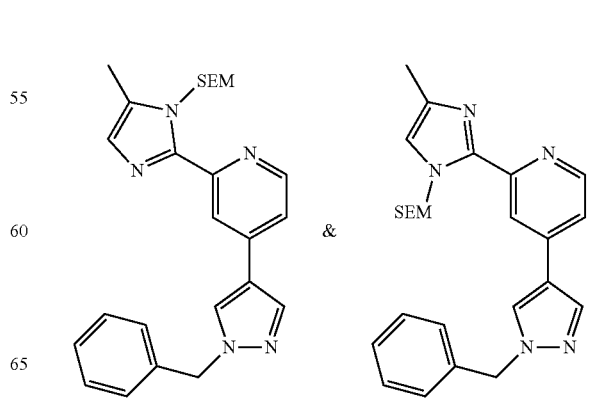

4-(1-Benzyl-1H-pyrazol-4-yl)-2-(5-methyl-1H-imidazol-2-yl)pyridine (0.50 g, 1.6 mmol, from Step 3) in DMF (9 mL) at 0° C. was treated with NaH (60% in mineral oil, 0.13 g, 3.2 mmol) for 20 minutes. [β-(Trimethylsilyl)ethoxy]methyl chloride (0.34 mL, 1.9 mmol, Aldrich) was added and the reaction was continued for 2 hours. Water was added and the reaction mixture was extracted with EtOAc. The combined organic extracts were washed with water and brine, dried over Na₂SO₄, filtered, and concentrated. The product was purified by flash chromatography, eluting with a gradient from 0-25% EtOAc/hexanes. Yield: 0.50 g, 70%. LCMS (M+H)⁺: 446.3.

Step 5. 2-(5-Methyl-1-{[2-(trimethylsilyl)ethoxy]methyl}-1H-imidazol-2-yl)-4-(1H-pyrazol-4-yl)pyridine and 2-(4-Methyl-1-{[2-(trimethylsilyl)ethoxy]methyl}-1H-imidazol-2-yl)-4-(1H-pyrazol-4-yl)pyridine (a Mixture of Isomers as the Trifluoroacetate Salts Prepared)

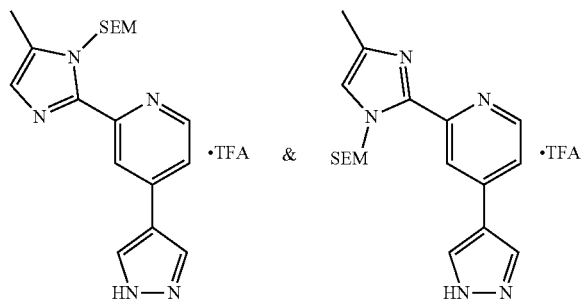 [SMILES: Cc1cnc(-c2cc(-c3cn[nH]c3)ccn2)n1COCC[Si](C)(C)C ; Cc1cn(COCC[Si](C)(C)C)c(-c2cc(-c3cn[nH]c3)ccn2)n1]

To a solution of 4-(1-benzyl-1H-pyrazol-4-yl)-2-(5-methyl-1-{[2-(trimethylsilyl)ethoxy]methyl}-1H-imidazol-2-yl)pyridine and 4-(1-benzyl-1H-pyrazol-4-yl)-2-(4-methyl-1-{[2-(trimethylsilyl)ethoxy]methyl}-1H-imidazol-2-yl)pyridine (0.400 g, 0.898 mmol, from Step 3) in DMSO (0.955 mL) was added 1.0 M KOᵗBu in THF (9.42 mL, 9.42 mmol) dropwise. Oxygen gas was introduced by bubbling the O₂ through the solution for 10 minutes. The reaction flask was then sealed and stirred for 30 minutes. Water and EtOAc were added to the reaction mixture. The pH was adjusted to neutral by the addition of 1.0 N HCl. The layers were shaken, separated, and the aqueous layer was extracted with two additional portions of EtOAc. The combined organic extracts were dried over Na₂SO₄, filtered, and concentrated. The product was purified by preparative HPLC (C-18 column eluting with a water:acetonitrile gradient buffered at pH 2 with 0.1% trifluoroacetic acid). Yield: 106 mg, 33%. LCMS (M+H)⁺: 356.2.

Step 6. 4-[1-(4-Chlorobenzyl)-1H-pyrazol-4-yl]-2-(5-methyl-1H-imidazol-2-yl)pyridine

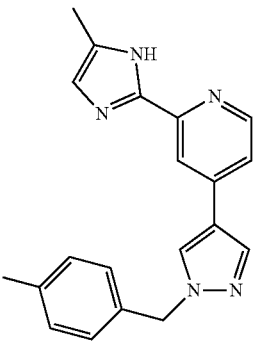

A mixture of 2-(5-methyl-1-{[2-(trimethylsilyl)ethoxy]methyl}-1H-imidazol-2-yl)-4-(1H-pyrazol-4-yl)pyridine and 2-(4-methyl-1-{[2-(trimethylsilyl)ethoxy]methyl}-1H-imidazol-2-yl)-4-(1H-pyrazol-4-yl)pyridine (0.132 g, 0.371 mmol, from Step 5) in DMF (2 mL) was treated with K₂CO₃ (0.154 g, 1.11 mmol) and 1-(bromomethyl)-4-chlorobenzene (0.0763 g, 0.371 mmol, Aldrich) overnight. Water was added and the reaction mixture was extracted with three portions of EtOAc. The combined organic extracts were washed with water twice, then dried over Na₂SO₄, filtered and concentrated. The product was used without further purification. LCMS (M+H)⁺: 480.3.

The alkylated mixture of products generated above (0.178 g, 0.371 mmol) was stirred in 1:1 TFA:DCM (4 mL) for 3 hours. Solvent was removed in vacuo. The residue was partitioned between saturated NaHCO₃ and EtOAc. The aqueous was extracted a total of three times with EtOAc. The combined organic extracts were dried over Na₂SO₄, filtered and concentrated. The product was used without further purification. LCMS (M+H)⁺: 350.2/352.1.

Step 7. 4-[1-(4-Chlorobenzyl)-1H-pyrazol-4-yl]-2-(4-iodo-5-methyl-1H-imidazol-2-yl)pyridine

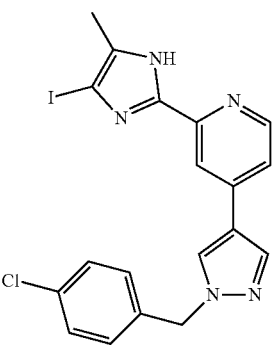 [SMILES: Cc1[nH]c(-c2cc(-c3cnn(Cc4ccc(Cl)cc4)c3)ccn2)nc1I]

4-[1-(4-Chlorobenzyl)-1H-pyrazol-4-yl]-2-(5-methyl-1H-imidazol-2-yl)pyridine (0.130 g, 0.372 mmol, from Step 6) in DMF (3 mL) was treated with N-Iodosuccinimide (0.0836 g, 0.372 mmol) for 1 hour. Water was added and the aqueous mixture was extracted with three portions of EtOAc. The combined organic extracts were washed with water, brine, dried over Na₂SO₄, filtered, and concentrated.

The product was purified by flash chromatography, eluting with a gradient from 0-40% EtOAc in hexanes. Yield: 50 mg, 28%. LCMS (M+H)+: 475.9/477.9.

Step 8. 2-{4-[1-(4-Chlorobenzyl)-1H-pyrazol-4-yl]pyridin-2-yl}-5-methyl-1H-imidazole-4-carboxylic acid trifluoroacetate salt

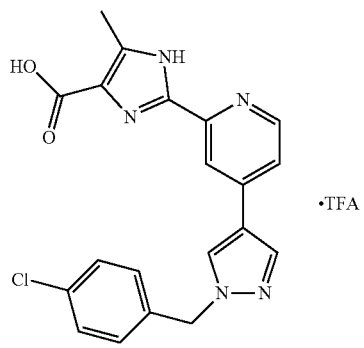 [SMILES: Cc1[nH]c(-c2cc(-c3cnn(Cc4ccc(Cl)cc4)c3)ccn2)nc1C(=O)O]

4-[1-(4-Chlorobenzyl)-1H-pyrazol-4-yl]-2-(4-iodo-5-methyl-1H-imidazol-2-yl)pyridine (0.050 g, 0.10 mmol, from Step 7) in DMF (0.8 mL) and water (0.09 mL) containing triethylamine (0.029 mL, 0.21 mmol) was degassed with a stream of nitrogen and [1,1'-bis(diphenylphosphino)ferrocene]dichloropalladium(II), complex with dichloromethane (1:1) (0.0086 g, 0.010 mmol, Aldrich) was added. The solution was saturated with carbon monoxide by bubbling the CO gas through the reaction subsurface for 3 minutes. The vessel was sealed and was heated to 60° C. for 5 hours. Additional CO was introduced, and water (0.3 mL, 20 mmol) and Na₂CO₃ (0.033 g, 0.32 mmol) were added and heating was continued for 8 hours. Upon cooling, the reaction mixture was diluted with MeOH and filtered. The product was partially purified by preparative HPLC (C-18 column eluting with a water:acetonitrile gradient buffered at pH 2 with 0.1% trifluoroacetic acid). The impure product was then used in Step 9. LCMS (M+H)+: 394.1/396.1.

Step 9. 2-{4-[1-(4-Chlorobenzyl)-1H-pyrazol-4-yl]pyridin-2-yl}-5-methyl-N-[(3S)-tetrahydrofuran-3-yl]-1H-imidazole-4-carboxamide A mixture containing 2-{4-[1-(4-chlorobenzyl)-1H-pyrazol-4-yl]pyridin-2-yl}-5-methyl-1H-imidazole-4-carboxylic acid trifluoroacetate salt (12 mg) in DMF (0.5 mL) was treated with N,N-diisopropylethylamine (0.010 mL, 0.058 mmol), (3S)-tetrahydrofuran-3-amine (0.003 g, 0.03 mmol, Advanced Chem Blocks) and HATU (0.009 g, 0.02 mmol). After 2.5 hours, additional N,N-diisopropylethylamine (0.010 mL, 0.057 mmol), HATU (0.009 g, 0.02 mmol), and (3S)-tetrahydrofuran-3-amine (0.003 g, 0.03 mmol) were added and the reaction was stirred overnight. The product was purified by preparative HPLC (C-18 column eluting with a water:acetonitrile gradient buffered at pH 10 with 0.15% ammonium hydroxide). Yield: 4 mg, 40% over 2 steps. ¹H NMR (400 MHz, CD₃OD) δ 8.52 (d, J=5.3 Hz, 1H), 8.34 (s, 1H), 8.27-8.17 (m, 1H), 8.10 (s, 1H), 7.53 (dd, J=5.2, 1.6 Hz, 1H), 7.43-7.33 (m, 2H), 7.33-7.17 (m, 2H), 5.40 (s, 2H), 4.61-4.50 (m, 1H), 4.02 (q, J=7.7 Hz, 1H), 3.96 (dd, J=9.1, 5.9 Hz, 1H), 3.86 (td, J=8.4, 5.9 Hz, 1H), 3.75 (dd, J=9.2, 3.8 Hz, 1H), 2.58 (s, 3H), 2.38-2.26 (m, 1H), 2.05-1.95 (m, 1H). LCMS (M+H)+: 463.1.

Example 296 was synthesized according to the procedure of Example 295 and the data are listed in Table 21.

TABLE 21

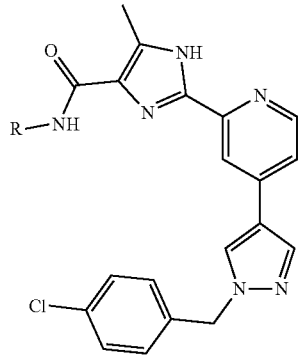

| Ex. No. | Name | R= | MS (M + H)+ | ¹H NMR |
|---|---|---|---|---|
| 296 | 2-{4-[1-(4-Chlorobenzyl)-1H-pyrazol-4-yl]pyridin-2-yl}-N,5-dimethyl-1H-imidazole-4-carboxamide (free base) | CH₃ | 407.1 | ¹H NMR (400 MHz, CD₃OD) δ 8.52 (d, J = 5.3 Hz, 1H), 8.28 (s, 1H), 8.23 (s, 1H), 8.08 (s, 1H), 7.80 (s, 1H), 7.51 (dd, J = 5.2, 1.6 Hz, 1H), 7.42-7.34 (m, 2H), 7.33-7.24 (m, 2H), 5.41 (s, 2H), 2.95 (s, 3H), 2.61 (s, 3H) |

Example 297. 2-{4-[1-(4-Chlorobenzyl)-1H-pyrazol-4-yl]pyridin-2-yl}-5-methyl-1H-imidazole-4-carbonitrile trifluoroacetate salt

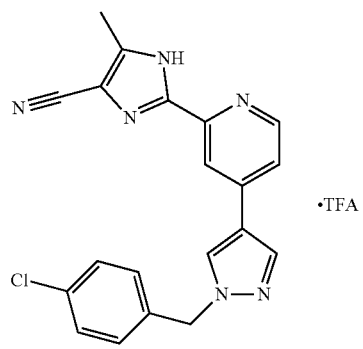 [SMILES: Cc1[nH]c(-c2cc(-c3cnn(Cc4ccc(Cl)cc4)c3)ccn2)nc1C#N]

Step 1. 4-[1-(4-Chlorobenzyl)-1H-pyrazol-4-yl]-2-(4-iodo-5-methyl-1-{[2-(trimethylsilyl)ethoxy]methyl}-1H-imidazol-2-yl)pyridine and 4-[1-(4-Chlorobenzyl)-1H-pyrazol-4-yl]-2-(5-iodo-4-methyl-1-{[2-(trimethylsilyl)ethoxy]methyl}-1H-imidazol-2-yl)pyridine

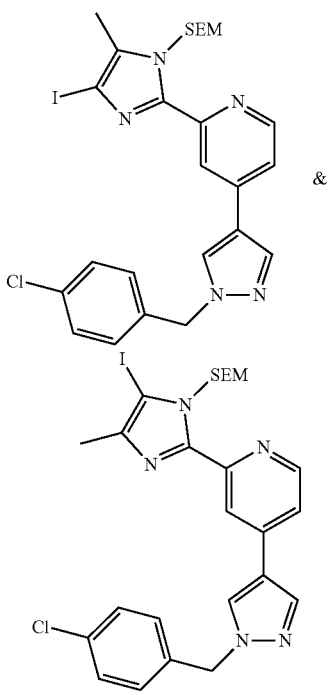

To 4-[1-(4-chlorobenzyl)-1H-pyrazol-4-yl]-2-(4-iodo-5-methyl-1H-imidazol-2-yl)pyridine (50.0 mg, 0.10 mmol, from Example 295, Step 7) in DMF (1 mL) at 0° C. was added NaH (60% in mineral oil, 8.4 mg, 0.21 mmol) and the reaction was stirred for 20 minutes. [β-(Trimethylsilyl)ethoxy]methyl chloride (28 μL, 0.16 mmol) was then added and the reaction was continued for 30 minutes. The reaction was quenched by the addition of water, and the reaction mixture was extracted with EtOAc (3×). The combined organic extracts were dried over $Na_2SO_4$, filtered, and concentrated. The product was purified by flash chromatography, eluting with a gradient of 0-30% EtOAc in hexanes. Two isomers were isolated: Peak 1 (first to elute, 4-[1-(4-Chlorobenzyl)-1H-pyrazol-4-yl]-2-(4-iodo-5-methyl-1-{[2-(trimethylsilyl)ethoxy]methyl}-1H-imidazol-2-yl)pyridine): 0.030 g, 47%. LCMS(M+H)$^+$: 606.1; Peak 2 (second to elute, 4-[1-(4-Chlorobenzyl)-1H-pyrazol-4-yl]-2-(5-iodo-4-methyl-1-{[2-(trimethylsilyl)ethoxy]methyl}-1H-imidazol-2-yl)pyridine): 0.019 g, 30%. LCMS(M+H)$^+$: 606.1.

Step 2. 2-{4-[1-(4-Chlorobenzyl)-1H-pyrazol-4-yl]pyridin-2-yl}-5-methyl-1H-imidazole-4-carbonitrile trifluoroacetate salt A degassed mixture of 4-[1-(4-chlorobenzyl)-1H-pyrazol-4-yl]-2-(4-iodo-5-methyl-1-{[2-(trimethylsilyl)ethoxy]methyl}-1H-imidazol-2-yl)pyridine (0.015 g, 0.025 mmol, Peak 1 from Step 1), zinc cyanide (29 mg, 0.25 mmol), and [1,1'-bis(diphenylphosphino)ferrocene]dichloropalladium (II) (2.7 mg, 0.0037 mmol) in DMF (0.5 mL) was heated to 150° C. for 35 minutes in a microwave reactor. Upon cooling, the reaction mixture was diluted with DCM, filtered, and concentrated. TFA (1 mL) was added, and the mixture was stirred overnight. Volatiles were then removed in vacuo and the product was purified by preparative HPLC/MS (pH 2). Yield: 11 mg. $^1$H NMR (400 MHz, $d_6$-DMSO) δ 8.72 (s, 1H), 8.57 (d, J=5.1 Hz, 1H), 8.21 (s, 1H), 8.20 (s, 1H), 7.66 (d, J=4.6 Hz, 1H), 7.44 (d, J=8.3 Hz, 2H), 7.34 (d, J=8.2 Hz, 2H), 5.38 (s, 2H), 2.40 (s, 3H). LCMS (M+H)$^+$: 375.1.

Example 298. N-((1r,4r)-4-Hydroxy-4-methylcyclohexyl)-2'-(4-methyl-1H-imidazol-2-yl)-[3,4'-bipyridine]-5-sulfonamide trifluoroacetate salt

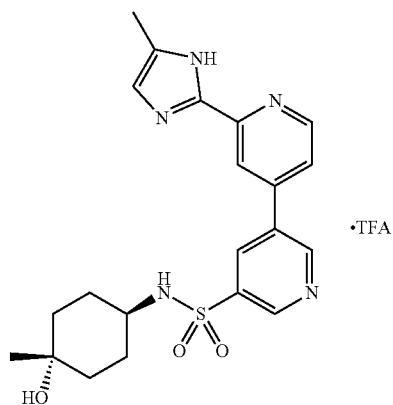 [SMILES: Cc1cnc(-c2cc(-c3cncc(S(=O)(=O)N[C@H]4CC[C@](C)(O)CC4)c3)ccn2)[nH]1]

Step 1. 5-Bromo-N-((1r,4r)-4-hydroxy-4-methylcyclohexyl)pyridine-3-sulfonamide

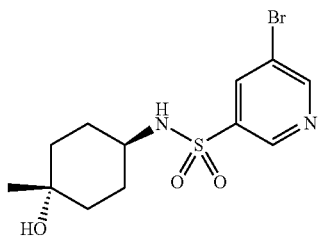 [SMILES: C[C@]1(O)CC[C@H](NS(=O)(=O)c2cncc(Br)c2)CC1]

To a mixture of (1r,4r)-4-amino-1-methylcyclohexan-1-ol (0.081 g, 0.62 mmol, PharmaBlock) and triethylamine (0.087 mL, 0.62 mmol) in DCM (3 mL) was added 5-bromopyridine-3-sulfonyl chloride (0.08 g, 0.3 mmol, Enamine Ltd) as a suspension in DCM (1 mL). The reaction was stirred for 16 hours and quenched by the addition of saturated $NaHCO_3$ (aq.) solution. The layers were separated and the aqueous layer was extracted with EtOAc. The combined organic extracts were dried over $MgSO_4$, filtered, and concentrated. The product was used without further purification. Yield: 0.08 g, 70%. LCMS(M+H)$^+$: 349.1.

249

Step 2. N-((1r,4r)-4-hydroxy-4-methylcyclohexyl)-5-(4,4,5,5-tetramethyl-1,3,2-dioxaborolan-2-yl)pyridine-3-sulfonamide

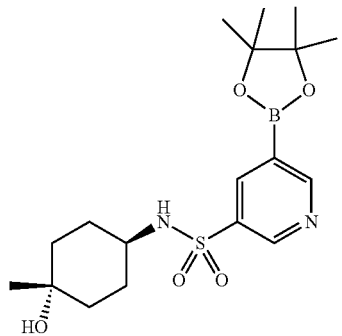

A degassed mixture of 5-bromo-N-((1r,4r)-4-hydroxy-4-methylcyclohexyl)pyridine-3-sulfonamide (0.050 g, 0.14 mmol), bis(pinacolato)diboron (0.036 g, 0.14 mmol), dichlorobis(triphenylphosphine)-palladium(II) (4.0 mg, 5.7 µmol) and potassium acetate (0.046 g, 0.47 mol) in THF (1.2 mL) was heated to 140° C. in a microwave reactor for 20 minutes. Upon cooling to room temperature, water and EtOAc were added and after filtration through Celite®, the layers were separated and the organic layer was washed with brine, dried over MgSO$_4$, filtered, and concentrated to afford N-((1r,4r)-4-hydroxy-4-methylcyclohexyl)-5-(4,4,5,5-tetramethyl-1,3,2-dioxaborolan-2-yl)pyridine-3-sulfonamide, which was used without further purification. Yield: 57 mg. LCMS (M+H)$^+$: 397.1.

Step 3. N-((1r,4r)-4-Hydroxy-4-methylcyclohexyl)-2'-(4-methyl-1H-imidazol-2-yl)-[3,4'-bipyridine]-5-sulfonamide trifluoroacetate salt A mixture of N-((1r,4r)-4-hydroxy-4-methylcyclohexyl)-5-(4,4,5,5-tetramethyl-1,3,2-dioxaborolan-2-yl)pyridine-3-sulfonamide (0.022 g, 0.071 mmol) and 4-bromo-2-(4-methyl-1-((2-(trimethylsilyl)ethoxy)methyl)-1H-imidazol-2-yl)pyridine (0.020 g, 0.054 mmol, prepared by treating the product of Example 75, Step 1 according to the method of Example 1, Step 2) in THF (1.0 mL) and 1.0 M K$_2$CO$_3$ (0.136 mL, 0.136 mmol) was degassed and dichloro[1,1'-bis(diphenylphosphino)ferrocene]palladium(II)-dichloromethane adduct (6.6 mg, 8.1 µmol) was added. The mixture was again degassed and heated to 80° C. for 3 hours. Upon cooling to room temperature, the reaction mixture was diluted with water and extracted with EtOAc. The organic layer was washed with brine, dried over MgSO$_4$, filtered, and concentrated. The crude product was dissolved in DCM (1 mL) and TFA (2 mL) was added. The mixture was stirred for 1 hour and volatiles were removed in vacuo. The product was purified by preparative HPLC/MS (pH 2). Yield: 4.0 mg, 14%. $^1$H NMR (400 MHz, d$_6$-DMSO) δ 9.34 (d, J=1.9 Hz, 1H), 9.14 (d, J=1.9 Hz, 1H), 8.92 (d, J=5.1 Hz, 1H), 8.64 (dd, J=1.9 Hz, 1.9 Hz, 1H), 8.58 (s, 1H), 8.10 (d, J=4.4 Hz, 1H), 8.00 (d, J=7.0 Hz, 1H), 7.50 (s, 1H), 3.29-3.18 (m, 1H), 2.37 (s, 3H), 1.72-1.56 (m, 2H), 1.54-1.38 (m, 2H), 1.37-1.17 (m, 4H), 1.07 (s, 3H). LCMS (M+H)$^+$: 428.1.

Example 299 was synthesized according to the procedure of Example 298 using (1r,4r)-4-aminocyclohexan-1-ol (Combi-Blocks) and the data are listed in Table 22.

TABLE 22

| Ex. No. | Name | R= | MS (M + H)$^+$ | $^1$H NMR |
|---|---|---|---|---|
| 299 | N-((1r,4r)-4-Hydroxycyclohexyl)-2'-(4-methyl-1H-imidazol-2-yl)-[3,4'-bipyridine]-5-sulfonamide trifluoroacetate salt |  | 414.1 | $^1$H NMR (400 MHz, d$_6$-DMSO) δ 9.35 (d, J = 1.9 Hz, 1H), 9.13 (d, J = 1.8 Hz, 1H), 8.92 (d, J = 5.1 Hz, 1H), 8.64 (dd, J = 1.9 Hz, 1.8 Hz, 1H), 8.58 (s, 1H), 8.13-8.08 (m, 1H), 8.03 (d, J = 7.3 Hz, 1H), 7.49 (s, 1H), 3.35-3.26 (m, 1H), 3.14-3.01 (m, 1H), 2.37 (s, 3H), 1.77- |

TABLE 22-continued

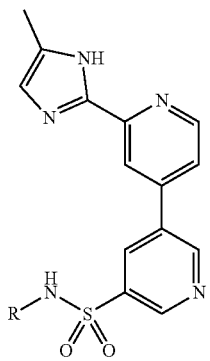

| Ex. No. | Name | R= | MS (M + H)+ | 1H NMR |
|---|---|---|---|---|
| | | | | 1.67 (m, 2H), 1.67-1.53 (m, 2H), 1.30-1.03 (m, 4H) |

Example 300. 4-[1-(4-Chlorobenzyl)-1H-pyrazol-4-yl]-2-{4-[1-(methylsulfonyl)pyrrolidin-3-yl]-1H-imidazol-2-yl}pyridine trifluoroacetate salt (Single Enantiomer Prepared)

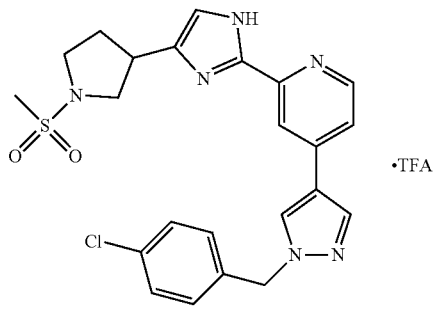 [SMILES: CS(=O)(=O)N1CCC(c2c[nH]c(-c3cc(-c4cnn(Cc5ccc(Cl)cc5)c4)ccn3)n2)C1]

Step 1. tert-Butyl 3-[2-(4-bromopyridin-2-yl)-1H-imidazol-4-yl]pyrrolidine-1-carboxylate (Racemic Mixture Prepared)

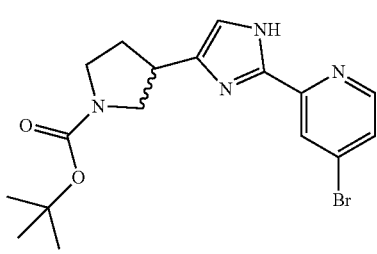 [SMILES: CC(C)(C)OC(=O)N1CCC(c2c[nH]c(-c3cc(Br)ccn3)n2)C1]

The title compound was prepared according to the procedure of Example 231, Step 1, using tert-butyl 3-(bromoacetyl)pyrrolidine-1-carboxylate (1.07 g, 3.66 mmol, prepared as described in WO2010/051245). The product was purified by flash chromatography, eluting with a gradient from 0-100% EtOAc/hexanes. Yield: 0.169 g, 12%. LCMS (M+H)+: 393.0.

Step 2. 1-(4-Chlorobenzyl)-4-(4,4,5,5-tetramethyl-1,3,2-dioxaborolan-2-yl)-1H-pyrazole

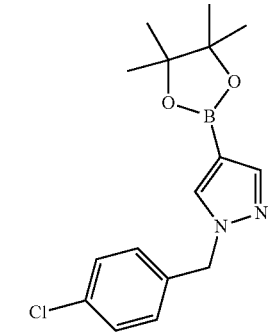 [SMILES: CC1(C)OB(c2cnn(Cc3ccc(Cl)cc3)c2)OC1(C)C]

4-(4,4,5,5-Tetramethyl-1,3,2-dioxaborolan-2-yl)-1H-pyrazole (0.300 g, 1.55 mmol, Aldrich) in DMF (8 mL) was treated with K₂CO₃ (0.64 g, 4.6 mmol) and 1-(bromomethyl)-4-chlorobenzene (0.35 g, 1.7 mmol, Aldrich). After stirring for 16 hours, the reaction mixture was diluted with water and extracted with EtOAc. The combined organic extracts were washed with water, followed by brine, dried over Na₂SO₄, filtered, and concentrated. The product was used without further purification in Step 3. LCMS (M+H)+: 319.1.

Step 3. tert-Butyl 3-(2-{4-[1-(4-chlorobenzyl)-1H-pyrazol-4-yl]pyridin-2-yl}-1-{[2-(trimethylsilyl)ethoxy]methyl}-1H-imidazol-4-yl)pyrrolidine-1-carboxylate (Single Enantiomers Isolated)

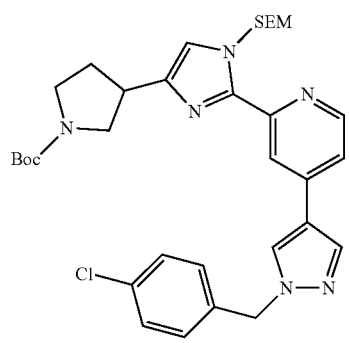 [SMILES: CC(C)(C)OC(=O)N1CCC(c2cn(COCC[Si](C)(C)C)c(-c3cc(-c4cnn(Cc5ccc(Cl)cc5)c4)ccn3)n2)C1]

Using tert-butyl 3-[2-(4-bromopyridin-2-yl)-1H-imidazol-4-yl]pyrrolidine-1-carboxylate (0.149 g, 0.379 mmol, racemic mixture from Step 1) and 1-(4-chlorobenzyl)-4-(4,4,5,5-tetramethyl-1,3,2-dioxaborolan-2-yl)-1H-pyrazole (0.14 g, 0.45 mmol, from Step 2), the methods of Example 231, Steps 2 and 3 were followed to afford the title compound. Yield: 0.100 g, 42%. LCMS(M+H)$^+$: 635.3. The enantiomers were separated by chiral preparative HPLC (CHIRALCEL AD-H, 5 μm, 20×250 mm, 20% EtOH in hexane @ 18 mL/min, loading 18 mg in 900 μL). Peak 1 (first to elute): 7.1 min; Peak 2 (second to elute): 9.5 min.

Step 4. 4-[1-(4-Chlorobenzyl)-1H-pyrazol-4-yl]-2-(4-pyrrolidin-3-yl-1H-imidazol-2-yl)pyridine (Single Enantiomer Prepared)

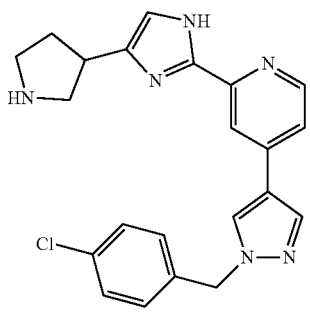 [SMILES: Clc1ccc(Cn2cc(-c3ccnc(-c4nc(C5CCNC5)c[nH]4)c3)cn2)cc1]

tert-Butyl 3-(2-{4-[1-(4-chlorobenzyl)-1H-pyrazol-4-yl]pyridin-2-yl}-1-{[2-(trimethylsilyl)ethoxy]methyl}-1H-imidazol-4-yl)pyrrolidine-1-carboxylate (Peak 2 from Step 3, 0.040 g, 0.063 mmol) was stirred with TFA (1 mL) in DCM (1 mL) for 1 hour. Volatiles were removed in vacuo and the product was used without further purification in Step 5. LCMS(M+H)$^+$: 405.1.

Step 5. 4-[1-(4-Chlorobenzyl)-1H-pyrazol-4-yl]-2-{4-[1-(methylsulfonyl)pyrrolidin-3-yl]-1H-imidazol-2-yl}pyridine trifluoroacetate salt (Single Enantiomer Prepared)

To 4-[1-(4-chlorobenzyl)-1H-pyrazol-4-yl]-2-(4-pyrrolidin-3-yl-1H-imidazol-2-yl)pyridine trifluoroacetate salt (from Step 4, 0.01 g, 0.02 mmol) in DCM (0.5 mL) was added N,N-diisopropylethylamine (0.017 mL, 0.099 mmol) followed by methanesulfonyl chloride (0.002 mL, 0.02 mmol, as an aliquot of a stock solution). A small quantity of water was added and DCM was then evaporated under a stream of nitrogen. The reaction mixture was diluted with MeOH and the product was purified by preparative HPLC/MS (pH 2). Yield: 7 mg, 50%. $^1$H NMR (400 MHz, CD$_3$OD) δ 8.71 (d, J=5.0 Hz, 1H), 8.37 (s, 1H), 8.30 (s, 1H), 8.13 (s, 1H), 7.78 (dd, J=5.1, 1.5 Hz, 1H), 7.62 (s, 1H), 7.43-7.37 (m, 2H), 7.37-7.19 (m, 2H), 5.44 (s, 2H), 3.86 (dd, J=9.7, 7.3 Hz, 1H), 3.73 (p, J=7.0 Hz, 1H), 3.67-3.57 (m, 1H), 3.57-3.44 (m, 2H), 2.98 (s, 3H), 2.60-2.45 (m, 1H), 2.34-2.22 (m, 1H). LCMS(M+H)$^+$: 483.0.

Examples 301-302 were synthesized according to the procedure of Example 300 using Peak 2 from Step 3 and alternative acyl chlorides or sulfonyl chlorides in Step 5, and the data are listed in Table 23.

TABLE 23

| Ex. No. | Name | R= | MS (M + H)$^+$ | $^1$H NMR |
|---|---|---|---|---|
| 301 | 2-[4-(1-Acetylpyrrolidin-3-yl)-1H-imidazol-2-yl]-4-[1-(4-chlorobenzyl)-1H-pyrazol-4-yl]pyridine trifluoroacetate salt | ![acetyl] | 447.1 | $^1$H NMR (400 MHz, CD$_3$OD, rotamers) δ 8.72 (d, J = 5.1 Hz, 1H), 8.37 (s, 1H), 8.31 (s, 1H), 8.13 (s, 1H), 7.79 (d, J = 5.2 Hz, 1H), 7.62 (s, 0.5H), 7.60 (s, 0.5H), 7.40 (d, J = 8.5 Hz, 2H), 7.33 (d, J = 8.4 Hz, 2H), 5.44 (s, 2H), 4.11-3.96 (m, 1H), 3.85-3.61 (m, 3H), 3.61-3.47 (m, 1H), 2.61-2.39 (m, 1H), 2.36-2.15 (m, 1H), 2.13 (s, 1.5H), 2.12 (s, 1.5H) |

TABLE 23-continued

| Ex. No. | Name | R= | MS (M + H)+ | ¹H NMR |
|---|---|---|---|---|
| 302 | 4-[1-(4-Chlorobenzyl)-1H-pyrazol-4-yl]-2-{4-[1-(phenylsulfonyl)pyrrolidin-3-yl]-1H-imidazol-2-yl}pyridine trifluoroacetate salt | phenylsulfonyl group | 545.1 | ¹H NMR (400 MHz, CD₃OD) δ 8.71 (d, J = 5.1 Hz, 1H), 8.36 (s, 1H0, 8.24 (s, 1H), 8.12 (s, 1H), 7.93-7.82 (m, 2H), 7.78 (dd, J = 5.2, 1.4 Hz, 1H), 7.72-7.62 (m, H), 7.62-7.55 (m, 2H), 7.43-7.30 (m, 5H), 5.45 (s, 2H), 3.84-3.71 (m, 1H), 3.64-3.39 (m, 4H), 2.44-2.27 (m, 1H), 2.22-2.06 (m, 1H) |

Examples 303-305 were synthesized according to the procedure of Example 300 using Peak 1 from Step 3 and alternative acyl chlorides or sulfonyl chlorides in Step 5, and the data are listed in Table 24.

TABLE 24

| Ex. No. | Name | R= | MS (M + H)+ | ¹H NMR |
|---|---|---|---|---|
| 303 | 2-[4-(1-Acetylpyrrolidin-3-yl)-1H-imidazol-2-yl]-4-[1-(4-chlorobenzyl)-1H-pyrazol-4-yl]pyridine trifluoroacetate salt | acetyl group | 447.1 | ¹H NMR (400 MHz, CD₃OD, rotamers) δ 8.71 (d, J = 5.4 Hz, 1H), 8.37 (s, 1H), 8.30 (s, 1H), 8.13 (s, 1H), 7.78 (dd, J = 5.3, 1.3 Hz, 1H), 7.61 (s, 0.5H), 7.59 (s, 0.5H), 7.41 (d, J = 8.5 Hz, 2H), 7.33 (d, J = 8.5 Hz, 2H), 5.45 (s, 2H), 4.11-3.94 (m, 1H), 3.84-3.60 (m, 3H), 3.60-3.46 (m, 1H), 2.60-2.38 (m, 1H), 2.37-2.16 (m, 1H), |

TABLE 24-continued

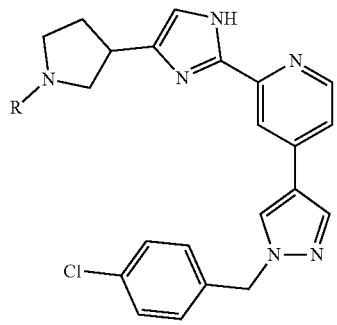

| Ex. No. | Name | R= | MS (M + H)+ | 1H NMR |
|---|---|---|---|---|
| | | | | 2.13 (s, 1.5H), 2.12 (s, 1.5H) |
| 304 | 4-[1-(4-Chlorobenzyl)-1H-pyrazol-4-yl]-2-{4-[1-(methylsulfonyl)pyrrolidin-3-yl]-1H-imidazol-2-yl}pyridine trifluoroacetate salt | methylsulfonyl group | 483.1 | 1H NMR (400 MHz, CD3OD) δ 8.71 (d, J = 5.2 Hz, 1H), 8.37 (s, 1H), 8.31 (s, 1H), 8.13 (s, 1H), 7.78 (dd, J = 5.0, 1.2 Hz, 1H), 7.61 (s, 1H), 7.40 (d, J = 8.5 Hz, 2H), 7.33 (d, J = 8.4 Hz, 2H), 5.44 (s, 2H), 3.86 (dd, J = 9.6, 7.4 Hz, 1H), 3.73 (p, J = 7.5 Hz, 1H), 3.66-3.57 (m, 1H), 3.57-3.45 (m, 2H), 2.98 (s, 3H), 2.59-2.42 (m, 1H), 2.34-2.20 (m, 1H) |
| 305 | 4-[1-(4-Chlorobenzyl)-1H-pyrazol-4-yl]-2-{4-[1-(phenylsulfonyl)pyrrolidin-3-yl]-1H-imidazol-2-yl}pyridine trifluoroacetate salt | phenylsulfonyl group | 545.1 | 1H NMR (400 MHz, CD3OD) δ 8.71 (d, J = 5.2 Hz, 1H), 8.37 (s, 1H), 8.25 (s, 1H), 8.13 (s, 1H), 7.90-7.84 (m, 2H), 7.78 (dd, J = 5.2, 1.4 Hz, 1H), 7.69-7.62 (m, 1H), 7.62-7.55 (m, 2H), 7.43-7.29 (m, 5H), 5.44 (s, 2H), 3.84-3.72 (m, 1H), 3.64-3.38 (m, 4H), 2.44-2.28 (m, 1H), 2.24-2.06 (m, 1H) |

Example 306. 4-[1-(4-Chlorobenzyl)-1H-pyrazol-4-yl]-2-(4-pyrrolidin-3-yl-1H-imidazol-2-yl)pyridine trifluoroacetate salt (Racemic Mixture Prepared)

The racemic product prepared in Example 300, Step 3 (before chiral separation), was deprotected as described in Example 300, Step 4, and the product was purified by preparative HPLC/MS (pH 2). 1H NMR (400 MHz, CD3OD) δ 8.67 (d, J=5.3 Hz, 1H), 8.39 (s, 1H), 8.36-8.31 (m, 1H), 8.14 (s, 1H), 7.76 (dd, J=5.3, 1.5 Hz, 1H), 7.56 (s, 1H), 7.46-7.36 (m, 2H), 7.36-7.28 (m, 2H), 5.44 (s, 2H), 3.88-3.70 (m, 2H), 3.66-3.54 (m, 1H), 3.54-3.40 (m, 2H), 2.67-2.51 (m, 1H), 2.40-2.18 (m, 1H).

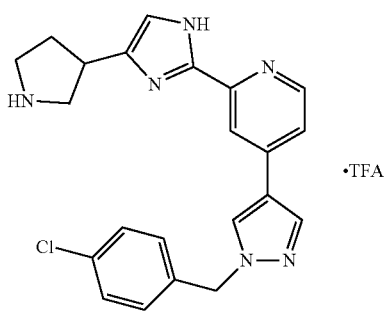 [SMILES: Clc1ccc(Cn2cc(-c3ccnc(-c4nc(C5CCNC5)c[nH]4)c3)cn2)cc1]

LCMS(M+H)+: 405.1.

Example 307. N-(2-Methoxyphenyl)-5-methyl-2-(5-morpholin-4-yl-3,4'-bipyridin-2'-yl)-1H-imidazol-4-amine trifluoroacetate salt

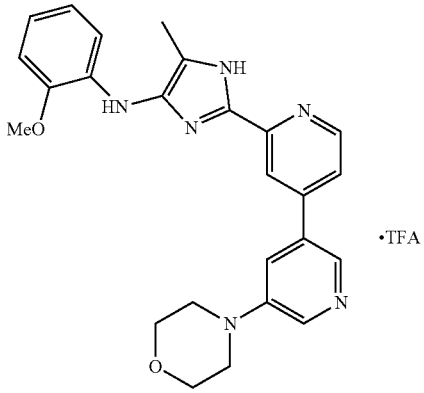 [SMILES: COc1ccccc1Nc1nc(-c2cc(-c3cncc(N4CCOCC4)c3)ccn2)[nH]c1C]

To a degassed mixture of 2'-(4-iodo-5-methyl-1H-imidazol-2-yl)-5-morpholin-4-yl-3,4'-bipyridine (30 mg, 0.067 mmol, from Example 257, Step 2), di-tert-butyl(2',4',6'-triisopropyl-3,6-dimethoxybiphenyl-2-yl)phosphine (2.0 mg, 0.0040 mmol), 'BuBrettPhos Pd G3 (3.4 mg, 0.0040 mmol), and 2-methoxyaniline (9.7 µL, 0.080 mmol) in THF (0.25 mL) was added 1.0 M LHMDS (lithium bis(trimethylsilyl)amide) in THF (150 µL, 0.15 mmol). The mixture was sealed and heated at 70° C. for 2 hours. Upon cooling to room temperature, the reaction mixture was quenched by the addition of 1N HCl (1 mL). The mixture was diluted with ACN/MeOH, filtered, and purified via preparative HPLC/MS (pH 2). Yield: 8.5 mg. $^1$H NMR (400 MHz, d$_6$-DMSO) δ 8.88 (d, J=5.2 Hz, 1H), 8.58-8.52 (m, 2H), 8.50 (d, J=2.2 Hz, 1H), 8.10-8.02 (m, 1H), 7.87-7.78 (m, 1H), 7.45 (br s, 1H), 7.05-6.95 (m, 1H), 6.86-6.73 (m, 2H), 6.64-6.53 (m, 1H), 3.89 (s, 3H), 3.85-3.72 (m, 4H), 3.43-3.27 (m, 4H), 2.21 (s, 3H). LCMS(M+H)$^+$: 443.1.

Example 308 was synthesized according to the procedure of Example 307 using alternative anilines, and the data are listed in Table 25.

TABLE 25

| Ex. No. | Name | R= | MS (M + H)$^+$ | $^1$H NMR |
|---|---|---|---|---|
| 308 | N-[5-Methyl-2-(5-morpholin-4-yl-3,4'-bipyridin-2'-yl)-1H-imidazol-4-yl]pyridazin-4-amine trifluoroacetate salt | pyridazin-4-yl | 415.2 | $^1$H NMR (400 MHz, d$_6$-DMSO) δ 13.21 (brs, 0.7H), 10.99 (s, 1H), 8.86 (d, J = 7.3 Hz, 1H), 8.74 (d, J = 5.2 Hz, 1H), 8.60-8.53 (m, 1H), 8.49 (d, J = 2.6 Hz, 1H), 8.29 (s, 1H), 8.12 (br s, 0.5H), 7.90 (s, 1H), 7.81 (dd, J = 5.2, 1.7 Hz, 1H), 3.93-3.65 (m, 4H), 3.51-3.13 (m, 4H), 2.32 (s, 3H) |

Example A. THP-1 RPS6 ELISA Assay

To measure the Phosphorylated Ribosomal Protein S6 (RPS6) in cell lysates, THP-1 cells (Human Acute Monocytic Leukemia) are purchased from ATCC (Manassas, VA) and maintained in RPMI with 10% FBS (Gibco/Life Technologies, Carlsbad, CA). For the assay, THP-1 cells are serum starved overnight in RPMI, then plated in RPMI (2×10$^5$ cells/well in 90 µL) into 96-well flat-bottom tissue culture treated plates (Corning, Corning, NY), in the presence or absence of a concentration range of test compounds.

Covered plates are incubated for 2 hours at 37° C., 5% $CO_2$ then treated with or without 10 nM MCP-1 (MYBioSource, San Diego, CA) for 15 minutes at 37° C., 5% $CO_2$. Plates are centrifuged at 1600 RPM and supernatants are removed. Cells are lysed in Lysis Buffer (Cell Signaling, Danvers, MA) with Protease Inhibitor (Calbiochem/EMD, Germany), PMSF (Sigma, St Louis MO), HALTS (Thermo Fisher, Rockford, IL) for 30 min on wet ice. Cell lysates are frozen at −80° C. before testing. The lysates are tested in the Human/Mouse/Rat Phospho-RPS6 ELISA (R&D Systems, Inc. Minn, MN). The plate is measured using a microplate reader (SpectraMax M5—Molecular Devices, LLC Sunnyvale, CA) set to 450 nm with a wavelength correction of 540. $IC_{50}$ determination is performed by fitting the curve of inhibitor percent inhibition versus the log of the inhibitor concentration using the GraphPad Prism 5.0 software.

Data for the Examples, obtained using the methods described in Example A, are provided in Table A.

TABLE A

| Example # | THP p-RPS6 ELISA IC50 (nM) |
|---|---|
| 1 | †††† |
| 5 | ††† |
| 6 | †††† |
| 7 | †††† |
| 8 | N/A |
| 9 | ††† |
| 10 | ††† |
| 11 | N/A |
| 12 | N/A |
| 13 | N/A |
| 14 | N/A |
| 16 | N/A |
| 17 | †† |
| 18 | †† |
| 19 | ††† |
| 20 | N/A |
| 21 | N/A |
| 25 | N/A |
| 26 | N/A |
| 30 | N/A |
| 31 | N/A |
| 32 | N/A |
| 33 | N/A |
| 34 | N/A |
| 35 | N/A |
| 37 | N/A |
| 40 | † |
| 41 | N/A |
| 43 | †††† |
| 44 | N/A |
| 45 | N/A |
| 46 | †††† |
| 47 | N/A |
| 48 | N/A |
| 49 | N/A |
| 50 | N/A |
| 51 | N/A |
| 52 | N/A |
| 53 | N/A |
| 54 | †††† |
| 55 | N/A |
| 56 | † |
| 57 | N/A |
| 58 | N/A |
| 59 | N/A |
| 60 | N/A |
| 61 | N/A |
| 62 | †††† |
| 63 | †††† |
| 64 | N/A |
| 65 | †††† |
| 66 | †††† |
| 67 | †††† |
| 68 | †††† |
| 70 | †††† |
| 71 | †††† |
| 72 | N/A |
| 73 | N/A |
| 74 | †††† |
| 75 | N/A |
| 76 | †† |
| 77 | †† |
| 78 | N/A |
| 79 | †††† |
| 80 | N/A |
| 81 | N/A |
| 82 | †††† |
| 83 | †††† |
| 84 | ††† |
| 85 | †††† |
| 86 | †† |
| 87 | †††† |
| 88 | †††† |
| 94 | ††† |
| 95 | N/A |
| 97 | †† |
| 98 | † |
| 99 | †††† |
| 100 | N/A |
| 101 | N/A |
| 102 | †† |
| 103 | ††† |
| 104 | † |
| 105 | † |
| 106 | † |
| 107 | † |
| 108 | † |
| 109 | †† |
| 110 | †† |
| 111 | †† |
| 112 | †† |
| 113 | † |
| 114 | † |
| 115 | † |
| 116 | † |
| 117 | † |
| 118 | †† |
| 119 | †††† |
| 120 | †††† |
| 121 | † |
| 122 | ††† |
| 123 | † |
| 124 | N/A |
| 125 | †† |
| 126 | N/A |
| 127 | ††† |
| 128 | N/A |
| 129 | N/A |
| 130 | †† |
| 131 | †††† |
| 132 | N/A |
| 133 | N/A |
| 134 | N/A |
| 135 | N/A |
| 136 | N/A |
| 137 | N/A |
| 138 | †††† |
| 139 | N/A |
| 140 | N/A |
| 141 | †††† |
| 142 | †††† |
| 143 | N/A |
| 144 | N/A |
| 145 | N/A |
| 145B | † |
| 145C | † |
| 146 | † |
| 147 | N/A |

TABLE A-continued

| Example # | THP p-RPS6 ELISA IC50 (nM) |
|---|---|
| 148 | N/A |
| 149 | N/A |
| 150 | N/A |
| 151 | † |
| 152 | †† |
| 153 | † |
| 154 | †† |
| 155 | † |
| 156 | ††† |
| 157 | ††† |
| 158 | ††† |
| 159 | ††† |
| 160 | ††† |
| 161 | † |
| 162 | N/A |
| 163 | † |
| 164 | N/A |
| 165 | † |
| 166 | N/A |
| 167 | N/A |
| 168 | † |
| 169 | ††† |
| 170 | N/A |
| 171 | N/A |
| 172 | †† |
| 173 | † |
| 174 | † |
| 175 | † |
| 176 | N/A |
| 177 | N/A |
| 178 | † |
| 179 | † |
| 180 | ††† |
| 181 | N/A |
| 182 | N/A |
| 183 | †† |
| 184 | †† |
| 185 | † |
| 186 | † |
| 187 | †† |
| 188 | N/A |
| 189 | N/A |
| 190 | †† |
| 191 | † |
| 192 | ††† |
| 193 | † |
| 194 | † |
| 195 | N/A |
| 196 | N/A |
| 197 | †† |
| 198 | †† |
| 199 | † |
| 200 | N/A |
| 201 | †† |
| 202 | †† |
| 203 | †† |
| 204 | N/A |
| 205 | †† |
| 206 | ††† |
| 207 | ††† |
| 208 | ††† |
| 209 | N/A |
| 210 | N/A |
| 211 | † |
| 212 | † |
| 212B | †† |
| 214 | †††† |
| 215 | N/A |
| 217 | N/A |
| 219 | N/A |
| 220 | N/A |
| 221 | †††† |
| 222 | N/A |
| 223 | N/A |
| 224 | N/A |
| 225 | N/A |
| 226 | N/A |
| 227 | N/A |
| 228 | N/A |
| 229 | N/A |
| 230 | N/A |
| 231 | †† |
| 232 | †† |
| 233 | ††† |
| 234 | N/A |
| 235 | N/A |
| 236 | N/A |
| 237 | † |
| 238 | N/A |
| 239 | N/A |
| 240 | ††† |
| 241 | †† |
| 242 | †††† |
| 243 | † |
| 244 | †††† |
| 245 | †††† |
| 246 | N/A |
| 247 | †††† |
| 248 | ††† |
| 249 | ††† |
| 250 | †† |
| 251 | N/A |
| 252 | † |
| 253 | † |
| 254 | † |
| 255 | †† |
| 256 | ††† |
| 257 | N/A |
| 258 | † |
| 259 | N/A |
| 260 | N/A |
| 261 | N/A |
| 262 | †† |
| 263 | N/A |
| 264 | ††† |
| 265 | †† |
| 266 | † |
| 267 | ††† |
| 268 | †† |
| 269 | †† |
| 270 | †† |
| 271 | †† |
| 272 | † |
| 273 | † |
| 274 | ††† |
| 275 | † |
| 276 | † |
| 277 | † |
| 278 | †† |
| 279 | † |
| 280 | N/A |
| 281 | † |
| 282 | †† |
| 283 | N/A |
| 284 | N/A |
| 285 | N/A |
| 286 | N/A |
| 287 | N/A |
| 288 | N/A |
| 289 | N/A |
| 290 | N/A |
| 291 | N/A |
| 292 | N/A |
| 293 | N/A |
| 294 | †††† |
| 295 | ††† |
| 296 | †††† |
| 297 | †††† |
| 298 | † |
| 299 | † |
| 300 | †† |
| 301 | N/A |

TABLE A-continued

| Example # | THP p-RPS6 ELISA IC50 (nM) |
|---|---|
| 302 | N/A |
| 303 | N/A |
| 304 | N/A |
| 305 | N/A |
| 306 | N/A |
| 307 | N/A |
| 308 | N/A |

† refers to IC$_{50}$ of ≤300 nM
†† refers to IC$_{50}$ of ≤1000 nM
††† refers to an IC$_{50}$ of ≤5000 nM
†††† refers to an IC$_{50}$ of >5000 nM
N/A refers to not available Example B. PI3K-γ Scintillation Proximity Assay Materials

[γ-$^{33}$P]ATP (10 mCi/mL) and Wheat Germ Agglutinin (WGA) YSi SPA Scintillation Beads was purchased from Perkin-Elmer (Waltham, MA). Lipid kinase substrate, D-myo-Phosphatidylinositol 4,5-bisphosphate (PtdIns(4,5)P2)D (+)-sn-1,2-di-O-octanoylglyceryl, 3-O-phospho linked (PIP2), CAS 204858-53-7, was purchased from Echelon Biosciences (Salt Lake City, UT). PI3Kγ (p110γ) Recombinant Human Protein was purchased from Life technology (Grand Island, NY). ATP, MgCl$_2$, DTT, EDTA, MOPS and CHAPS were purchased from Sigma-Aldrich (St. Louis, MO).

The kinase reaction was conducted in polystyrene 384-well Greiner Bio-one white plate from Thermo Fisher Scientific in a final volume of 25 μL. Inhibitors were first diluted serially in DMSO and added to the plate wells before the addition of other reaction components. The final concentration of DMSO in the assay was 2%. The PI3Kγ assay was carried out at room temperature in 20 mM MOPS, pH 6.7, 10 mM MgCl$_2$, 5 mM DTT and CHAPS 0.03%. Reactions were initiated by the addition of ATP, the final reaction mixture consisted of 20 μM PIP2, 2 μM ATP, 0.5 Ci [γ-$^{33}$P] ATP, 13 nM PI3Kα. Reactions were incubated for 120 min and terminated by the addition of 40 μL SPA beads suspended in quench buffer: 163 mM potassium phosphate pH 7.8, 20% glycerol, 25 mM EDTA. The final concentration of SPA beads is 1.0 mg/mL. After the plate sealing, plates were shaken overnight at room temperature and centrifuged at 1500 rpm for 10 min, the radioactivity of the product was determined by scintillation counting on Topcount (Perkin-Elmer). IC$_{50}$ determination was performed by fitting the curve of percent of the solvent control activity versus the log of the inhibitor concentration using the GraphPad Prism 6.0 software. Data for the Examples, obtained using the methods described in Example B, are provided in Table B.

Example C. PI3Kδ Scintillation Proximity Assay

Materials

[γ-$^{33}$P]ATP (10 mCi/mL) and Wheat Germ Agglutinin (WGA) YSi SPA Scintillation Beads was purchased from Perkin-Elmer (Waltham, MA). Lipid kinase substrate, D-myo-Phosphatidylinositol 4,5-bisphosphate (PtdIns(4,5)P2)D (+)-sn-1,2-di-O-octanoylglyceryl, 3-O-phospho linked (PIP2), CAS 204858-53-7, was purchased from Echelon Biosciences (Salt Lake City, UT). PI3Kδ (p110δ/p85α) Recombinant Human Protein was purchased from Eurofins (St Charles, MO). ATP, MgCl$_2$, DTT, EDTA, MOPS and CHAPS were purchased from Sigma-Aldrich (St. Louis, MO).

The kinase reaction was conducted in polystyrene 384-well Greiner Bio-one white plate from Thermo Fisher Scientific in a final volume of 25 μL. Inhibitors were first diluted serially in DMSO and added to the plate wells before the addition of other reaction components. The final concentration of DMSO in the assay was 2%. The PI3Kδ assay was carried out at room temperature in 20 mM MOPS, pH 6.7, 10 mM MgCl$_2$, 5 mM DTT and CHAPS 0.03%. Reactions were initiated by the addition of ATP, the final reaction mixture consisted of 20 μM PIP2, 2 μM ATP, 0.5 Ci [γ-$^{33}$P] ATP, 3.4 nM PI3Kδ. Reactions were incubated for 120 min and terminated by the addition of 40 μL SPA beads suspended in quench buffer: 163 mM potassium phosphate pH 7.8, 20% glycerol, 25 mM EDTA. The final concentration of SPA beads is 1.0 mg/mL. After the plate sealing, plates were shaken overnight at room temperature and centrifuged at 1500 rpm for 10 min, the radioactivity of the product was determined by scintillation counting on Topcount (Perkin-Elmer). IC$_{50}$ determination was performed by fitting the curve of percent of the solvent control activity versus the log of the inhibitor concentration using the GraphPad Prism 6.0 software.

Data for the Examples, obtained using the methods described in Example C, are provided in Table B.

TABLE B

| Example # | PI3K-gamma SPA IC50 (nM) | PI3K-delta SPA IC50 (nM) |
|---|---|---|
| 1 | † | †††† |
| 5 | †† | † |
| 6 | †† | ††† |
| 7 | †† | ††† |
| 8 | ††† | ††† |
| 9 | †† | ††† |
| 10 | ††† | ††† |
| 11 | †††† | †††† |
| 12 | ††† | ††† |
| 13 | †††† | †††† |
| 14 | †††† | †††† |
| 16 | †††† | †††† |
| 17 | † | † |
| 18 | † | † |
| 19 | † | † |
| 20 | ††† | †††† |
| 21 | ††† | †††† |
| 25 | †††† | †††† |
| 26 | †††† | †††† |
| 30 | †††† | †††† |
| 31 | ††† | †††† |
| 32 | ††† | †††† |
| 33 | †††† | ††† |
| 34 | ††† | ††† |
| 35 | ††† | ††† |
| 37 | †††† | †††† |
| 40 | † | † |
| 41 | †††† | † |
| 43 | ††† | †††† |
| 44 | †††† | ††† |
| 45 | ††† | ††† |
| 46 | †† | ††† |
| 47 | ††† | † |
| 48 | †††† | †††† |
| 49 | †††† | †††† |
| 50 | †††† | †††† |
| 51 | †††† | †††† |
| 52 | †††† | ††† |
| 53 | †††† | †††† |
| 54 | †† | †† |
| 55 | ††† | ††† |

TABLE B-continued

| Example # | PI3K-gamma SPA IC50 (nM) | PI3K-delta SPA IC50 (nM) |
|---|---|---|
| 56 | †† | †† |
| 57 | ††† | †† |
| 58 | †††† | †††† |
| 59 | †††† | †††† |
| 60 | ††† | ††† |
| 61 | †††† | †††† |
| 62 | †† | †††† |
| 63 | ††† | †††† |
| 64 | ††† | †††† |
| 65 | ††† | †††† |
| 66 | ††† | †††† |
| 67 | ††† | ††† |
| 68 | ††† | †††† |
| 70 | ††† | ††† |
| 71 | ††† | ††† |
| 72 | †††† | †††† |
| 73 | †††† | †††† |
| 74 | † | † |
| 75 | †††† | †††† |
| 76 | † | †† |
| 77 | † | ††† |
| 78 | ††† | ††† |
| 79 | † | ††† |
| 80 | †††† | †††† |
| 81 | †††† | †††† |
| 82 | † | † |
| 83 | † | † |
| 84 | †† | ††† |
| 85 | ††† | †††† |
| 86 | † | ††† |
| 87 | †† | † |
| 88 | ††† | † |
| 94 | ††† | †††† |
| 95 | †††† | †††† |
| 97 | † | ††† |
| 98 | †† | †† |
| 99 | † | ††† |
| 100 | ††† | ††† |
| 101 | ††† | ††† |
| 102 | †† | † |
| 103 | †† | † |
| 104 | † | † |
| 105 | †† | †† |
| 106 | † | † |
| 107 | †† | †† |
| 108 | † | † |
| 109 | † | † |
| 110 | † | † |
| 111 | † | † |
| 112 | † | † |
| 113 | † | † |
| 114 | † | † |
| 115 | † | † |
| 116 | † | † |
| 117 | † | † |
| 118 | † | † |
| 119 | † | †††† |
| 120 | †† | † |
| 121 | † | † |
| 122 | ††† | ††† |
| 123 | † | † |
| 124 | ††† | ††† |
| 125 | †† | † |
| 126 | ††† | ††† |
| 127 | † | † |
| 128 | ††† | ††† |
| 129 | †† | †† |
| 130 | † | † |
| 131 | † | † |
| 132 | ††† | ††† |
| 133 | ††† | †† |
| 134 | †††† | †††† |
| 135 | †††† | ††† |
| 136 | ††† | ††† |
| 137 | ††† | ††† |
| 138 | ††† | †† |
| 139 | ††† | †† |
| 140 | †† | † |
| 141 | † | † |
| 142 | † | † |
| 143 | †† | †† |
| 144 | †† | †† |
| 145 | † | ††† |
| 145B | † | † |
| 145C | † | † |
| 146 | † | † |
| 147 | ††† | ††† |
| 148 | †† | †† |
| 149 | †† | †††† |
| 150 | ††† | ††† |
| 151 | † | † |
| 152 | † | † |
| 153 | † | † |
| 154 | † | †† |
| 155 | † | † |
| 156 | † | † |
| 157 | †† | ††† |
| 158 | † | †† |
| 159 | † | †† |
| 160 | † | ††† |
| 161 | † | †† |
| 162 | ††† | ††† |
| 163 | † | † |
| 164 | ††† | † |
| 165 | † | †† |
| 166 | †† | † |
| 167 | ††† | ††† |
| 168 | † | † |
| 169 | †† | † |
| 170 | †† | † |
| 171 | †† | †† |
| 172 | † | † |
| 173 | † | † |
| 174 | † | † |
| 175 | † | † |
| 176 | †† | ††† |
| 177 | ††† | †† |
| 178 | † | † |
| 179 | † | †† |
| 180 | † | † |
| 181 | †† | † |
| 182 | ††† | ††† |
| 183 | † | † |
| 184 | † | † |
| 185 | † | †† |
| 186 | † | † |
| 187 | † | †† |
| 188 | ††† | ††† |
| 189 | †† | † |
| 190 | † | † |
| 191 | † | † |
| 192 | †† | †† |
| 193 | † | † |
| 194 | † | † |
| 195 | ††† | ††† |
| 196 | ††† | † |
| 197 | †† | † |
| 198 | † | † |
| 199 | † | † |
| 200 | ††† | ††† |
| 201 | † | ††† |
| 202 | †† | †† |
| 203 | † | †† |
| 204 | †† | † |
| 205 | † | †† |
| 206 | †† | †† |
| 207 | † | ††† |
| 208 | † | † |
| 209 | †† | †† |
| 210 | †† | ††† |
| 211 | † | † |
| 212 | † | † |

TABLE B-continued

| Example # | PI3K-gamma SPA IC50 (nM) | PI3K-delta SPA IC50 (nM) |
|---|---|---|
| 212B | † | †† |
| 214 | † | ††† |
| 215 | ††† | †††† |
| 217 | †††† | †††† |
| 219 | †††† | †††† |
| 220 | ††† | †††† |
| 221 | †† | ††† |
| 222 | †††† | †††† |
| 223 | †††† | †††† |
| 224 | †††† | †††† |
| 225 | †††† | †††† |
| 226 | †††† | †††† |
| 227 | †††† | †††† |
| 228 | †††† | †††† |
| 229 | †††† | †††† |
| 230 | †††† | †††† |
| 231 | † | †† |
| 232 | †† | ††† |
| 233 | † | ††† |
| 234 | †† | †† |
| 235 | ††† | †††† |
| 236 | †††† | †††† |
| 237 | † | † |
| 238 | †††† | ††† |
| 239 | ††† | ††† |
| 240 | †† | ††† |
| 241 | †† | † |
| 242 | † | †††† |
| 243 | † | † |
| 244 | †† | † |
| 245 | † | † |
| 246 | ††† | ††† |
| 247 | † | † |
| 248 | † | † |
| 249 | † | † |
| 250 | † | † |
| 251 | ††† | †† |
| 252 | † | † |
| 253 | † | † |
| 254 | † | † |
| 255 | † | † |
| 256 | † | † |
| 257 | ††† | †††† |
| 258 | † | † |
| 259 | ††† | ††† |
| 260 | ††† | ††† |
| 261 | ††† | ††† |
| 262 | † | † |
| 263 | †† | † |
| 264 | †† | † |
| 265 | † | † |
| 266 | † | † |
| 267 | † | † |
| 268 | † | † |
| 269 | † | † |
| 270 | † | † |
| 271 | † | † |
| 272 | † | † |
| 273 | † | † |
| 274 | † | † |
| 275 | † | † |
| 276 | †† | † |
| 277 | † | † |
| 278 | † | † |
| 279 | †† | † |
| 280 | ††† | † |
| 281 | † | † |
| 282 | † | † |
| 283 | †††† | †† |
| 284 | †††† | †† |
| 285 | †††† | ††† |
| 286 | †††† | ††† |
| 287 | †††† | ††† |
| 288 | †††† | ††† |
| 289 | †††† | † |
| 290 | †††† | †† |
| 291 | †††† | † |
| 292 | ††† | †† |
| 293 | N/A | N/A |
| 294 | † | †††† |
| 295 | † | ††† |
| 296 | † | †††† |
| 297 | † | †††† |
| 298 | † | † |
| 299 | † | † |
| 300 | † | ††† |
| 301 | ††† | †††† |
| 302 | ††† | ††† |
| 303 | ††† | †††† |
| 304 | †† | ††† |
| 305 | ††† | ††† |
| 306 | †††† | †††† |
| 307 | ††† | † |
| 308 | ††† | † |

† refers to IC$_{50}$ of ≤50 nM
†† refers to IC$_{50}$ of ≤100 nM
††† refers to an IC$_{50}$ of ≤500 nM
†††† refers to an IC$_{50}$ of >500 nM
N/A refers to not available Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A method of treating a disease or disorder in a patient, wherein said disease or disorder is associated with abnormal expression or activity of PI3Kγ kinase, wherein the disease or disorder is selected from cancer or tumors, sarcomas, lymphomas, and leukemias, the method comprising administering to said patient a therapeutically effective amount of a compound of Formula IIb:

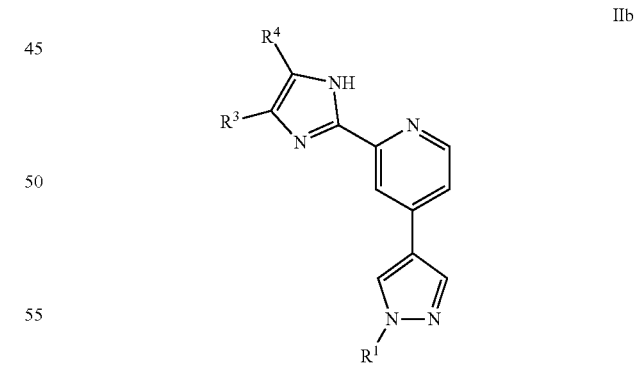

IIb or a pharmaceutically acceptable salt or tautomer thereof, wherein:
$R^1$ is independently selected from halo, CN, $NO_2$, $C_{1-6}$ alkyl, $C_{2-6}$ alkenyl, $C_{2-6}$ alkynyl, $C_{1-4}$ haloalkyl, $Cy^{1a}$, —$C_{1-4}$ alkylene-Cy, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cOR^d$, $NR^cC(O)R^b$, $NR^cC(O)OR^b$, $NR^cC(O)NR^c$ $R^d$, $NR^cS(O)R^b$, $NR^cS(O)_2R^b$ $NR^cS(O)_2NR^cR^d$, $S(O)R^b$, $S(O)NR^cR^d$, $S(O)_2R^b$, and $S(O)_2NR^cR^d$;

wherein said $C_{1-6}$ alkyl, $C_{2-6}$ alkenyl, $C_{2-6}$ alkynyl, and $C_{1-4}$ haloalkyl are optionally substituted with 1, 2, or 3 independently selected $R^{11}$ groups;

$R^3$ is selected from H, $C_{1-6}$ alkyl, $C_{1-4}$ haloalkyl, $Cy^1$, $C(O)NR^{c1}R^{d1}$, and $C(O)OR^{a1}$, wherein said $C_{1-6}$ alkyl is optionally substituted with 1, 2, or 3 independently selected $R^{13}$ groups;

$R^4$ is selected from H, $C_{1-6}$ alkyl, $C_{1-4}$ haloalkyl, $Cy^1$, —$C_{1-4}$ alkylene-$Cy^1$, $NR^{c1}R^{d1}$, and $NR^{c1}C(O)R^{b1}$, wherein said $C_{1-6}$ alkyl is optionally substituted with 1, 2, or 3 independently selected $R^{13}$ groups;

each $R^{11}$ is independently selected from halo, CN, $NO_2$, $C_{1-6}$ alkyl, $C_{2-6}$ alkenyl, $C_{2-6}$ alkynyl, $C_{1-4}$ haloalkyl, $Cy^2$, —$C_{1-4}$ alkylene-$Cy^2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}OR^{d2}$, $NR^{c2}C(O)R^{b2}$, $NR^{c2}C(O)OR^{a2}$ $NR^{c2}C(O)NR^{c2}R^{d2}$ $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$; wherein said $C_{1-6}$ alkyl, $C_{2-6}$ alkenyl, $C_{2-6}$ alkynyl, and $C_{1-4}$ haloalkyl are each optionally substituted with 1, 2, or 3 independently selected $R^g$ groups;

each $R^{13}$ is independently selected from halo, CN, $NO_2$, $C_{1-6}$ alkyl, $C_{2-6}$ alkenyl, $C_{2-6}$ alkynyl, $C_{1-4}$ haloalkyl, $Cy^3$, —$C_{1-4}$ alkylene-$Cy^3$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}OR^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$; wherein said $C_{1-6}$ alkyl, $C_{2-6}$ alkenyl, $C_{2-6}$ alkynyl, and $C_{1-4}$ haloalkyl are each optionally substituted with 1, 2, or 3 independently selected $R^g$ groups;

$Cy^{1a}$ is selected from 5-6 membered heterocycloalkyl having 1 or 2 ring atoms independently selected from N and O, which is optionally substituted by 1, 2, or 3 independently selected $R^{11}$ groups;

each Cy is independently selected from 3-6 membered cycloalkyl, phenyl, 5-6 membered heteroaryl having 1 or 2 ring atoms independently selected from N and O, and 4-8 membered heterocycloalkyl having 1 or 2 ring atoms independently selected from N and O, each of which is optionally substituted by 1, 2, or 3 independently selected $R^{11}$ groups;

each $Cy^1$ is independently selected from 3-10 membered cycloalkyl, 6-9 membered aryl, 5-6 membered heteroaryl having 1 or 2 ring atoms independently selected from N and O, and 5-6 membered heterocycloalkyl having 1 ring atom selected from N, O, and S, each of which is optionally substituted by 1, 2, or 3 independently selected $R^{13}$ groups;

each $Cy^2$ is independently selected from 3-6 membered cycloalkyl, phenyl, 5-6 membered heteroaryl having 1 or 2 ring atoms independently selected from N and O, and 5-6 membered heterocycloalkyl having 1 or 2 ring atoms independently selected from N and O, each of which is optionally substituted by 1, 2, or 3 independently selected $R^g$ groups;

each $Cy^3$ is independently selected from 3-6 membered cycloalkyl, phenyl, and 5-6 membered heterocycloalkyl having 1 ring atom selected from N and O, each of which is optionally substituted by 1, 2, or 3 independently selected $R^g$ groups;

$R^a$, $R^c$, and $R^d$ are each independently selected from H, $C_{1-6}$ alkyl, $C_{2-6}$ alkenyl, $C_{2-6}$ alkynyl, $C_{1-4}$ haloalkyl, Cy, and —$C_{1-4}$ alkylene-Cy; wherein said $C_{1-6}$ alkyl, $C_{2-6}$ alkenyl, $C_{2-6}$ alkynyl, and $C_{1-4}$ haloalkyl are each optionally substituted with 1, 2, or 3 independently selected $R^{11}$ groups;

$R^b$ is independently selected from $C_{1-6}$ alkyl, $C_{2-6}$ alkenyl, $C_{2-6}$ alkynyl, $C_{1-4}$ haloalkyl, Cy, and —$C_{1-4}$ alkylene-Cy; wherein said $C_{1-6}$ alkyl, $C_{2-6}$ alkenyl, $C_{2-6}$ alkynyl, and $C_{1-4}$ haloalkyl are each optionally substituted with 1, 2, or 3 independently selected $R^{11}$ groups;

alternatively, any $R^c$ and $R^d$ attached to the same N atom, together with the N atom to which they are attached, form a 4-10 membered heterocycloalkyl group having 1 or 2 ring atoms independently selected from N and O, optionally substituted with 1, 2, or 3 independently selected $R^{11}$ groups;

$R^{a1}$, $R^{c1}$, and $R^{d1}$ are each independently selected from H, $C_{1-6}$ alkyl, $C_{2-6}$ alkenyl, $C_{2-6}$ alkynyl, $C_{1-4}$ haloalkyl, $Cy^1$, and —$C_{1-4}$ alkylene-$Cy^1$; wherein said $C_{1-6}$ alkyl, $C_{2-6}$ alkenyl, $C_{2-6}$ alkynyl, and $C_{1-4}$ haloalkyl are each optionally substituted with 1, 2, or 3 independently selected $R^{13}$ groups;

$R^{b1}$ is independently selected from $C_{1-6}$ alkyl, $C_{2-6}$ alkenyl, $C_{2-6}$ alkynyl, $C_{1-4}$ haloalkyl, $Cy^1$, and —$C_{1-4}$ alkylene-$Cy^1$; wherein said $C_{1-6}$ alkyl, $C_{2-6}$ alkenyl, $C_{2-6}$ alkynyl, and $C_{1-4}$ haloalkyl are each optionally substituted with 1, 2, or 3 independently selected $R^{13}$ groups; or alternatively, any $R^{c1}$ and $R^{d1}$ attached to the same N atom, together with the N atom to which they are attached, form a 4-, 5-, or 6-membered heterocycloalkyl group having 1 or 2 ring atoms independently selected from N and O optionally substituted with 1, 2 or 3 independently selected $R^{13}$ groups;

each $R^{a2}$, $R^{c2}$, and $R^{d2}$ are independently selected from H, $C_{1-6}$ alkyl, $C_{2-6}$ alkenyl, $C_{2-6}$ alkynyl, $C_{1-4}$ haloalkyl, $Cy^2$, and —$C_{1-4}$ alkylene-$Cy^2$; wherein said $C_{1-6}$ alkyl, $C_{2-6}$ alkenyl, $C_{2-6}$ alkynyl, and $C_{1-4}$ haloalkyl are each optionally substituted with 1, 2, or 3 independently selected $R^g$ groups;

each $R^{b2}$ is independently selected from $C_{1-6}$ alkyl, $C_{2-6}$ alkenyl, $C_{2-6}$ alkynyl, $C_{1-4}$ haloalkyl, $Cy^2$, and —$C_{1-4}$ alkylene-$Cy^2$; wherein said $C_{1-6}$ alkyl, $C_{2-6}$ alkenyl, $C_{2-6}$ alkynyl, and $C_{1-4}$ haloalkyl are each optionally substituted with 1, 2, or 3 independently selected $R^g$ groups; or each $R^{a3}$, $R^{c3}$, and $R^{d3}$ are independently selected from H, $C_{1-6}$ alkyl, $C_{2-6}$ alkenyl, $C_{2-6}$ alkynyl, $C_{1-4}$ haloalkyl, $Cy^3$, and —$C_{1-4}$ alkylene-$Cy^3$; wherein said $C_{1-6}$ alkyl, $C_{2-6}$ alkenyl, $C_{2-6}$ alkynyl, and $C_{1-4}$ haloalkyl are each optionally substituted with 1, 2, or 3 independently selected $R^g$ groups;

each $R^{b3}$ is independently selected from $C_{1-6}$ alkyl, $C_{2-6}$ alkenyl, $C_{2-6}$ alkynyl, $C_{1-4}$ haloalkyl, $Cy^3$, and —$C_{1-4}$ alkylene-$Cy^3$; wherein said $C_{1-6}$ alkyl, $C_{2-6}$ alkenyl, $C_{2-6}$ alkynyl, and $C_{1-4}$ haloalkyl are each optionally substituted with 1, 2, or 3 independently selected $R^g$ groups; or alternatively, any $R^{c3}$ and $R^{d3}$ attached to the same N atom, together with the N atom to which they are attached, form a 5- or 6-membered heterocycloalkyl group having 1 or 2 ring atoms independently selected from N and O optionally substituted with 1, 2 or 3 independently selected $R^g$ groups; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO-$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

2. The method of claim 1, wherein $R^1$ is selected from halo, $C_{1-6}$ alkyl, $C_{2-6}$ alkenyl, $C_{2-6}$ alkynyl, $C_{1-4}$ haloalkyl, $Cy^{1a}$, —$C_{1-4}$ alkylene-Cy, $OR^a$, $C(O)R^b$, $C(O)NR^cR^d$, $C(O)OR^a$, $OC(O)R^b$, $OC(O)NR^cR^d$, $NR^cR^d$, $NR^cOR^d$, $NR^cC(O)R^b$, $NR^cC(O)OR^b$, $NR^cC(O)NR^cR^d$, $NR^cS(O)_2R^b$, $NR^cS(O)_2NR^cR^d$, $S(O)_2R^b$, and $S(O)_2NR^cR^d$; wherein said $C_{1-6}$ alkyl, $C_{2-6}$ alkenyl, $C_{2-6}$ alkynyl, and $C_{1-4}$ haloalkyl are optionally substituted with 1, 2, or 3 independently selected $R^{11}$ groups.

3. The method of claim 1, wherein $R^a$, $R^c$, and $R^d$ are each independently selected from H, $C_{1-6}$ alkyl, Cy, and —$C_{1-4}$ alkylene-Cy; wherein said $C_{1-6}$ alkyl is optionally substituted with 1 or 2 independently selected $R^{11}$ groups; $R^b$ is independently selected from $C_{1-6}$ alkyl, Cy, and —$C_{1-4}$ alkylene-Cy; wherein said $C_{1-6}$ alkyl is optionally substituted with 1 or 2 independently selected $R^{11}$ groups; alternatively, any $R^c$ and $R^d$ attached to the same N atom, together with the N atom to which they are attached, form a 4-10 membered heterocycloalkyl group having 1 or 2 ring atoms independently selected from N and O, which is optionally substituted with 1 or 2 independently selected $R^{11}$ groups.

4. The method of claim 1, wherein each Cy is independently 3-6 membered cycloalkyl, 4-6 membered heterocycloalkyl having 1 or 2 ring atoms independently selected from N and O, phenyl or 5-6 membered heteroaryl having 1 or 2 ring atoms independently selected from N and O, each of which is optionally substituted by 1, 2, or 3 independently selected $R^{11}$ groups.

5. The method of claim 1, wherein each Cy is independently cyclopropyl, cyclobutyl, cyclopentyl,

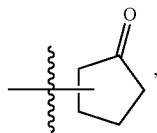

tetrahydrofuranyl, tetrahydropyranyl, morpholinyl, or phenyl, each of which is optionally substituted by 1 or 2 independently selected $R^{11}$ groups.

6. The method of claim 1, wherein $Cy^{1a}$ is 5-6 membered heterocycloalkyl having 1 or 2 ring atoms independently selected from N and O, which is optionally substituted by 1, 2, or 3 independently selected $R^{11}$ groups.

7. The method of claim 1, wherein each $R^{11}$ is independently selected from halo, CN, $C_{1-6}$ alkyl, $C_{2-6}$ alkenyl, $C_{2-6}$ alkynyl, $C_{1-4}$ haloalkyl, $Cy^2$, —$C_{1-4}$ alkylene-$Cy^2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}OR^{d2}$, $NR^{c2}C(O)R^{b2}$, $NR^{c2}C(O)OR^{a2}$, $NR^{c2}C(O)NR^{c2}R^{d2}$, $NR^{c2}S(O)_2R^{b2}$, $NR^{c2}S(O)_2NR^{c2}R^{d2}$, $S(O)_2R^{b2}$, and $S(O)_2NR^{c2}R^{d2}$; wherein said $C_{1-6}$ alkyl, $C_{2-6}$ alkenyl, $C_{2-6}$ alkynyl, and $C_{1-4}$ haloalkyl are each optionally substituted with 1, 2, or 3 independently selected $R^g$ groups.

8. The method of claim 1, wherein each $R^{a2}$, $R^{c2}$, and $R^{d2}$ are independently selected from H, $C_{1-6}$ alkyl, and $Cy^2$; wherein said $C_{1-6}$ alkyl is optionally substituted with 1 or 2 independently selected $R^g$ groups; and each $R^{b2}$ is independently selected from $C_{1-6}$ alkyl and $Cy^2$; wherein said $C_{1-6}$ alkyl is optionally substituted with 1 or 2 independently selected $R^g$ groups.

9. The method of claim 1, wherein each $Cy^2$ is independently selected from 3-6 membered cycloalkyl, phenyl, and 5-6 membered heterocycloalkyl having 1 or 2 ring atoms independently selected from N and O, each of which is optionally substituted by 1, 2, or 3 independently selected $R^g$ groups.

10. The method of claim 1, wherein $R^{a1}$, $R^{c1}$, and $R^{d1}$ are each independently selected from H, $C_{1-6}$ alkyl, $Cy^1$, and —$C_{1-4}$ alkylene-$C^{y1}$; wherein said $C_{1-6}$ alkyl is optionally substituted with 1, 2, 3, or 4 independently selected $R^{13}$ groups; $R^{b1}$ is independently selected from $C_{1-6}$ alkyl, $Cy^1$, and —$C_{1-4}$ alkylene-$Cy^1$; wherein said $C_{1-6}$ alkyl is optionally substituted with 1, 2, 3, or 4 independently selected $R^{13}$ groups; alternatively, any $R^{c1}$ and $R^{d1}$ attached to the same N atom, together with the N atom to which they are attached, form a 4-, 5-, or 6-membered heterocycloalkyl group having 1 or 2 ring atoms independently selected from N and O optionally substituted with 1, 2 or 3 independently selected $R^{13}$ groups.

11. The method of claim 1, wherein each $Cy^1$ is independently selected from 3-10 membered cycloalkyl, 5-6 membered heterocycloalkyl, 5-6 membered heteroaryl having 1 or 2 ring atoms independently selected from N and O, and phenyl, each of which is optionally substituted by 1, 2, or 3 independently selected $R^{13}$ groups.

12. The method of claim 1, wherein each $R^{13}$ is independently selected from halo, CN, $C_{1-6}$ alkyl, $C_{2-6}$ alkenyl, $C_{2-6}$ alkynyl, $C_{1-4}$ haloalkyl, $Cy^3$, —$C_{1-4}$ alkylene-$Cy^3$, $OR^{a3}$, $C(O)R^{b3}$, $C(O)NR^{c3}R^{d3}$, $C(O)OR^{a3}$, $NR^{c3}R^{d3}$, $NR^{c3}OR^{d3}$, $NR^{c3}C(O)R^{b3}$, $NR^{c3}C(O)OR^{a3}$, $NR^{c3}C(O)NR^{c3}R^{d3}$, $S(O)_2R^{b3}$, and $S(O)_2NR^{c3}R^{d3}$; wherein said $C_{1-6}$ alkyl, $C_{2-6}$ alkenyl, $C_{2-6}$ alkynyl, and $C_{1-4}$ haloalkyl are each optionally substituted with 1, 2, or 3 independently selected $R^g$ groups.

13. The method of claim 1, wherein each $R^{a3}$, $R^{c3}$, and $R^{d3}$ are independently selected from H and $C_{1-6}$ alkyl; wherein said $C_{1-6}$ alkyl is optionally substituted with 1, 2, 3, or 4 independently selected $R^g$ groups; each $R^{b3}$ is independently selected from $C_{1-6}$ alkyl, which is optionally substituted with 1, 2, 3, or 4 independently selected $R^g$ groups; alternatively, any $R^{c3}$ and $R^{d3}$ attached to the same N atom, together with the N atom to which they are attached, form a 5- or 6-membered heterocycloalkyl group having 1 or 2 ring atoms independently selected from N and O optionally substituted with 1, 2 or 3 independently selected $R^g$ groups.

14. The method of claim 1, wherein each $Cy^3$ is independently selected from 3-6 membered cycloalkyl and 5-6 membered heterocycloalkyl having 1 ring atom selected from N and O, each of which is optionally substituted by 1 or 2 independently selected $R^g$ groups.

15. The method of claim 1, wherein each $R^g$ is independently selected from OH, CN, halo, $C_{1-6}$ alkyl, $C_{1-4}$ haloalkyl, $C_{1-6}$ alkoxy, $C_{1-6}$ haloalkoxy, cyano-$C_{1-3}$ alkyl, HO-$C_{1-3}$ alkyl, amino, $C_{1-6}$ alkylamino, and di($C_{1-6}$ alkyl)amino.

16. The method of claim 1, wherein the compound of Formula IIb is selected from:
4-[1-(4-Chlorobenzyl)-1H-pyrazol-4-yl]-2-(5-phenyl-1H-imidazol-2-yl)pyridine;
4-(1-Benzyl-1H-pyrazol-4-yl)-2-(5-phenyl-1H-imidazol-2-yl)pyridine;

2-((4-(2-(5-Phenyl-1H-imidazol-2-yl)pyridin-4-yl)-1H-pyrazol-1-yl)methyl)benzonitrile;
4-(1-(2-Chlorobenzyl)-1H-pyrazol-4-yl)-2-(5-phenyl-1H-imidazol-2-yl)pyridine;
4-(1-Methyl-1H-pyrazol-4-yl)-2-(5-phenyl-1H-imidazol-2-yl)pyridine;
4-(3-Methyl-1H-pyrazol-4-yl)-2-(5-phenyl-1H-imidazol-2-yl)pyridine;
4-(1-Ethyl-1H-pyrazol-4-yl)-2-(5-phenyl-1H-imidazol-2-yl)pyridine;
2-(5-Phenyl-1H-imidazol-2-yl)-4-(1-propyl-1H-pyrazol-4-yl)pyridine;
3-((4-(2-(5-Phenyl-1H-imidazol-2-yl)pyridin-4-yl)-1H-pyrazol-1-yl)methyl)benzonitrile;
4-(1-(3-Chlorobenzyl)-1H-pyrazol-4-yl)-2-(5-phenyl-1H-imidazol-2-yl)pyridine;
2-(5-Phenyl-1H-imidazol-2-yl)-4-(1-(piperidin-4-yl)-1H-pyrazol-4-yl)pyridine;
4-(2-(4-(2-(5-Phenyl-1H-imidazol-2-yl)pyridin-4-yl)-1H-pyrazol-1-yl)ethyl)morpholine;
Methyl 2-((4-(2-(5-phenyl-1H-imidazol-2-yl)pyridin-4-yl)-1H-pyrazol-1-yl)methyl)benzoate;
Methyl 3-((4-(2-(5-phenyl-1H-imidazol-2-yl)pyridin-4-yl)-1H-pyrazol-1-yl)methyl)benzoate;
Methyl 4-((4-(2-(5-phenyl-1H-imidazol-2-yl)pyridin-4-yl)-1H-pyrazol-1-yl)methyl)benzoate;
2-((4-(2-(5-Phenyl-1H-imidazol-2-yl)pyridin-4-yl)-1H-pyrazol-1-yl)methyl)benzoic acid;
3-((4-(2-(5-Phenyl-1H-imidazol-2-yl)pyridin-4-yl)-1H-pyrazol-1-yl)methyl)benzoic acid;
4-((4-(2-(5-Phenyl-1H-imidazol-2-yl)pyridin-4-yl)-1H-pyrazol-1-yl)methyl)benzoic acid;
4-((4-(2-(5-Phenyl-1H-imidazol-2-yl)pyridin-4-yl)-1H-pyrazol-1-yl)methyl)benzonitrile;
4-(1-(Methylsulfonyl)-1H-pyrazol-4-yl)-2-(5-phenyl-1H-imidazol-2-yl)pyridine;
4-(1-(Ethylsulfonyl)-1H-pyrazol-4-yl)-2-(5-phenyl-1H-imidazol-2-yl)pyridine;
4-(1-(Cyclopropylsulfonyl)-1H-pyrazol-4-yl)-2-(5-phenyl-1H-imidazol-2-yl)pyridine;
2-(5-Phenyl-1H-imidazol-2-yl)-4-(1-(tetrahydro-2H-pyran-4-yl)-1H-pyrazol-4-yl)pyridine;
2-(4-(2-(5-Phenyl-1H-imidazol-2-yl)pyridin-4-yl)-1H-pyrazol-1-yl)acetamide;
N,N-Dimethyl-2-(4-(2-(5-phenyl-1H-imidazol-2-yl)pyridin-4-yl)-1H-pyrazol-1-yl)acetamide;
2-(4-(2-(5-Phenyl-1H-imidazol-2-yl)pyridin-4-yl)-1H-pyrazol-1-yl)-1-(pyrrolidin-1-yl)ethanone;
1-Morpholino-2-(4-(2-(5-phenyl-1H-imidazol-2-yl)pyridin-4-yl)-1H-pyrazol-1-yl)ethanone;
3-(4-(2-(5-Phenyl-1H-imidazol-2-yl)pyridin-4-yl)-1H-pyrazol-1-yl)propanenitrile;
3-(4-(2-(5-Phenyl-1H-imidazol-2-yl)pyridin-4-yl)-1H-pyrazol-1-yl)propanamide;
4-(1-(Cyclopentylsulfonyl)-1H-pyrazol-4-yl)-2-(5-phenyl-1H-imidazol-2-yl)pyridine;
Ethyl 3-(4-(2-(5-phenyl-1H-imidazol-2-yl)pyridin-4-yl)-1H-pyrazol-1-yl)propanoate;
2-(4-(2-(5-Phenyl-1H-imidazol-2-yl)pyridin-4-yl)-1H-pyrazol-1-yl)acetonitrile;
3-(4-(2-(5-Phenyl-1H-imidazol-2-yl)pyridin-4-yl)-1H-pyrazol-1-yl)propanoic acid;
N-Methyl-3-(4-(2-(5-phenyl-1H-imidazol-2-yl)pyridin-4-yl)-1H-pyrazol-1-yl)propanamide;
N-cyclopentyl-3-(4-(2-(5-phenyl-1H-imidazol-2-yl)pyridin-4-yl)-1H-pyrazol-1-yl)propanamide;
2-(5-Phenyl-1H-imidazol-2-yl)-4-(1-(tetrahydrofuran-3-yl)-1H-pyrazol-4-yl)pyridine;
4-(1-(4-Chlorobenzyl)-1H-pyrazol-4-yl)-2-(4,5-dimethyl-1H-imidazol-2-yl)pyridine; and
(2-{4-[1-(4-Chlorobenzyl)-1H-pyrazol-4-yl]pyridin-2-yl}-5-methyl-N-[(3S)-tetrahydrofuran-3-yl]-1H-imidazole-4-carboxamide;
or a pharmaceutically acceptable salt or tautomer of any of the aforementioned.

17. The method of claim 1, wherein the compound of Formula IIb is selected from:
2'-(4,5-Dimethyl-1H-imidazol-2-yl)-N-(tetrahydrofuran-3-ylmethyl)-3,4'-bipyridin-5-amine;
2'-(4,5-Dimethyl-1H-imidazol-2-yl)-N-(1-phenylethyl)-3,4'-bipyridin-5-amine;
2'-(4,5-Dimethyl-1H-imidazol-2-yl)-5-{[(3S)-3-methoxypyrrolidin-1-yl]carbonyl}-3,4'-bipyridine;
2-{4-[1-(4-Chlorobenzyl)-1H-pyrazol-4-yl]pyridin-2-yl}-N,5-dimethyl-1H-imidazole-4-carboxamide;
4-[1-(4-Chlorobenzyl)-1H-pyrazol-4-yl]-2-{4-[1-(methylsulfonyl)pyrrolidin-3-yl]-1H-imidazol-2-yl}pyridine;
2-[4-(1-Acetylpyrrolidin-3-yl)-1H-imidazol-2-yl]-4-[1-(4-chlorobenzyl)-1H-pyrazol-4-yl]pyridine;
4-[1-(4-Chlorobenzyl)-1H-pyrazol-4-yl]-2-{4-[1-(phenylsulfonyl)pyrrolidin-3-yl]-1H-imidazol-2-yl}pyridine; and
4-[1-(4-Chlorobenzyl)-1H-pyrazol-4-yl]-2-(4-pyrrolidin-3-yl-1H-imidazol-2-yl)pyridine;
or a pharmaceutically acceptable salt or tautomer of any of the aforementioned.

18. The method of claim 1, wherein the compound of Formula IIb is selected from:
4-[1-(4-Chlorobenzyl)-1H-pyrazol-4-yl]-2-(5-phenyl-1H-imidazol-2-yl)pyridine;
4-(1-Benzyl-1H-pyrazol-4-yl)-2-(5-phenyl-1H-imidazol-2-yl)pyridine;
2-((4-(2-(5-Phenyl-1H-imidazol-2-yl)pyridin-4-yl)-1H-pyrazol-1-yl)methyl)benzonitrile;
4-(1-(2-Chlorobenzyl)-1H-pyrazol-4-yl)-2-(5-phenyl-1H-imidazol-2-yl)pyridine;
4-(1-Methyl-1H-pyrazol-4-yl)-2-(5-phenyl-1H-imidazol-2-yl)pyridine;
4-(3-Methyl-1H-pyrazol-4-yl)-2-(5-phenyl-1H-imidazol-2-yl)pyridine;
4-(1-Ethyl-1H-pyrazol-4-yl)-2-(5-phenyl-1H-imidazol-2-yl)pyridine;
4-(3,5-Dimethyl-1H-pyrazol-4-yl)-2-(5-phenyl-1H-imidazol-2-yl)pyridine;
2-(5-Phenyl-1H-imidazol-2-yl)-4-(1-propyl-1H-pyrazol-4-yl)pyridine;
4-(1-Methyl-1H-pyrazol-5-yl)-2-(5-phenyl-1H-imidazol-2-yl)pyridine;
4-(1-Methyl-3-(trifluoromethyl)-1H-pyrazol-5-yl)-2-(5-phenyl-1H-imidazol-2-yl)pyridine;
4-(1-Methyl-1H-imidazol-2-yl)-2-(5-phenyl-1H-imidazol-2-yl)pyridine;
N-(2'-(5-Phenyl-1H-imidazol-2-yl)-3,4'-bipyridin-5-yl)acetamide;
4-(2'-(5-Phenyl-1H-imidazol-2-yl)-3,4'-bipyridin-5-yl)morpholine;
5-Methoxy-2'-(5-phenyl-1H-imidazol-2-yl)-3,4'-bipyridine;
3-((4-(2-(5-Phenyl-1H-imidazol-2-yl)pyridin-4-yl)-1H-pyrazol-1-yl)methyl)benzonitrile;
4-(1-(3-Chlorobenzyl)-1H-pyrazol-4-yl)-2-(5-phenyl-1H-imidazol-2-yl)pyridine;

2-(5-Phenyl-1H-imidazol-2-yl)-4-(1-(piperidin-4-yl)-1H-pyrazol-4-yl)pyridine;
4-(2-(4-(2-(5-Phenyl-1H-imidazol-2-yl)pyridin-4-yl)-1H-pyrazol-1-yl)ethyl)morpholine;
Methyl 2-((4-(2-(5-phenyl-1H-imidazol-2-yl)pyridin-4-yl)-1H-pyrazol-1-yl)methyl)benzoate;
Methyl 3-((4-(2-(5-phenyl-1H-imidazol-2-yl)pyridin-4-yl)-1H-pyrazol-1-yl)methyl)benzoate;
Methyl 4-((4-(2-(5-phenyl-1H-imidazol-2-yl)pyridin-4-yl)-1H-pyrazol-1-yl)methyl)benzoate;
2-((4-(2-(5-Phenyl-1H-imidazol-2-yl)pyridin-4-yl)-1H-pyrazol-1-yl)methyl)benzoic acid;
3-((4-(2-(5-Phenyl-1H-imidazol-2-yl)pyridin-4-yl)-1H-pyrazol-1-yl)methyl)benzoic acid;
4-((4-(2-(5-Phenyl-1H-imidazol-2-yl)pyridin-4-yl)-1H-pyrazol-1-yl)methyl)benzoic acid;
5-(4-Methylpiperazin-1-yl)-2'-(5-phenyl-1H-imidazol-2-yl)-3,4'-bipyridine;
5-(Methylsulfonyl)-2'-(5-phenyl-1H-imidazol-2-yl)-3,4'-bipyridine;
4-(2'-(5-Phenyl-1H-imidazol-2-yl)-3,4'-bipyridin-6-yl)morpholine;
4-((4-(2-(5-Phenyl-1H-imidazol-2-yl)pyridin-4-yl)-1H-pyrazol-1-yl)methyl)benzonitrile;
4-(1-(Methylsulfonyl)-1H-pyrazol-4-yl)-2-(5-phenyl-1H-imidazol-2-yl)pyridine;
4-(1-(Ethylsulfonyl)-1H-pyrazol-4-yl)-2-(5-phenyl-1H-imidazol-2-yl)pyridine;
4-(1-(Cyclopropylsulfonyl)-1H-pyrazol-4-yl)-2-(5-phenyl-1H-imidazol-2-yl)pyridine;
2-(5-Phenyl-1H-imidazol-2-yl)-4-(1-(tetrahydro-2H-pyran-4-yl)-1H-pyrazol-4-yl)pyridine;
2-(4-(2-(5-Phenyl-1H-imidazol-2-yl)pyridin-4-yl)-1H-pyrazol-1-yl)acetamide;
N,N-Dimethyl-2-(4-(2-(5-phenyl-1H-imidazol-2-yl)pyridin-4-yl)-1H-pyrazol-1-yl)acetamide;
2-(4-(2-(5-Phenyl-1H-imidazol-2-yl)pyridin-4-yl)-1H-pyrazol-1-yl)-1-(pyrrolidin-1-yl)ethanone;
1-Morpholino-2-(4-(2-(5-phenyl-1H-imidazol-2-yl)pyridin-4-yl)-1H-pyrazol-1-yl)ethanone;
3-(4-(2-(5-Phenyl-1H-imidazol-2-yl)pyridin-4-yl)-1H-pyrazol-1-yl)propanenitrile;
3-(4-(2-(5-Phenyl-1H-imidazol-2-yl)pyridin-4-yl)-1H-pyrazol-1-yl)propanamide;
4-(1-(Cyclopentylsulfonyl)-1H-pyrazol-4-yl)-2-(5-phenyl-1H-imidazol-2-yl)pyridine;
Ethyl 3-(4-(2-(5-phenyl-1H-imidazol-2-yl)pyridin-4-yl)-1H-pyrazol-1-yl)propanoate;
2-(4-(2-(5-Phenyl-1H-imidazol-2-yl)pyridin-4-yl)-1H-pyrazol-1-yl)acetonitrile;
3-(4-(2-(5-Phenyl-1H-imidazol-2-yl)pyridin-4-yl)-1H-pyrazol-1-yl)propanoic acid;
N-Methyl-3-(4-(2-(5-phenyl-1H-imidazol-2-yl)pyridin-4-yl)-1H-pyrazol-1-yl)propanamide;
N-cyclopentyl-3-(4-(2-(5-phenyl-1H-imidazol-2-yl)pyridin-4-yl)-1H-pyrazol-1-yl)propanamide;
2-(5-Phenyl-1H-imidazol-2-yl)-4-(1-(tetrahydrofuran-3-yl)-1H-pyrazol-4-yl)pyridine;
5-(5-Methoxy-3,4'-bipyridin-2'-yl)-1H-imidazol-2-amine;
N-Ethyl-5-(5-methoxy-3,4'-bipyridin-2'-yl)-1H-imidazol-2-amine;
5-(5-Methoxy-3,4'-bipyridin-2'-yl)-N-pentyl-1H-imidazol-2-amine;
N-Isobutyl-5-(5-methoxy-3,4'-bipyridin-2'-yl)-1H-imidazol-2-amine;
N-(Cyclobutylmethyl)-5-(5-methoxy-3,4'-bipyridin-2'-yl)-1H-imidazol-2-amine;
N-Butyl-5-(5-methoxy-3,4'-bipyridin-2'-yl)-4H-1,2,4-triazol-3-amine;
N-Isopropyl-5-(5-methoxy-3,4'-bipyridin-2'-yl)-4H-1,2,4-triazol-3-amine;
5-(5-Methoxy-3,4'-bipyridin-2'-yl)-N-methyl-4H-1,2,4-triazol-3-amine;
5-(5-Methoxy-3,4'-bipyridin-2'-yl)-N-phenyl-4H-1,2,4-triazol-3-amine;
5-Methoxy-2'-(5-phenyl-4H-1,2,4-triazol-3-yl)-3,4'-bipyridine;
5-Methoxy-2'-(4H-1,2,4-triazol-3-yl)-3,4'-bipyridine;
5-Methoxy-2'-(5-methyl-4H-1,2,4-triazol-3-yl)-3,4'-bipyridine;
5-Methoxy-2'-(2-phenyl-1H-imidazol-5-yl)-3,4'-bipyridine;
N-[2-(5-Methoxy-3,4'-bipyridin-2'-yl)-4-methyl-1H-imidazol-5-yl]acetamide;
2'-(4,5-Dimethyl-1H-imidazol-2-yl)-5-methoxy-3,4'-bipyridine;
5-Methoxy-2'-(5-methyl-1H-imidazol-2-yl)-3,4'-bipyridine;
2-(5-Methoxy-3,4'-bipyridin-2'-yl)-1,4,5,6-tetrahydrocyclopenta[d]imidazole;
5-Methoxy-2'-(5-(trifluoromethyl)-1H-imidazol-2-yl)-3,4'-bipyridine;
Ethyl 2-(5-methoxy-3,4'-bipyridin-2'-yl)-5-(trifluoromethyl)-1H-imidazole-4-carboxylate;
2-(5-Methoxy-3,4'-bipyridin-2'-yl)-5-(trifluoromethyl)-1H-imidazole-4-carboxylic acid;
5-Methoxy-2'-(4-methyl-5-phenyl-1H-imidazol-2-yl)-3,4'-bipyridine;
4-(2-(5-Methoxy-3,4'-bipyridin-2'-yl)-1H-imidazol-5-yl)-N,N-dimethylbenzenesulfonamide;
2'-(5-Isopropyl-1H-imidazol-2-yl)-5-methoxy-3,4'-bipyridine;
2'-(5-Ethyl-1H-imidazol-2-yl)-5-methoxy-3,4'-bipyridine;
2'-(5-Cyclopropyl-1H-imidazol-2-yl)-5-methoxy-3,4'-bipyridine;
5-Methoxy-2'-(5-(pyridin-2-yl)-1H-imidazol-2-yl)-3,4'-bipyridine;
2'-(5-tert-Butyl-1H-imidazol-2-yl)-5-methoxy-3,4'-bipyridine;
2'-(5-Methyl-1H-imidazol-2-yl)-5-morpholin-4-yl-3,4'-bipyridine;
4-(2'-(4,5-Dimethyl-1H-imidazol-2-yl)-3,4'-bipyridin-5-yl)morpholine;
4-(2'-(5-(Trifluoromethyl)-1H-imidazol-2-yl)-3,4'-bipyridin-5-yl)morpholine;
4-(2'-(5-Ethyl-1H-imidazol-2-yl)-3,4'-bipyridin-5-yl)morpholine;
4-(2'-(5-Isopropyl-1H-imidazol-2-yl)-3,4'-bipyridin-5-yl)morpholine;
4-(2'-(5-Cyclopropyl-1H-imidazol-2-yl)-3,4'-bipyridin-5-yl)morpholine;
4-(2'-(5-Cyclobutyl-1H-imidazol-2-yl)-3,4'-bipyridin-5-yl)morpholine;
4-(2'-(5-Cyclopropyl-4-methyl-1H-imidazol-2-yl)-3,4'-bipyridin-5-yl)morpholine;
4-(2'-(5-Ethyl-4-methyl-1H-imidazol-2-yl)-3,4'-bipyridin-5-yl)morpholine;
2'-(5-Cyclohexyl-1H-imidazol-2-yl)-5-(methylsulfonyl)-3,4'-bipyridine;
2'-(5-Methyl-1H-imidazol-2-yl)-5-(methylsulfonyl)-3,4'-bipyridine;

2'-(4,5-Dimethyl-1H-imidazol-2-yl)-5-(methylsulfonyl)-3,4'-bipyridine;
5-(Methylsulfonyl)-2'-(5-(trifluoromethyl)-1H-imidazol-2-yl)-3,4'-bipyridine;
2'-(5-Ethyl-1H-imidazol-2-yl)-5-(methylsulfonyl)-3,4'-bipyridine;
2'-(5-Isopropyl-1H-imidazol-2-yl)-5-(methylsulfonyl)-3,4'-bipyridine;
2'-(5-Cyclopropyl-1H-imidazol-2-yl)-5-(methylsulfonyl)-3,4'-bipyridine;
2'-(5-Cyclobutyl-1H-imidazol-2-yl)-5-(methylsulfonyl)-3,4'-bipyridine;
2'-(5-Cyclopentyl-1H-imidazol-2-yl)-5-(methylsulfonyl)-3,4'-bipyridine;
2'-(5-Benzyl-1H-imidazol-2-yl)-5-(methylsulfonyl)-3,4'-bipyridine;
2'-(5-Cyclopropyl-4-methyl-1H-imidazol-2-yl)-5-(methylsulfonyl)-3,4'-bipyridine;
2'-(5-Ethyl-4-methyl-1H-imidazol-2-yl)-5-(methylsulfonyl)-3,4'-bipyridine;
5-(Methylsulfonyl)-2'-(5-(pyridin-2-yl)-1H-imidazol-2-yl)-3,4'-bipyridine;
5-Methyl-2-(5-(methylsulfonyl)-3,4'-bipyridin-2'-yl)-1H-imidazole-4-carboxylic acid;
4-Cyclohexyl-2-[5-(methylsulfonyl)-3,4'-bipyridin-2'-yl]-1H-imidazol-5-amine;
2'-[4-(Difluoromethyl)-5-methyl-1H-imidazol-2-yl]-5-(methylsulfonyl)-3,4'-bipyridine;
[5-Methyl-2-(5-morpholin-4-yl-3,4'-bipyridin-2'-yl)-1H-imidazol-4-yl]methanol;
2-[5-Methyl-2-(5-morpholin-4-yl-3,4'-bipyridin-2'-yl)-1H-imidazol-4-yl]ethanol;
1-[5-Methyl-2-(5-morpholin-4-yl-3,4'-bipyridin-2'-yl)-1H-imidazol-4-yl]ethanol;
Methyl 5-methyl-2-(5-morpholin-4-yl-3,4'-bipyridin-2'-yl)-1H-imidazole-4-carboxylate;
tert-Butyl [2'-(5-phenyl-1H-imidazol-2-yl)-3,4'-bipyridin-5-yl]carbamate;
2'-(5-Phenyl-1H-imidazol-2-yl)-3,4'-bipyridin-5-amine;
tert-Butyl [2'-(4,5-dimethyl-1H-imidazol-2-yl)-3,4'-bipyridin-5-yl]carbamate;
2'-(4,5-Dimethyl-1H-imidazol-2-yl)-3,4'-bipyridin-5-amine;
N-[2'-(5-Phenyl-1H-imidazol-2-yl)-3,4'-bipyridin-5-yl]ethanesulfonamide;
2-Methoxy-N-[2'-(5-phenyl-1H-imidazol-2-yl)-3,4'-bipyridin-5-yl]acetamide;
N-(2'-(5-Phenyl-1H-imidazol-2-yl)-3,4'-bipyridin-5-yl)benzamide;
2-Chloro-N-(2'-(5-phenyl-1H-imidazol-2-yl)-3,4'-bipyridin-5-yl)benzamide;
3-Chloro-N-(2'-(5-phenyl-1H-imidazol-2-yl)-3,4'-bipyridin-5-yl)benzamide;
4-Chloro-N-(2'-(5-phenyl-1H-imidazol-2-yl)-3,4'-bipyridin-5-yl)benzamide;
3-Cyano-N-(2'-(5-phenyl-1H-imidazol-2-yl)-3,4'-bipyridin-5-yl)benzamide;
4-Cyano-N-(2'-(5-phenyl-1H-imidazol-2-yl)-3,4'-bipyridin-5-yl)benzamide;
N-(2'-(5-Phenyl-1H-imidazol-2-yl)-3,4'-bipyridin-5-yl)cyclopentanecarboxamide;
N-Ethyl-N'-[2'-(5-phenyl-1H-imidazol-2-yl)-3,4'-bipyridin-5-yl]urea;
Ethyl 2'-(5-phenyl-1H-imidazol-2-yl)-3,4'-bipyridin-5-yl-carbamate;
2'-(5-Phenyl-1H-imidazol-2-yl)-N-(tetrahydro-2H-pyran-4-ylmethyl)-3,4'-bipyridin-5-amine;
2'-(5-Phenyl-1H-imidazol-2-yl)-N-(tetrahydro-2H-pyran-4-yl)-3,4'-bipyridin-5-amine;
N-(1-Methylpiperidin-4-yl)-2'-(5-phenyl-1H-imidazol-2-yl)-3,4'-bipyridin-5-amine;
N-((1-Methylpiperidin-4-yl)methyl)-2'-(5-phenyl-1H-imidazol-2-yl)-3,4'-bipyridin-5-amine;
2'-(4,5-Dimethyl-1H-imidazol-2-yl)-N-(tetrahydro-2H-pyran-4-ylmethyl)-3,4'-bipyridin-5-amine;
(S)-(2'-(4,5-Dimethyl-1H-imidazol-2-yl)-3,4'-bipyridin-5-yl)(3-hydroxypyrrolidin-1-yl)methanone;
(2'-(4,5-Dimethyl-1H-imidazol-2-yl)-3,4'-bipyridin-5-yl)(4-methylpiperazin-1-yl)methanone;
(2'-(4,5-Dimethyl-1H-imidazol-2-yl)-3,4'-bipyridin-5-yl)(morpholino)methanone;
2'-(4,5-Dimethyl-1H-imidazol-2-yl)-N-(3-(dimethylamino)propyl)-3,4'-bipyridine-5-carboxamide;
4-(2'-(4,5-Dimethyl-1H-imidazol-2-yl)-3,4'-bipyridine-5-carbonyl)piperazine-1-carboxamide;
(2'-(4,5-Dimethyl-1H-imidazol-2-yl)-3,4'-bipyridin-5-yl)(pyrrolidin-1-yl)methanone;
(2'-(4,5-Dimethyl-1H-imidazol-2-yl)-3,4'-bipyridin-5-yl)(3-hydroxyazetidin-1-yl)methanone;
1-(2'-(4,5-Dimethyl-1H-imidazol-2-yl)-3,4'-bipyridine-5-carbonyl)azetidine-3-carbonitrile;
(2'-(4,5-Dimethyl-1H-imidazol-2-yl)-3,4'-bipyridin-5-yl)(3-hydroxypiperidin-1-yl)methanone;
(R)-(2'-(4,5-Dimethyl-1H-imidazol-2-yl)-3,4'-bipyridin-5-yl)(3-fluoropyrrolidin-1-yl)methanone;
(2'-(4,5-Dimethyl-1H-imidazol-2-yl)-3,4'-bipyridin-5-yl)(3-oxa-9-azaspiro[5.5]undecan-9-yl)methanone;
2'-(4,5-Dimethyl-1H-imidazol-2-yl)-N-isopropyl-3,4'-bipyridine-5-carboxamide;
(2'-(4,5-Dimethyl-1H-imidazol-2-yl)-3,4'-bipyridin-5-yl)(4-(1-methylpiperidin-4-yl)piperazin-1-yl)methanone;
1-(4-(2'-(4,5-Dimethyl-1H-imidazol-2-yl)-3,4'-bipyridine-5-carbonyl)piperazin-1-yl)ethanone;
2'-(4,5-Dimethyl-1H-imidazol-2-yl)-N-(tetrahydro-2H-pyran-4-yl)-3,4'-bipyridine-5-carboxamide;
(R)-(2'-(4,5-Dimethyl-1H-imidazol-2-yl)-3,4'-bipyridin-5-yl)(3-(dimethylamino)pyrrolidin-1-yl)methanone;
2'-(4,5-Dimethyl-1H-imidazol-2-yl)-N-((tetrahydro-2H-pyran-4-yl)methyl)-3,4'-bipyridine-5-carboxamide;
(R)-(2'-(4,5-Dimethyl-1H-imidazol-2-yl)-3,4'-bipyridin-5-yl)(3-hydroxypyrrolidin-1-yl)methanone;
2'-(4,5-Dimethyl-1H-imidazol-2-yl)-N-(2-(tetrahydro-2H-pyran-4-yl)ethyl)-3,4'-bipyridine-5-carboxamide;
(2'-(4,5-Dimethyl-1H-imidazol-2-yl)-3,4'-bipyridin-5-yl)(2-oxa-7-azaspiro[3.5]nonan-7-yl)methanone;
2'-(4,5-Dimethyl-1H-imidazol-2-yl)-N-(2-methoxyethyl)-3,4'-bipyridine-5-carboxamide;
2'-(4,5-Dimethyl-1H-imidazol-2-yl)-N-((tetrahydrofuran-2-yl)methyl)-3,4'-bipyridine-5-carboxamide;
1-(2'-(4,5-Dimethyl-1H-imidazol-2-yl)-3,4'-bipyridine-5-carbonyl)pyrrolidin-3-one;
(2'-(4,5-Dimethyl-1H-imidazol-2-yl)-3,4'-bipyridin-5-yl)(3-(2-hydroxyethyl)pyrrolidin-1-yl)methanone;
(2'-(4,5-Dimethyl-1H-imidazol-2-yl)-3,4'-bipyridin-5-yl)(3-(pyridin-2-yl)pyrrolidin-1-yl)methanone;
2-(2'-(4,5-Dimethyl-1H-imidazol-2-yl)-3,4'-bipyridine-5-carbonyl)-6-methyl-2,6-diazaspiro[3.4]octan-5-one;
((3R,4R)-1-{[2'-(4,5-Dimethyl-1H-imidazol-2-yl)-3,4'-bipyridin-5-yl]carbonyl}-4-methylpyrrolidin-3-yl)methanol;
5-[(3,3-Difluoropyrrolidin-1-yl)carbonyl]-2'-(4,5-dimethyl-1H-imidazol-2-yl)-3,4'-bipyridine;
2'-(4,5-Dimethyl-1H-imidazol-2-yl)-5-[(3-methoxypyrrolidin-1-yl)carbonyl]-3,4'-bipyridine;

Methyl 1-{[2'-(4,5-dimethyl-1H-imidazol-2-yl)-3,4'-bipyridin-5-yl]carbonyl}pyrrolidine-3-carboxylate;
2'-(4,5-Dimethyl-1H-imidazol-2-yl)-N-[(3R)-tetrahydrofuran-3-yl]-3,4'-bipyridine-5-carboxamide;
1-{[2'-(4,5-Dimethyl-1H-imidazol-2-yl)-3,4'-bipyridin-5-yl]carbonyl}piperidin-4-ol;
2'-(4,5-Dimethyl-1H-imidazol-2-yl)-5-{[3-(trifluoromethyl)pyrrolidin-1-yl]carbonyl}-3,4'-bipyridine;
5-(7-Azabicyclo[2.2.1]hept-7-ylcarbonyl)-2'-(4,5-dimethyl-1H-imidazol-2-yl)-3,4'-bipyridine;
1-{[2'-(4,5-Dimethyl-1H-imidazol-2-yl)-3,4'-bipyridin-5-yl]carbonyl}-3-methylpyrrolidin-3-ol;
2'-(4,5-Dimethyl-1H-imidazol-2-yl)-5-[(3-phenylpyrrolidin-1-yl)carbonyl]-3,4'-bipyridine;
2'-(4,5-Dimethyl-1H-imidazol-2-yl)-5-[(3-pyridin-4-ylpyrrolidin-1-yl)carbonyl]-3,4'-bipyridine;
1-{[2'-(4,5-Dimethyl-1H-imidazol-2-yl)-3,4'-bipyridin-5-yl]carbonyl}pyrrolidine-3-carbonitrile;
2'-(4,5-Dimethyl-1H-imidazol-2-yl)-5-{[2-(trifluoromethyl)azetidin-1-yl]carbonyl}-3,4'-bipyridine;
5-[(3,3-Dimethylazetidin-1-yl)carbonyl]-2'-(4,5-dimethyl-1H-imidazol-2-yl)-3,4'-bipyridine;
2'-(4,5-Dimethyl-1H-imidazol-2-yl)-5-[(4-phenylpiperidin-1-yl)carbonyl]-3,4'-bipyridine;
2'-(4,5-Dimethyl-1H-imidazol-2-yl)-5-[(4aR,8aS)-octahydroisoquinolin-2(1H)-ylcarbonyl]-3,4'-bipyridine;
2'-(4,5-Dimethyl-1H-imidazol-2-yl)-5-[(3-phenylpiperidin-1-yl)carbonyl]-3,4'-bipyridine;
5-[(4-Benzylpiperidin-1-yl)carbonyl]-2'-(4,5-dimethyl-1H-imidazol-2-yl)-3,4'-bipyridine;
2'-(4,5-Dimethyl-1H-imidazol-2-yl)-5-[(2-methylpiperidin-1-yl)carbonyl]-3,4'-bipyridine;
5-(Azetidin-1-ylcarbonyl)-2'-(4,5-dimethyl-1H-imidazol-2-yl)-3,4'-bipyridine;
N-Benzyl-2'-(4,5-dimethyl-1H-imidazol-2-yl)-3,4'-bipyridine-5-carboxamide;
N-Benzyl-2'-(4,5-dimethyl-1H-imidazol-2-yl)-N-methyl-3,4'-bipyridine-5-carboxamide;
2'-(4,5-Dimethyl-1H-imidazol-2-yl)-N-methyl-N-phenyl-3,4'-bipyridine-5-carboxamide;
2'-(4,5-Dimethyl-1H-imidazol-2-yl)-N-[(1S)-1-phenylethyl]-3,4'-bipyridine-5-carboxamide;
4-Benzyl-1-{[2'-(4,5-dimethyl-1H-imidazol-2-yl)-3,4'-bipyridin-5-yl]carbonyl}piperidin-4-ol;
2'-(4,5-Dimethyl-1H-imidazol-2-yl)-5-[(3-pyrazin-2-ylpyrrolidin-1-yl)carbonyl]-3,4'-bipyridine;
2'-(4,5-Dimethyl-1H-imidazol-2-yl)-N-ethyl-N-methyl-3,4'-bipyridine-5-carboxamide;
2'-(4,5-Dimethyl-1H-imidazol-2-yl)-5-[(3-methoxyazetidin-1-yl)carbonyl]-3,4'-bipyridine;
2'-(4,5-Dimethyl-1H-imidazol-2-yl)-5-[(4-methyl-1,4-diazepan-1-yl)carbonyl]-3,4'-bipyridine;
2'-(4,5-Dimethyl-1H-imidazol-2-yl)-N-(2-hydroxyethyl)-N-methyl-3,4'-bipyridine-5-carboxamide;
N-(Cyclopropylmethyl)-2'-(4,5-dimethyl-1H-imidazol-2-yl)-3,4'-bipyridine-5-carboxamide;
N-(Cyanomethyl)-2'-(4,5-dimethyl-1H-imidazol-2-yl)-N-methyl-3,4'-bipyridine-5-carboxamide;
2'-(4,5-Dimethyl-1H-imidazol-2-yl)-N-(2-methoxyethyl)-N-methyl-3,4'-bipyridine-5-carboxamide;
2'-(4,5-Dimethyl-1H-imidazol-2-yl)-N-{[1-(hydroxymethyl)cyclopropyl]methyl}-N-methyl-3,4'-bipyridine-5-carboxamide;
N-(Cyclobutylmethyl)-2'-(4,5-dimethyl-1H-imidazol-2-yl)-3,4'-bipyridine-5-carboxamide;
N-(Cyclopentylmethyl)-2'-(4,5-dimethyl-1H-imidazol-2-yl)-3,4'-bipyridine-5-carboxamide;
N-(tert-Butyl)-2'-(4,5-dimethyl-1H-imidazol-2-yl)-3,4'-bipyridine-5-carboxamide;
2'-(4,5-Dimethyl-1H-imidazol-2-yl)-N-(3-hydroxypropyl)-N-methyl-3,4'-bipyridine-5-carboxamide;
2'-(4,5-Dimethyl-1H-imidazol-2-yl)-N-methyl-N-propyl-3,4'-bipyridine-5-carboxamide;
2'-(4,5-Dimethyl-1H-imidazol-2-yl)-5-[(3-ethylpyrrolidin-1-yl)carbonyl]-3,4'-bipyridine;
5-(5-Azaspiro[2.4]hept-5-ylcarbonyl)-2'-(4,5-dimethyl-1H-imidazol-2-yl)-3,4'-bipyridine;
2'-(4,5-Dimethyl-1H-imidazol-2-yl)-1-(phenylsulfonyl)-1,2,5,6-tetrahydro-3,4'-bipyridine;
2-(4,5-Dimethyl-1H-imidazol-2-yl)-4-[1-(phenylsulfonyl)piperidin-3-yl]pyridine;
1-(4-(2-(4,5-Dimethyl-1H-imidazol-2-yl)pyridin-4-yl)-5,6-dihydropyridin-1(2H)-yl)ethanone;
1-(3-(2-(4,5-Dimethyl-1H-imidazol-2-yl)pyridin-4-yl)-5,6-dihydropyridin-1(2H)-yl)ethanone;
2-(4,5-Dimethyl-1H-imidazol-2-yl)-4-(1-(methylsulfonyl)-1,2,5,6-tetrahydropyridin-3-yl)pyridine;
4-(1-(4-Chlorophenylsulfonyl)-1,2,5,6-tetrahydropyridin-3-yl)-2-(4,5-dimethyl-1H-imidazol-2-yl)pyridine;
(3-(2-(4,5-Dimethyl-1H-imidazol-2-yl)pyridin-4-yl)-5,6-dihydropyridin-1(2H)-yl)(phenyl)methanone;
4-(1-Benzyl-1,2,5,6-tetrahydropyridin-3-yl)-2-(4,5-dimethyl-1H-imidazol-2-yl)pyridine;
4-(1-(4-Chlorobenzyl)-1,2,5,6-tetrahydropyridin-3-yl)-2-(4,5-dimethyl-1H-imidazol-2-yl)pyridine;
2-(4,5-Dimethyl-1H-imidazol-2-yl)-4-(1-((tetrahydro-2H-pyran-4-yl)methyl)-1,2,5,6-tetrahydropyridin-3-yl)pyridine;
1-(3-(2-(4,5-Dimethyl-1H-imidazol-2-yl)pyridin-4-yl)-2,5-dihydro-1H-pyrrol-1-yl)ethanone;
2-(4,5-Dimethyl-1H-imidazol-2-yl)-4-(1-(methylsulfonyl)-2,5-dihydro-1H-pyrrol-3-yl)pyridine;
4-(1-Benzyl-2,5-dihydro-1H-pyrrol-3-yl)-2-(4,5-dimethyl-1H-imidazol-2-yl)pyridine;
4-(1-(4-Chlorobenzyl)-2,5-dihydro-1H-pyrrol-3-yl)-2-(4,5-dimethyl-1H-imidazol-2-yl)pyridine;
2-(4,5-Dimethyl-1H-imidazol-2-yl)-4-(1-((tetrahydro-2H-pyran-4-yl)methyl)-2,5-dihydro-1H-pyrrol-3-yl)pyridine;
(3R)-1-[2'-(4,5-Dimethyl-1H-imidazol-2-yl)-3,4'-bipyridin-5-yl]pyrrolidin-3-ol;
(3S)-1-[2'-(4,5-Dimethyl-1H-imidazol-2-yl)-3,4'-bipyridin-5-yl]pyrrolidin-3-ol;
2'-(4,5-Dimethyl-1H-imidazol-2-yl)-N-phenyl-3,4'-bipyridin-5-amine;
5-Chloro-2'-(4,5-dimethyl-1H-imidazol-2-yl)-3,4'-bipyridine;
tert-Butyl 3-[2'-(4,5-dimethyl-1H-imidazol-2-yl)-3,4'-bipyridin-5-yl]-2,5-dihydro-1H-pyrrole-1-carboxylate;
5-(2,5-Dihydro-1H-pyrrol-3-yl)-2'-(4,5-dimethyl-1H-imidazol-2-yl)-3,4'-bipyridine;
2'-(4,5-Dimethyl-1H-imidazol-2-yl)-5-[1-(methylsulfonyl)-2,5-dihydro-1H-pyrrol-3-yl]-3,4'-bipyridine;
1-(3-(2'-(4,5-Dimethyl-1H-imidazol-2-yl)-3,4'-bipyridin-5-yl)-2,5-dihydro-1H-pyrrol-1-yl)ethanone;
Methyl 3-(2'-(4,5-dimethyl-1H-imidazol-2-yl)-3,4'-bipyridin-5-yl)-2,5-dihydro-1H-pyrrole-1-carboxylate;
2'-(4,5-Dimethyl-1H-imidazol-2-yl)-5-[1-(methylsulfonyl)pyrrolidin-3-yl]-3,4'-bipyridine;
Ethyl 5-methyl-2-[5-(methylsulfonyl)-3,4'-bipyridin-2'-yl]-1H-imidazole-4-carboxylate;
5-Methyl-2-[5-(methylsulfonyl)-3,4'-bipyridin-2'-yl]-1H-imidazole-4-carboxylic acid;

N-Cyclopentyl-5-methyl-2-[5-(methylsulfonyl)-3,4'-bipyridin-2'-yl]-1H-imidazole-4-carboxamide;
2'-[5-Methyl-4-(morpholin-4-ylcarbonyl)-1H-imidazol-2-yl]-5-(methylsulfonyl)-3,4'-bipyridine;
(3R)-1-({5-Methyl-2-[5-(methylsulfonyl)-3,4'-bipyridin-2'-yl]-1H-imidazol-4-yl}carbonyl)pyrrolidin-3-ol;
(3S)-1-({5-Methyl-2-[5-(methylsulfonyl)-3,4'-bipyridin-2'-yl]-1H-imidazol-4-yl}carbonyl)pyrrolidin-3-ol;
1-({5-Methyl-2-[5-(methylsulfonyl)-3,4'-bipyridin-2'-yl]-1H-imidazol-4-yl}carbonyl)azetidin-3-ol;
1-({5-Methyl-2-[5-(methylsulfonyl)-3,4'-bipyridin-2'-yl]-1H-imidazol-4-yl}carbonyl)azetidine-3-carbonitrile;
5-Methyl-2-[5-(methylsulfonyl)-3,4'-bipyridin-2'-yl]-1H-imidazole-4-carboxamide;
N,5-Dimethyl-2-[5-(methylsulfonyl)-3,4'-bipyridin-2'-yl]-1H-imidazole-4-carboxamide;
N,N,5-Trimethyl-2-[5-(methylsulfonyl)-3,4'-bipyridin-2'-yl]-1H-imidazole-4-carboxamide;
N-Ethyl-5-methyl-2-[5-(methylsulfonyl)-3,4'-bipyridin-2'-yl]-1H-imidazole-4-carboxamide;
N-Isopropyl-5-methyl-2-[5-(methylsulfonyl)-3,4'-bipyridin-2'-yl]-1H-imidazole-4-carboxamide;
5-Methyl-2-[5-(methylsulfonyl)-3,4'-bipyridin-2'-yl]-N-(tetrahydro-2H-pyran-4-yl)-1H-imidazole-4-carboxamide;
5-Methyl-2-[5-(methylsulfonyl)-3,4'-bipyridin-2'-yl]-N-[(3S)-tetrahydrofuran-3-yl]-1H-imidazole-4-carboxamide;
5-Methyl-2-[5-(methylsulfonyl)-3,4'-bipyridin-2'-yl]-N-[(3R)-tetrahydrofuran-3-yl]-1H-imidazole-4-carboxamide;
5-Methyl-2-(5-morpholin-4-yl-3,4'-bipyridin-2'-yl)-1H-imidazole-4-carboxylic acid;
N-Cyclopentyl-5-methyl-2-(5-morpholin-4-yl-3,4'-bipyridin-2'-yl)-1H-imidazole-4-carboxamide;
N-Isopropyl-N,5-dimethyl-2-(5-morpholin-4-yl-3,4'-bipyridin-2'-yl)-1H-imidazole-4-carboxamide;
N-Ethyl-N,5-dimethyl-2-(5-morpholin-4-yl-3,4'-bipyridin-2'-yl)-1H-imidazole-4-carboxamide;
N,5-Dimethyl-2-(5-morpholin-4-yl-3,4'-bipyridin-2'-yl)-N-(tetrahydrofuran-3-yl)-1H-imidazole-4-carboxamide;
2'-(5-Methyl-4-{[3-(trifluoromethyl)azetidin-1-yl]carbonyl}-1H-imidazol-2-yl)-5-morpholin-4-yl-3,4'-bipyridine;
2'-{4-[(3-Methoxyazetidin-1-yl)carbonyl]-5-methyl-1H-imidazol-2-yl}-5-morpholin-4-yl-3,4'-bipyridine;
tert-Butyl (1-{[5-methyl-2-(5-morpholin-4-yl-3,4'-bipyridin-2'-yl)-1H-imidazol-4-yl]carbonyl}azetidin-3-yl)carbamate;
N-Cyclohexyl-5-methyl-2-(5-morpholin-4-yl-3,4'-bipyridin-2'-yl)-1H-imidazole-4-carboxamide;
N-(tert-Butyl)-5-methyl-2-(5-morpholin-4-yl-3,4'-bipyridin-2'-yl)-1H-imidazole-4-carboxamide;
2'-{4-[(3,3-Dimethylazetidin-1-yl)carbonyl]-5-methyl-1H-imidazol-2-yl}-5-morpholin-4-yl-3,4'-bipyridine;
N-Isopropyl-5-methyl-2-(5-morpholin-4-yl-3,4'-bipyridin-2'-yl)-1H-imidazole-4-carboxamide;
5-Methyl-2-(5-morpholin-4-yl-3,4'-bipyridin-2'-yl)-N-(tetrahydro-2H-pyran-4-yl)-1H-imidazole-4-carboxamide;
5-Methyl-2-(5-morpholin-4-yl-3,4'-bipyridin-2'-yl)-N-[(3R)-tetrahydrofuran-3-yl]-1H-imidazole-4-carboxamide;
5-Methyl-2-(5-morpholin-4-yl-3,4'-bipyridin-2'-yl)-N-[(3S)-tetrahydrofuran-3-yl]-1H-imidazole-4-carboxamide;
N-Benzyl-5-methyl-2-(5-morpholin-4-yl-3,4'-bipyridin-2'-yl)-1H-imidazole-4-carboxamide;
5-Methyl-2-(5-morpholin-4-yl-3,4'-bipyridin-2'-yl)-N-[(1S)-1-phenylethyl]-1H-imidazole-4-carboxamide;
5-Methyl-2-(5-morpholin-4-yl-3,4'-bipyridin-2'-yl)-N-[(1R)-1-phenylethyl]-1H-imidazole-4-carboxamide;
N-[(1R)-2-Methoxy-1-phenylethyl]-5-methyl-2-(5-morpholin-4-yl-3,4'-bipyridin-2'-yl)-1H-imidazole-4-carboxamide;
N-[(1S)-2-Methoxy-1-phenylethyl]-5-methyl-2-(5-morpholin-4-yl-3,4'-bipyridin-2'-yl)-1H-imidazole-4-carboxamide;
N-[1-(3-Fluorophenyl)ethyl]-5-methyl-2-(5-morpholin-4-yl-3,4'-bipyridin-2'-yl)-1H-imidazole-4-carboxamide;
N-2-Adamantyl-5-methyl-2-(5-morpholin-4-yl-3,4'-bipyridin-2'-yl)-1H-imidazole-4-carboxamide;
N-[(3S)-1-Benzylpyrrolidin-3-yl]-5-methyl-2-(5-morpholin-4-yl-3,4'-bipyridin-2'-yl)-1H-imidazole-4-carboxamide;
N-[(3R)-1-Benzylpyrrolidin-3-yl]-5-methyl-2-(5-morpholin-4-yl-3,4'-bipyridin-2'-yl)-1H-imidazole-4-carboxamide;
5-Methyl-2-(5-morpholin-4-yl-3,4'-bipyridin-2'-yl)-N-(tetrahydro-2H-thiopyran-4-yl)-1H-imidazole-4-carboxamide;
N-(2,3-Dihydro-1H-inden-2-yl)-5-methyl-2-(5-morpholin-4-yl-3,4'-bipyridin-2'-yl)-1H-imidazole-4-carboxamide;
N-{[5-Methyl-2-(5-morpholin-4-yl-3,4'-bipyridin-2'-yl)-1H-imidazol-4-yl]methyl}tetrahydro-2H-pyran-4-amine;
N-{[5-Methyl-2-(5-morpholin-4-yl-3,4'-bipyridin-2'-yl)-1H-imidazol-4-yl]methyl}cyclopentanamine;
N-{[5-Methyl-2-(5-morpholin-4-yl-3,4'-bipyridin-2'-yl)-1H-imidazol-4-yl]methyl}propan-2-amine;
(3S)-N-{[5-Methyl-2-(5-morpholin-4-yl-3,4'-bipyridin-2'-yl)-1H-imidazol-4-yl]methyl}tetrahydrofuran-3-amine;
(3R)-N-{[5-Methyl-2-(5-morpholin-4-yl-3,4'-bipyridin-2'-yl)-1H-imidazol-4-yl]methyl}tetrahydrofuran-3-amine;
N-Methyl-1-[5-methyl-2-(5-morpholin-4-yl-3,4'-bipyridin-2'-yl)-1H-imidazol-4-yl]methanamine;
N,N-Dimethyl-1-[5-methyl-2-(5-morpholin-4-yl-3,4'-bipyridin-2'-yl)-1H-imidazol-4-yl]methanamine;
2-Methoxy-N-{[5-methyl-2-(5-morpholin-4-yl-3,4'-bipyridin-2'-yl)-1H-imidazol-4-yl]methyl}ethanamine;
3-Methoxy-N-{[5-methyl-2-(5-morpholin-4-yl-3,4'-bipyridin-2'-yl)-1H-imidazol-4-yl]methyl}propan-1-amine;
2'-[5-Methyl-4-(morpholin-4-ylmethyl)-1H-imidazol-2-yl]-5-morpholin-4-yl-3,4'-bipyridine;
2'-(4,5-Dimethyl-1H-imidazol-2-yl)-3,4'-bipyridin-5-yl]methanol;
4-(1-(4-Chlorobenzyl)-1H-pyrazol-4-yl)-2-(4,5-dimethyl-1H-imidazol-2-yl)pyridine; and
(2-{4-[1-(4-Chlorobenzyl)-1H-pyrazol-4-yl]pyridin-2-yl}-5-methyl-N-[(3S)-tetrahydrofuran-3-yl]-1H-imidazole-4-carboxamide;
or a pharmaceutically acceptable salt or tautomer of any of the aforementioned.

19. The method of claim 1, wherein the compound of Formula IIb is 4-[1-(4-Chlorobenzyl)-1H-pyrazol-4-yl]-2-{4-[1-(methylsulfonyl)pyrrolidin-3-yl]-1H-imidazol-2-yl}pyridine, or a pharmaceutically acceptable salt or tautomer thereof.

20. The method of claim 1, wherein the compound of Formula IIb is 4-[1-(4-Chlorobenzyl)-1H-pyrazol-4-yl]-2-{4-[1-(methylsulfonyl)pyrrolidin-3-yl]-1H-imidazol-2-yl}pyridine, or a pharmaceutically acceptable salt thereof.

21. The method of claim 1, wherein the disease or disorder is lung cancer, melanoma, pancreatic cancer, breast cancer, prostate cancer, liver cancer, colon cancer, endometrial cancer, bladder cancer, skin cancer, cancer of the uterus, renal cancer, or gastric cancer.

22. The method of claim 1, wherein the sarcoma is Askin's tumor, sarcoma botryoides, chondrosarcoma, Ewing's sarcoma, malignant hemangioendothelioma, malignant schwannoma, osteosarcoma, alveolar soft part sarcoma, angiosarcoma, cystosarcoma phyllodes, dermatofibrosarcoma protuberans, desmoid tumor, desmoplastic small round cell tumor, epithelioid sarcoma, extraskeletal chondrosarcoma, extraskeletal osteosarcoma, fibrosarcoma, gastrointestinal stromal tumor (GIST), hemangiopericytoma, hemangiosarcoma, Kaposi's sarcoma, leiomyosarcoma, liposarcoma, lymphangiosarcoma, lymphosarcoma, malignant peripheral nerve sheath tumor (MPNST), neurofibrosarcoma, rhabdomyosarcoma, synovial sarcoma, or undifferentiated pleomorphic sarcoma.

23. The method of claim 1, wherein the disease or disorder is acute myeloid leukemia, acute monocytic leukemia, small lymphocytic lymphoma, chronic lymphocytic leukemia (CLL), chronic myelogenous leukemia (CML), multiple myeloma, T-cell acute lymphoblastic leukemia (T-ALL), cutaneous T-cell lymphoma, large granular lymphocytic leukemia, mature (peripheral) t-cell neoplasm (PTCL), anaplastic large cell lymphoma (ALCL), or lymphoblastic lymphoma.

24. The method of claim 23, wherein the mature (peripheral) t-cell neoplasm (PTCL) is T-cell prolymphocytic leukemia, T-cell granular lymphocytic leukemia, aggressive NK-cell leukemia, mycosis fungoides/Sezary syndrome, anaplastic large cell lymphoma (T-cell type), enteropathy type T-cell lymphoma, adult T-cell leukemia/lymphoma, or angioimmunoblastic T-cell lymphoma.

25. The method of claim 23, wherein the anaplastic large cell lymphoma (ALCL) is systemic ALCL or primary cutaneous ALCL.

26. The method of claim 1, wherein the disease or disorder is Burkitt's lymphoma, acute myeloblastic leukemia, chronic myeloid leukemia, non-Hodgkin's lymphoma, Hodgkin's lymphoma, hairy cell leukemia, Mantle cell lymphoma, small lymphocytic lymphoma, follicular lymphoma, lymphoplasmacytic lymphoma, extranodal marginal zone lymphoma, Waldenstrom's macroglobulinemia, prolymphocytic leukemia, acute lymphoblastic leukemia, myelofibrosis, mucosa-associated lymphatic tissue (MALT) lymphoma, mediastinal (thymic) large B-cell lymphoma, lymphomatoid granulomatosis, splenic marginal zone lymphoma, primary effusion lymphoma, intravascular large B-cell lymphoma, plasma cell leukemia, extramedullary plasmacytoma, smoldering myeloma, monoclonal gammopathy of undetermined significance (MGUS), or diffuse large B cell lymphoma.

27. The method of claim 26, wherein non-Hodgkin's lymphoma (NHL) is relapsed NHL, refractory NHL, recurrent follicular NHL, indolent NHL (iNHL), or aggressive NHL (aNHL).

28. The method of claim 26, wherein the diffuse large B cell lymphoma is activated B-cell like (ABC) diffuse large B cell lymphoma, or germinal center B cell (GCB) diffuse large B cell lymphoma.

29. The method of claim 26, wherein the Burkitt's lymphoma is endemic Burkitt's lymphoma, sporadic Burkitt's lymphoma, or Burkitt's-like lymphoma.

* * * * *

UNITED STATES PATENT AND TRADEMARK OFFICE
CERTIFICATE OF CORRECTION

PATENT NO. : 11,952,367 B2
APPLICATION NO. : 17/705079
DATED : April 9, 2024
INVENTOR(S) : Richard B. Sparks et al.

It is certified that error appears in the above-identified patent and that said Letters Patent is hereby corrected as shown below:

On the Title Page

Column 1 (Title), Line 1, delete "PYRIDIMINE" and insert -- PYRIMIDINE --.

In the Specification

Column 1, Line 1, delete "PYRIDIMINE" and insert -- PYRIMIDINE --.

In the Claims

Column 270, Line 66, Claim 1, after "$NR^cS(O)_2R^b$" insert -- , --;

Column 271, Line 17, Claim 1, after "$NR^{c2}C(O)OR^{a2}$" insert -- , --;

Column 271, Line 17, Claim 1, after "$NR^{c2}C(O)NR^{c2}R^{d2}$" insert -- , --;

Column 271, Line 33, Claim 1, delete "3independently" and insert -- 3 independently --;

Column 273, Line 61, Claim 7, delete "$C(O)OR\ ^{a2}$," and insert -- $C(O)OR^{a2}$, --;

Column 273, Line 62, Claim 7, after "$NR^{c2}R^{d2}$" insert -- , --;

Column 274, Line 17, Claim 10, delete "alkylene-$C^{y1}$;" and insert -- alkylene-$Cy^1$; --.

Signed and Sealed this
First Day of October, 2024

Katherine Kelly Vidal
Director of the United States Patent and Trademark Office